United States Patent [19]
Freidinger et al.

[11] Patent Number: 5,356,904
[45] Date of Patent: Oct. 18, 1994

[54] CARBOSTYRIL OXYTOCIN RECEPTOR ANTAGONISTS

[75] Inventors: Roger M. Freidinger, Lansdale; Joseph M. Pawluczyk, Warminster; Douglas J. Pettibone, Shalfont; Peter D. Williams, Harleysville, all of Pa.

[73] Assignee: Merck & Co., Inc., Rahway, N.J.

[21] Appl. No.: 957,491

[22] Filed: Oct. 7, 1992

[51] Int. Cl.$^5$ ............................................. A61K 31/47
[52] U.S. Cl. ................................. 514/312; 514/802; 514/935
[58] Field of Search ........................ 514/312, 807, 935

[56] References Cited
U.S. PATENT DOCUMENTS
5,095,003 3/1992 Goetz et al. ........................... 514/9

FOREIGN PATENT DOCUMENTS
0382185A2 8/1990 .
0470514A1 2/1992 .
WO94/01113 1/1994 PCT Int'l Appl. ........ A61K 31/535

OTHER PUBLICATIONS

Ogawa et al. 114 CA:81619f 1990.
The Pharmacological Basis of Therapeutics 7th Ed. Goodman & Gilmans Eds., The Macmillan Publ. Co. N.Y. 1987.
Life Sciences, vol. 50, pp. 1953–1958, Pergamon Press, (1992) By D. J. Pettibone, et al., entitled *Radioligand Binding Studies Reveal Marked Species Differences in the Vasopressin $V_1$ Receptor of Rat, Rhesus and Human Tissues*.
Science, vol. 252, pp. 572–574 (Apr. 26, 1991) by Y. Yamamura, et al., entitled *OPC-21268, An Orally Effective, Nonpeptide Vasopressin V1 Receptor Antagonist*.
Biochemical & Biophysical Research Communications, vol. 178, No. 2, pp. 707–712 (Jul. 31, 1991) by K. Okada, et al., entitled *Effect of a New $V_1$ Antagonist (OPC-21268) on Vascular Action of Vasopressin in Cultured Rat Vascular Smooth Muscle Cells*.
Hypertension, vol. 18 (3), p. 383 (1991) by Y. Uehara, et al., entitled *Alterations in Receptor–Mediated Activation of Phospholipase $A_2$ in Dahl Salt-Sensitive Rats*.

*Primary Examiner*—Marianne M. Cintins
*Assistant Examiner*—Russell Travers
*Attorney, Agent, or Firm*—Mary A. Appollina; Joseph F. DiPrima

[57] ABSTRACT

A method of inhibiting oxytocin from acting at its receptor site by administering oxytocin receptor antagonist compounds of the formula

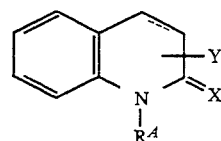

wherein X is oxygen or sulfur; Y is hydrogen or lower alkyl; $R^4$ is

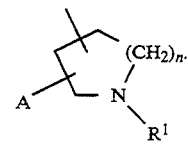

5 Claims, No Drawings

CARBOSTYRIL OXYTOCIN RECEPTOR ANTAGONISTS

FIELD OF THE INVENTION

This invention relates to treatment of preterm labor, stopping labor preparatory to Caesarean delivery and to the treatment of dysmenorrhea through the use of agents that are oxytocin receptor antagonists. The present invention provides a novel use of piperidinyl carbostyril compounds previously known to be useful as vasopressin receptor antagonists. The aforementioned pharmacologic activities are useful in the treatment of mammals.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and calsium antagonists. Ritodrine, the leading $\beta_2$-adrenergic agonists, causes a number of cardiovascular and metabolic side effects in the mother, including tachycardia, increased renin secretion, hyperglycemia (and reactive hypoglycemia in the infant) and pulmonary edema. Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Calcium antagonists have been used to inhibit uterine activity of preterm labor but also produce unwanted cardiovascular side effects.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part from a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds used in the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens. Additional uses for the present invention are for the stoppage of labor preparatory to Caesarean delivery and to control uterine activity during fetal surgery.

It is, therefore, a purpose of this invention to provide substances which more effectively antagonize the function of oxytocin in disease states in animals, preferably mammals, especially in humans. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of formula I, below, are antagonists of oxytocin and bind to the oxytocin receptor. When the oxytocin receptor is bound by the compounds used in the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find utility for the stoppage of labor preparatory to Caesarean delivery.

SUMMARY OF THE INVENTION

The invention is a method of antagonizing binding of oxytocin to mammalian oxytocin receptors, comprising the step of administering to a mammal in need thereof, in an amount effective to antagonize said binding, an antagonist compound of the formula:

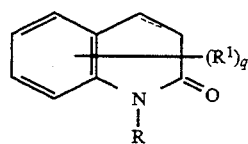

I wherein $R^1$ is hydrogen; nitro; lower alkoxy; lower alkoxycarbonyl; lower alkyl; halogen; amino having one to two substituents selected from the group consisting of lower alkanoyl, lower alkyl, benozyl and phenyl lower alkoxycarbonyl; hydroxy; cyano; carboxy; lower alkanoyloxy; or hydrazinocarbonyl;

q is an integer of 1 to 3 and

R is a group of the formula

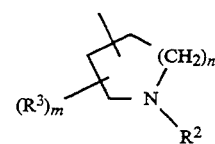

or

-continued

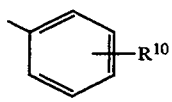

wherein

R² is hydrogen; lower alkoxycarbonyl; phenoxycarbonyl which phenyl ring may be substituted by one to three substituents selected from nitro and an amino having optionally one or two substituents selected from a lower alkanoyl, lower alkyl or benzoyl; phenyl lower alkenylcarbonyl; phenyl lower alkanoyl substituted by amino which in turn is substituted by lower alkoxycarbonyl; alkanoyl; alkenylcarbonyl; phenylsulfonyl substituted by lower alkoxy; a group of the formula

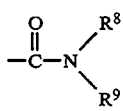

wherein

R⁸ and R⁹ are the same or different and are each hydrogen or phenyl substituted by lower alkoxy, lower alkyl, halogen, amino substituted by lower alkyl, lower alkanoyl or nitro; carbonyl substituted by a heterocyclic ring substituted by one to three substituents selected from phenyl lower alkoxycarbonyl, phenyl lower alkoxy, oxo, lower alkyl or lower alkylenedioxy; a group of the formula

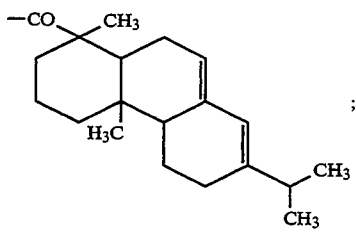

naphthylcarbonyl; thienyl lower alkanoyl; tricyclo[3.3.1.1]decanyl(lower)alkanoyl; tricyclo[3.3.1.1.]-decanylcarbonyl; or a group of the formula

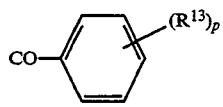

wherein p is 0 or an integer of 1 to 3, and R¹³ is hydroxy; alkoxy; alkoxy having one or two substituents selected from hydroxy, lower alkanoyloxy, tri-lower alkylammonium, lower alkoxy, or a group of the formula

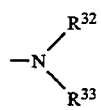

wherein R³² and R³³ are the same or different and are each hydrogen, lower alkyl, hydroxy-substituted lower alkyl, lower alkanoyl, tetrahydropyranyl lower alkyl, phenyl, phenyl lower alkyl wherein the alkyl moiety may optionally be substituted by hydroxy and the phenyl ring may optionally be substituted by a lower alkoxy, or a pyridyl lower alkyl; or R³² and R³³ may be bound to nitrogen to form a 5 or 6 membered saturated heterocyclic ring which may be intervened with nitrogen, oxygen or sulfur wherein the heterocyclic group may optionally be substituted by a member selected from carbamoyl, lower alkyl, phenyl lower alkyl, phenyl or hydroxy-substituted lower alkyl; carboxy-substituted alkoxy; halogen-substituted lower alkoxy; lower alkoxycarbonyl-substituted alkoxy; lower alkanoyloxy-substituted lower alkoxy; lower alkenyloxy substituted lower alkoxy; lower alkoxy lower alkoxy; lower alkylsulfonyloxy-substituted lower alkoxy; benzoyloxy-substituted lower alkoxy; tricyclo[3.3.1.1]decanyl-substituted lower alkoxy; lower alkoxy lower alkoxy substituted by one or two substituents selected from hydroxy and an amino being optionally substituted by lower alkyl; morpholinyl-substituted lower alkoxy; benzimidazolylsulfinyl-substituted lower alkoxy; a group of the formula

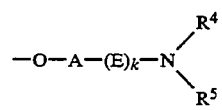

wherein A is alkylene, k is an integer of 0 or 1, E is —CO— or —OCO—, R⁴ and R⁵ are the same or different and are each hydrogen; lower alkyl which may optionally be substituted by hydroxy or cyano; lower alkenyl, lower alkynyl; phenyl lower alkyl; lower alkanoyl which may optionally have one to three substituents of a halogen atom; benzoyl which phenyl ring may optionally be substituted by a member selected from nitro and an amino having optionally one or more substituents selected from lower alkyl, lower alkanoyl or phenyl lower alkoxycarbonyl; phenyl; lower alkoxycarbonyl; lower alkoxycarbonyl lower alkyl wherein the lower alkyl moiety may optionally be substituted by hydroxy or an amino having optionally a phenyl lower alkoxycarbonyl substituent; an amido having optionally a lower alkyl substituent; a pyrrolidinyl-substituted carbonyl which pyrrodinyl ring may optionally be substituted by phenyl lower alkoxycarbonyl; amino-substituted lower alkanoyl wherein the lower alkanoyl moiety may optionally be substituted by a member selected from phenyl lower alkoxycarbonyl amino, hydroxy, phenyl optionally having a hydroxy substituent, carbamoyl, imidazolyl or a lower alkylthio, and the amino group may optionally have a substituent selected from a lower alkyl optionally having a hydroxy substituent, lower alkenyl, phenyl lower alkyl optionally having a lower alkoxy substituent on the phenyl ring, lower alkylsulfonyl, lower alkanoyl, lower alkylsulfonyl, a phenylsulfonyl which phenyl ring may optionally be substituted by a lower alkyl group, nitro or amino having optionally one or two substituents selected from a lower alkyl and a lower alkanoyl; amido-substituted lower alkyl wherein the lower alkyl moiety optionally has a substituent selected from phenyl optionally having a hydroxy substituent, imidazolyl, carbamoyl or a lower alkylthio, and the amido group may optionally have a lower alkyl substituent; amino-substituted lower alkyl which may optionally be substituted by a lower alkyl or a lower alkanoyl; anilinocarbonyl; piperidinyl which may optionally be substituted by phenyl lower alkyl; cycloalkyl, cycloalkenylcarbonyl; cycloalkylcarbonyl which may optionally have one to three substituents selected from hydroxy and a lower alkanoyloxy; tetrahydropyranyl-substituted lower alkyl wherein the tetrahydropyranyl ring may optionally have one to four substituents selected from hydroxy and a lower alkoxy; lower alkanoyl which is substituted by a 5 or 6 membered saturated heterocyclic group selected from pyrrolidinyl, piperazinyl, piperidinyl and morpholinyl wherein the heterocyclic group may have optionally a substituted selected from a lower alkyl and phenyl; piperidinyl-substituted carbonyl which may optionally be substituted by a lower alkanoyl; lower alkanoyloxy lower alkyl; pyridyl-substituted lower alkyl; or an amino acid residue which can form an amido group with its amino group or $R^4$ and $R^5$ may bind together with the nitrogen atom to which they bond to form a 5 or 6 membered saturated or unsaturated heterocyclic group which may be intervened or not with nitrogen, oxygen, or sulfur, wherein the heterocyclic group may optionally be substituted by a member selected from a phenyl having optionally a substituted selected from a lower alkoxy and a halogen atom, oxo, hydroxy, lower alkenyl, carboxy, phenyl lower alkyl having an optional hydroxy substituent on the lower alkyl moiety, lower alkanoyl lower alkyl having optionally a hydroxy substituent, benzoyl, an amido having optionally a lower alkyl substituent, anilinocarbonyl, benzoyl lower alkyl lower alkylsulfonyl, piperidinyl, pyrimidyl, pyridyl, and lower alkoxycarbonyl; carbamoyloxy-substituted lower alkoxy; lower alkylthio-substituted lower alkoxy; alkenyloxy; phenoxy; lower alkanoyloxy; lower alkylsulfonyloxy; lower alkynyl; phenyl lower alkoxy; cycloalkyl; cycloalkyloxy; cycloalkenyloxy; imidazo[4,5-c]pyridyl-carbonyl lower alkoxy; a group of the formula

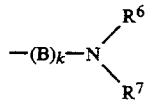

wherein k is as defined above, B is a lower alkylene or a group —CO— and $R^6$ and $R^7$ are the same or different and are each hydrogen, lower alkyl, lower alkanoyl having optionally one to three halogen substituents, carboxy lower alkyl, lower alkoxycarbonyl, lower alkoxycarbonyl lower alkyl, lower alkenyl, amido-substituted lower alkyl having an optional lower alkyl substituent, or a phenyl lower alkoxycarbonyl, or $R^6$ and $R^7$ may bind together with a nitrogen atom to which they bond to form a 5 or 6 membered, saturated or unsaturated heterocyclic group which may be intervened or not with nitrogen, oxygen or sulfur, wherein the heterocyclic group may optionally have a substituent selected from a lower alkoxycarbonyl, lower alkyl, lower alkylthio, or oxo; nitro; halogen; lower alkylsulfonyl; lower alkyl which may optionally have one to three substituents selected from a halogen, hydroxy, phenyl and lower alkoxy; cyano-substituted lower alkoxy, pyrrolyl-substituted lower alkoxy; cyano; lower alkoxycarbonyl; amidino; carbamoyl; carboxy; lower alkanoyl; benzoyl; lower alkoxycarbonyl lower alkyl; carboxy lower alkyl; lower alkoxy lower alkyl; lower alkanoyloxy lower alkyl; hydroxyimino; substituted lower alkyl; phenyl; lower alkylthio; lower alkylsulfinyl; lower alkenyl optionally having a hydroxy substituent; lower alkylenedioxy, lower alkylsilyl; pyrimidylthio-substituted lower alkoxy; pyrimidylsulfinyl-substituted lower alkoxy; pyrimidylsulfonyl-substituted lower alkoxy; imidazolylthio-substituted lower alkoxy which may optionally have a lower alkyl substituent; imidazolylsulfonyl-substituted lower alkoxy which may optionally have a lower alkyl substituent; ammonium-lower alkoxy having three substituents selected from lower alkoxy, lower alkenyl and oxo; phenylthio-substituted lower alkoxy which phenyl ring may optionally have a substituent selected from nitro and amino; phenylsulfonyl-substituted lower alkoxy which phenyl ring may optionally have a substituent selected from nitro and an amino having optionally one or two substituents selected from a lower alkanoyl and lower alkyl; pyridylthio-substituted lower alkoxy; or a pyridylsulfonyl-substituted lower alkoxy which pyridyl ring may optionally be substituted by oxo; n is an integer of 1 or 2; m is 0 or an integer of 1 to 3; $R^3$ is a lower alkyl; $R^{10}$ is a group of the formula

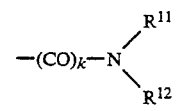

wherein k is as defined above and $R^{11}$ and $R^{12}$ are the same or different and are each hydrogen, lower alkyl, phenyl lower alkyl, lower alkenyl, benzoyl which may optionally have a lower alkoxy substituent, tricyclo[3.3.1.1]decanyl, a phenyl which may optionally have a lower alkoxy substituent or a cycloalkyl, or $R^{11}$ and $R^{12}$ may bind together with the nitrogen atom to which they bond to form a saturated or unsaturated heterocyclic group which may be intervened or not with nitrogen, oxygen or sulfur, wherein the heterocyclic group may optionally have a substituent selected from a benzoyl, a lower alkanoyl, phenyl lower alkyl and a phenyl which may optionally be substituted by a lower alkoxy and a lower alkonoyl; the bond between 3 and 4 positions of the carbostyril ring is a single bond or double bond; provided that when $R^1$ is hydrogen and the k in the formula

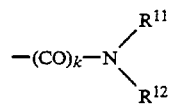

is 0, $R^{11}$ and $R^{12}$ are not simultaneously hydrogen atoms.

The method of the invention can also be practiced with compounds of formula II

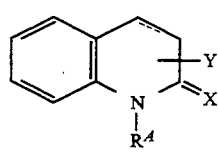

wherein X is oxygen or sulfur;

Y is hydrogen or lower alkyl;

$R^4$ is a group of the formula

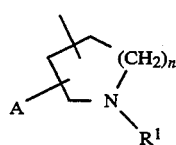

wherein n is 1 or 2, A is a lower alkylene, and $R^1$ is a benzoyl which phenyl may optionally have one to three substituents selected from a lower alkoxy and an amino having optionally a lower alkyl substituent; or $R^A$ is a group of the formula

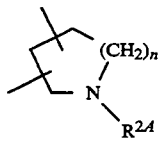

wherein n is as defined above, and $R^{2A}$ is a group of the formula

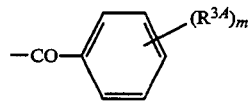

wherein $R^{3A}$ is a lower alkoxy; or a 5 or 6 membered heterocyclic ring having 1 to 2 hetero atoms selected from nitrogen, oxygen, or sulfur which may optionally have a substituent selected from lower alkyl, oxo, phenyl optionally having a substituent selected from halogen and a lower alkoxy on the phenyl ring and a phenylthio optionally having a substituent selected from nitro and amino; lower alkynylthio; pyrrolidinyl-substituted lower alkylthio; pyrrolidinyl-substituted lower alkylsulfinyl; pyrrolidinyl-substituted lower alkylsulfonyl; a group of the formula

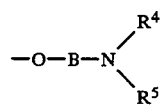

wherein B is a lower alkylene having optionally a hydroxy substituent, $R^4$ is hydrogen and $R^5$ is tricyclo[3.3.1.1]decanyl, tricyclo[3.3.1.1]decanyl-lower alkyl, halogen-substituted lower alkyl, lower alkoxycarbonyl-lower alkanoyloxy-lower alkyl, lower alkanyl, or lower alkenyl, or $R^4$ and $R^5$ may bind together with the nitrogen atom to which then bond to form a group of the formula

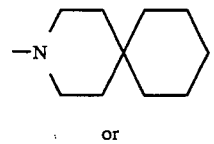

or

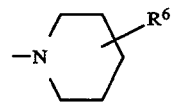

wherein $R^6$ is an amino which may optionally be substituted by a lower alkanoyl having optionally one to three halogen substituents; or lower alkoxy having two substituents selected from an aminocarbonyloxy having optionally a lower alkyl substituent or a group of the formula

wherein $R^7$ and $R^8$ are the same of different and are each hydrogen or lower alkyl;

m is an integer of 1 to 3;

the bond between the 3 and 4 positions of the carbostyril ring is a single bond or a double bond; provided that when all of $R^{3A}$ are lower alkoxy or when $R^5$ is a lower alkanoyl, X is sulfur and that when $R^5$ is lower alkenyl and X is oxygen, B is a lower alkylene having a hydroxy substituent, and further that when $R^{3A}$ is a heterocyclic group having a lower alkyl or oxo substituent, the heterocyclic group is bound to the phenyl ring at the position other than the hetero atom, or a pharmaceutically acceptable salt thereof.

Most preferred compounds for use in the present method are those represented in the following table:

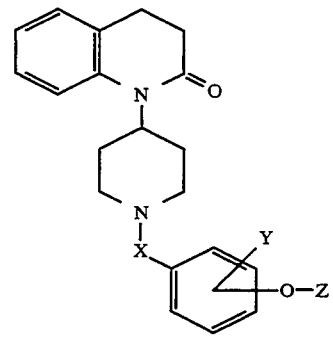

| Example | X | Y | Z |
|---------|---|---|---|
| 1 | —C(=O)— | | —CH₂CH₂CH₂CH₂—N(H)—C(=O)—CH₃ |
| 2 | —C(=O)— | | —CH₂CH₂CH₂—N(phthalimide) |
| 3 | —C(=O)— | | —H |
| 4 | —C(=O)— | | —CH₃ |

-continued

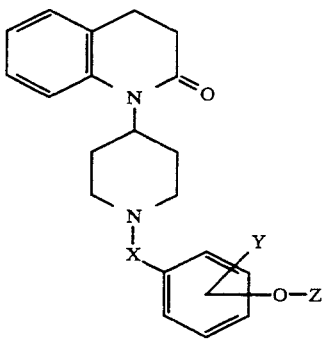

| Example | X | Y | Z |
|---|---|---|---|
| 5 | ![C=O] | —OCH₃ | —CH₃ |
| 6 | ![S(=O)₂] | | —CH₃ |
| 7 | ![H₂C] | | —H |

DETAILED DESCRIPTION OF THE INVENTION

Compounds of formula I are prepared as taught in European patent application EP 0 382 185, published Aug. 16, 1990. The carbostryril derivatives of formula I of the present invention can be prepared by various processes, for example, by the processes shown in the following reaction schemes.

[Reaction Scheme-1]

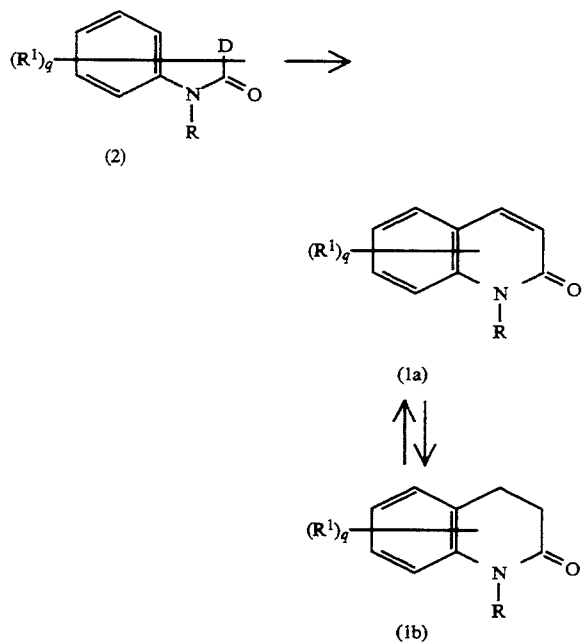

wherein R, q and $R^1$ are the same as defined above, and D is a group of the formula: —CH=CHR$^{14}$ ($R^{14}$ is a lower alkoxy, phenyl or a halogen atom), a group of the formula:

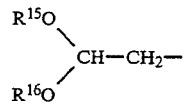

($R^{15}$ and $R^{16}$ are each a lower alkyl), or a group of the formula: —CH=CH, and the D group may optionally be substituted by the group $R^1$.

The cyclization reaction of the compound of the formula (2) is carried out in an appropriate solvent or without solvent in the presence of an acid. The acid includes any conventional inorganic acids and organic acids, for example, inorganic acids (e.g. hydrochloric acid, hydrobromic acid, sulfuric acid, etc.), Lewis acids (e.g. aluminum chloride, boron trifluoride, titanium tetra chloride, etc.), organic acids (e.g. formic acid, acetic acid, ethanesulfonic acid, p-toluenesulfonic acid, etc.), phosphorus pentoxide, polyphosphoric acid, among which hydrochloric acid, hydrobromic acid and sulfuric acid are preferable. The acid is usually used in at least equivalent amount, preferably in an amount of 10 to 50 times by weight, as much as the amount of the compound (2). The solvent includes any conventional inert solvents, for example, water, lower alcohols (e.g. methanol, ethanol, propanol, etc.), ethers (e.g. dioxane, tetrahydrofuran, etc.), aromatic hydrocarbons (e.g. benzene, chlorobenzene, toluene, etc.), halogenated hydrocarbons (e.g. methylene chloride, chloroform, carbon tetrachloride, etc.), acetone, dimethylsulfoxide, dimethylformamide, hexamethylphosphoric triamide, and the like. The reaction is usually carried out at a temperature of from about 0° to about 200° C., preferably from room temperature to about 150° C., for about 5 minutes to 6 hours.

The reduction of the compound of the formula (1a) is usually carried out under conventional conditions for the usual catalytic reduction. The catalyst includes metals such as palladium, palladium-carbon, platinum, Raney nickel, etc. The solvent used therein includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.). The reduction reaction can be carried out at atmospheric pressure or under pressure, usually under atmospheric pressure to 20 kg/cm², preferably atmospheric pressure to 10 kg/cm². The reaction temperature is usually in the range of from about 0° C. to about 150° C., preferably from room temperature to about 100° C.

The dehydration reaction of the compound of the formula (1b) is usually carried out in an appropriate solvent with an oxidizing agent. The oxidizing agent includes, for example, benzoquinones (e.g. 2,3-dichloro-5,6-dicyanobenzoquinone, chloranil (=2,3,5,6-tetrachlorobenzoquinone), etc.), halogenating agents (e.g. N-bromosuccinimide, N-chlorosuccinimide, bromine, etc.), hydrogenating catalysts (e.g. selenium oxide, palladium-carbon, palladium black, palladium oxide, Raney nickel, etc.). When a halogenating agent is used, it is usually used in an amount of 1 to 5 moles, preferably 1 to 2 moles, to 1 mole of the compound (1b). When a hydrogenating catalyst is used, it is used in a catalytic amount as usual. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar solvents (e.g. acetic acid, etc.), aprotic polar solvents (e.g. dimethylformamide, dimethylsulfoxide, hexamethylphosphoric triamide, etc.). The reaction is usually carried out at a temperature of from room temperature to about 300° C., preferably from room temperature to about 200° C., for 1 to 40 hours.

[Reaction Scheme-2]

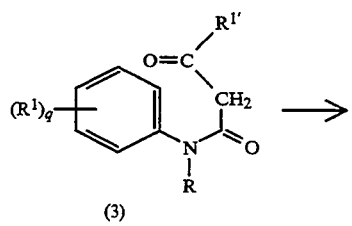

(3)

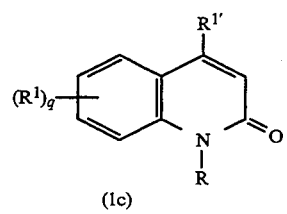

(1c)

wherein $R^1$, q and R are the same as defined above, and $R^{1'}$ is hydrogen atom or a lower alkyl, provided that when $R^{1'}$ is a lower alkyl, q is 1 or 2.

The cyclization reaction of the compound (3) is carried out in an appropriate solvent in the presence of a condensation agent. The concensation agent includes, for example, Lewis acids, such as phosphorus pentoxide, hydrogen fluoride, sulfuric acid, polyphosphoric acid, aluminum chloride, zinc chloride, etc. The solvent includes, for example, halogenated hydrocarbons (e.g. chloroform, dichloromethane, 1,2-dichloroethane, etc.), ethers (e.g. diethyl ether, dioxane, etc.), aromatic hydrocarbons (e.g. nitrobenzene, chlorobenzene, etc.). The condensation agent is usually used in an amount of about 1 to 10 moles, preferably about 3 to 6 moles, to 1 mole of the compound (3). The reaction is usually carried out at a temperature of about 50° C. to about 250° C., preferably about 70° C. to about 200° C., for about 20 minutes to about 6 hours.

[Reaction Scheme-3]

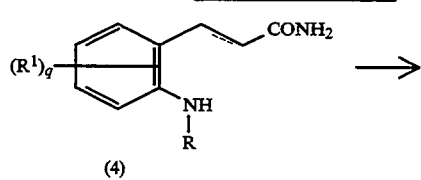

-continued
[Reaction Scheme-3]

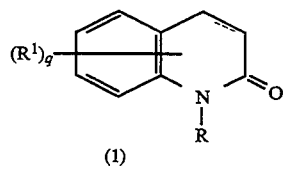

(1)

wherein R, $R^1$, q, and the bond between 3- and 4-positions of the carbonstyril nucleus are the same as defined above.

The cyclization reaction of the compound (4) is carried out in an appropriate solvent or without using a solvent in the presence of an acid. The acid includes, for example, inorganic acids (e.g. hydrochloric acid, sulfuric acid, hydrobromic acid, nitric acid, polyphosphoric acid, etc.), organic acids (e.g. p-toluenesulfonic acid, ethanesulfonic acid, trifluoroacetic acid, etc.). The solvent includes any conventional solvents unless they affect on the reaction, for example, water, lower alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, diphenyl ether, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The reaction is usually carried out at a temperature of from about −20° C. to about 150° C., preferably from about 0° C. to about 150° C., for about 5 minutes to about 30 hours.

[Reaction Scheme-4]

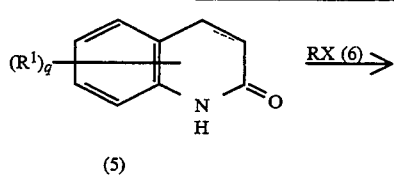

(5)

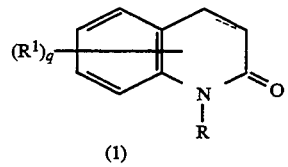

(1)

wherein R, $R^1$, q and the bond between 3- and 4-positions of the carbostyril nucleus are the same as defined above.

The reaction of the compound of the formula (5) and the compound of the formula (6) is usually carried out in an appropriate inert solvent in the presence or absence of a basic compound. The inert solvent includes, for example, aromatic hydrocarbons (e.g. benzene, toluene, xylene, etc.), alcohols (e.g. methanol, ethanol, propanol, butanol, 3-methoxy-1-butanol, ethylcellosolve, methylcellosolve, etc.), pyridine, acetone, N-methylpyrrolidone, dimethylsulfoxide, dimethylformamide, hexamethylphosphoric triamide, etc. The basic compound includes, for example, sodium carbonate, potassium carbonate, sodium hydrogen carbonate, potassium hydrogen carbonate, sodium hydroxide, potassium hydroxide, sodium hydride, potassium hydride, triethylamine, etc.

The amounts of the compound (5) and the compound (6) are not critical, but the compound (6) is usually used at least in equimolar amount, preferably in an amount of 1 to 5 moles to 1 mole of the compound (5). The reaction is usually carried out at a temperature of from room temperature to about 200° C., preferably about 100° C. to about 180° C., for about 3 to 30 hours. In the above reaction, a copper powder may also be used as a catalyst, by which the reaction can proceed advantageously.

[Reaction Scheme-5]

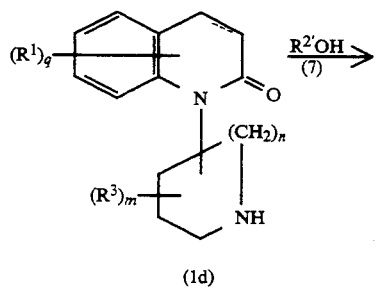

(1d)

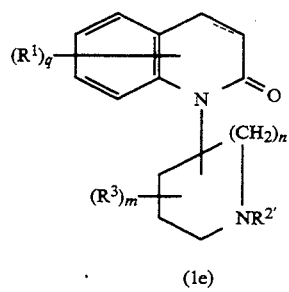

(1e)

wherein $R^1$, q, $R^3$, m, n and the bond between 3- and 4-positions of the carbostyril nucleus are the same as defined above, and $R^2$ is the same groups as $R^2$ other than hydrogen atom and a group of the formula:

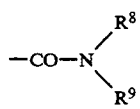

($R^8$ and $R^9$ are the same as defined above).

The process of Reaction Scheme-5 is carried out by reacting a carbostyril derivative of the formula (1d) and a carboxylic acid compound of the formula (7) by a conventional amido bond producing reaction. The amido bond producing reaction can be carried out under the conditions for the conventional amido bond producing reaction, for example, (a) a mixed acid anhydride process, i.e. a process of reacting the carboxylic acid compound (7) with an alkylhalocarboxylic acid to form a mixed acid anhydride and reacting the resultant with the amine compound (1d), (b) an activated ester process, i.e. a process of converting the carboxylic acid compound (7) into an activated ester, such as p-nitrophenyl ester, N-hydroxysuccinimide ester, 1-hydroxybenzotriazole ester, etc., and reacting the resultant with the amine compound (1d), (c) a carbodiimide process, i.e. a process of condensing the carboxylic acid compound (7) and the amine compound (1d) in the presence of an activating agent such as dicyclohexylcarbodiimide, carbonyldimidazole, etc., (d) other processes, i.e. a process of converting the carboxylic acid compound (7) into a carboxylic anhydride by treating it with a dehydrating agent such as acetic anhydride, and reacting the resultant with the amine compound (1d); a process of reacting an ester of the carboxylic acid compound (7) with a lower alcohol and the amine compound (1d) at a high temperature under high pressure; a process of reacting an acid halide compound of the carboxylic acid compound (7), i.e. a carboxylic acid halide, with the amine compound (1d), and the like.

The mixed acid anhydride used in the above mixed acid anhydride process is obtained by the known Schötten-Baumann reaction, and the reaction product is used without isolation from the reaction mixture for the reaction with the amine compound (1d) to give the desired compound of the formula (1e). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about −20° C. to about 100° C., preferably from about 0° C. to about 50° C., for about 5 minutes to about 10 hours, preferably about 5 minutes to about 2 hours.

The reaction of the thus obtained mixed acid anhydride with the amine compound (1d) is usually carried out at a temperature of from about −20° C. to about 150° C., preferably about 10° C. to about 50° C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (7), the alkylhalocarboxylic acid and the amine (1d) are usually used in each equimolar amount, but preferably, the alkylhalocarboxylic acid and the carboxylic acid compound (7) are used each in an amount of about 1 to 1.5 mole to 1 mole of the amine (1d).

Among the above other processes (d), in case of the process of reacting the carboxylic acid halide with the amine compound (1d), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride, etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, and the like. The amount of the amine compound (1d) and the carboxylic acid halide is not critical, but the carboxylic acid halide is usually used at least in equimolar amount, preferably about 1 to 5 moles to 1 mole of the amine compound (1d). The reaction is usually carried out at a temperature of from about −20° C. to about 180° C., preferably from about 0° C. to about 150° C., for about 5 minutes to about 30 hours.

The amido bond producing reaction in the above Reaction Scheme-5 may also be carried out by reacting the carboxylic acid compound (7) and the amine (1d) in the presence of a condensation agent such as triphenylphosphine, diphenylphosphinyl chloride, phenyl-N-phenylphosphoramide chloridate, diethyl chlorophosphate, diethyl cyanophosphate, bis(2-oxo-3-oxazolidinyl)phosphinic chloride, etc. The reaction is usually carried out in the presence of the solvent and basic compound as used in the above reaction of the carboxylic acid halide and the amine (1d) at a temperature of from about −20° C. to about 150° C., preferably about 0° C. to about 100° C., for about 5 minutes to about 30 hours. The condensation agent and the carboxylic acid compound (7) are used at least in equimolar amount, preferably about 1 to 2 moles, to 1 mole of the amine (1d).

wherein $R^1$, q, $R^3$, m, n and the bond between 3- and 4-positions of the carbostyril nucleus are the same as defined above, and $R^8$ is the same as $R^2$ other than hydrogen atom.

The reaction of the compound (1d) and the compound (8) can be carried out in the presence or preferably absence of a basic compound in an appropriate solvent or without solvent. The solvent and the basic compound used therein are the same as the solvent and basic compound as used in the reaction of the carboxylic acid halide and the amine (1d) of the above Reaction Scheme-5. The compound (8) is usually used in an amount of about 1 to 5 moles, preferably about 1 to 3 moles, to 1 mole of the compound (1d). The reaction is usually carried out at a temperature of about 0° to 200° C., preferably from room temperature to about 15° C., for about 5 minutes to about 30 hours. In the above reaction, a boron compound (e.g. borone trifluoride etherate, etc.) may be added to the reaction system.

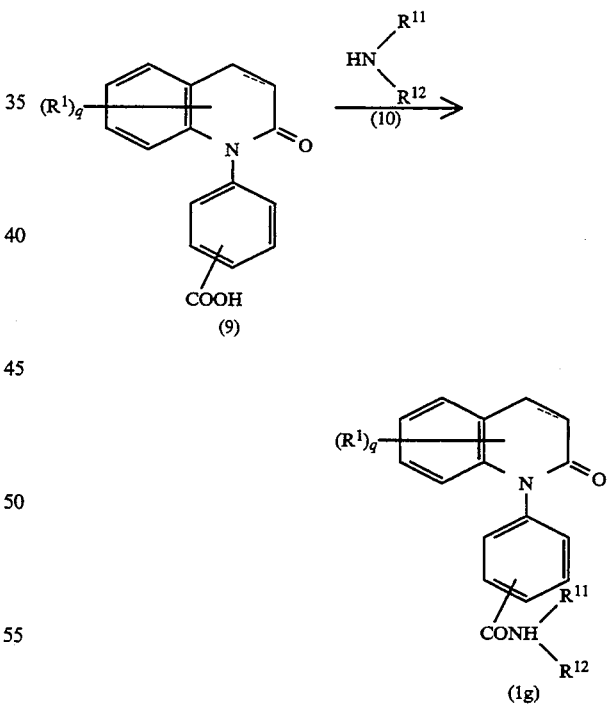

[Reaction Scheme-7]

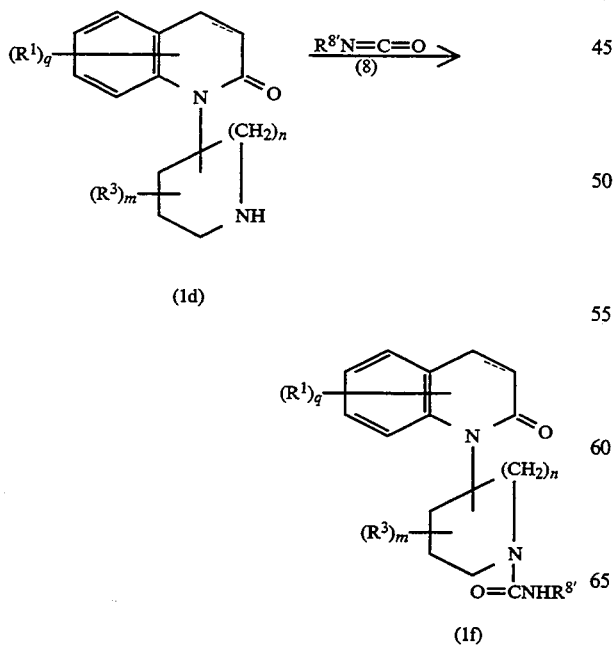

[Reaction Scheme-6]

wherein $R^1$, q, $R^{11}$, $R^{12}$ and the bond between 3- and 4-positions of the carbostyril nucleus are the same as defined above.

The reaction of the compound (9) and the compound (10) is carried out under the same conditions as used in the reaction of the compound (1d) and the compound (7) in the above Reaction Scheme-5.

[Reaction Scheme-8]

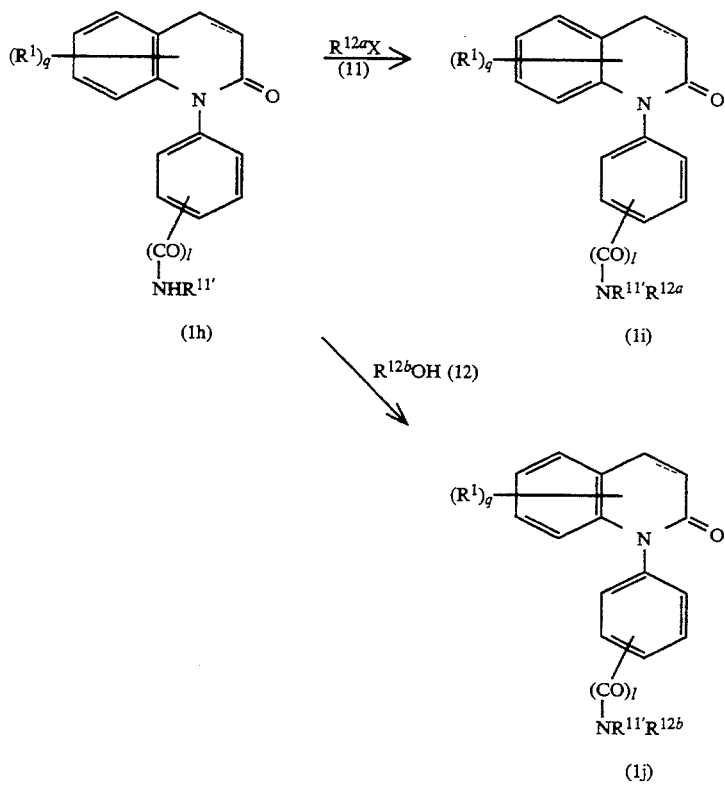

wherein $R^1$, q, X, l and the bond between 3- and 4-positions of carbostyril nucleus are the same as defined above, and $R^{11}$ is hydrogen atom, a lower alkyl, a phenyl(lower)alkyl, a lower alkenyl, a benzoyl which may optionally have a lower alkoxy substituent, tricyclo[3.3.1.1]decanyl, a phenyl which may optionally have a lower alkoxy substituent, or a cycloalkyl, $R^{12a}$ is a lower alkyl, a phenyl(lower)alkyl, a lower alkenyl, tricyclo[3.3.1.1]decanyl, a phenyl which may optionally have a lower alkoxy substituent, or a cycloalkyl, and $R^{12b}$ is a benzoyl which may optionally have a lower alkoxy substituent.

The reaction of the compound (1h) and the compound (11) is usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), acetic acid, ethyl acetate, acetone, acetonitrile, dimethylsulfoxide, dimethylformamide, hexamethylphosphoric triamide, and the like. The basic compound includes, for example, carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium sodium, sodium amide, metal alcoholates (e.g. sodium methoxide, sodium ethoxide, etc.), and organic basic compounds (e.g. pyridine, ethyldiisopropylamine, dimethylaminopyridine, triethylamine, 1,5-diazabicyclo[4.3.0]nonene-(5) (DBN), 1,8-diazabicyclo[5.4.0]undecene-7 (DBU), 1,4-diazabicyclo[2.2.2]octane (DABCO), etc.). The amount of the compound (1h) and the compound (11) is not critical, but the compound (11) is usually used at least in equivalent amount, preferably 1 to 5 moles, to 1 mole of the compound (1h). The reaction is usually carried out at a temperature of from about 0° C. to about 200° C., preferably from about 0° C. to about 170° C., for about 30 minutes to about 30 hours.

The reaction of the compound (1h) and the compound (12) is carried out under the same conditions in the reaction of the compound (1d) and the compound (7) in the above Reaction Scheme-5.

In case of the compound of the formula (1) wherein $R^{11}$ and $R^{12}$ combine together with the nitrogen atom to which they bond to form a saturated or unsaturated heterocyclic group which may be intervened or not with nitrogen, oxygen or sulfur atom and said heterocyclic group contains a secondary amino group, the compound can be converted into a compound where said heterocyclic group is substituted on said secondary amine group by a substituent selected from a phenyl(lower)alkyl and a phenyl having optionally a substituent selected from a lower alkoxy and a lower alkanoyl by treating it in the same manner as in the reaction of the compound (1h) and the compound (11) in the above Reaction Scheme-8.

Besides, said compound can also be converted into a compound where the heterocyclic group is substituted on said secondary amine by a substituent selected from benzoyl and a lower alkanoyl by treating it in the same manner as in the reaction of the compound (1h) and the compound (12) in the above Reaction Scheme-8.

[Reaction Scheme-9A]

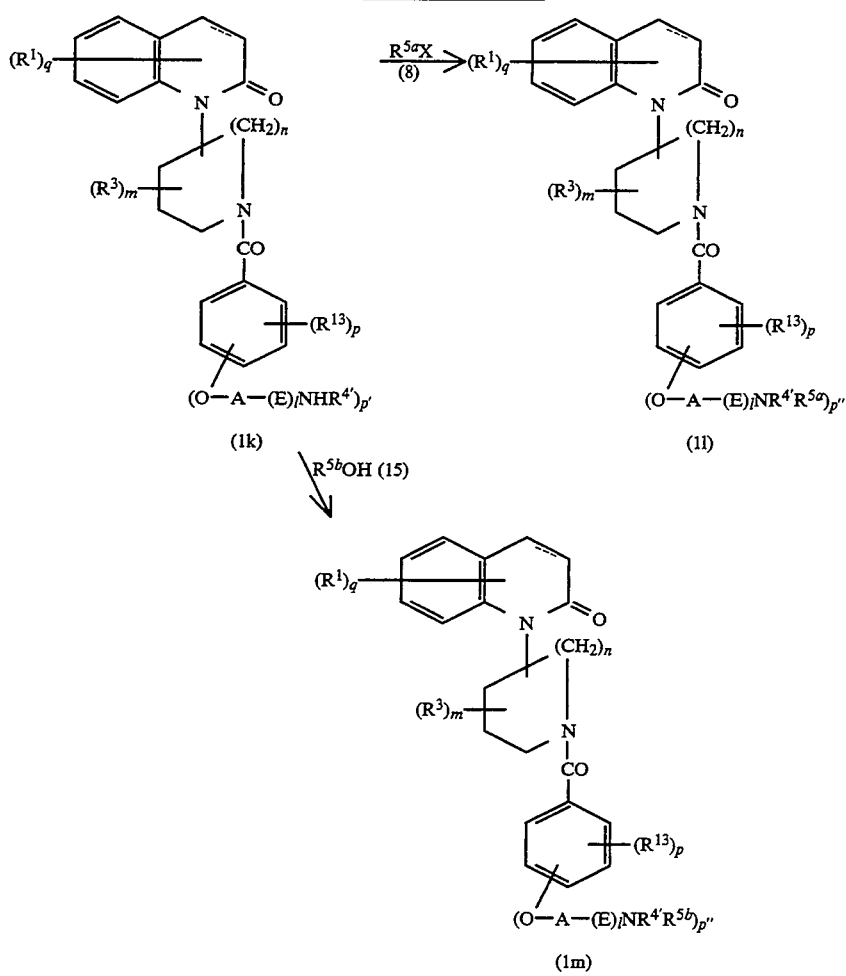

wherein R¹, q, R³, n, R¹³, p, X, A, E, l, and the bond between 3- and 4-positions of the carbostyril nucleus are the same as defined above, and R⁴ is hydrogen atom; a lower alkyl which may optionally be substituted by hydroxy or cyano; a lower alkenyl; a lower alkynyl; a phenyl(lower)alkyl; a lower alkanoyl which may optionally have one to three substituents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower-)alkoxycarbonyl substituent; an amido having optionally a lower alkyl substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, a phenyl having optionally a hydroxy substituent, carbamoyl, imidazolyl or a lower alkylthio, and the amino group may optionally have a substituent selected from a lower alkyl having optionally a hydroxy substituent, a lower alkenyl, a phenyl(-lower)alkyl having optionally a lower alkoxy substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by nitro or an amino having optionally one or two substituents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have substituent selected from a lower alkyl and a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholino wherein the heterocyclic group may optionally have substituent selected from a lower alkyl and phenyl; a piperidinyl-substituted carbonyl which may optionally be substituted by a lower alkanoyl; a lower alkanoyloxy(lower)alkyl; a pyridyl-substituted lower alkyl; or an amino acid residue which can form an amido group with its amino group, $R^{5a}$ is a lower alkyl which may optionally be substituted by hydroxy or cyano; a lower alkenyl; a lower alkynyl; a phenyl(lower)alkyl; phenyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a lower alkylsulfonyl; a phenylsulfonyl which phenyl ring may optionally be substituted by nitro or an amino having optionally one or two substituents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have a substituent selected from a lower alkyl and a lower alkanoyl; anilinocarbonyl; a piperidinyl which may optionally be substituted by a phenyl(lower)alkyl; a cycloalkyl, a tetrahydropyranyl-substituted lower alkyl wherein the tetrahydropyranyl ring may optionally have one to four substituents selected from hydroxy and a lower alkoxy; a lower alkanoyloxy(lower)alkyl; or a pyridyl-substituted lower alkyl, $R^{5b}$ is a lower alkanoyl which may optionally have one to three substituents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; a lower alkoxycarbonyl; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxy carbonylamino, hydroxy, a phenyl having optionally a hydroxy substituent, carbamoyl, imidazolyl or a lower alkylthio, and the amino group may optionally have a substituent selected from a lower alkyl having optionally a hydroxy substituent, a lower alkenyl, a lower alkanoyl, or a phenyl(lower)alkoxycarbonyl; a hydroxy-substituted lower alkanoyl; a lower alkanoyloxy(lower)alkanoyl; a cycloalkenylcarbonyl; a cycloalkylcarbonyl which may optionally have one to three substituents selected from hydroxy and a lower alkanoyloxy; a lower alkanoyl which is substituted by a 5- or 6-membered saturated heterocyclic group selected from pyrrolidinyl, piperazinyl, piperidinyl and morpholino wherein the heterocyclic group may optionally be substituted by a lower alkyl or phenyl; a piperidinyl-substituted carbonyl which may optionally be substituted by a lower alkanoyl; or an amino acid residue which can form an amido group with its amino group, p' and p'' are each an integer of 1 to 3, provided that p+p' and p+p'' are each an integer not more than 3.

[Reaction Scheme-9B]

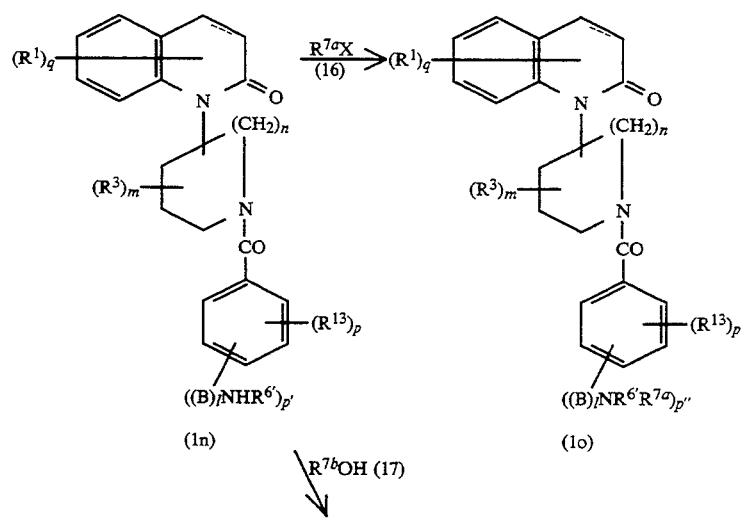

[Reaction Scheme-9B]

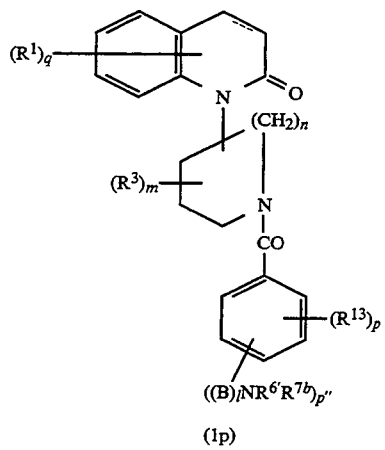

(1p)

wherein $R^1$, q, $R^3$, m, n, $R^{13}$, p, X, B, l, and the bond between 3- and 4-positions of the carbostyril nucleus are the same as defined above, and $R^6$ is hydrogen atom, a lower alkyl, a lower alkanoyl having optionally one to three halogen substituents, a lower alkoxycarbonyl, a carboxy(lower)alkyl, a lower alkoxycarbonyl(lower)alkyl, a lower alkenyl, an amido-substituted lower alkyl having optionally a lower alkyl substituent, or a phenyl(lower)alkoxycarbonyl, $R^{7a}$ is a lower alkyl, a lower alkoxycarbonyl(lower)alkyl, carboxy(lower)alkyl, a lower alkenyl, or an amido-substituted lower alkyl having optionally a lower alkyl substituent, $R^{7b}$ is a lower alkanoyl having optionally one to three halogen substituents, a lower alkoxycarbonyl, or a phenyl(lower)alkoxycarbonyl, p' and p'' are each an integer of 1 to 3, provided that p+p' and p+p'' are each an integer not more than 3.

The reaction of the compound (1k) and the compound (14) in the Reaction Scheme-9A and the reaction of the compound (1n) and the compound (16) in the Reaction Scheme-9B can be carried out under the same conditions as in the reaction of the compound (1h) and the compound (12) in the above Reaction Scheme-8.

Besides, the compound (1m) wherein $R^{5b}$ is a lower alkanoyl or the compound (1p) wherein $R^{7b}$ is a lower alkanoyl having optionally one to three substituents of a halogen atom can also be obtained by reacting the compound (1k) or the compound (1n) with an alkanoylating agent of the formula: $(R^{5b})_2O$ or $(R^{7b})_2O$ (wherein $R^{5b}$ is a lower alkanoyl, and $R^{7b}$ is a lower alkanoyl having optionally one to three substituents of a halogen atom) in an appropriate solvent or without solvent in the presence or absence, preferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, etc. The basic compound includes, for example, tertiary amines (e.g. triethylamine, pyridine, etc.), sodium hydroxide, potassium hydroxide, sodium hydride, and the like. The above reaction can also be carried out in a solvent such as acetic acid in the presence of a mineral acid (e.g. sulfuric acid, etc.). The alkanoylating agent is usually used in an equimolar amount or more, preferably 1 to 10 moles, to 1 mole of the staring compound, and the reaction is usually carried out at a temperature of about 0° C. to about 200° C., preferably from about 0° C. to about 150° C., for about 0.5 to 15 hours.

Moreover, the compound (1l) wherein $R^{5a}$ is a lower alkyl or a phenyl(lower)alkyl) and the compound (1o) wherein $R^{7a}$ is a lower alkyl can also be obtained by reacting the compound (1k) or the compound (1n) with a compound of the formula: $R^{18}$—CO—$R^{19}$ (18) (wherein $R^{18}$ and $R^{19}$ are each hydrogen atom, phenyl, or a lower alkyl), respectively. In case of the compound (1n), however, the compound to be reacted should be the compound (18) wherein $R^{18}$ and $R^{19}$ are other than phenyl. The reaction is usually carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium boro hydride, sodium cyanoboro hydride, lithium aluminum hydride, etc.), catalystic reducing agents (e.g. palladium black, palladium-carbon, platinum oxide, platinum black, Raney nickel, etc.). When formic acid is used as the reducing agent, the reaction is usually carried out at a temperature of from room temperature to about 200° C., preferably about 50° C. to about 150° C., for about 1 to 10 hours. The formic acid is usually used in a large excess amount to the compound (1k) or the compound (1n).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (1k) or the compound (1n). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40% by weight, preferably about 1 to 20% by weight, of the amount of the compound (1k) or the compound (1n). The compound (18) is usually used at least in equivalent amount, preferably equivalent to a large excess amount, to the compound (1k) or the compound (1n).

In case of the compound of the formula (1) wherein $R^6$ and $R^7$ combine together with the nitrogen atom to which they bond to form a 5- or 6-membered, saturated or unsaturated heterocyclic which may be intervened or not with nitrogen, oxygen or sulfur atom and said heterocyclic group contains a secondary amino group, and/or $R^4$ and $R^5$ combine together with the nitrogen atom to which they bond to form a 5- or 6-membered, saturated heterocyclic group which may be intervened or not with nitrogen, oxygen or sulfur atom and said heterocyclic group contains a secondary amino group, the compound can be converted into a compound where said heterocyclic groups are substituted on said secondary amino group by a substituent selected from a lower alkyl (in case of forming a heterocyclic group by $R^6$ and $R^7$) or a phenyl having optionally a substituent selected from a halogen atom and a lower alkoxy (in case of forming a heterocyclic group by $R^4$ and $R^5$) by treating it in the same manner as in the reaction of the compound (1k) and the compound (14) in the above Reaction Scheme-9A.

Besides, said compound (where $R^6$ and $R^7$ form a heterocyclic group) can also be converted into a compound where the heterocyclic group is substituted on said secondary amino group by a substituent selected from a lower alkoxycarbonyl by treating it in the same manner as in the reaction of the compound (1k) and the compound (15) in the above Reaction Scheme-9A.

[Reaction Scheme-10A]

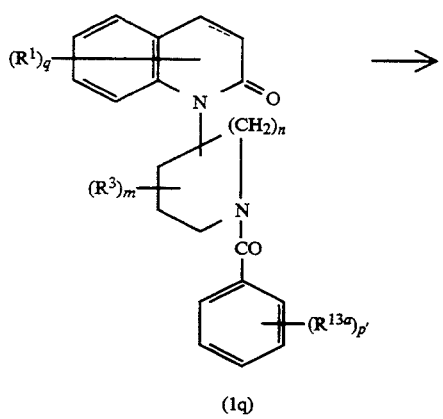

(1q)

[Reaction Scheme-10A] -continued

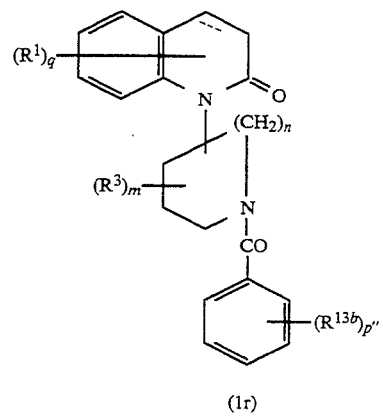

(1r)

wherein $R^1$, q, $R^3$, m, n, p', p'', and the bond between 3- and 4-positions of the carbostyril nucleus are the same as defined above, and $R^{13a}$ is the same groups as $R^{13}$ provided that at least one of the $R^{13a}$ is cyano, and $R^{13b}$ is the same groups as $R^{13}$ provided that at least one of the $R^{13b}$ is amidino.

[Reaction Scheme-10B]

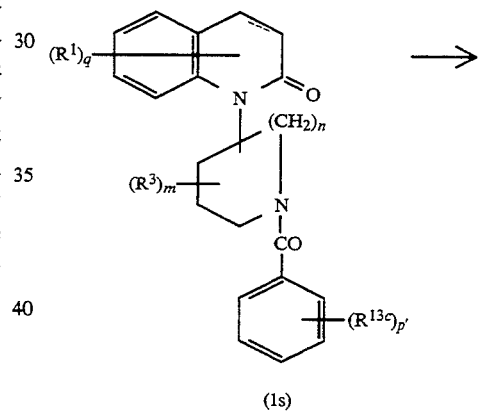

(1s)

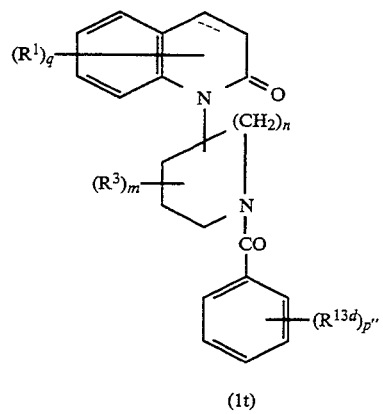

(1t)

wherein $R^1$, q, $R^3$, m, n, p', p'', and the bond between 3- and 4-positions of the carbostyril nucleus are the same as defined above, and $R^{13c}$ is the same groups as $R^{13}$ provided that at least one of the $R^{13c}$ is a cyano-substituted lower alkoxy, and $R^{13d}$ is the same groups as $R^{13}$ provided that at least one of the $R^{13d}$ is an amidino-substituted lower alkoxy.

The reaction of converting the compound (1q) to the compound (1r) in the above Reaction Scheme-10A and of converting the compound (1s) to the compound (1t) in the above Reaction Scheme-10B is carried out by reacting the compound (1q) and the compound (1s) with various alcohols, phenols, and thiols, respectively in an appropriate solvent or without solvent in the co-presence of a basic compound and hydrogen chloride, followed by reacting the resultant imidate compounds with aqueous ammonia in an appropriate solvent. The solvent used in the reaction for obtaining an imidate compound includes, for example, halogenated hydrocarbons (e.g. dichloromethane, chloroform, etc.), aromatic hydrocarbons (e.g. benzene, toluene, etc.), and the like. The alcohols used therein include, preferably lower alcohols such as methanol, ethanol, etc. These alcohols are usually used in an amount of 1 mole or more, preferably 1 to 2 moles, to 1 mole of the starting compound. The basic compound includes, preferably metal alcoholates such as sodium methylate, sodium ethylate, etc., particularly preferably the alcoholates with the same alcohols as above. The reaction for forming imidate compound is usually carried out at a temperature of about −10° C. to about 50° C., preferably about 0° C. to room temperature, for about 1 to 200 hours. The imidate compound thus obtained can be used in the subsequent reaction without being isolated from the reaction mixture.

The solvent used in the reaction of converting the imidate compound to the desired amidine compound includes, for example, water soluble solvents such as lower alcohols (e.g. methanol, ethanol, isopropanol, etc.), acetone, dimethylformamide, acetonitrile, and the like. The aqueous ammonium used in the reaction is usually used in an amount of 1 mole or more, preferably 5 to 50 moles, to 1 mole of imidate compound. The reaction is usually carried out at a temperature of about 0° C. to about 100° C., preferably 0° C. to room temperature, for about 10 minutes to about 15 hours. In the above reaction of converting the imidate compound to the amidine compound, there may occasionally be produced a compound where $R^{13d}$ is the same groups as $R^{13}$ provided that at least one of the $R^{13d}$ is a carbamoyl-substituted lower alkoxy, or $R^{13b}$ is the same groups as $R^{13}$ provided that at least one of $R^{13b}$ is a carbamoyl group, but these compounds can easily be separated from the reaction system.

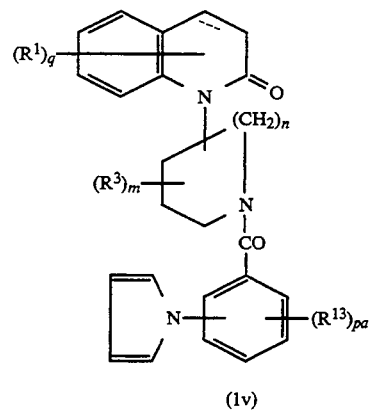

(1v)

wherein $R^1$, q, $R^3$, m, n, $R^{13}$, and the bond between 3- and 4-positions of the carbostyril nucleus are the same as defined above, and $R^{20}$ and $R^{21}$ are each lower alkoxy, and pa is 0 or an integer of 1 to 2.

The reaction of the compound (1u) and the compound (19) can be carried out in an appropriate solvent in the presence of an acid. The solvent includes, for example, water, lower alcohols (e.g. methanol, ethanol, isopropanol, etc.), ketones (e.g. acetone, methyl ethyl keton, etc.), ethers (e.g. dioxane, tetrahydrofuran, ethylene glycol dimethyl ether, etc.), fatty acids (e.g. acetic acid, formic acid. etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.). The reaction is usually carried out at a temperature of from room temperature to about 200° C., preferably from room temperature to about 150° C., for about 0.5 to 5 hours. The compound (19) is usually used in an amount of at least 1 mole, preferably 1 to 2 moles, to 1 mole of the compound (1u).

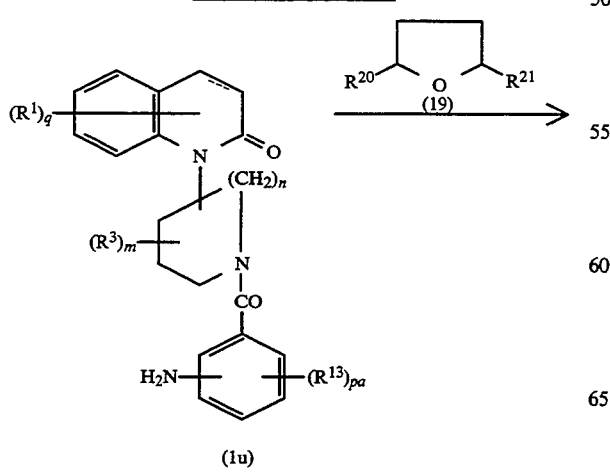

(1u)

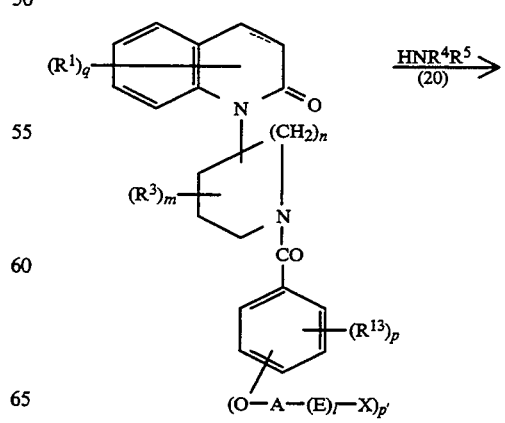

(1w)

-continued

[Reaction Scheme-12A]

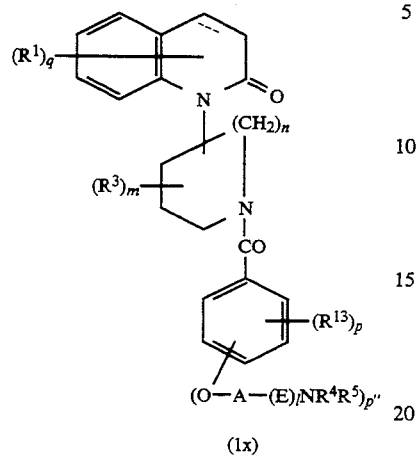

(1x)

wherein $R^1$, q, $R^3$, m, n, $R^4$, $R^5$, $R^{13}$, p, p', p'', X, A, E, l, and the bond between 3- and 4-positions of the carbostyril nucleus are the same as defined above.

[Reaction Scheme-12B]

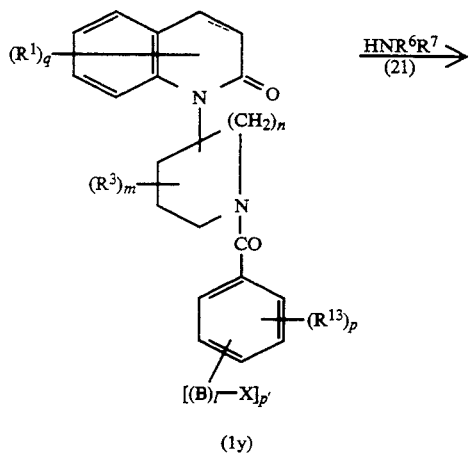

(1y)

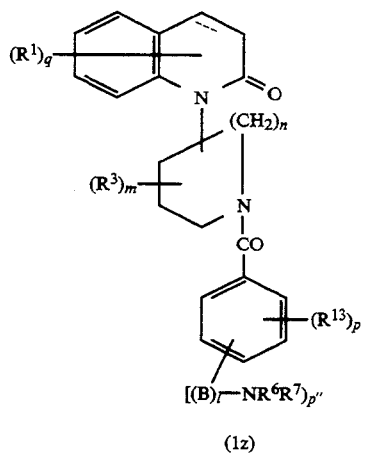

(1z)

wherein $R^1$, q, $R^3$, m, n, $R^6$, $R^7$, $R^{13}$, p, p', p'', X, B, l, and the bond between 3- and 4-positions of the carbostyril nucleus are the same as defined above.

[Reaction Scheme-12C]

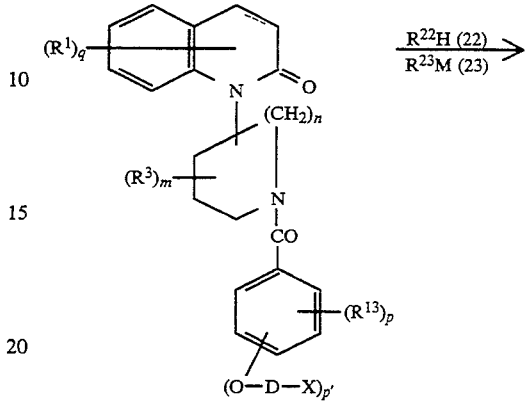

(1A)

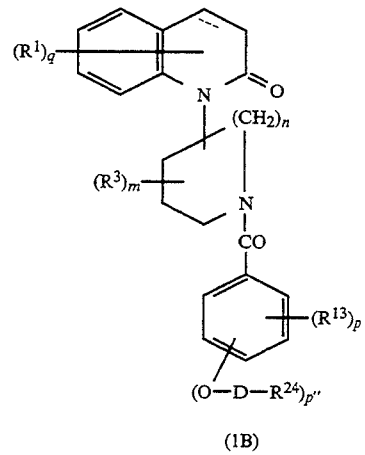

(1B)

wherein $R^1$, q, $R^3$, m, n, $R^{13}$, p, p', p'', X, and the bond between 3- and 4-positions of the carbostyril nucleus are the same as defined above, and D is a lower alkylene, $R^{22}$ is a group of the formula:

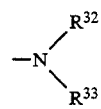

($R^{32}$ and $R^{33}$ are the same as defined above), benzoyloxy, a lower alkylsulfonyloxy, a lower alkanoyloxy, a lower alkylthio, benzimidazolylthio, pyrimidylthio, an imidazolylthio having optionally a lower alkyl substituent, a phenylthio having optionally a substituent selected from nitro and amino on the phenyl ring, pyridylthio, or pyrrolyl, $R^{23}$ is hydroxy, a lower alkoxy, benzoyloxy, a lower alkylsulfonyloxy, a lower alkanoyloxy, or a lower alkoxy having one or two substituents selected from cyano, hydroxy and an amino having optionally a lower alkyl substituent, $R^{24}$ is the same as the above $R^{22}$ or $R^{23}$, and M is an alkali metal (e.g. potassium, sodium, etc.).

[Reaction Scheme-12D]

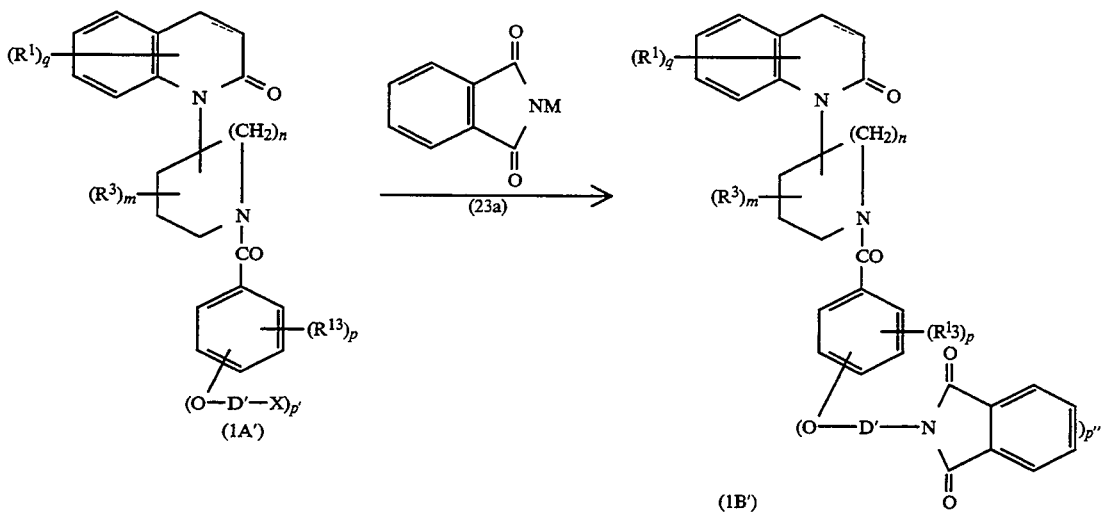

wherein R¹, q, R³, m, n, R¹³, p, p', p", X, M and the bond between 3- and 4-positions of the carbostyril nucleus are the same as defined above, and D' is a lower alkylene.

The reaction of the compound (1w) and the compound (20) in Reaction Scheme-12A, of the compound (1y) and the compound (21) in Reaction Scheme-12B, of the compound (1A) and the compound (22) or (23) in Reaction Scheme-12C, and of the compound (1A) and the compound (23a) in Reaction Scheme-12D is carried out under the same conditions as in the reaction of the compound (1h) and the compound (11) in the above Reaction Scheme-8.

Scheme-8. The reaction is usually carried out at a temperature of from room temperature to about 120° C., preferably about 0° C. to about 100° C., for about 0.5 to 5 hours. Hydrazine is usually used in an amount of at least 1 mole, preferably about 1 to 5 moles, to 1 mole of the compound (1C). The hydrolysis is carried out under the same conditions as in the hydrolysis of the compound (1) wherein R⁴ or R⁵ is a lower alkoxycarbonyl as described hereinafter.

[Reaction Scheme-13]

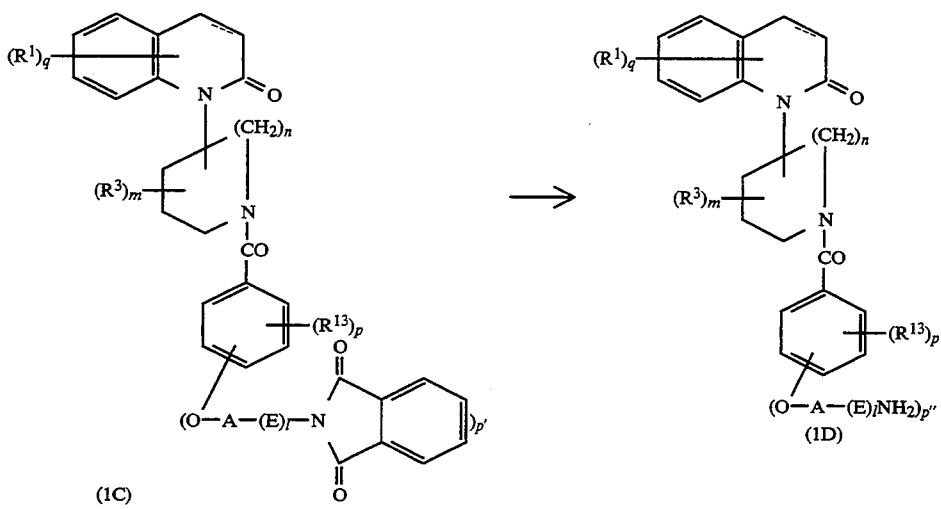

wherein R¹, q, R³, m, n, R¹³, p, p', p", A, E, l, and the bond between 3- and 4-positions of the carbostyril nucleus are the same as defined above.

The reaction of converting the compound (1C) into the compound (1D) can be carried out by reacting the compound (1C) with hydrazine in an appropriate solvent or by hydrolyzing the compound (1C). The solvent used in the reaction with hydrazine includes the same solvent as used in the reaction of the compound (1h) and the compound (11) in the above Reaction

[Reaction Scheme-14]

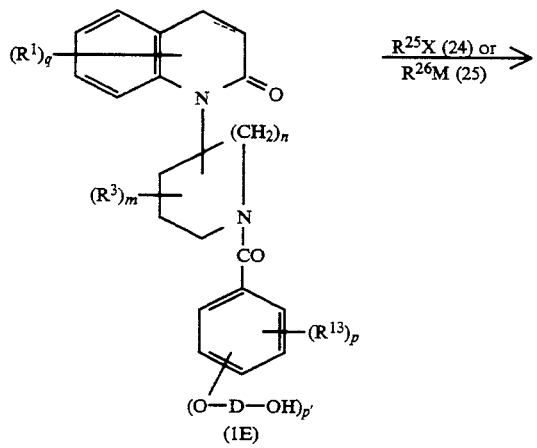

(1E)

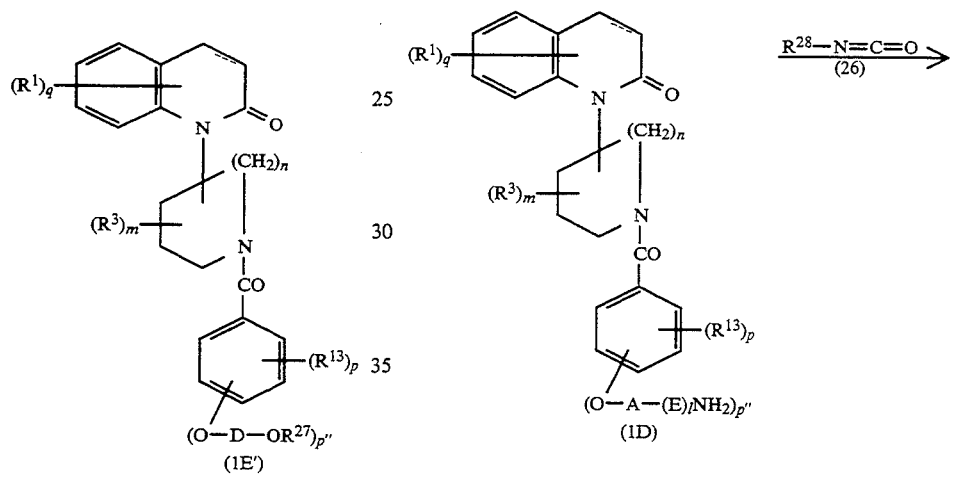

wherein $R^1$, q, $R^3$, m, n, $R^{13}$, p, p', p", X, D, M, and the bond between 3- and 4-positions of the carbostyril nucleus are the same as defined above, and $R^{25}$ is a lower alkanoyl, a lower alkenyl, a lower alkyl, a lower alkylsulfonyl, a lower alkyl having one or two substituents selected from hydroxy and an amino having optionally a lower alkyl substituent, or benzoyl, $R^{26}$ is a group of —OCN, and $R^{27}$ is the same groups as the above $R^{25}$ or a carbamoyl.

The reaction of the compound (1E) and the compound (24) is carried out under the same conditions as in the reaction of the compound (1h) and the compound (11) in the above Reaction Scheme-8. In said reaction, an alkali metal halide (e.g., sodium iodide, potassium iodide, etc.) may be added to the reaction system.

The reaction of the compound (1E) and the compound (25) is carried out in an appropriate solvent in the presence of an acid. The solvent includes the same solvents as used in the reaction of the compound (1h) and the compound (11) in the above Reaction Scheme-8. In addition thereto, there may also be used halogenated hydrocarbons (e.g. methylene chloride, chloroform, carbon tetrachloride, etc.). The acid includes, for example, mineral acids (e.g. hydrochloric acid, sulfuric acid, hydrobromic acid, etc.) and organic acids (e.g. formic acid, acetic acid, trifluoroacetic acid, aromatic sulfonic acids, etc.). The reaction is usually carried out at a temperature of about 0° C. to about 150° C., preferably, from room temperature to about 100° C., for about 1 to 15 hours. The compound (25) is usually used in an amount of 1 to 5 moles, preferably 1 to 3 moles, to 1 mole of the compound (1E).

[Reaction Scheme-15]

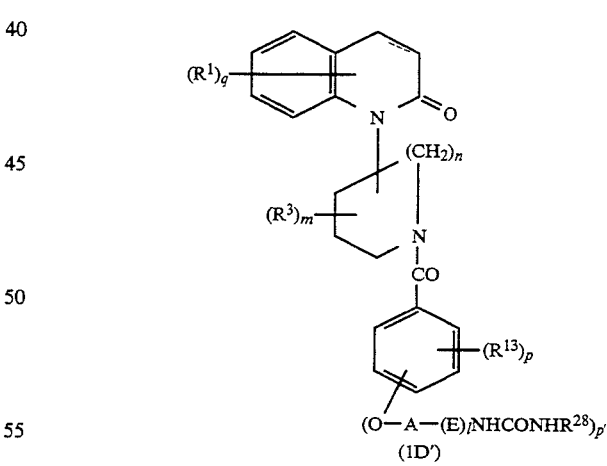

wherein $R^1$, q, $R^3$, m, n, $R^{13}$, p, p', p", A, E, l, and the bond between 3- and 4-positions of the carbostyril nucleus are the same as defined above, and $R^{28}$ is hydrogen atom, phenyl or a lower alkyl.

The reaction of the compound (1D) and the compound (26) is carried out under the same conditions as in the reaction of the compound (1d) and the compound (8) in the above Reaction Scheme-6.

[Reaction Scheme-16]

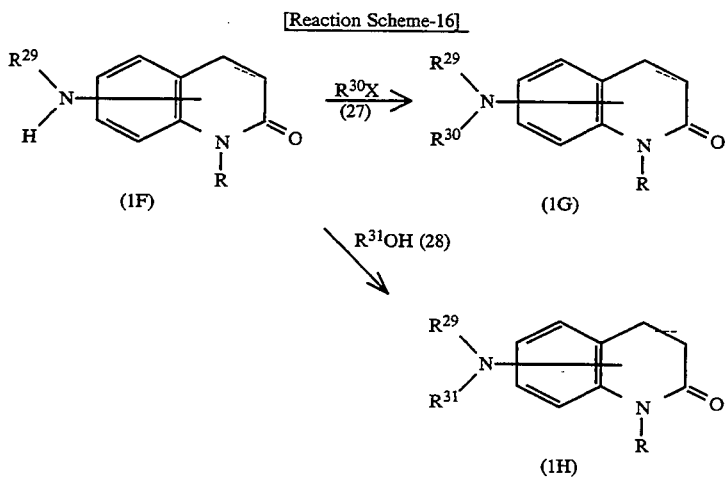

wherein R, X, and the bond between 3- and 4-positions of the carbostyril nucleus are the same as defined above, and $R^{29}$ is hydrogen atom, a lower alkanoyl, a lower alkyl or benzoyl, $R^{30}$ is a lower alkyl, and $R^{31}$ is a lower alkanoyl or benzoyl.

The reaction of the compound (1F) and the compound (27) is carried out under the same conditions as in the reaction of the compound (1k) and the compound (14) in the above Reaction Scheme-9A.

The reaction of the compound (1F) and the compound (28) is carried out under the same conditions as in the reaction of the compound (1k) and the compound (15) in the above Reaction Scheme-9A.

[Reaction Scheme-17]

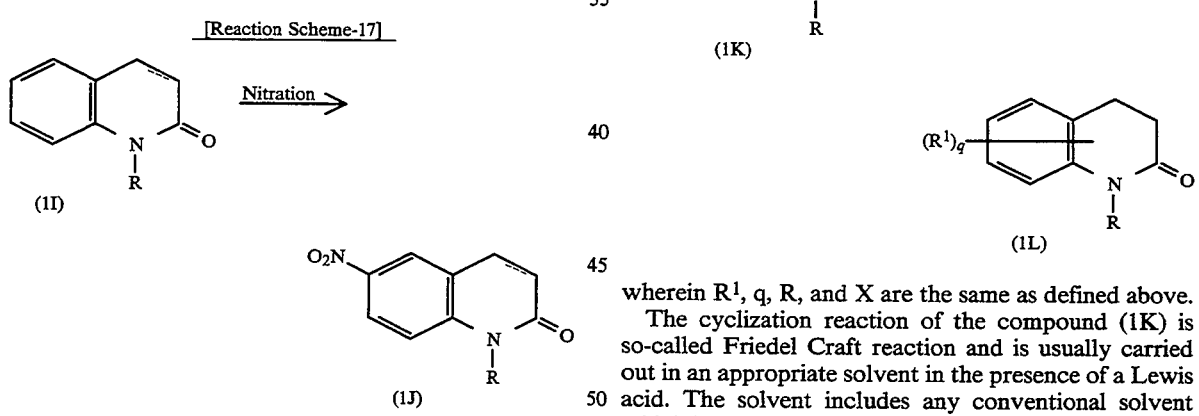

wherein R and the bond between 3- and 4-positions of the carbostyril nucleus are the same as defined above.

The nitration of the compound (1i) can be carried our under the same conditions as used in the conventional nitration reaction of an aromatic compound. That is, it can be carried out by using a nitrating agent in an appropriate inert solvent or without solvent. The inert solvent includes, for example, acetic acid, acetic anhydride, conc. sulfuric acid, and the like. The nitrating agent includes, for example, fuming nitric acid, conc. nitric acid, mixed acid (e.g. a mixture of nitric acid with sulfuric acid, fuming sulfuric acid, phosphoric acid, or acetic anhydride), a mixture of an alkali metal nitrate (e.g. potassium nitrate, sodium nitrate, etc.) with sulfuric acid, and the like. The nitrating agent is used in an equimolar amount or more, usually in an excess amount, to the amount of the starting compound. The reaction is advantageously carried out at a temperature of about 0° C. to room temperature for about 0.5 to 4 hours.

[Reaction Scheme-18]

wherein $R^1$, q, R, and X are the same as defined above.

The cyclization reaction of the compound (1K) is so-called Friedel Craft reaction and is usually carried out in an appropriate solvent in the presence of a Lewis acid. The solvent includes any conventional solvent which is usually used in this kind of reaction, for example, carbon disulfide, nitrobenzene, chlorobenzene, dichloromethane, dichloroethane, trichloroethane, tetrachloroethane, and the like. The Lewis acid includes any conventional acid, for example, aluminum chloride, zinc chloride, iron chloride, tin chloride, boron tribromide, boron trifluoride, conc. sulfuric acid, and the like. The amount of Lewis acid is not critical but is usually in the range of about 2 to 6 moles, preferably about 3 to 4 moles, to 1 mole of the compound (1K). The reaction temperature is usually in the range of about 20° C. to 200° C., preferably 40° C. to 180° C. The reaction period of time may vary depending on the kinds of the starting compound, catalyst and reaction temperature, etc., but is usually in the range of about 0.5 to 6 hours. Besides, sodium chloride may be added to the reaction system in order to proceed the reaction advantageously.

[Reaction Scheme-19]

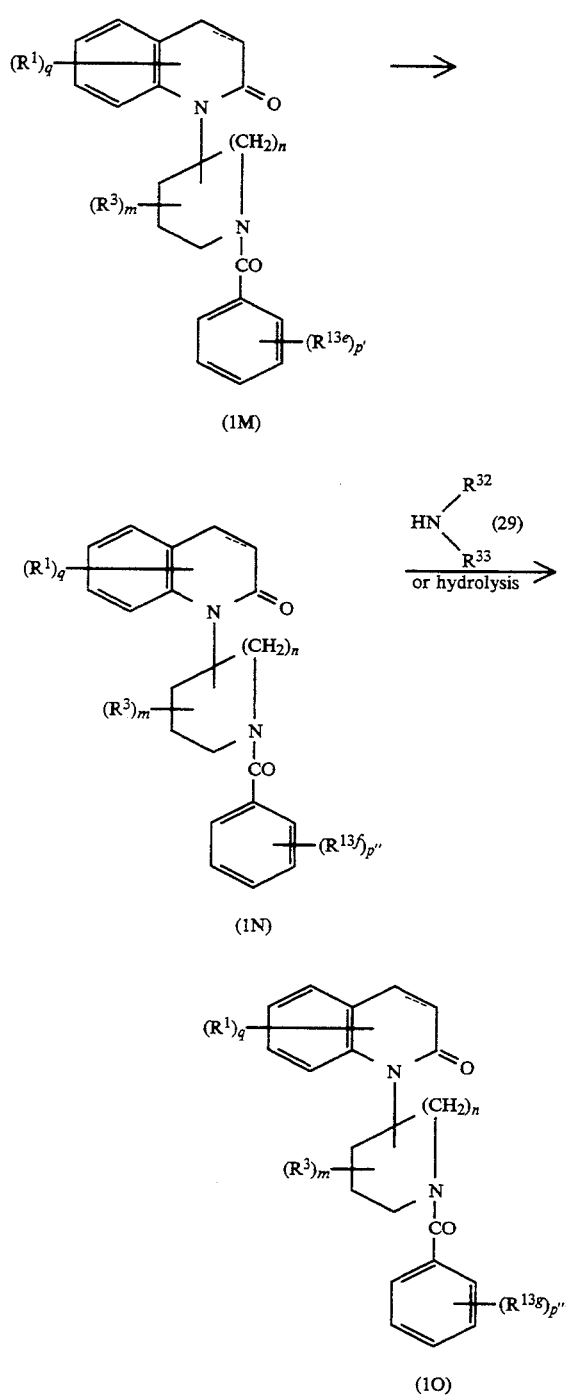

(1M)

(1N)

(1O)

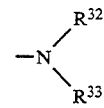

($R^{32}$ and $R^{33}$ are as defined above), and p'' is an integer of 1 to 3.

The reaction of converting the compound (M) into the compound (N) is carried out under the same conditions as in the reaction of oxidizing lower alkylthio into lower alkylsulfonyl as mentioned above. The reaction of the compound (1N) and the compound (29) is carried out under the same conditions as in the reaction of the compound (1h) and the compound (11) in the above Reaction Scheme-8. Besides, the hydrolysis of the compound (1N) can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

[Reaction Scheme-20]

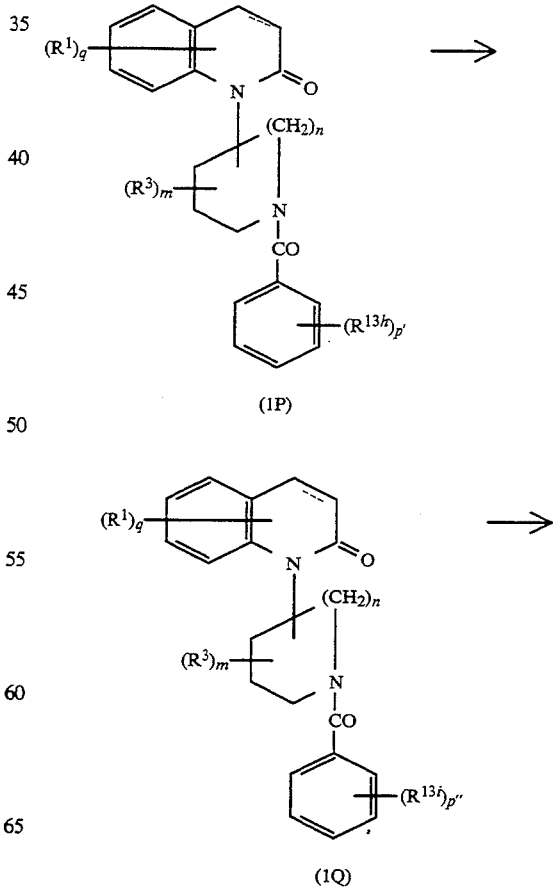

(1P)

(1Q)

wherein $R^1$, q, $R^3$, m, n, p', p'', and the bond between 3- and 4-positions of the carbostyril nucleus are the same as defined above, and $R^{13e}$ is the same groups as $R^{13}$ provided that at least one of the $R^{13e}$ is a lower alkenyloxy, $R^{13f}$ is the same groups as $R^{13}$ provided that at least one of the $R^{13f}$ is an oxilanyl-substituted lower alkoxy, $R^{13g}$ is the same groups as $R^{13}$ provided that at least one of the $R^{13g}$ is a lower alkoxy having a substituent selected from hydroxy and a group of the formula:

-continued
[Reaction Scheme-20]

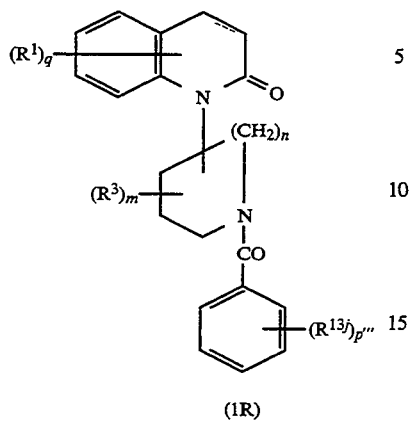

(1R)

wherein R¹, q, R³, m, n, p', p", and the bond between 3- and 4-positions of the carbostyril nucleus are the same as defined above, and $R^{13h}$ is the same groups as $R^{13}$ provided that at least one of the $R^{13h}$ is a lower alkanoyl, $R^{13i}$ is the same groups as $R^{13}$ provided that at least one of the $R^{13i}$ is a lower alkenyl having optionally a substituent selected from a lower alkoxycarbonyl, carboxyl or hydroxy, $R^{13j}$ is the same groups as $R^{13}$ provided that at least one of the $R^{13j}$ is a lower alkyl having optionally a substituent selected from a lower alkoxycarbonyl, carboxyl and hydroxy.

The reaction of converting the compound (1P) into the compound (1Q) is carried out in an appropriate solvent in the presence of a Wittig reagent and a basic compound. The Wittig reagent includes, for example, a phosphoric compound of the formula:

wherein $R^{34}$ is phenyl, $R^{35}$ is a lower alkyl having optionally a substituent selected from a lower alkoxycarbonyl, carboxyl and hydroxy, and X is a halogen atom, and a phosphoric compound of the formula:

wherein $R^{36}$ is a lower alkoxy, and $R^{37}$ is a lower alkyl.

The basic compound includes inorganic bases (e.g. metallic sodium, metallic potassium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about −80° C. to about 150° C., preferably about −80° C. to about 120° C., for about 0.5 to 15 hours.

The reaction of converting the compound (1Q) into the compound (1R) is carried out under the same conditions as in the catalytic hydrogenation as described hereinbefore.

The starting compound (2) can be prepared, for example, by the processes as shown in the following Reaction Schemes-21 and -22.

[Reaction Scheme-21]

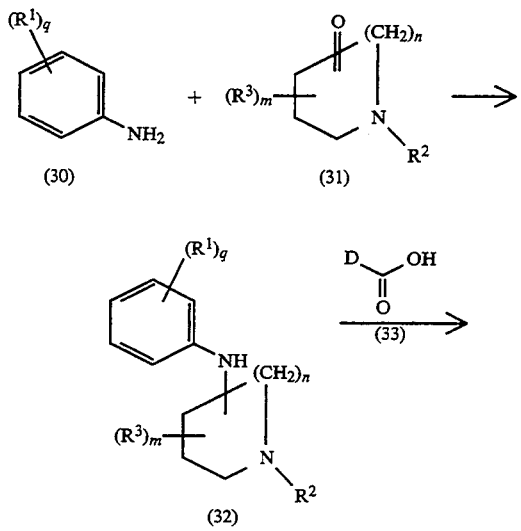

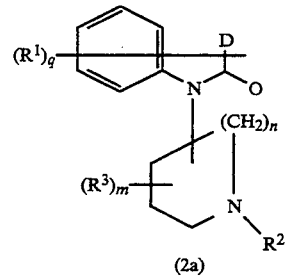

(2a)

wherein R¹, q, R², R³, m, n and D are the same as defined above, provided that the group R¹ may substitute on either of the benzene ring or the group D of the compound (2a).

The reaction of the compound (30) and the compound (31) is carried out under the same conditions as in the reaction of the compound (1k) and the compound (18) in the above Reaction Scheme-9A.

The reaction of the compound (32) and the compound (33) is carried out under the same conditions as in the reaction of the compound (1d) and the compound (7) in the above Reaction Scheme-5.

[Reaction Scheme-22]

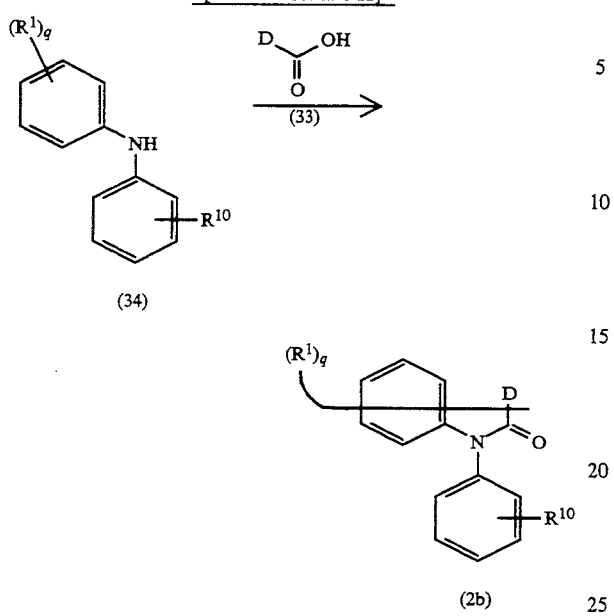

(2b)

wherein $R^1$, q, $R^{10}$, and D are the same as defined above, provided that the group $R^1$ may substitute on either of the benzene ring or the group D of the compound (2b).

The reaction of the compound (34) and the compound (33) is carried out under the same conditions as the above reaction of the compound (32) and the compound (33).

The starting compound (3) can be prepared, for example, by the process of the following Reaction Scheme-23.

[Reaction Scheme-23]

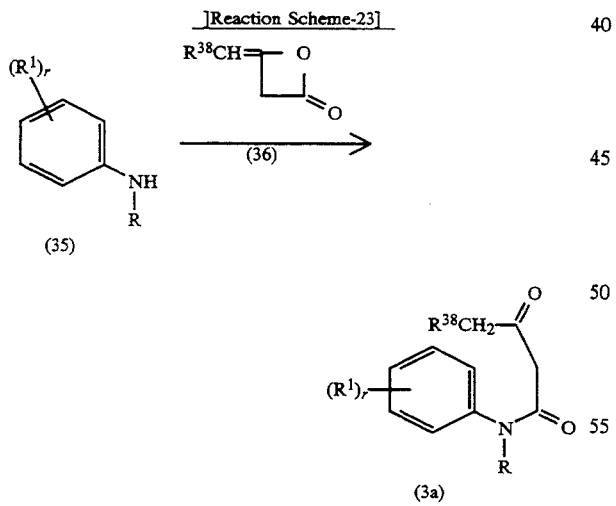

wherein $R^1$ and R are the same as defined above, $R^{38}$ is hydrogen atom or a lower alkyl, and r is 1 or 2.

The reaction of the compound (35) and the compound (36) is carried out in a solvent as used in the reaction of the compound (1E) and the compound (25) in the above Reaction Scheme-14. The compound (36) is usually used in an amount of at least 1 mole, preferably 1 to 2 moles, to 1 mole of the compound (35). The reaction is usually carried out at a temperature of 0° C. to 150° C., preferably from room temperature to about 100° C., for about 0.5 to 5 hours.

The starting compound (4) can be prepared, for example, by the process of the following Reaction Scheme-24.

[Reaction Scheme-24]

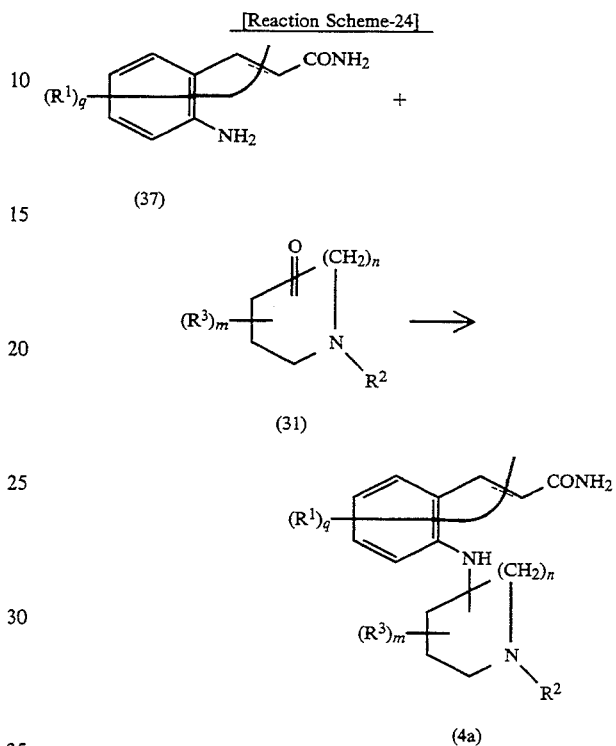

wherein $R^1$, q, $R^2$, $R^3$, m, and n are the same as defined above.

The reaction of the compound (37) and the compound (31) is carried out under the same conditions as in the reaction of the compound (30) and the compound (31) in the above Reaction Scheme-21.

The starting compound (1K) can be prepared, for example, by the process of the following Reaction Scheme-25.

[Reaction Scheme-25]

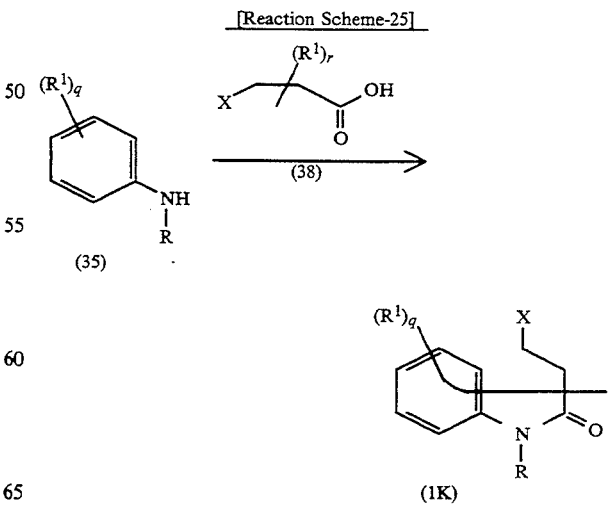

wherein $R^1$, q, r, R and X are as defined above, provided that the total of q and r is not more than 3.

The reaction of the compound (35) and the compound (38) is carried out under the same conditions as in the reaction of the compound (32) and the compound (33) in the above Reaction Scheme-21.

[Reaction Scheme-26]

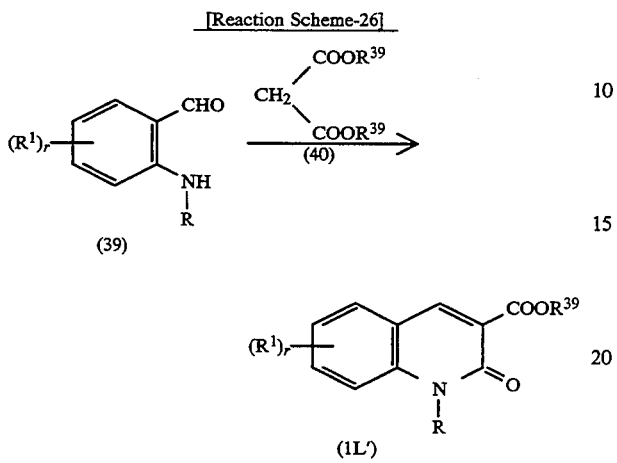

(1L')

wherein $R^1$, r and R are as defined above, and $R^{39}$ is a lower alkyl.

The reaction of the compound (39) and the compound (40) is carried out in an appropriate solvent in the presence of a basic compound. The basic compound includes, inorganic bases (e.g. sodium hydroxide, potassium hydroxide, sodium hydrogen carbonate, potassium hydrogen carbonate, potassium carbonate, sodium carbonate, sodium hydride, etc.), alkali metal alcoholates (e.g. sodium methylate, sodium ethylate, etc.), and organic bases (e.g. triethylamine, pyridine, α-picoline, N,N-dimethylaniline, N-methylmorpholine, piperidine, pyrrolidine, etc.). The solvent includes, for example, ethers (e.g. dioxane, tetrahydrofuran, monoglyme, diglyme, etc.), aromatic hydrocarbons (e.g. benzene, toluene, xylene, etc.), lower alcohols (e.g. methanol, ethanol, isopropanol, etc.), polar solvents (e.g. dimethylsulfoxide, dimethylformamide, etc.), and the like. The reaction is usually carried out at a temperature of from room temperature to 150° C., preferably from 60° C. to 120° C., for about 1 to 24 hours. The compound (40) is usually used in an equimolar to large excess amount, preferably 1 to 5 moles to 1 mole of the compound (39). A lower alkane (e.g. acetic acid, etc.) or molecular sieves may be added to the reaction system to proceed the reaction advantageously.

The compound (39) can be prepared, for example, by the process of the following reaction scheme.

[Reaction Scheme-27]

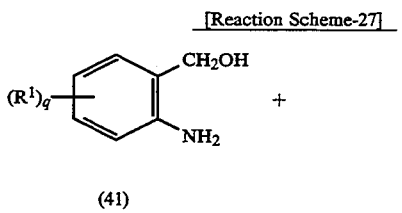

(41)

-continued
[Reaction Scheme-27]

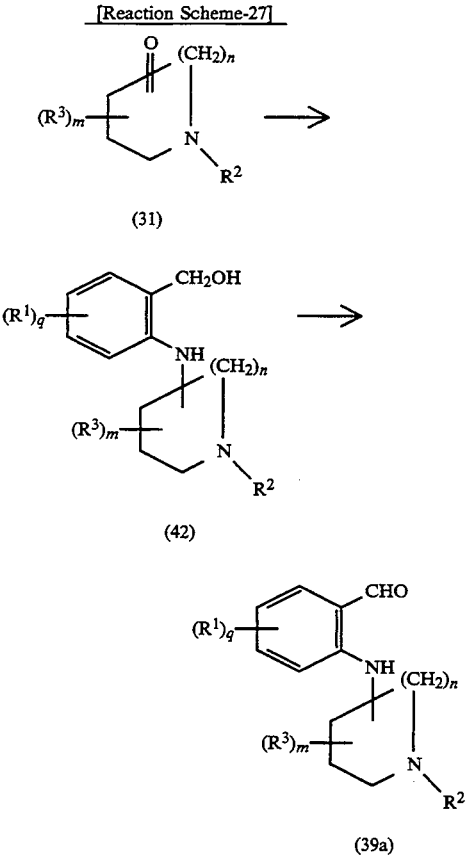

wherein $R^1$, q, $R^2$, $R^3$, m and n are as defined above.

The reaction of the compound (41) and the compound (31) is carried out under the same conditions as in the reaction of the compound (30) and the compound (31) in the above Reaction Scheme-21.

The reaction of converting the compound (42) into the compound (39a) is carried out in an appropriate solvent or without solvent in the presence of an oxidizing agent. The solvent includes the above-mentioned aromatic hydrocarbons, lower alcohols, halogenated hydrocarbons, ethers, polar solvents (e.g. dimethylsulfoxide, dimethylformamide, hexamethylphosphoric triamide, etc.). The oxidizing agent includes acetic anhydride-dimethylsulfoxide, phosphorus pentoxide-dimethylsulfoxide, sulfur trioxide, pyridine complex-dimethylsulfoxide, dicyclohexylcarbodiimide-dimethylsulfoxide, oxalyl chloride-dimethylsulfoxide, chromic acid, chromic acid complexes (e.g. chromic acid-pyridine complex, chromic acid-2-pyridine complex, etc.), manganese dioxide, and the like. When oxalyl chloride-dimethylsulfoxide is used as the oxidizing agent, there may be added to the reaction system the basic compound as used in the reaction of the compound (1d) and the carboxylic halide in the above Reaction Scheme-5. The reaction is usually carried out at a temperature of 0° C. to 150° C., preferably from room temperature to about 100° C., for about 1 to 30 hours. The oxidizing agent is usually used in an amount of 1 to 20 moles; preferably 1 to 15 moles, to 1 mole of the compound (42).

[Reaction Scheme-28]

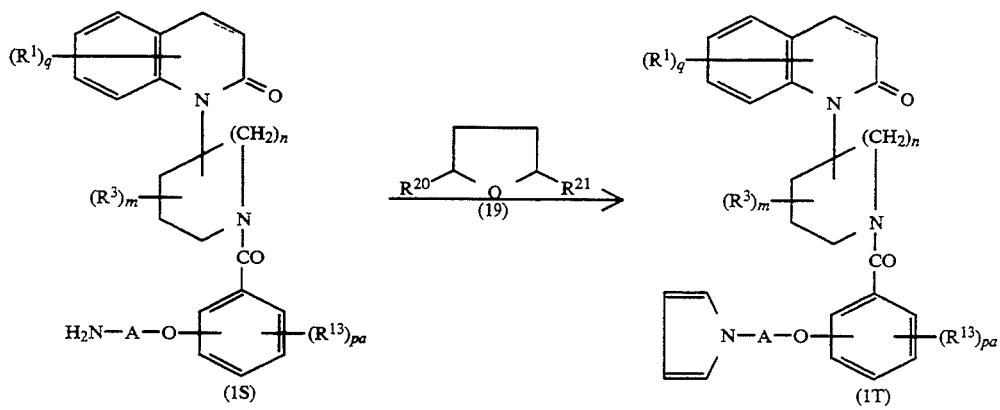

wherein $R^1$, q, $R^3$, m, n, $R^{13}$, pa, A, $R^{20}$, $R^{21}$ and the bond between 3- and 4-positions of the carbostyril nucleus are the same as defined above.

The reaction of the compound (1S) and the compound (19) is carried out under the same conditions as in the reaction of the compound (1u) and the compound (19) in the above Reaction Scheme-11.

alkyl or a lower alkanoyl, $R^{41}$ is a lower alkyl, $R^{42}$ is a lower alkanoyl; $R^{43}$ is a lower alkoxy, a halogen atom, an amino having optionally one or two substituents selected from a lower alkyl and a lower alkanoyl, or nitro, t is 0, 1 or 2, s is an integer of 1 to 3, provided that total of t and s is not more than 3.

The reaction of the compound (1U) and the com-

[Reaction Scheme-29]

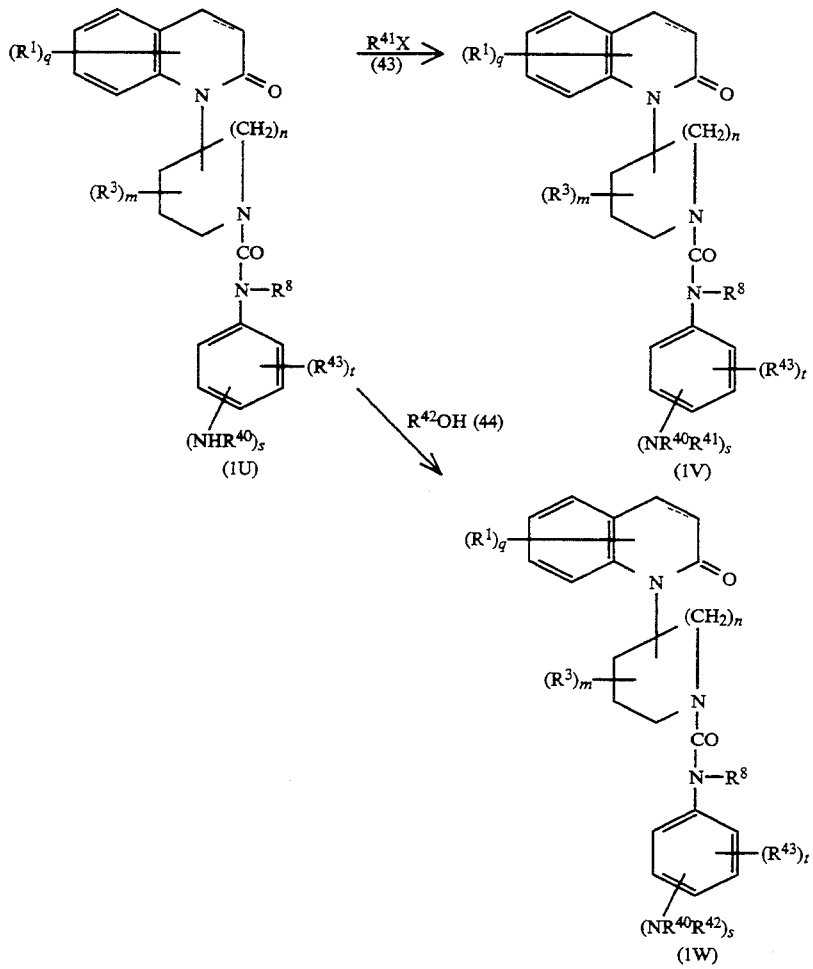

wherein $R^1$, q, $R^3$, m, n, $R^8$, X, and the bond between 3- and 4-positions of the carbostyril nucleus are the same as defined above, and $R^{40}$ is hydrogen atom, a lower pound (43) is carried out under the same conditions as in the reaction of the compound (1k) and the compound (14) in the above Reaction Scheme-9A.

The reaction of the compound (1U) and the compound (44) is carried out under the same conditions as in the reaction of the compound (1k) and the compound (15) in the above Reaction Scheme-9A.

phosphorus pentoxide, polyphosphoric acid, etc.), and organic acids (e.g. p-toluenesulfonic acid, ethanesulfonic acid, methanesulfonic acid, trifluoroacetic acid, etc.), or a mixture of these acids. The solvent includes the same solvents as used in the cyclization reaction of the compound (4) in the above Reaction Scheme-3. The

[Reaction Scheme-30]

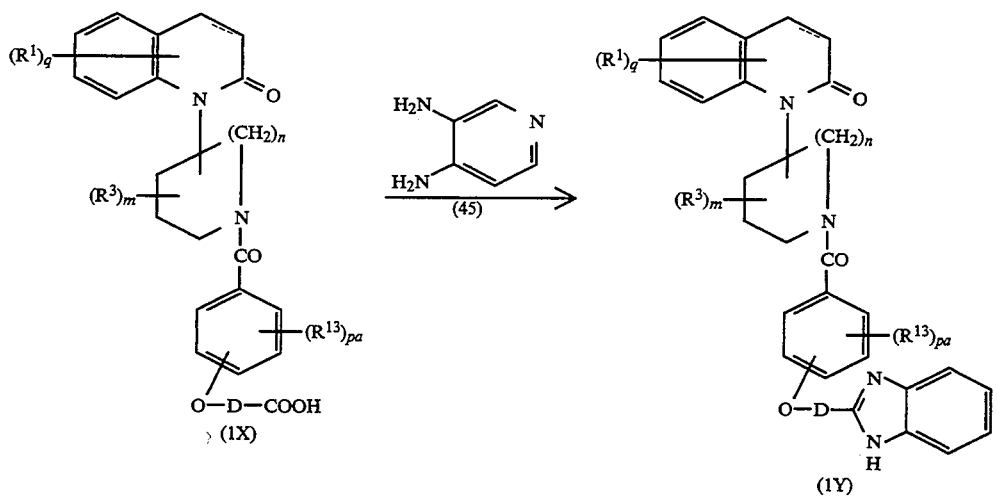

wherein $R^1$, q, $R^3$, m, n, $R^{13}$, pa, D, and the bond between 3- and 4-positions of the carbostyril nucleus are the same as defined above.

The reaction of the compound (1X) and the compound (45) is carried out in an appropriate solvent or without solvent in the presence of an acid. The acid includes, for example, inorganic acids (e.g. hydrochloric acid, sulfuric acid, hydrobromic acid, nitric acid, compound (45) is usually used in an amount of at least 1 mole, preferably 1 to 1.5 mole, to 1 mole of the compound (1X). The reaction is usually carried out at a temperature of from room temperature to about 200° C., preferably from room temperature to about 150° C., for about 1 to 5 hours.

[Reaction Scheme-31]

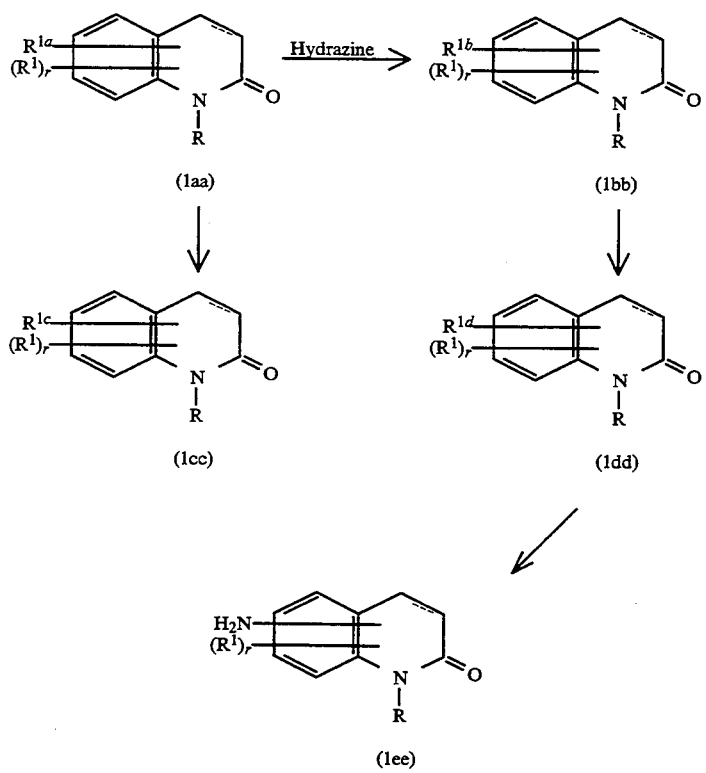

wherein R, $R^1$ and the bond between 3- and 4-positions of the carbostyril nucleus are the same as defined above, and $R^{1a}$ is a lower alkoxycarbonyl, $R^{1b}$ is hydroazinocarbonyl, $R^{1c}$ is carboxyl, $R^{1d}$ is a phenyl(lower)alkoxycarbonyl-substituted amino, and r is 1 or 2.

The reaction of the compound (1aa) and hydrazine is carried out in an appropriate solvent. The solvent includes the same solvents as used in the reaction of the compound (1d) and the halide (7) in the above Reaction Scheme-5. Hydrazine is used in a large excess amount, preferably in 8 to 20 moles to 1 mole of the compound (1aa). The reaction is usually carried out at a temperature of from room temperature to about 150° C., preferably from room temperature to about 100° C., for about to 10 hours.

The reaction of converting the compound (1aa) into the compound (1cc) is carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

The reaction of converting the compound (1bb) into the compound (1dd) is carried out by reacting the compound (1bb) with a metal nitrite (e.g. sodium nitrite, potassium nitrite, etc.) in an appropriate solvent in the presence of an acid, followed by reacting the resultant with a phenyl lower alcohol (e.g. benzyl alcohol, α-phenethyl alcohol, β-phenethyl alcohol, etc.). The acid used therein includes, for example, hydrochloric acid, hyrobromic acid, sulfuric acid, tetrafluoroboric acid, hexafluorophosphoric acid, and the like. The solvent used in the reaction with a metal nitrite includes, for example, water dichloromethane, chloroform, carbon tetrachloride or a mixture of these solvents. The reaction is usually carried out at a temperature of about −20° C. to about 10° C., preferably about −5° C. to about 5° C., for about 5 minutes to about one hour. The nitrite is usually used in an amount of at least 1 mole, preferably 1 to 1.5 mole, to 1 mole of the compound (1bb). The solvent used in the reaction with a phenyl lower alcohol includes, for example, aromatic hydrocarbons (e.g. benzene, toluene, xylene, etc.), ketones (e.g. acetone, methyl ethyl ketone, etc.), ethers (e.g. dioxane, tetrahydrofuran, diethyl ether, ethylene glycol dimethyl ether, etc.), and the like. The reaction is carried out at a temperature of from room temperature to about 200° C., preferably from room temperature to about 150° C., for about 0.5 to 10 hour. The phenyl lower alcohol is usually used in an amount of at least 1 mole, preferably 1 to 2 moles, to 1 mole of the compound (1bb).

The reaction of converting the compound (1dd) into the compound (1ee) is carried out under the same conditions as in the reduction reaction of the compound (1) wherein $R^2$ is a heterocyclic group-substituted carbonyl having a phenyl(lower)alkoxycarbonyl on at least one nitrogen atom thereof as described hereinafter.

[Reaction Scheme-32]

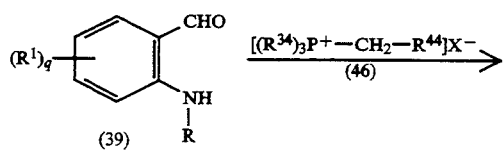

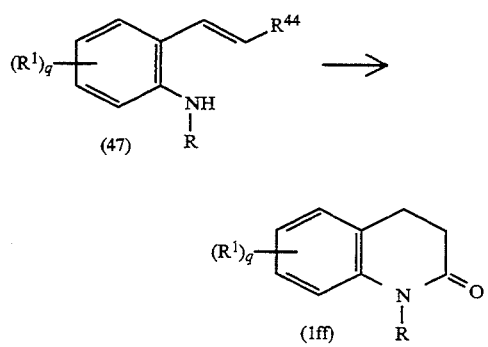

wherein $R^1$, q, R, $R^{34}$, and X are the same as defined above, and $R^{44}$ is a lower alkoxycarbonyl.

The reaction of the compound (39) and the compound (46) is carried out under the same conditions as in the reaction of converting the compound (1P) into the compound (1Q) in the above Reaction Scheme-20.

The cyclization reaction of the compound (47) is carried out in the presence of a catalytic reducing agent and in the presence or absence of a basic compound or an acid, preferably in the presence of an acid, in an appropriate solvent. The basic compound includes, for example, organic bases (e.g. triethylamine, trimethylamine, pyridine, dimethylaniline, N-methylmorpholine, DBN, DBU, DABCO, etc.), and inorganic bases (e.g. potassium carbonate, sodium carbonate, sodium hydroxide, potassium hydroxide, sodium hydride, potassium hydride, potassium hydrogen carbonate, sodium hydrogen carbonate, etc.), and the acid includes, for example, inorganic acids (e.g. hydrochloric acid, sulfuric acid, phosphoric acid, etc.), organic acids (e.g. acetic acid, etc.), or a mixture of these acids. The solvent includes, for example, water, alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. tetrahydrofuran, diethyl ether, dimethoxyethane, etc.), esters (e.g. methyl acetate, ethyl acetate, etc.), N,N-dimethylformamide, dimethylsulfoxide, hexamethylphosphoric triamide, or a mixture of these solvents. The catalytic reducing agent includes the same catalysts as used in the reduction reaction of the compound (1a) in the above Reaction Scheme-1. The reaction is usually carried out under atmospheric pressure to about 20 kg/cm², preferably atmospheric pressure to about 10 kg/cm², at a temperature of about 0° C. to about 200° C., preferably from room temperature to about 150° C., for about 1 to 10 hours. The catalytic reducing agent is preferably used in an amount of 0.02 to 1 part by weight to 1 part of the compound (47).

[Reaction Scheme-33]

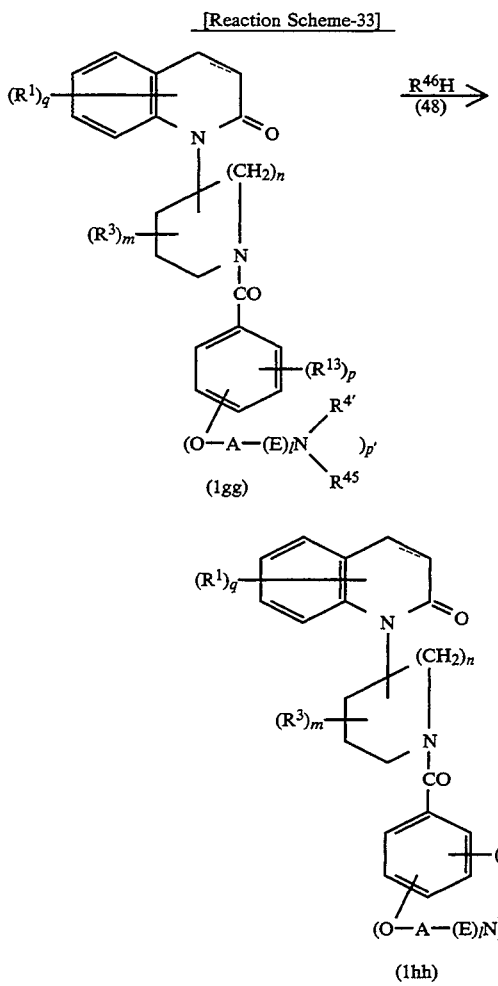

wherein $R^1$, q, $R^3$, m, n, $R^{13}$, p', p'', A, E, l, and the bond between 3- and 4-positions of the carbostyril nucleus are the same as defined above, and $R^{45}$ is a lower alkanoyl which has one halogen substituent and may optionally have a further substituent selected from a phenyl(lower)alkoxycarbonylamino, hydroxy, a phenyl having optionally a hydroxy substituent, carbamoyl, imidazolyl and a lower alkylthio, $R^{46}$ is an amino which may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower)alkoxycarbonyl, and $R^{47}$ is an amino-substituted lower alkanoyl wherein the lower alkanoyl moiety may optionally have a substituent selected from a phenyl(lower)alkoxycarbonylamino, hydroxy, a phenyl having optionally a hydroxy substituent, carbamoyl, imidazolyl, and a lower alkylthio, and the amino group may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower)alkoxycarbonyl.

The reaction of the compound (1gg) and the compound (48) is carried out under the same conditions as in the reaction of the compound (1h) and the compound (11) in the above Reaction Scheme-8.

[Reaction Scheme-34]

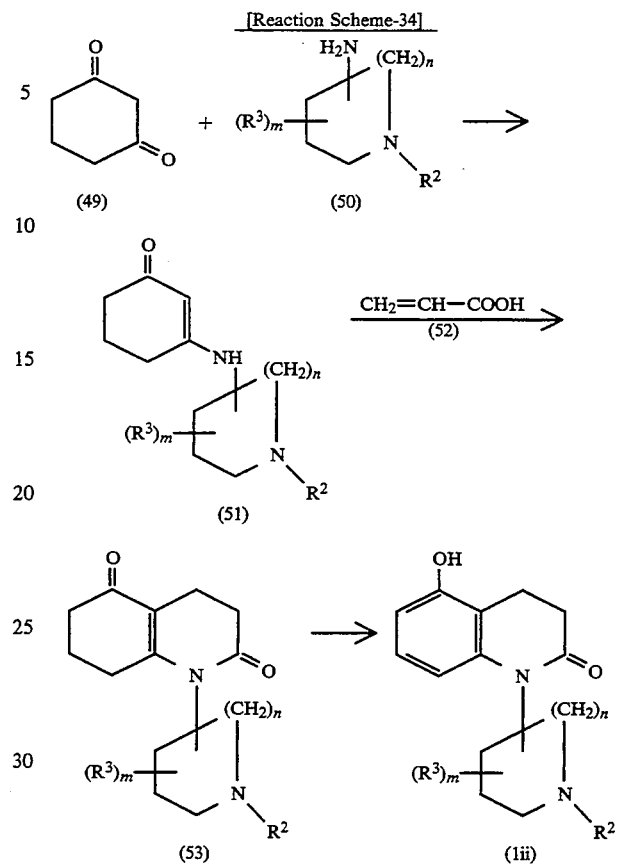

wherein $R^2$, $R^3$, m, and n are the same as defined above.

The reaction of the compound (49) and the compound (50) is carried out by heating them in an appropriate solvent. The solvent includes, for example, alcohols (e.g. methanol, ethanol, isopropanol, etc.), acetonitrile, ethers (e.g. dioxane, diethyl ether, diglyme, tetrahydrofuran, etc.), aromatic hydrocarbons (e.g. benzene, toluene, xylene, etc.), or a mixture of these solvents. The reaction is usually carried out at a temperature of from room temperature to about 200° C., preferably about 50° C. to about 150° C., for about 1 to 10 hours. The compound (50) is usually used in an amount of at least 1 mole, preferably 1 to 1.5 mole, to 1 mole of the compound (49).

The reaction of the compound (51) and the compound (52) is usually carried out without using any solvent at a temperature of about 50° C. to about 200° C., preferably from about 50° C. to about 150° C., for about 1 to 10 hours.

The reaction of converting the compound (53) into the compound (1bb) is carried out in an appropriate solvent in the presence of a halogenating agent and a basic compound. The solvent includes, for example, halogenated hydrocarbons (e.g. dichloromethane, dichloroethane, chloroform, carbon tetrachloride, etc.), alcohols (e.g. methanol, ethanol, propanol, etc.), and the like. The halogenating agent includes N-halogenated succinimides (e.g. N-bromosuccinimide, N-chlorosuccinimide, etc.), halogen molecules (e.g. bromine, chlorine, etc.), N-bromoacetamide, pyrrolidinium bromide perbromide, and the like. The basic compound includes the compounds as used in the reaction of the compound (1h) and the compound (11) in the above Reaction Scheme-8. The reaction is usually carried out at a temperature of about 0° C. to about 150° C., preferably from room temperature to about 100° C., for about 1 to 10 hours. The halogenating agent is usually used in an amount of at least 1 mole, preferably 1 to 3 moles, to 1 mole of the compound (53).

-continued
[Reaction Scheme-36]

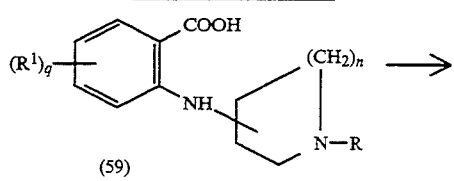

(59)

[Reaction Scheme-35]

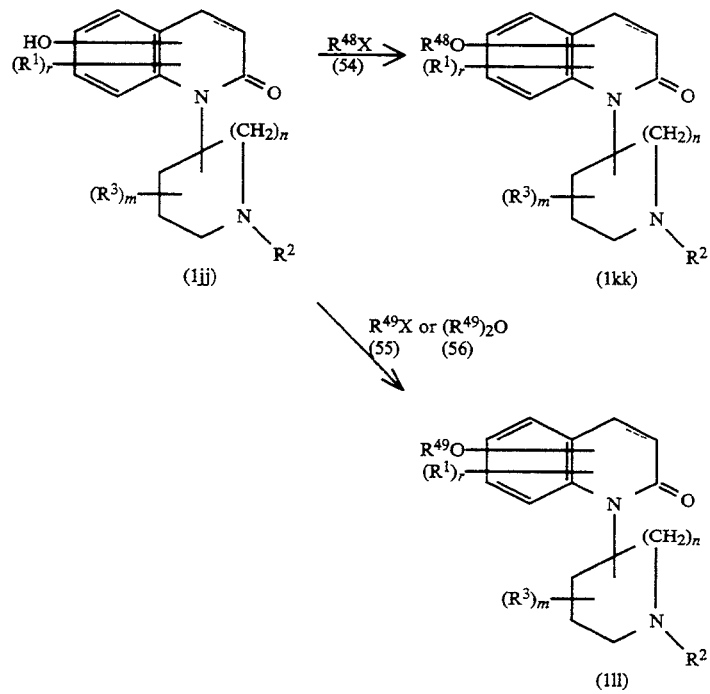

wherein $R^1$, r, $R^2$, $R^3$, m, n, X, and the bond between 3- and 4-positions of the carbostyril nucleus are the same as defined above, and $R^{48}$ is a lower alkyl, and $R^{49}$ is a lower alkanoyl.

The reaction of the compound (1jj) and the compound (54) is carried out under the same conditions as in the reaction of the compound (1h) and the compound (11) in the above Reaction Scheme-8.

The reaction of the compound (1jj) and the compound (55) is carried out under the same conditions as in the reaction of the compound (1h) and the compound (12), wherein a carboxylic halide is used, in the above Reaction Scheme-8, and the reaction of the compound (1jj) and the compound (56) is carried out under the same conditions as in the reaction of the compound (1k) and the compound of the formula: $(R^{5b})_2O$ in the above Reaction Scheme-9A.

[Reaction Scheme-36]

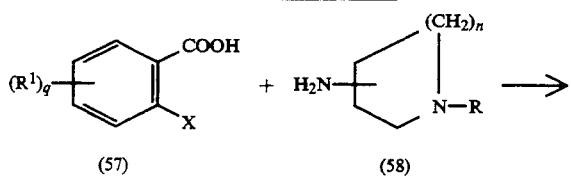

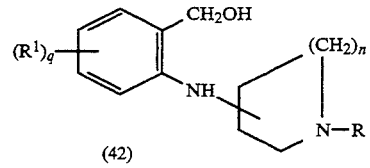

(42)

wherein $R^1$, q, n, R and X are as defined above.

The reaction of the compound (57) and the compound (58) is carried out under the same conditions as in the reaction of the compound (5) and the compound (6) in the above Reaction Scheme-4. In this reaction, copper monoxide may be added to the reaction system in order to proceed the reaction advantageously.

The reaction of converting the compound (59) into the compound (42) can be carried out under the same conditions as used in the reduction reaction of the compound (1) wherein $R^{13}$ is a lower alkanoyl or benzoyl as described hereinafter.

In case of the compounds of the formula (1) wherein (a) $R^2$ is a phenyl(lower)alkanoyl wherein the lower alkanoyl moiety is substituted by an amino having a lower alkoxycarbonyl substituent, (b) $R^4$ or $R^5$ is a lower alkoxy carbonyl, (c) $R^6$ or $R^7$ is a lower alkoxycarbonyl, or (d) $R^6$ and $R^7$ form a heterocyclic group which has a lower alkoxycarbonyl substituent on at least one nitrogen atom of the heterocyclic group, these compound can be subjected to hydrolysis to obtain the corresponding compounds of the formula (1) wherein (a) $R^2$ is a phenyl(lower)alkanoyl wherein the lower alkanoyl moiety is substituted by an amino, (b) $R^4$ or $R^5$ is hydrogen atom, (c) $R^6$ or $R^7$ is hydrogen atom, or (d) $R^6$ and $R^7$ form a heterocyclic group where at least one nitrogen has no substituent, respectively.

The hydrolysis can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature of from room temperature to about 200° C., preferably from room temperature to about 150° C., for about 0.5 to 25 hours.

In the case of the compounds of the formula (1) wherein $R^2$ is a heterocyclic group-substituted carbonyl which has a phenyl(lower)alkoxycarbonyl on at least one nitrogen atom thereof; $R^{13}$ is a benzoyl which is substituted by at least one amino group having at least one phenyl(lower)alkoxycarbonyl substituent on the phenyl ring; $R^4$ or $R^5$ is a pyrrolidinylcarbonyl having at least one phenyl(lower)alkoxycarbonyl substituent on the nitrogen atom of the pyrrolidine ring, or an amino-substituted lower alkanoyl wherein the amino has at least one phenyl(lower)alkoxycarbonyl substituent and the lower alkanoyl moiety may optionally have a substituent; or $R^6$ or $R^7$ is a phenyl(lower)alkoxycarbonyl, these compounds can be subjected to a reduction reaction to obtain the corresponding compounds of the formula (1) wherein $R^2$ is a heterocyclic group-substituted carbonyl wherein at least one nitrogen has hydrogen substituent; $R^{13}$ is a benzoyl which has at least one amino group having no phenyl(lower)alkoxycarbonyl substituent; $R^4$ or $R^5$ is a pyrrolidinylcarbonyl having no substituent on the nitrogen atom thereof or an amino-substituted lower alkanoyl having no substituent on the amino group thereof; or $R^6$ or $R^7$ is hydrogen atom. The reduction is carried out by catalytic reduction in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 100° C., preferably from about 0° C. to about 80° C., under atmospheric pressure to 10 atm., for about 0.5 to 20 hours.

The compound of the formula (1) wherein $R^{13}$ is a phenyl(lower)alkoxy can be converted into the corresponding compound (1) wherein $R^{13}$ is hydroxy by reduction thereof. The reduction can be carried out under the same conditions as in the reduction of the compound (1) wherein $R^2$ is a heterocyclic group-substituted carbonyl having a phenyl(lower)alkoxycarbonyl substituent on at least one nitrogen atom as described above.

In the case of the compounds of the formula (1) wherein $R^1$ is nitro; $R^2$ is a phenoxycarbonyl having at least one nitro substituent; $R^8$ or $R^9$ is a phenyl having at least one nitro substituent; $R^{13}$ is nitro, a phenylthio-substituted lower alkoxy having at least one nitro substituent on the phenyl ring, or a phenylsulfonyl-substituted lower alkoxy having at least one nitro substituent on the phenyl ring; or $R^4$ or $R^5$ is a benzoyl having at least one nitro substituent, or a phenylsulfonyl having at least one nitro substituent on the phenyl ring, these compounds can be subjected to a reduction reaction to obtain the corresponding compounds of the formula (1) wherein $R^1$ is amino; $R^2$ is a phenoxycarbonyl having at least one amino substituent; $R^8$ or $R^9$ is a phenyl having at least one amino substituent; $R^{13}$ is amino, or a phenylthio-substituted lower alkoxy having at least one amino substituent on the phenyl ring, or a phenylsulfonyl-substituted lower alkoxy having at least one amino substituent on the phenyl ring; or $R^4$ or $R^5$ is a benzoyl having at least one amino substituent, or a phenylsulfonyl having at least one amino substituent on the phenyl ring.

The reduction reaction can be carried out, for example, (1) by reducing them in an appropriate solvent with a catalytic reducing agent, or (2) by reducing them in an appropriate inert solvent with a reducing agent, such as a combination of a metal or metal salt and an acid, or a metal or metal salt and an alkali metal hydroxide, sulfide, ammonium salt, and the like.

In the case of reduction using a catalytic reducing agent (1), the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), and the like. The catalytic reducing agent includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 150° C., preferably from about 0° C. to about 100° C., under atmospheric hydrogen pressure to 10 atm., for about 0.5 to 10 hours.

In the case of the reduction (2), the reducing agent includes a combination of iron, zinc, tin or stannous chloride with a mineral acid (e.g. hydrochloric acid, etc.), or of iron, ferrous sulfate, zinc or tin with an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example, water, acetic acid, methanol, ethanol, dioxane, and the like. The conditions of the reduction reaction are determined depending on the kinds of the reducing agent, for example, in case of a combination of stannous chloride and hydrochloric acid, it is advantageously carried out at a temperature of about 0° C. to room temperature for about 0.5 to 10 hours. The reducing agent is usually used in an amount of at least 1 mole, preferably 1 to 5 moles, to 1 mole of the starting compound.

The compound of the formula (1) wherein $R^{13}$ is a lower alkanoyl or benzoyl can be converted into the corresponding compound (1) wherein $R^{13}$ is a lower alkyl substituted by hydroxy and/or phenyl by reduction thereof. The reduction reaction can advantageously be carried out by using a hydrogenating reducing agent. The hydrogenating reducing agent includes, for example, lithium aluminum hydride, sodium boro hydride, diborane, and the like. The reducing agent is usually used in an amount of at least 1 mole, preferably 1 to 15 moles, to 1 mole of the starting compound. The reduction reaction is usually carried out in an appropriate solvent such as water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about $-60°$ C. to about 150° C., preferably about $-30°$ C. to about 100° C., for about 10 minutes to about 5 hours. In case of using lithium aluminum hydride or diborane as the reducing agent, it is preferable to proceed the reaction in an anhydrous solvent such as tetrahydrofuran, diethyl ether, diisopropyl ether, diglyme, or the like.

The compound of the formula (1) wherein $R^{13}$ is hydroxy can be converted into the corresponding compound (1) wherein $R^{13}$ is a group of the formula: $-OR^{17}$ (wherein $R^{17}$ is as defined below) by reacting it with a compound of the formula:

$$R^{17}X$$

wherein $R^{17}$ is a carboxy-substituted alkyl, a lower alkoxycarbonyl-substituted alkyl, a lower alkanoyloxy-substituted lower alkyl, a lower alkenyloxy-substituted lower alkyl, a lower alkoxy(lower)alkyl, an alkyl, a lower alkyl having one or two substituents selected from hydroxy, a lower alkanoyloxy, a tri(lower)alkylammonium, a lower alkoxy, or a group of the formula:

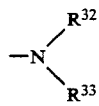

(wherein $R^{32}$ and $R^{33}$ are as defined above), a halogen-substituted lower alkyl, a lower alkylsulfonyloxy-substituted lower alkyl, a benzoyloxy-substituted lower alkyl, a tricyclo[3.3.1.1]decanyl-substituted lower alkyl, a group of the formula:

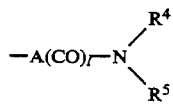

(wherein A, l, $R^4$ and $R^5$ are as defined above), a carbamoyloxy-substituted lower alkyl, a lower alkylthio-substituted lower alkyl, a lower alkylsulfonyl-substituted lower alkyl, a lower alkylsulfinyl-substituted lower alkyl, an alkenyl, a lower alkanoyl, a lower alkylsulfonyl, a lower alkynyl, a phenyl(lower)alkyl, a cycloalkyl, a cycloalkenyl, a cyano-substituted lower alkyl, an oxilanyl-substituted lower alkyl, a phthalimido-substituted alkyl, a pyrrolyl-substituted lower alkyl, an amidino-substituted lower alkyl, a lower alkoxy(lower)alkyl having one or two substituents selected from hydroxy and an amino having optionally a lower alkyl-substituent, a morpholino-substituted lower alkyl which may optionally have a substituent selected from a lower alkyl and oxo, a benzimidazolylthio-substituted lower alkyl, a benzimidazolylsulfinyl-substituted lower alkyl, an imidazo[4,5-c]pyridylcarbonyl-substituted lower alkyl, a pyrimidylthio-substituted lower alkyl, a pyrimidylsulfinyl-substituted lower alkyl, a pyrimidylsulfonyl-substituted lower alkyl, an imidazolylthio-substituted lower alkyl which may optionally have a lower alkyl substituent on the imidazole ring, an imidazolylsulfonyl-substituted lower alkyl which may optionally have a lower alkyl substituent on the imidazole ring, a phenylthio-substituted lower alkyl which may optionally have a substituent selected from nitro and amino on the phenyl ring, a phenylsulfonyl-substituted lower alkyl which may optionally have a substituted selected from nitro and an amino having optionally one or two substituents selected from a lower alkanoyl and a lower alkyl on the phenyl ring, a pyridylthio-substituted lower alkyl, a pyridylsulfonyl-substituted lower alkyl having optionally an oxo substituent on the pyridine ring, and X is as defined above.

The above reaction is carried out under the same conditions as in the reaction of the compound (1h) and the compound (11) in the above Reaction Scheme-8. Besides, an alkali metal halide (e.g. sodium iodide, potassium iodide, etc.) may be added to the reaction system.

The compounds of the formula (1) wherein $R^{13}$ is a lower alkylthio, a lower alkylthio-substituted lower alkoxy, a benzimidazolylthio-substituted lower alkoxy, a pyrimidyl thio-substituted lower alkoxy, an imidazolylthio-substituted lower alkoxy having optionally a lower alkyl substituent on the imidazole ring, a phenylthio-substituted lower alkoxy which may optionally have a substituent selected from nitro and amino on the phenyl ring, or a pyridylthio-substituted lower alkoxy can be converted into the corresponding compounds of the formula (1) wherein $R^{13}$ is a lower alkylsulfinyl or a lower alkylsulfonyl; or a lower alkylsulfinyl-substituted lower alkoxy or a lower alkylsulfonyl-substituted lower alkoxy; a benzimidazolylsulfinyl-substituted lower alkoxy; a pyrimidylsulfinyl-substituted lower alkoxy or a pyrimidylsulfonyl-substituted lower alkoxyl; an imidazolylsulfonyl-substituted lower alkoxy which may optionally have a lower alkyl substituent on the imidazole ring; a phenylsulfonyl-substituted lower alkoxy which may optionally have a substituent selected from nitro and amino on the phenyl ring; or pyridylsulfonyl-substituted lower alkoxy, by oxidation thereof.

The oxidation of converting the lower alkylthio into the lower alkylsulfinyl; the oxidation of converting the lower alkylsulfinyl into the lower alkylsulfonyl; the oxidation of converting the lower alkylthio-substituted lower alkoxy into the lower alkylsulfinyl-substituted lower alkoxy; the oxidation of converting the lower alkylsulfinyl-substituted lower alkoxy into the lower alkylsulfonyl-substituted lower alkoxy; the oxidation of converting the pyrimidylthio-substituted lower alkoxy into the pyridylsulfinyl-substituted lower alkoxy; and the oxidation of converting the pyrimidylsulfinyl-substituted lower alkoxy into the pyrmidylsulfonyl-substituted lower alkoxy are carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. Besides, in cases of the oxidation of converting the lower alkylthio into the lower alkylsulfonyl; the oxidation of converting the lower alkylthio-substituted lower alkoxy into the lower alkylsulfonyl-substituted lower alkoxy; the oxidation of converting the pyrimidylthio-substituted lower alkoxy into the pyrmidylsulfonyl-substituted lower alkoxy; the oxidation of converting the imidazolylthio-substituted lower alkoxy having optionally a lower alkyl substituent on the imidazole ring into the imidazolylsulfonyl-substituted lower alkoxy having optionally a lower alkyl substituent on the imidazole ring; the oxidation of converting the phenylthio-substituted lower alkoxy which may optionally have a substituent selected from nitro and amino on the phenyl ring into the phenylsulfonyl-substituted lower alkoxy which may optionally have a substituent selected from nitro and amino on the phenyl ring; and the oxidation of converting the pyridylthio-substituted lower alkoxy into the pyridylsulfonyl-substituted lower alkoxy, the oxidizing agent is usually used at least 2 moles, preferably 2 to 4 moles, to 1 mole of the starting compound. The above reaction is usually carried out at a temperature of about 0° C. to about 40° C., preferably from about 0° C. to room temperature, for about 1 to 15 hours. In the above reaction, in case of the compound wherein $R^{13}$ is a pyridylthio-substituted lower alkoxy, the pyridyl group may occasionally also be oxidized to give the corresponding pyridine N-oxide compound.

The compound of the formula (1) wherein $R^{13}$ is a lower alkenyl, an alkenyloxy or a cycloalkenyloxy can be converted into the corresponding compound (1) wherein $R^{13}$ is a lower alkyl, an alkoxy or a cycloalkyloxy by reduction thereof. The reduction reaction is carried out under the same conditions as in the above-mentioned reaction of converting the compound (1) wherein $R^6$ or $R^7$ is a phenyl(lower)alkoxycarbonyl into the compound (1) wherein $R^6$ or $R^7$ is hydrogen atom.

The compound of the formula (1) wherein $R^{13}$ is a lower alkanoyl can be converted into the corresponding compound (1) wherein $R^{13}$ is a hydroxyimino-substituted lower alkyl by reacting it with hydroxylamine. The reaction is carried out in an inert solvent in the presence or absence of a basic compound. The basic compound includes, for example, inorganic basic compounds (e.g. sodium hydroxide, potassium hydroxide, sodium carbonate, potassium carbonate, etc.), lower alkanic acid alkali metal salts (e.g. sodium acetate, etc.), organic bases (e.g. piperidine, pyridine, 4-dimethylaminopyridine, triethylamine, DBN, DBU, DABCO, etc.), and the like. The solvent includes any solvent which does not affect on the reaction, for example, water, lower alcohols (e.g. methanol, ethanol; isopropanol, etc.), fatty acids (e.g. acetic acid, etc.), ethers (e.g. dioxane, tetrahydrofuran, diethyl ether, ethylene glycol monomethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylsulfoxide, hexamethylphosphoric triamide, etc.), or a mixture of these solvents. The hydroxylamine is usually used in an amount of at least 1 mole, preferably 1 to 5 moles, to 1 mole of the starting compound. The reaction is usually carried out at a temperature of from room temperature to about 200° C., preferably from room temperature to about 150° C., for about 1 to 15 hours.

In case of the compounds of the formula (1) wherein $R^{13}$ is a lower alkoxycarbonyl-substituted alkoxy, a lower alkanoyloxy-substituted lower alkoxy, a lower alkanoyloxy-substituted lower alkyl, a lower alkanoyloxy, a lower alkoxycarbonyl, a lower alkoxycarbonyl(lower)alkyl, $R^6$ or $R^7$ is a lower alkoxycarbonyl(lower)alkyl, $R^4$ or $R^5$ is a lower alkanoyloxy(lower)alkanoyl, a cycloalkylcarbonyl having at least one substituent of a lower alkanoyloxy on the cycloalkyl group, or a lower alkanoyloxy(lower)alkyl, or $R^1$ is a lower alkanoyloxy, these compounds can be converted by hydrolysis thereof into the corresponding compounds (1) wherein $R^{13}$ is a carboxy-substituted lower alkoxy, a hydroxy-substituted lower alkoxy, a hydroxy-substituted lower alkyl, hydroxy, carboxy, a carboxy-substituted lower alkyl, $R^6$ or $R^7$ is a carboxy-substituted lower alkyl, $R^4$ or $R^5$ is a hydroxy-substituted lower alkanoyl, a cycloalkylcarbonyl having at least one hydroxy substituent on the cycloalkyl group, or a hydroxy-substituted lower alkyl, or $R^1$ is hydroxy. The above hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described herebefore.

In the case of the compounds of the formula (1) wherein $R^1$ is a lower alkanoyl-substituted amino; $R^2$ is a an alkanoyl; $R^2$ is a group of the formula:

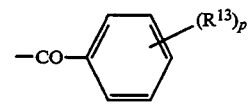

(wherein $R^{13}$ and p are as defined above), or a phenoxycarbonyl having at least one lower alkanoyl-substituted amino on the phenyl ring; $R^4$ or $R^5$ is a lower alkanoyl having optionally one to three substituents of a halogen atom, an amino-substituted lower alkanoyl having a lower alkanoyl substituent, an amino-substituted lower alkyl having a lower alkanoyl substituent, a piperidinylcarbonyl having a lower alkanoyl substituent on the nitrogen atom of the piperidine ring, or a phenylsulfonyl having at least one lower alkanoyl-substituted amino on the phenyl ring; $R^6$ or $R^7$ is a lower alkanoyl having one to three substituents of a halogen atom; or $R^4$ and $R^5$ or $R^{11}$ and $R^{12}$ form a heterocyclic group which has a lower alkanoyl substituent on the nitrogen atom of said heterocyclic group, these compounds can be converted by hydrolysis into the corresponding compounds of the formula (1) wherein $R^1$ is amino; $R^2$ is hydrogen atom; $R^2$ is a phenoxycarbonyl having at least one amino substituent on the phenyl ring; $R^4$ or $R^5$ is hydrogen atom, an amino-substituted lower alkanoyl, an amino-substituted lower alkyl, unsubstituted piperidinylcarbonyl, or a phenylsulfonyl having at least one amino substituent on the phenyl group; $R^6$ or $R^7$ is hydrogen atom; or $R^4$ and $R^5$ or $R^{11}$ and $R^{12}$ form a heterocyclic group which have an substituent on the nitrogen atom of said heterocyclic group. The hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinbefore.

In the case of the compounds of the formula (1) wherein $R^4$ or $R^5$ is a phenyl(lower)alkyl; $R^{11}$ or $R^{12}$ is a phenyl(lower)alkyl; or $R^4$ and $R^5$ or $R^{11}$ and $R^{12}$ form a heterocyclic group which has a phenyl(lower)alkyl substituent on the nitrogen atom of said heterocyclic group, these compounds can be subjected to a reduction reaction to obtain the corresponding compounds of the formula (1) wherein $R^4$ or $R^5$ is hydrogen, atom; $R^{11}$ or $R^{12}$ is hydrogen atom; or $R^4$ and $R^5$ or $R^{11}$ and $R^{12}$ form a heterocyclic group which has no substituent on the nitrogen atom of said heterocyclic group. The reduction is carried out under the same conditions as in the above-mentioned reduction of converting a compound (1) wherein $R^6$ or $R^7$ is a phenyl(lower)alkoxycarbonyl into the compound (1) wherein $R^6$ or $R^7$ is hydrogen atom. Besides, the reduction reaction can also be carried out by using the same solvent and catalyst as in the catalytic hydrogenation reaction together with a hydrogen donor (e.g. formic acid, cyclohexane, hydrazine hydrate, ammonium formate, etc.), at a temperature of from room temperature to 150° C., preferably from room temperature to 100° C., for about 1 to 6 hours.

The compound of the formula (1) wherein $R^2$ is a benzoyl having at least one lower alkenyloxy substituent can be converted into the corresponding compound (1) wherein $R^2$ has at least two substituents of hydroxy and a lower alkenyl by subjecting it to Claisen rearrangement. The reaction is carried out by heating said compound in an appropriate solvent. The solvent includes solvents having a high boiling point, such as dimethylformamide, diphenyl ether, dimethylaniline, tetrahydronaphthalene, etc.. The reaction is usually carried out at a temperature of 100° C. to 250° C., preferably from 150° C. to 250° C. for about 1 to 30 hours.

In the case of the compounds of the formula (1) wherein $R^{13}$ is a carboxy-substituted alkoxy, carboxy or a carboxy-substituted lower alkyl; $R^6$ or $R^7$ is a carboxy-substituted lower alkyl; $R^4$ and $R^5$ form a heterocyclic group which has at least one carboxyl substituent on the heterocyclic group, these compounds can be converted by esterification thereof into the corresponding compounds of the formula (1) wherein $R^{13}$ is a lower alkoxycarbonyl-substituted alkoxy, a lower alkoxycarbonyl, or a lower alkoxycarbonyl(lower)alkyl; $R^6$ or $R^7$ is a lower alkoxycarbonyl(lower)alkyl; or $R^4$ and $R^5$ form a heterocyclic group which has at least one lower alkoxycarbonyl substituent on the heterocyclic group. The esterification is usually carried out by reacting the compound with an alcohol (e.g. methanol, ethanol, isopropanol, etc.) in the presence of a mineral acid (e.g. hydrochloric acid, sulfuric acid, etc.) and a halogenating agent (e.g. thionyl chloride, phosphorus oxychloride, phosphorus pentoxide, phosphorus trichloride, etc.), at a temperature of 0° C. to about 150° C., preferably from 50° C. to 100° C., for about 1 to 10 hours.

In the case of the compounds of the formula (1) wherein $R^4$ or $R^5$ is a lower alkoxycarbonyl or a lower alkoxycarbonyl(lower)alkyl; $R^6$ or $R^7$ is a lower alkoxycarbonyl(lower)alkyl or a carboxy(lower)alkyl; or $R^4$ and $R^5$ form a heterocyclic group which has at least one substituent of carboxy or a lower alkoxycarbonyl on the heterocyclic group, these compounds can be reacted with an amine having optionally a lower alkyl-substituent or an amine having optionally a substituent selected from a lower alkyl and a lower alkanoyl under the same conditions as in the reaction of the compound (1d) and the compound (7) in the above Reaction Scheme-5 to obtain the corresponding compounds (1) wherein $R^4$ or $R^5$ is an amido having optionally a lower alkyl substituent, or an amido-substituted lower alkyl which has optionally a substituent selected from a lower alkyl and a lower alkanoyl; $R^6$ or $R^7$ is an amido-substituted lower alkyl having optionally a lower alkyl substituent on the amido group; or $R^4$ and $R^5$ form a heterocyclic group being substituted by at least one amido group which has optionally a lower alkyl substituent. In this reaction, when the $R^6$ in the compound (1) is hydrogen atom and the $R^7$ is a carboxy(lower)alkyl, these groups may occasionally form an intermolecular amido bond to give the compound wherein $R^6$ and $R^7$ form a group of the formula:

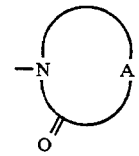

(wherein A is as defined above).

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding compounds (1) wherein $R^4$ or $R^5$ is a benzoyl which has at least one amino having one or two lower alkyl substituents; a phenylsulfonyl which phenyl ring is substituted by at least one amino having one or two lower alkyl substituents; an amino-substituted lower alkyl wherein the amino group has one or two lower alkyl substituents; or $R^{13}$ is a phenylsulfonyl-substituted lower alkoxy which phenyl ring is substituted by at least one amino having one or two lower alkyl substituents by treating them under the same conditions as in the reaction of the compound (1k) and the compound (14) in the above Reaction Scheme-9A.

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding components (1) wherein $R^4$ or $R^5$ is a benzoyl which has a substituent selected from a lower alkanoyl and a lower alkoxycarbonyl and further at least one amino having optionally one lower alkyl substituent; a phenylsulfonyl which phenyl ring is substituted by a lower alkanoyl and further by at least one amino having optionally one lower alkyl substituent; an amino-substituted lower alkyl wherein the amino group has a lower alkanoyl substituent and further at least one amino having optionally a lower alkyl substituent; or $R^{13}$ is a phenylsulfonyl-substituted lower alkoxy which phenyl ring is substituted by a lower alkanoyl and further by at least one amino having optionally one lower alkyl substituent by treating them under the same conditions as in the reaction of the compound (1k) and the compound (15) in the above Reaction Scheme-9A.

The compound of the formula (1d) can also be prepared by reducing the compound (1) wherein $R^2$ is a phenyl(lower)alkyl under the same conditions as in the above-mentioned reduction of the compound (1) wherein $R^2$ is a heterocyclic group-substituted carbonyl which has at least one phenyl(lower)alkoxycarbonyl on the nitrogen atom. The reduction reaction may be carried out in the presence of an acid (e.g. hydrochloric acid, etc.).

The compound (1) wherein $R^{13}$ is a tri(lower)alkylammonium can also be prepared by reacting a compound (1) wherein $R^{13}$ is a di(lower)alkylamino with a compound of the formula: $R^{50}X$ (wherein $R^{50}$ is a lower alkyl and X is a halogen atom) under the same conditions as in the reaction of the compound (1h) and the compound (11) in the above Reaction Scheme-8.

The compound (1) wherein $R^{13}$ is an ammonium(lower)alkoxy having three substituents selected from a lower alkyl, a lower alkenyl and oxo can also be prepared by reacting a compound (1) wherein $R^{13}$ is an amino-substituted lower alkoxy which has two substituents selected from a lower alkyl and/or a lower alkenyl on the amino group with a compound of the formula: $R^{51}X$ (wherein $R^{51}$ is a lower alkyl or a lower alkenyl, and X is as defined above) under the same conditions as in the reaction of the compound (1h) and the compound (11) of the above Reaction Scheme-8. Besides, said compound can be converted into a compound (1) wherein $R^{13}$ is an ammonium(lower)alkoxy having oxo substituent by oxidizing the compound under the same conditions as in the above-mentioned oxidization reaction for converting the compound (1) wherein $R^{13}$ is a lower alkylthio into the corresponding compound (1) wherein $R^{13}$ is a lower alkylsulfonyl.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, citric acid, succinic acid, benzoic acid, etc. Among the active compounds (1) of the invention, the compounds having an ammonium group can be converted into a salt thereof with a pharmaceutically acceptable halogen anion (e.g. chlorine anion, bromine anion, fluorine anion, or iodine anion). These salts are useful as an active ingredient as like as the compounds (1) in the free form.

In addition, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromatography, preparative thin layer chromatography, extraction with a solvent, and the like.

The compounds and their salts of this invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspensions are sterilized and are preferably made isotonic with the blood. In the preparation of these solutions, emulsions and suspensions, there are used conventional diluents, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes, and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Components | Amount |
|---|---|
| 1-[1-(4-Dimethylaminobenzoyl)-4-piperidinyl]-3,4-dihydrocarbostyril | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
|---|---|
| 1-[1-(2-Methoxy-4-ethoxybenzoyl)-4-piperidinyl]-3,4-dihydrocarbostyril | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
|---|---|
| 7-Fluoro-1-[1-(2,4-dimethoxybenzoyl)-4-piperidinyl]-3,4-dihydrocarbostyril | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |

| Components | Amount |
| --- | --- |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

A mixture of aniline (28.0 g), 1-benzyl-4-piperidone (56.7 g), acetic acid (55 ml), platinum oxide (0.9 g) and ethanol (420 ml) is subjected to catalytic reduction at room temperature at normal pressure for 2 hours. The catalyst is removed by filtration and the filtrate is concentrated.

The resulting residue is made alkaline with a 10% aqueous sodium hydroxide solution and extracted with dichloromethane. After the extract is dried and concentrated, n-hexane is added to the residue and the formed crystals are separated by filtration and recrystallized from n-hexane to give N-(1-benzyl-4-piperidinyl)aniline (63.3 g) as colorless prisms, m.p. 73°–75° C.

Using appropriate starting materials, the same procedure as in Reference Example 1 is repeated to give the following compounds:

N-(1-Benzyl-4-piperidinyl)-4-methoxyaniline, m.p. 75°–76° C. (recrystallized from n-hexane), colorless prisms N-(1-Benzyl-4-piperidinyl)-4-methylaniline, m.p. 95°–96° C. (recrystallized from n-hexane), colorless prisms N-(1-Benzyl-4-piperidinyl)-4-fluoroaniline, m.p. 87°–88° C. (recrystallized from n-hexane), colorless prisms N-(1-Benzyl-4-piperidinyl)-3-methylaniline
NMR (CDCl$_3$) δ: 1.38 1.64 (2H, m), 2.00–2.20 (4H, m), 2.26 (3H, s), 2.72–2.94 (2H, m), 3.20–3.40 (1H, m), 3.62 (2H, s), 3.55–3.70 (1H, m), 6.39 (2H, d, J=6.2 Hz), 6.49 (1H, d, J=7.4 Hz), 7.04 (1H, t, J=7.4 Hz), 7.20–7.45 (6H, m)

N-(1-Benzyl-4-piperidinyl)-3-fluoroaniline, m.p. 72°–74° C. (recrystallized from n-hexane), colorless prisms N-(1-Benzyl-4-piperidinyl)-2-methylaniline, m.p. 100°–102° C. (recrystallized from n-hexane), colorless prisms N-(1-Benzyl-4-piperidinyl)-3-acetaminoaniline
NMR (CDCl$_3$) δ: 1.34–2.73 (2H, m), 1.82–2.25 (7H, m), 2.68–2.95 (2H, m), 3.28 (1H, brs), 3.51 (2H, s), 3.58–3.80 (1H, m), 6.30–6.60 (2H, m), 7.01–7.53 (7H, m)

N-(1-Benzoyl-4-piperidinyl)aniline, m.p. 161°–163° C. (recrystallized from ethanol), white powders N-(1-Benzyl-3-piperidinyl)aniline.

Example 1

To N-(1-benzoyl-4-piperidinyl)-2-(2-carbamoylethyl)aniline (85 g) prepared in Reference Example 4 is added 5% hydrochloric acid (500 ml) and the mixture is refluxed for 5 hours. After cooling, the reaction mixture is extracted with diethyl ether and the aqueous layer is made alkaline with a 50% aqueous sodium hydroxide solution and extracted with ethyl acetate. The extract is dried over sodium carbonate and concentrated. The concentrate is purified by silica gel column chromatography (eluent; n-hexane/ethyl acetate=1/10–10/1) and recrystallized from ethanol/n-hexane to give 1-(1-benzoyl-4-piperidinyl)-3,4-dihydrocarbostyril (35 g) as white powders, m.p. 108°–111° C.

Examples 2 to 383C

Using appropriate starting materials, the procedure of Example 1 is repeated to give the following compounds as shown in Table 1. Table 2 shows the NMR analysis of these compounds.

TABLE 1

[Structure: carbostyril ring system with R$^1$ substituent and N-R group]

Example 2
Structure

R: [piperidinyl]—N—COCH$_2$CH$_3$

R$^1$: H
Bond between 3- and 4-positions in the carbostyril ring: single bond
Crystalline form: white powders
Recrystallization solvent: ethanol/n-hexane
Melting point: 82–83° C.
Form: Free Example 3
Structure R: [piperidinyl]—N—C(=O)—[phenyl]—NO$_2$ R$^1$: H
Bond between 3- and 4-positions in the carbostyril ring: single bond
Crystalline form: pale yellow powders
Recrystalllization solvent: ethanol/n-hexane
Melting point: 142–145° C.
Form: Free Example 4
Structure R: [piperidinyl]—N—C(=O)—[furyl]

R$^1$: H
Bond between 3- and 4-positions in the carbostyril ring: single bond
Crystalline form: white powders
Recrystallization solvent: ethanol/n-hexane
Melting point: 108–111° C.
Form: Free Example 5
Structure R: [piperidinyl]—N—C(=O)—[pyridyl]

R$^1$: H
Bond between 3- and 4-positions in the carbostyril ring: single bond
Crystalline form: white powders
Recrystallization solvent: ethanol/n-hexane
Melting point: 113–116° C.
Form: Free TABLE 1-continued

[Structure: carbostyril with R¹ substituent and R on N]

Example 6
Structure

R: —[piperidine]—N—C(=O)—[pyridine]

R¹: H
Bond between 3- and 4-positions in the carbostyril ring: single bond
Crystalline form: white powders
Recrystallization solvent: ethanol/n-hexane
Melting point: 105–108° C.
Form: Free

Example 7
Structure

R: —[piperidine]—N—C(=O)—[thiophene]

R¹: H
Bond between 3- and 4-positions in the carbostyril ring: single bond
Crystalline form: white powders
Recrystallization solvent: ethanol/n-hexane
Melting point: 129–132° C.
Form: Free

Example 8
Structure

R: —[piperidine]—N—C(=O)—[pyrrole-NH]

R¹: H
Bond between 3- and 4-positions in the carbostyril ring: single bond
Crystalline form: white powders
Recrystallization solvent: ethanol/n-hexane
Melting point: 161–162° C. (decomposition)
Form: Free

Example 9
Structure

R: —[piperidine]—N—C(=O)—NH—[phenyl]

R¹: H
Bond between 3- and 4-positions in the carbostyril ring: single bond
Crystalline form: white powders
Recrystallization solvent: ethanol/n-hexane
Melting point: 194–196° C.
Form: Free

Example 10
Structure

R: —[piperidine]—N—C(=O)—[phenyl with OC₂H₅ and OCH₃]

R¹: H
Bond between 3- and 4-positions in the carbostyril ring: double bond
Crystalline form: white powders
Recrystallization solvent: ethanol/n-hexane
Melting point: 172–174° C.
Form: Free

Example 11
Structure

R: —[piperidine]—N—C(=O)—CH=CH—[phenyl]

R¹: H
Bond between 3- and 4-positions in the carbostyril ring: single bond
Crystalline form: white powders
Recrystallization solvent: ethanol/n-hexane
Melting point: 144–147° C.
Form: Free

Example 12
Structure

R: —[piperidine]—N—C(=O)—CH$_2$—[phenyl]

R¹: H
Bond between 3- and 4-positions in the carbostyril ring: single bond
NMR analysis: 1)
Form: Free

Example 13
Structure

R: —[piperidine]—N—C(=O)—CH(H)—[pyrrolidine-N—COOCH$_2$—phenyl]

R¹: H
Bond between 3- and 4-positions in the carbostyril ring: single bond
Crystalline form: white powders
Recrystallization solvent: ethanol/n-hexane
Melting point: 143–147° C.
Form: Free

Example 14
Structure

R: —[piperidine]—N—C(=O)—CH(phenyl)—NHCOC(CH$_3$)$_3$

R¹: H
Bond between 3- and 4-positions in the carbostyril ring: single bond
Crystalline form: white powders
Recrystallization solvent: ethanol/n-hexane
Melting point: 143–146° C.
Form: Free

Example 15
Structure

R: —[piperidine]—N—C(=O)—O—[phenyl]

R¹: H
Bond between 3- and 4-positions in the carbostyril ring: single bond
Crystalline form: white powders
Recrystallization solvent: diethyl ether/n-hexane
Melting point: 138–140° C.
Form: Free

Example 16

TABLE 1-continued

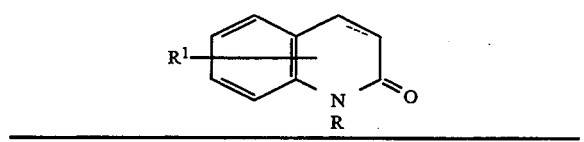

Structure

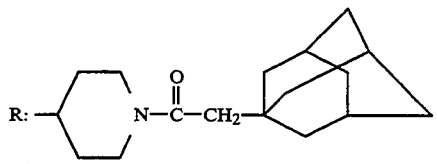

R¹: H
Bond between 3- and 4-positions in the carbostyril ring: single bond
Crystalline form: white powders
Recrystallization solvent: n-hexane
Melting point: 143–145° C.
Form: Free Example 17
Structure

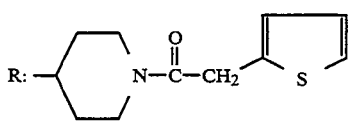

R¹: H
Bond between 3- and 4-positions in the carbostyril ring: single bond
NMR analysis. 2)
Form: Free Example 18
Structure

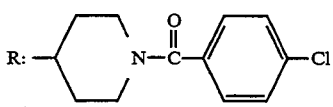

R¹: H
Bond between 3- and 4-positions in the carbostyril ring: single bond
Crystalline form: white powders
Recrystallization solvent: n-hexane/ethanol
Melting point: 111–112° C.
Form: Free Example 19
Structure

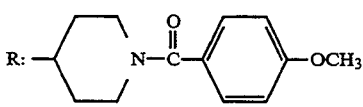

R¹: H
Bond between 3- and 4-positions in the carbostyril ring: single bond
Crystalline form: white powders
Recrystallization solvent: n-hexane/ethanol
Melting point: 93–96° C.
Form: Free Example 20
Structure

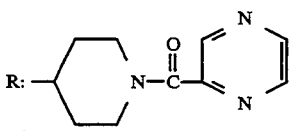

R¹: H
Bond between 3- and 4-positions in the carbostyril ring: single bond
NMR analysis: 3)
Form: Free Example 21
Structure TABLE 1-continued

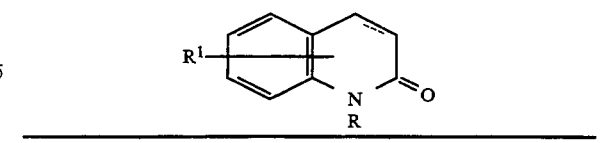

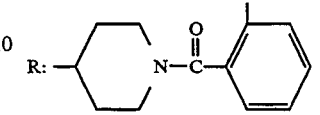

R¹: H
Bond between 3- and 4-positions in the carbostyril ring: single bond
Crystalline form: white powders
Recrystallization solvent: n-hexane/ethanol
Melting point: 175–178° C.
Form: Free Example 22
Structure

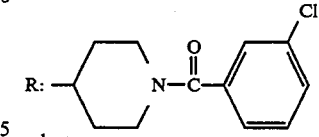

R¹: H
Bond between 3- and 4-positions in the carbostyril ring: single bond
Crystalline form: white powders
Recrystallization solvent: n-hexane/ethanol
Melting point: 123–126° C.
Form: Free Example 23
Structure

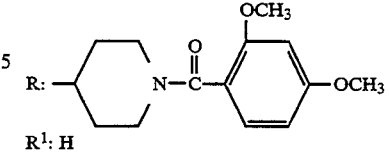

R¹: H
Bond between 3- and 4-positions in the carbostyril ring: single bond
Crystalline form: white powders
Recrystallization solvent: n-hexane/ethanol
Melting point: 141–143° C.
Form: Free Example 24
Structure

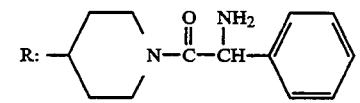

R¹: H
Bond between 3- and 4-positions in the carbostyril ring: single bond
Crystalline form: white powders
Recrystallization solvent: diethyl ether
Melting point: 116–120° C.
Form: Free Example 25
Structure

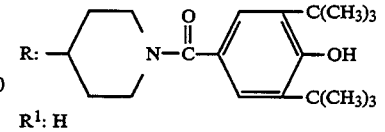

R¹: H
Bond between 3- and 4-positions in the carbostyril ring: single bond
Crystalline form: white powders
Recrystallization solvent: n-hexane/ethanol
Melting point: 134–136° C.
Form: Free Example 26
Structure

TABLE 1-continued

[Structure: carbostyril with R¹ and R substituents]

R: —[piperidine]—N—C(=O)—[phenyl]—O(CH₂)₃CH₃

R¹: H
Bond between 3- and 4-positions in the carbostyril ring: single bond
NMR analysis: 4)
Form: Free

Example 27
Structure

R: —[piperidine]—N—C(=O)—[phenyl]—N(CH₃)₂

R¹: H
Bond between 3- and 4-positions in the carbostyril ring: single bond
Crystalline form: white powders
Recrystallization solvent: n-hexane/ethanol
Melting point 153–155° C.
Form: Free

Example 28
Structure

R: —[piperidine]—N—C(=O)—[sugar-like ring with CH₂–O–phenyl and C(CH₃)₂]

R¹: H
Bond between 3- and 4-positions in the carbostyril ring: single bond
NMR analysis: 5)
Form: Free

Example 29
Structure

R: —[piperidine]—N—C(=O)—[phenyl]—SCH₃

R¹: H
Bond between 3- and 4-positions in the carbostyril ring: single bond
NMR analysis: 6)
Form: Free

Example 30
Structure

R: —[piperidine]—N—C(=O)—[phenyl with OCH₃, OCH₃]

R¹: H
Bond between 3- and 4-positions in the carbostyril ring: single bond
Crystalline form: white powders
Recrystallization solvent: n-hexane/ethanol
Melting point: 121–124° C.
Form: Free

Example 31
Structure

R: —[piperidine]—N—C(=O)—[phenyl]—O—[phenyl]

R¹: H
Bond between 3- and 4-positions in the carbostyril ring: single bond
Crystalline form: white powders

TABLE 1-continued

[Structure: carbostyril with R¹ and R substituents]

Recrystallization solvent: n-hexane/ethanol
Melting point: 205–208° C.
Form: Free

Example 32
Structure

R: —[piperidine]—N—C(=O)—[phenyl]—NHC(=O)CH₃

R¹: H
Bond between 3- and 4-positions in the carbostyril ring: single bond
Crystalline form: white amorphous
NMR analysis: 7)
Recrystallization solvent: n-hexane
Melting point: 85–90° C.
Form: Free

Example 33
Structure

R: —[piperidine]—N—C(=O)—[phenyl]—OC(=O)CH₃

R¹: H
Bond between 3- and 4-positions in the carbostyril ring: single bond
Crystalline form: white powders
Recrystallization solvent: n-hexane/ethanol
Melting point: 170–171 ° C.
Form: Free

Example 34
Structure

R: —[piperidine]—N—C(=O)—CH=C(CH₃)—CH₂—CH₂—CH=C(CH₃)CH₃

R¹: H
Bond between 3- and 4-positions in the carbostyril ring: single bond
NMR analysis: 8)
Form: Free

Example 35
Structure

R: —[piperidine]—N—C(=O)—[phenyl]—Br

R¹: H
Bond between 3- and 4-positions in the carbostyril ring: single bond
Crystalline form: white powders
Recrystallization solvent: n-hexane/ethanol
Melting point: 124–128° C.
Form: Free

Example 36
Structure

R: —[piperidine]—N—C(=O)—[phenyl]—F

R¹: H
Bond between 3- and 4-positions in the carbostyril ring: single bond
Crystalline form: white powders
Recrystallization solvent: n-hexane/ethanol
Melting point: 105–107° C.
Form: Free TABLE 1-continued

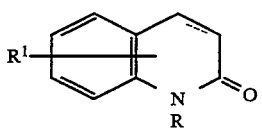

Example 37
Structure

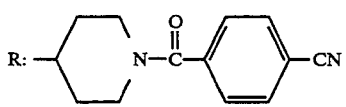

R¹: H
Bond between 3- and 4-positions in the carbostyril ring: single bond
Crystalline form: pale yellow powders
Recrystallization solvent: n-hexane/ethanol
Melting point: 169–172° C.
Form: Free

Example 38
Structure

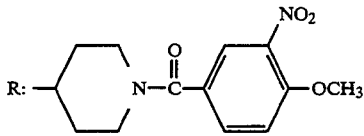

R¹: H
Bond between 3- and 4-positions in the carbostyril ring: single bond
Crystalline form: pale yellow amorphous
Recrystallization solvent: n-hexane/ethanol
Melting point: 85–90° C.
Form: Free
NMR analysis: 9)

Example 39
Structure

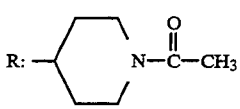

R¹: H
Bond between 3- and 4-positions in the carbostyril ring: single bond
NMR analysis: 10)
Form: Free

Example 44
Structure

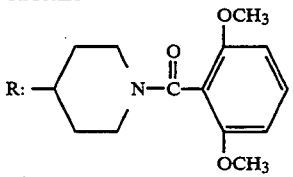

R¹: H
Bond between 3- ind 4-positions in the carbostyril ring: single bond
Crystalline form: white powders
Recrystallization solvent: n-hexane/ethanol
Melting point: 202–204° C.
Form: Free

Example 45
Structure

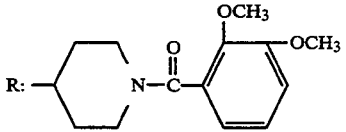

R¹: H
Bond between 3- and 4-positions in the carbostyril ring: single bond
Crystalline form: white powders
Recrystallization solvent: n-hexane/ethanol
Melting point: 194–195° C.
Form: Free TABLE 1-continued

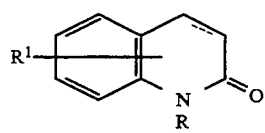

Example 46
Structure

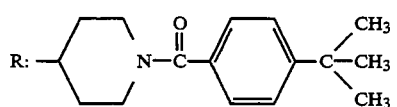

R¹: H
Bond between 3- and 4-positions in the carbostyril ring: single bond
Crystalline form: white powders
Recrystallization solvent: n-hexane/ethanol
Melting point: 110–112° C.
Form: Free

Example 47
Structure

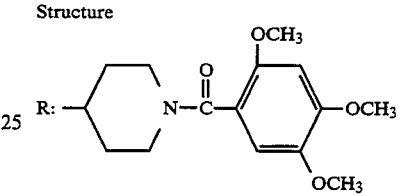

R¹: H
Bond between 3- and 4-positions in the carbostyril ring: single bond
Crystalline form: white powders
Recrystallization solvent: n-hexane/ethanol
Melting point: 123–126° C.
Form: Free

Example 48
Structure

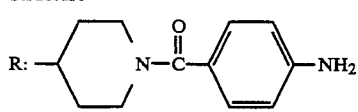

R¹: H
Bond between 3- and 4-positions in the carbostyril ring: single bond
Crystalline form: white powders
Recrystallization solvent: n-hexane/ethanol
Melting point: 198–199° C.
Form: Free

Example 49
Structure

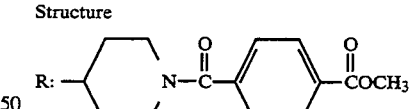

R¹: H
Bond between 3- and 4-positions in the carbostyril ring: single bond
Crystalline form: white powders
Recrystallization solvent: n-hexane/ethanol
Melting point: 160–162° C.
Form: Free

Example 50
Structure

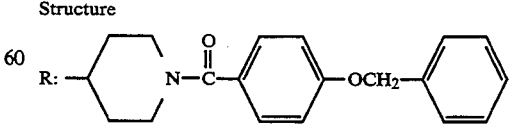

R¹: H
Bond between 3- and 4-positions in the carbostyril ring: single bond
NMR analysis: 12)
Form: Free

Example 51
Structure

TABLE 1-continued

[Carbostyril structure with R¹ and N-R]

R: —[piperidine]—N—C(=O)—[phenyl]—SO₂CH₃

R¹: H
Bond between 3- and 4-positions in the carbostyril ring: single bond
Crystalline form: white powders
Recrystallization solvent: n-hexane/ethanol
Melting point: 194–196° C.
Form: Free Example 52
Structure R: —[piperidine]—N—C(=O)—[phenyl]—OH R¹: H
Bond between 3- and 4-positions in the carbostyril ring: single bond
Crystalline form: white powders
Recrystallization solvent: n-hexane/ethanol
Melting point: 182–183° C.
Form: Free Example 53
Structure R: —[piperidine]—N—C(=O)—[phenyl]—COOH R¹: H
Bond between 3- and 4-positions in the carbostyril ring: single bond
Crystalline form: white powders
Recrystallization solvent: n-hexane/ethanol
Melting point: 232–235° C.
Form: Free Example 54
Structure R: —[piperidine]—N—C(=O)—[phenyl with OCH₃]—SCH₃

R¹: H
Bond between 3- and 4-positions in the carbostyril ring: single bond
NMR analysis: 13)
Form: Free Example 55
Structure R: —[piperidine]—N—C(=O)—[phenyl]—O(CH₂)₂N(CH₃)₂

R¹: H
Bond between 3- and 4-positions in the carbostyril ring: single bond
NMR analysis: 14)
Form: Free Example 56
Structure R: —[piperidine]—N—C(=O)—[phenyl]—OCH₂CH(CH₃)₂

R¹: H
Bond between 3- and 4-positions in the carbostyril ring: single bond

TABLE 1-continued

[Carbostyril structure with R¹ and N-R]

NMR analysis: 15)
Form: Free

Example 57
Structure

R: —[piperidine]—N—C(=O)—[phenyl]—N(CH₃)(COOC(CH₃)₃)

R¹: H
Bond between 3- and 4-positions in the carbostyril ring: single bond
NMR analysis: 16)
Form: Free Example 58
Structure R: —[piperidine]—N—C(=O)—[phenyl]—N[piperazine]N—COOC(CH₃)₃

R¹: H
Bond between 3- and 4-positions in the carbostyril ring: single bond
Crystalline form: white powders
Recrystallization solvent: n-hexane
Melting point: 136–138° C.
Form: Free Example 59
Structure R: —[piperidine]—N—C(=O)—[phenyl]—N(COOC(CH₃)₃)(CH₂CH=C(CH₃)₂)

R¹: H
Bond between 3- and 4-positions in the carbostyril ring: single bond
NMR analysis: 17)
Form: Free Example 60
Structure R: —[piperidine]—N—C(=O)—[phenyl]—N[piperazine]NH R¹: H
Bond between 3- and 4-positions in the carbostyril ring: single bond
NMR analysis: 18)
Form: Free Example 61
Structure R: —[piperidine]—N—C(=O)—[phenyl]—OCH₂CH=C(CH₃)₂

R¹: H
Bond between 3- and 4-positions in the carbostyril ring: single bond
NMR analysis: 19)
Form: Free Example 62
Structure TABLE 1-continued

[Structure: R¹-substituted carbostyril with N-R, 3,4-bond]

R: piperidine-N—C(=O)—C₆H₄—NHCH₃ (para)
R¹: H
Bond between 3- and 4-positions in he carbostyril ring: single bond
Crystalline form: white powders
Recrystallization solvent: n-hexane/ethanol
Melting point: 184–186° C.
Form: Free Example 63
Structure

R: piperidine-N—C(=O)—C₆H₄—N(C₂H₅)₂ (para)
R¹: H
Bond between 3- and 4-positions in the carbostyril ring: single bond
Crystalline form: white powders
Recrystallization solvent: n-hexane/ethanol
Melting point: 139–140° C.
Form: Free Example 64
Structure

R: piperidine-N—C(=O)— attached to 6-position of carbostyril
R¹: H
Bond between 3- and 4-positions in the carbostyril ring: single bond
Crystalline form: white powders
Recrystallization solvent: n-hexane/ethanol
Melting point: 238–240° C.
Form: Free Example 65
Structure

R: piperidine-N—C(=O)—benzene with N—CH₃ amide and N—H carbostyril fusion
R¹: H
Bond between 3- and 4-positions in the carbostyril ring: single bond
Crystalline form: white powders
Recrystallization solvent: n-hexane/ethanol
Melting point: 224–226° C.
Form: Free Example 66
Structure

R: piperidine-N—C(=O)—C₆H₄—O(CH₂)₂CH₃ (para)
R¹: H
Bond between 3- and 4-positions in the carbostyril ring: single bond
Crystalline form: white powders
Recrystallization solvent: n-hexane/ethanol
Melting point: 110–111° C.
Form: Free Example 67
Structure

R: piperidine-N—C(=O)—C₆H₄—N(COCH₂Cl)(CH₃) (para)
R¹: H
Bond between 3- and 4-positions in the carbostyril ring: single bond
Crystalline form: white powders
Recrystallization solvent: n-hexane/ethanol
Melting point: 220–222° C.
Form: Free Example 68
Structure

R: piperidine-N—C(=O)—C₆H₄—N(piperazine)N—CH₃ (para)
R¹: H
Bond between 3- and 4-positions in the carbostyril ring: single bond
NMR analysis: 20)
Form: Free Example 69
Structure

R: piperidine-N—C(=O)—C₆H₄—CH(CH₃)₂ (para)
R¹: H
Bond between 3- and 4-positions in the carbostyril ring: single bond
NMR analysis: 21)
Form: Free Example 70
Structure

R: piperidine-N—C(=O)—C₆H₄—CHO (para)
R¹: H
Bond between 3- and 4-positions in the carbostyril ring: single bond
NMR analysis: 22)
Form: Free Example 71
Structure

R: piperidine-N—C(=O)—C₆H₄—SC₂H₅ (para)
R¹: H
Bond between 3- and 4-positions in the carbostyril ring: single bond
Crystalline form: white powders
Recrystallization solvent: n-hexane/ethanol
Melting point: 98–99° C.
Form: Free Example 72
Structure

R: piperidine-N—C(=O)—C₆H₃(2-OCH₃)(4-Cl)
R¹: H
Bond between 3- and 4-positions in the carbostyril ring: single bond
Crystalline form: white powders

TABLE 1-continued

[Structure: carbostyril core with R¹ substituent and N-R]

Recrystallization solvent: n-hexane/ethanol
Melting point: 84–87° C.
Form: Free

Example 73
Structure

R: piperidine-N–C(=O)–C₆H₄–CH₂OH

R¹: H
Bond between 3- and 4-positions in the carbostyril ring: single bond
Crystalline form: white powders
Recrystallization solvent: n-hexane/ethanol
Melting point: 138–139° C.
Form: Free Example 74
Structure R: piperidine-N–C(=O)–C₆H₃(OCH₃)(S(=O)CH₃)

R¹: H
Bond between 3- and 4-positions in the carbostyril ring: single bond
Crystalline form: white powders
Recrystallization solvent: n-hexane/ethanol
Melting point: 95–98° C.
Form: Free Example 75
Structure R: piperidine-N–C(=O)–C₆H₄–C(=O)–C₆H₅

R¹: H
Bond between 3- and 4-positions in the carbostyril ring: single bond
Crystalline form: white powders
Recrystallization solvent: n-hexane/ethanol
Melting point: 240–243° C.
Form: Free Example 76
Structure R: piperidine-N–C(=O)–C₆H₃(OCH₃)₂–N(CH₃)₂

R¹: H
Bond between 3- and 4-positions in the carbostyril ring: single bond
Crystalline form: white powders
Recrystallization solvent: n-hexane/ethanol
Melting point: 93–96° C.
Form: Free Example 77
Structure R: piperidine-N–C(=O)–(pyrrolidine-NH)

R¹: H
Bond between 3- and 4-positions in the carbostyril ring: single bond
NMR analysis: 23)
Form: Free Example 78
Structure R: piperidine-N–C(=O)–C₆H₄–NHCOCF₃

R¹: H
Bond between 3- and 4-positions in the carbostyril ring: single bond
Crystalline form: pale red powders
Recrystallization solvent: n-hexane
Melting point: 104–107° C.
Form: Free Example 79
Structure R: piperidine-N–C(=O)–C₆H₄–NHCH₂CH=CH₂

R¹: H
Bond between 3- and 4-positions in the carbostyril ring: single bond
NMR analysis: 24)
Form: Free Example 80
Structure R: piperidine-N–C(=O)–C₆H₃(NH₂)–NH₂

R¹: H
Bond between 3- and 4-positions in the carbostyril ring: single bond
Crystalline form: white powders
Recrystallization solvent: n-hexane/ethanol
Melting point: 113–116° C.
Form: Free Example 81
Structure R: piperidine-N–C(=O)–C₆H₃(N(CH₃)₂)–N(CH₃)₂

R¹: H
Bond between 3- and 4-positions in the carbostyril ring: single bond
Crystalline form: pale grey powders
Recrystallization solvent: n-hexane/ethanol
Melting point: 162–164° C.
Form: Free Example 82
Structure R: piperidine-N–C(=O)–C₆H₄–N(CH₂CH=CH₂)(CH₃)

R¹: H
Bond between 3- and 4-positions in the carbostyril ring: single bond
NMR analysis: 25)
Form: Free Example 83

TABLE 1-continued

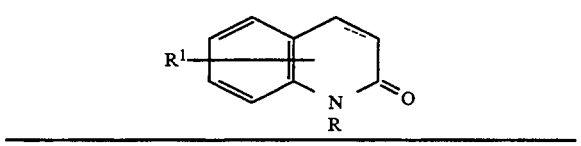

Structure

R: 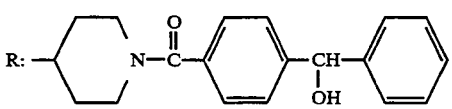

R[1]: H
Bond between 3- and 4-positions in the carbostyril ring: single bond
Crystalline form: white powders
Recrystallization solvent: n-hexane/ethanol
Melting point: 93–96° C.
Form: Free Example 84
Structure R: 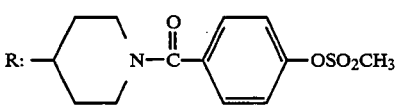

R[1]: H
Bond between 3- and 4-positions in the carbostyril ring: single bond
NMR analysis: 26)
Form: Free Example 85
Structure R: 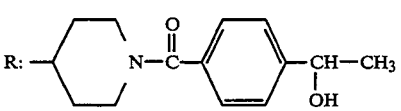

R[1]: H
Bond between 3- and 4-positions in the carbostyril ring: single bond
Crystalline form: white powders
Recrystallization solvent: n-hexane/ethanol
Melting point: 144–146° C.
Form: Free Example 86
Structure R: 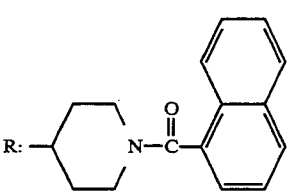

R[1]: H
Bond between 3- and 4-positions in the carbostyril ring: single bond
Crystalline form: white powders
Recrystallization solvent: n-hexane/ethanol
Melting point: 197–199° C.
Form: Free Example 87
Structure R: 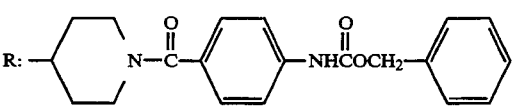

R[1]: H
Bond between 3- and 4-positions in the carbostyril ring: single bond
NMR analysis: 27)
Form: Free Example 88
Structure TABLE 1-continued

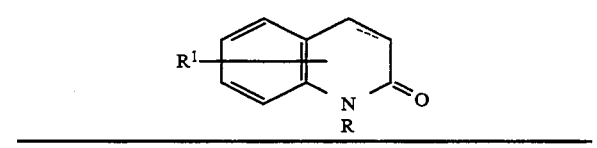

R: 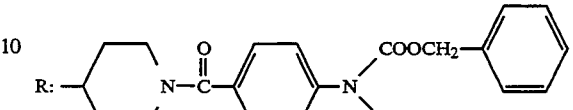

R[1]: H
Bond between 3- and 4-positions in the carbostyril ring: single bond
NMR analysis: 28)
Form: Free Example 89
Structure R: 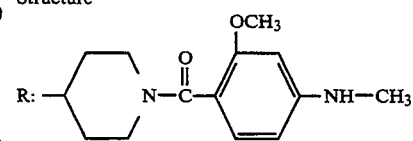

R[1]: H
Bond between 3- and 4-positions in the carbostyril ring: single bond
NMR analysis: 29)
Form: Free Example 90
Structure R: 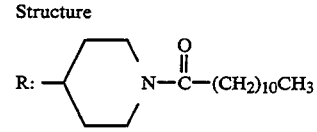

R[1]: H
Bond between 3- and 4-positions in the carbostyril ring: single bond
NMR analysis: 30)
Form: Free Example 91
Structure R: 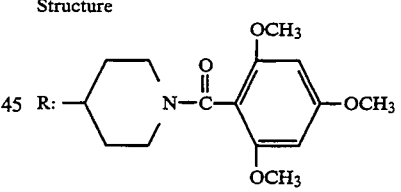

R[1]: H
Bond between 3- and 4-positions in the carbostyril ring: single bond
Crystalline form: white powders
Recrystallization solvent: n-hexane/ethanol
Melting point: 193–196° C.
Form: Free Example 92
Structure R: 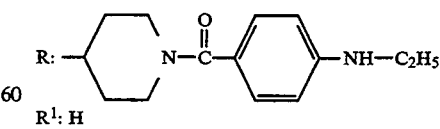

R[1]: H
Bond between 3- and 4-positions in the carbostyril ring: single bond
Crystalline form: white powders
Recrystallization solvent: n-hexane/ethanol
Melting point: 82–85° C.
Form: Free Example 93
Structure TABLE 1-continued

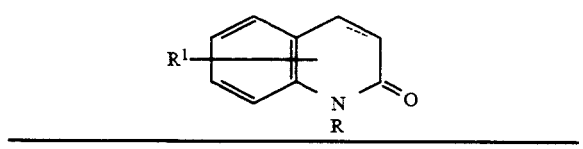

R: 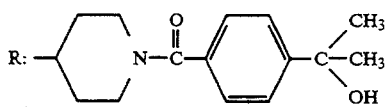

R¹: H
Bond between 3- and 4-positions in the carbostyril ring: single bond
NMR analysis: 31)
Form: Free Example 94
Structure R: 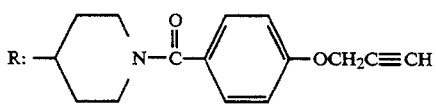

R¹: H
Bond between 3- and 4-positions in the carbostyril ring: single bond
NMR analysis: 32)
Form: Free Example 95
Structure R: 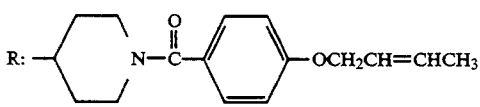

R¹: H
Bond between 3- and 4-positions in the carbostyril ring: single bond
Crystalline form: white powders
Recrystallization solvent: n-hexane
Melting point: 122–125° C.
Form: Free Example 96
Structure R: 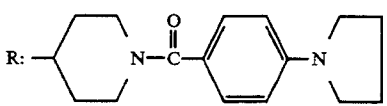

R¹: H
Bond between 3- and 4-positions in the carbostyril ring: single bond
Crystalline form: pale yellow powders
Recrystallization solvent: n-hexane/ethanol
Melting point: 168–171° C.
Form: Free Example 97
Structure R: 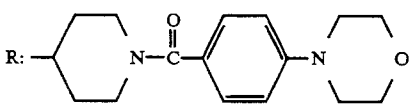

R¹: H
Bond between 3- and 4-positions in the carbostyril ring: single bond
Crystalline form: pale yellow powders
Recrystallization solvent: n-hexane/ethanol
Melting point: 213–215° C.
Form: Free Example 98
Structure R: 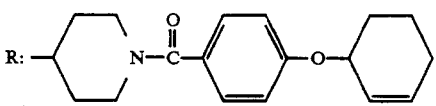

R¹: H
Bond between 3- and 4-positions in the carbostyril ring: single bond
Crystalline form: white powders TABLE 1-continued

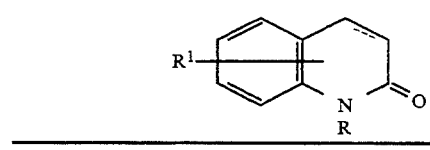

Recrystallization solvent: n-hexane
Melting point: 111–114° C.
Form: Free

Example 99
Structure

R: 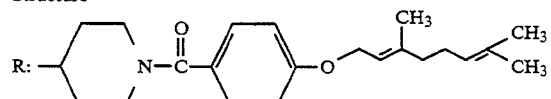

R¹: H
Bond between 3- and 4-positions in the carbostyril ring: single bond
NMR analysis: 33)
Form: Free Example 100
Structure R: 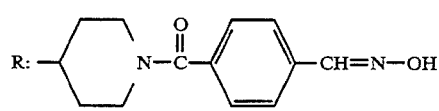

R¹: H
Bond between 3- and 4-positions in the carbostyril ring: single bond
Crystalline form: white powders
Recrystallization solvent: n-hexane/ethanol
Melting point: 222–224° C.
Form: Free Example 101
Structure R: 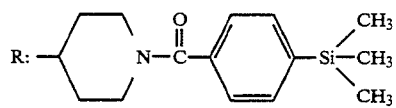

R¹: H
Bond between 3- and 4-positions in the carbostyril ring: single bond
Crystalline form: white powders
Recrystallization solvent: n-hexane
Melting point: 149–151° C.
Form: Free Example 102
Structure R: 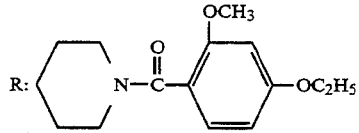

R¹: H
Bond between 3- and 4-positions in the carbostyril ring: single bond
Crystalline form: colorless prisms
Recrystallization solvent: n-hexane/ethanol
Melting point: 174–175° C.
Form: Free Example 103
Structure R: 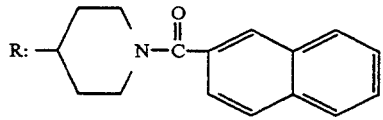

R¹: H
Bond between 3- and 4-positions in the carbostyril ring: single bond
Crystalline form: white powders
Recrystallization solvent: n-hexane/ethanol
Melting point: 130–132° C.
Form: Free TABLE 1-continued

[Structure: R¹-substituted carbostyril with N-R, 3,4-bond]

Example 104
Structure

R: —[piperidine]—N—C(=O)—[phenyl]—N[pyrrole]

R¹: H
Bond between 3- and 4-positions in the carbostyril ring: single bond
Crystalline form: pale grey powders
Recrystallization solvent: n-hexane
Melting point: 153–156° C.
Form: Free

Example 105
Structure

R: —[piperidine]—N—C(=O)—[phenyl]—CH(OCH$_3$)$_2$

R¹: H
Bond between 3- and 4-positions in the carbostyril ring: single bond
Crystalline form: white powders
Recrystallization solvent: n-hexane
Melting point: 134–136° C.
Form: Free

Example 106
Structure

R: —[piperidine]—N—C(=O)—[phenyl]—O—[cyclohexyl]

R¹: H
Bond between 3- and 4-positions in the carbostyril ring: single bond
NMR analysis: 34)
Form: Free

Example 107
Structure

R: —[piperidine]—N—C(=O)—[phenyl]—C(=NH)—NH$_2$

R¹: H
Bond between 3- and 4-positions in the carbostyril ring: single bond
Crystalline form: white powders
Recrystallization solvent: water
Melting point: 92–97° C.
Form: Free
NMR analysis: 35)

Example 108
Structure

R: —[piperidine]—N—C(=O)—[phenyl]—O(CH$_2$)$_5$CH$_3$

R¹: H
Bond between 3- and 4-positions in the carbostyril ring: single bond
NMR analysis: 36)
Form: Free

Example 109
Structure

R: —[piperidine]—N—C(=O)—[phenyl]—O(CH$_2$)$_{11}$CH$_3$

R¹: H
Bond between 3- and 4-positions in the carbostyril ring: single bond
NMR analysis: 37)
Form: Free

Example 110
Structure

R: —[piperidine]—N—C(=O)—[phenyl]—O(CH$_2$)$_3$CN

R¹: H
Bond between 3- and 4-positions in the carbostyril ring: single bond
NMR analysis: 38)
Form: Free

Example 111
Structure

R: —[piperidine]—N—C(=O)—[phenyl]—N(H)(CH$_2$)$_3$C(=O)OC$_2$H$_5$

R¹: H
Bond between 3- and 4-positions in the carbostyril ring: single bond
NMR analysis: 40)
Form: Free

Example 112
Structure

R: —[piperidine]—N—C(=O)—[phenyl]—O(CH$_2$)$_2$CONH—CH$_2$COOC$_2$H$_5$

R¹: H
Bond between 3- and 4-positions in the carbostyril ring: single bond
NMR analysis: 41)
Form: Free

Example 113
Structure

R: —[piperidine]—N—C(=O)—[phenyl]—O(CH$_2$)$_3$C(=NH)—NH$_2$

R¹: H
Bond between 3- and 4-positions in the carbostyril ring: single bond
NMR analysis: 42)
Form: Free

Example 114
Structure

R: —[piperidine]—N—C(=O)—[phenyl]—O(CH$_2$)$_3$N[piperazine]N—[phenyl]—OCH$_3$

R¹: H
Bond between 3- and 4-positions in the carbostyril ring: single bond
NMR analysis: 43)
Form: Free

Example 115
Structure

R: —[piperidine]—N—C(=O)—[phenyl]—O(CH$_2$)$_3$N[piperazine]N—[phenyl]—Cl

R¹: H
Bond between 3- and 4-positions in the carbostyril ring: single bond

TABLE 1-continued

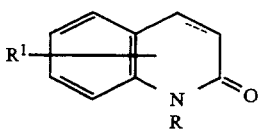

NMR analysis: 44)
Form: Free

Example 116
Structure

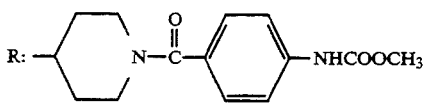

R¹: H
Bond between 3- and 4-positions in the carbostyril ring: single bond
NMR analysis: 45)
Form: Free Example 117
Structure

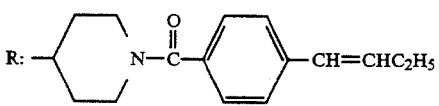

R¹: H
Bond between 3- and 4-positions in the carbostyril ring: single bond
NMR analysis: 46)
Form: Free Example 118
Structure

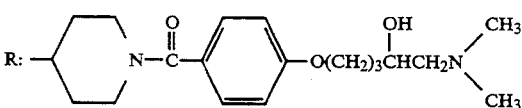

R¹: H
Bond between 3- and 4-positions in the carbostyril ring: single bond
NMR analysis: 47)
Form: Free Example 119
Structure

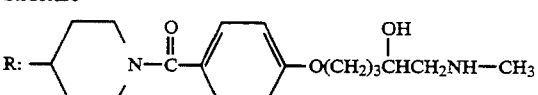

R¹: H
Bond between 3- and 4-positions in the carbostyril ring: single bond
NMR analysis: 48)
Form: Free Example 120
Structure

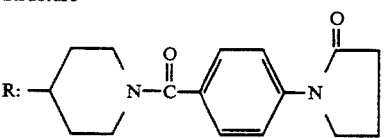

R¹: H
Bond between 3- and 4-positions in the carbostyril ring: single bond
NMR analysis: 49)
Form: Free Example 121
Structure

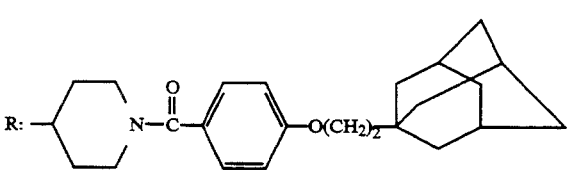

TABLE 1-continued

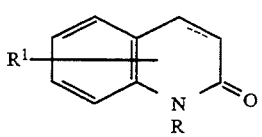

R¹: H
Bond between 3- and 4-positions in the carbostyril ring: single bond
NMR analysis: 50)
Form: Free Example 122
Structure

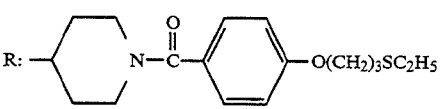

R¹: H
Bond between 3- and 4-positions in the carbostyril ring: single bond
NMR analysis: 51)
Form: Free Example 123
Structure

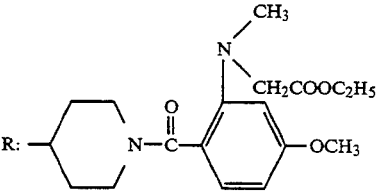

R¹: H
Bond between 3- and 4-positions in the carbostyril ring: single bond
NMR analysis: 52)
Form: Free Example 124
Structure

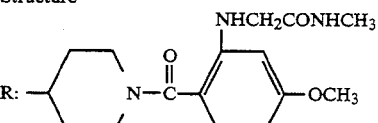

R¹: H
Bond between 3- and 4-positions in the carbostyril ring: single bond
NMR analysis: 53)
Form: Free Example 125
Structure

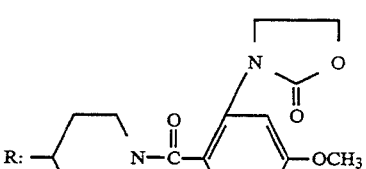

R¹: H
Bond between 3- and 4-positions in the carbostyril ring: single bond
NMR analysis: 54)
Form: Free Example 126
Structure

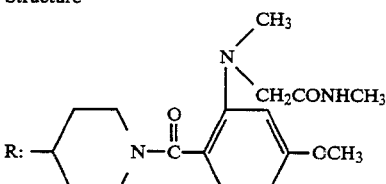

TABLE 1-continued

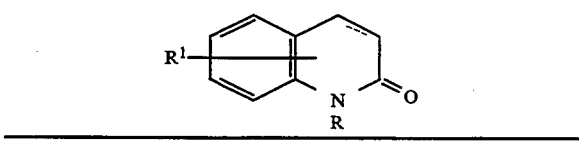

R¹: H
Bond between 3- and 4-positions in the carbostyril ring: single bond
NMR analysis: 55)
Form: Free Example 127
Structure

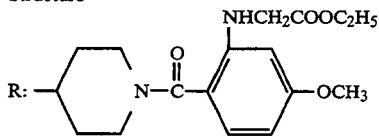

R¹: H
Bond between 3- and 4-positions in the carbostyril ring: single bond
NMR analysis: 56)
Form: Free Example 128
Structure

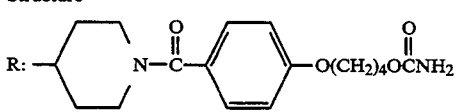

R¹: H
Bond between 3- and 4-positions in the carbostyril ring: single bond
NMR analysis: 57)
Form: Free Example 129
Structure

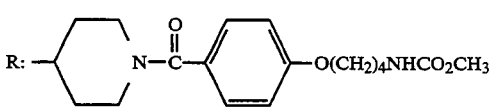

R¹: H
Bond between 3- and 4-positions in the carbostyril ring: single bond
NMR analysis: 58)
Form: Free Example 130
Structure

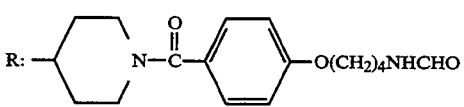

R¹: H
Bond between 3- and 4-positions in the carbostyril ring: single bond
NMR analysis: 59)
Form: Free Example 131
Structure

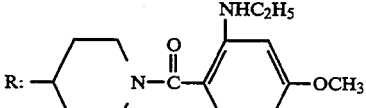

R¹: H
Bond between 3- and 4-positions in the carbostyril ring: single bond
NMR analysis: 60)
Form: Free Example 132
Structure TABLE 1-continued

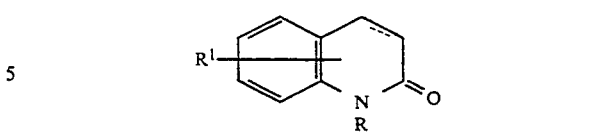

R: 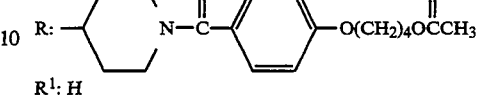

R¹: H
Bond between 3- and 4-positions in the carbostyril ring: single bond
Crystalline form: white powders
Recrystallization solvent: diethyl ether/n-hexane
Melting point: 67–69° C.
Form: Free Example 133
Structure R: 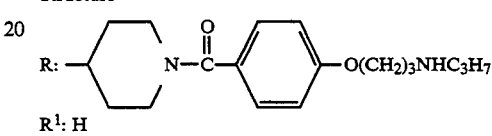

R¹: H
Bond between 3- and 4-positions in the carbostyril ring: single bond
NMR analysis: 61)
Form: Free Example 134
Structure R: 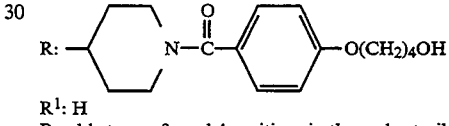

R¹: H
Bond between 3- and 4-positions in the carbostyril ring: single bond
Crystalline form: colorless needles
Recrystallization solvent: diethyl ether n-hexane
Melting point: 138–138° C.
Form: Free Example 135
Structure R: 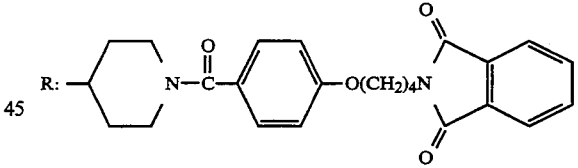

R¹: H
Bond between 3- and 4-positions in the carbostyril ring: single bond
Crystalline form: colorless needles
Recrystallization solvent: ethanol/diethyl ether
Melting point: 171–173° C. Form: Free Example 136
Structure R: 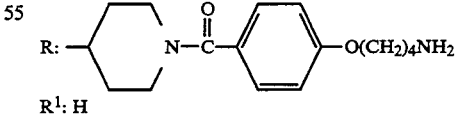

R¹: H
Bond between 3- and 4-positions in the carbostyril ring: single bond
NMR analysis: 62)
Form- Free Example 137
Structure R: 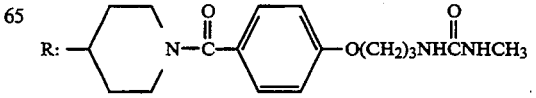

TABLE 1-continued

[Structure: carbostyril core with R¹ substituent on benzene ring and R on N]

R¹: H
Bond between 3- and 4-positions in the carbostyril ring: single bond
NMR analysis: 63)
Form: Free

Example 138
Structure

R: [piperidine]–N–C(=O)–[phenyl]–O(CH₂)₃NHCH₂–[phenyl]

R¹: H
Bond between 3- and 4-positions in the carbostyril ring: single bond
NMR analysis: 64)
Form: Free

Example 139
Structure

R: [piperidine]–N–C(=O)–[phenyl]–O(CH₂)₃NHSO₂CH₃

R¹: H
Bond between 3- and 4-positions in the carbostyril ring: single bond
NMR analysis: 65)
Form: Free

Example 140
Structure

R: [piperidine]–N–C(=O)–[phenyl]–O(CH₂)₃NHCOCH₃

R¹: H
Bond between 3- and 4-positions in the carbostyril ring: single bond
NMR analysis: 66)
Form: Free

Example 141
Structure

R: [piperidine]–N–C(=O)–[phenyl]–O(CH₂)₃NHCCH₃ (with C=O)

R¹: H
Bond between 3- and 4-positions in the carbostyril ring: single bond
Crystalline form: colorless needles
Recrystallizaton solvent: ethanol/diethyl ether
Melting point: 147.5–149° C.
Form: Free
NMR analysis: 67)

Example 142
Structure

R: [piperidine]–N–C(=O)–[phenyl]–O(CH₂)₃OCNH₂ (with C=O)

R¹: H
Bond between 3- and 4-positions in the carbostyril ring: single bond
Crystalline form: colorless needles
Recrystallization solvent: ethanol
Melting point: 136–138° C.
Form: Free
NMR analysis: 68)

Example 143
Structure

R: [piperidine]–N–C(=O)–[phenyl]–O(CH₂)₃N(CH₂–phenyl)(CH₂)₂CH₃

R¹: H
Bond between 3- and 4-positions in the carbostyril ring: single bond
NMR analysis: 69)
Form: Free

Example 144
Structure

R: [piperidine]–N–C(=O)–[phenyl with 2-N(CH₃)(CH₂CH₃), 4-OCH₃]

R¹: H
Bond between 3- and 4-positions in the carbostyril ring: single bond
NMR analysis: 70)
Form: Free

Example 145
Structure

R: [piperidine]–N–C(=O)–[phenyl]–O(CH₂)₄NHCCH₂NHCCH₃ (with two C=O)

R¹: H
Bond between 3- and 4-positions in the carbostyril ring: single bond
NMR analysis: 71)
Form: Free

Example 146
Structure

R: [piperidine]–N–C(=O)–[phenyl]–O(CH₂)₅OCCH₃ (with C=O)

R¹: H
Bond between 3- and 4-positions in the carbostyril ring: single bond
NMR analysis: 72)
Form: Free

Example 147
Structure

R: [piperidine]–N–C(=O)–[phenyl]–O(CH₂)₅N–phthalimide

R¹: H
Bond between 3- and 4-positions in the carbostyril ring: single bond
NMR analysis: 73)
Form: Free

Example 148
Structure

R: [piperidine]–N–C(=O)–[phenyl]–O(CH₂)₅NH₂

TABLE 1-continued

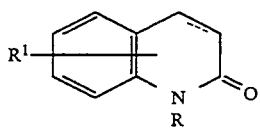

R¹: H
Bond between 3- and 4-positions in the carbostyril ring: single bond
NMR analysis: 74)
Form: Free Example 149
Structure

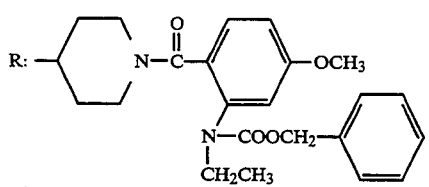

R¹: H
Bond between 3- and 4-positions in the carbostyril ring: single bond
NMR analysis: 75)
Form: Free Example 150
Structure

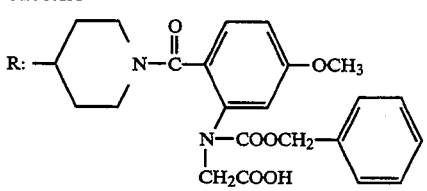

R¹: H
Bond between 3- and 4-positions in the carbostyril ring: single bond
NMR analysis: 76)
Form: Free Example 151
Structure

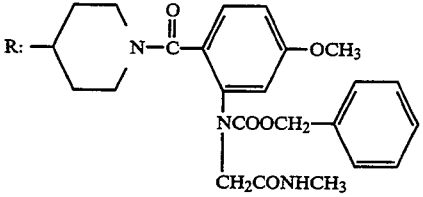

R¹: H
Bond between 3- and 4-positions in the carbostyril ring: single bond
NMR analysis: 77)
Form: Free Example 152
Structure

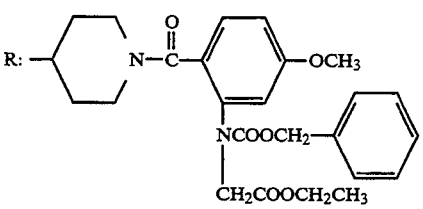

R¹: H
Bond between 3- and 4-positions in the carbostyril ring: single bond
NMR analysis: 78)
Form: Free Example 153
Structure TABLE 1-continued

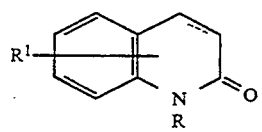

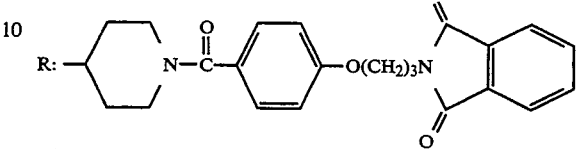

R¹: 7-F
Bond between 3- and 4-positions in the carbostyril ring: single bond
NMR analysis: 79)
Form: Free Example 154
Structure

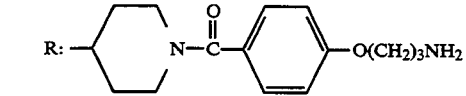

R¹: 7-F
Bond between 3- and 4-positions in the carbostyril ring: single bond
NMR analysis: 80)
Form: Free Example 155
Structure

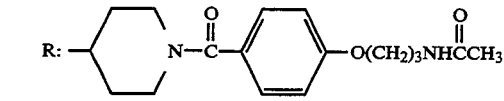

R¹: 7-F
Bond between 3- and 4-positions in the carbostyril ring: single bond
NMR analysis: 81)
Form: Free Example 156
Structure

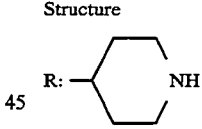

R¹: 7-C₂H₅
Bond between 3- and 4-positions in the carbostyril ring: single bond
NMR analysis: 82)
Form: Free Example 157
Structure

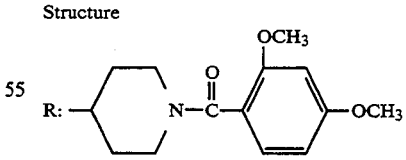

R¹: 7-C₂H₅
Bond between 3- and 4-positions in the carbostyril ring: single bond
NMR analysis: 83)
Form: Free Example 158
Structure

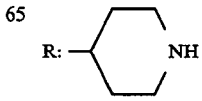

TABLE 1-continued

R¹: 7-OCH₃
Bond between 3- and 4-positions in the carbostyril ring: single bond
NMR analysis: 84)
Form: Free Example 159
Structure R: —[piperidine]—N—C(=O)—[phenyl with 2-OCH₃, 4-OCH₃]

R¹: 7-OCH₃
Bond between 3- and 4-positions in the carbostyril ring: single bond
NMR analysis: 85)
Form: Free Example 160
Structure R: —[piperidine]—N—C(=O)—[phenyl with 2-OCH₃, 4-OCH₃]

R¹: 6-NHCO—[phenyl]

Bond between 3- and 4-positions in the carbostyril ring: single bond
NMR analysis: 86)
Form: Free Example 161
Structure R: —[piperidine]—N—C(=O)—[phenyl with 2-OCH₃, 4-OCH₃]

R¹: 6-NHCOCH₃
Bond between 3- and 4-positions in the carbostyril ring: single bond
Crystalline form: white powders
Recrystallization solvent: ethanol
Melting point: 271–272° C.
Form: Free Example 162
Structure R: —[piperidine]—N—C(=O)—[phenyl with 2-OCH₃, 4-OCH₃]

R¹: 6-NH₂
Bond between 3- and 4-positions in the carbostyril ring: single bond
NMR analysis: 87)
Form: Free Example 163
Structure R: —[piperidine]—N—C(=O)—[phenyl with 2-OCH₃, 4-OCH₃]

R¹: 6-NO₂
Bond between 3- and 4-positions in the carbostyril ring: single bond
Crystalline form: pale yellow powders
Recrystallization solvent: ethanol
Melting point: 197–199° C.
Form: Free Example 164
Structure R: —[piperidine]—N—C(=O)—[phenyl with 2-OCH₃]

R¹: H
Bond between 3- and 4-positions in the carbostyril ring: single bond
Crystalline form: white powders
Recrystallization solvent: dichloromethane/n-hexane
Melting point: 151.5–152.5° C.
Form: Free Example 165
Structure R: —[piperidine]—N—C(=O)—[phenyl]

R¹: H
Bond between 3- and 4-positions in the carbostyril ring: double bond
NMR analysis: 88)
Form: Free Example 166
Structure R: —[piperidine]—N—C(=O)—[phenyl with 4-OCH₃]

R¹: H
Bond between 3- and 4-positions in the carbostyril ring: double bond
NMR analysis: 89)
Form: Free Example 167
Structure R: —[piperidine]—N—C(=O)—[phenyl with 2-OCH₃, 4-OCH₃]

R¹: H
Bond between 3- and 4-positions in the carbostyril ring: double bond
NMR analysis: 90)
Form: Free Example 168
Structure R: —[piperidine]—NH TABLE 1-continued

[Carbostyril structure with R¹ substituent and N-R]

R¹: H
Bond between 3- and 4-positions in the carbostyril ring: double bond
NMR analysis: 91)
Form: Free Example 169
Structure R: [piperidine-N-C(=O)-phenyl-N(CH₃)₂]

R¹: H
Bond between 3- and 4-positions in the carbostyril ring: single bond
Crystalline form: white powders
Recrystallization solvent: ethanol/diethyl ether/n-hexane
Melting point: 181–183° C.
Form: Free Example 170
Structure R: [piperidine-N-C(=O)-phenyl(2-OCH₃, 4-OCH₃)]

R¹: 6-F
Bond between 3- and 4-positions in the carbostyril ring: single bond
NMR analysis: 92)
Form: Free Example 171
Structure R: [piperidine-NH]

R¹: 6-F
Bond between 3- and 4-positions in the carbostyril ring: single bond
NMR analysis: 93)
Form: Free Example 172
Structure R: [phenyl-C(=O)-N(CH₃)-phenyl-OCH₃]

R¹: H
Bond between 3- and 4-positions -in the carbostyril ring: single bond
NMR analysis: 94)
Form: Free Example 173
Structure R: [piperidine-N-C(=O)-phenyl(2-OCH₃, 4-OCH₃)]

R¹: 7-F
Bond between 3- and 4-positions in the carbostyril ring: single bond
NMR analysis: 95)
Form: Free Example 174
Structure TABLE 1-continued

[Carbostyril structure with R¹ substituent and N-R]

R: [piperidine-N-C(=O)-phenyl(2-NHCOOCH₂-phenyl, 4-OCH₃)]

R¹: H
Bond between 3- and 4-positions in the carbostyril ring: single bond
NMR analysis: 96)
Form: Free Example 175
Structure R: [piperidine-N-C(=O)-phenyl(2-NO₂, 4-OCH₃)]

R¹: H
Bond between 3- and 4-positions in the carbostyril ring: single bond
Crystalline form: colorless needles
Recrystallization solvent: ethanol/diethyl ether
Melting point: 151–154° C.
Form: Free Example 176
Structure R: [piperidine-N-C(=O)-phenyl(2-NH₂, 4-OCH₃)]

R¹: H
Bond between 3- and 4-positions in the carbostyril ring: single bond
Crystalline form: colorless needles
Recrystallization solvent: ethanol
Melting point: 169-171° C.
Form: Free Example 177
Structure R: [piperidine-N-C(=O)-phenyl(2-OCH₃, 4-OCH₃)]

R¹: 7-F
Bond between 3- and 4-positions in the carbostyril ring: single bond
NMR analysis: 97)
Form: Free Example 178
Structure R: [piperidine-N-C(=O)-phenyl(2-OCH₃, 4-OCH₃)]

R¹: 6-CH₃
Bond between 3- and 4-positions in the carbostyril ring: single bond
NMR analysis: 98)
Form: Free Example 179
Structure TABLE 1-continued

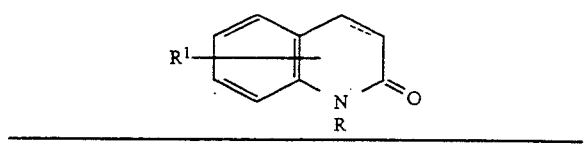

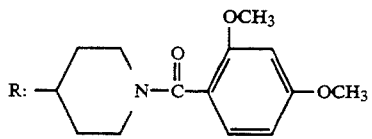

R¹: 8-CH₃
Bond between 3- and 4-positions in the carbostyril ring: single bond
NMR analysis: 99)
Form: Free Example 180
Structure

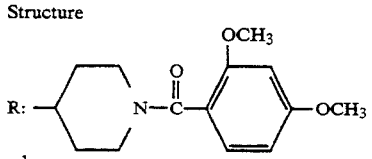

R¹: 7-CH₃
Bond between 3- and 4-positions in the carbostyril ring: single bond
NMR analysis: 100)
Form: Free Example 181
Structure

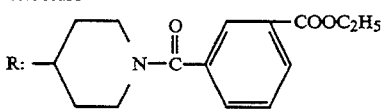

R¹: H
Bond between 3- and 4-positions in the carbostyril ring: single bond
NMR analysis: 101)
Form: Free Example 182
Structure

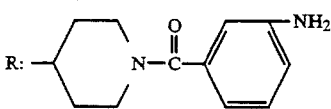

R¹: H
Bond between 3- and 4-positions in the carbostyril ring: single bond
Crystalline form: white powders
Recrystallization solvent: ethanol/n-hexane
Melting point: 183–183·5° C.
Form: Free Example 183
Structure

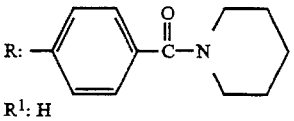

R¹: H
Bond between 3- and 4-positions in the carbostyril ring: single bond
Crystalline form: white powders
Recrystallization solvent: ethanol/diethyl ether/n-hexane
Melting point: 175–176° C.
Form: Free Example 184
Structure

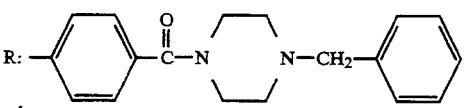

R¹: H
Bond between 3- and 4-positions in the carbostyril ring: single bond
NMR analysis: 102)
Form: Free TABLE 1-continued

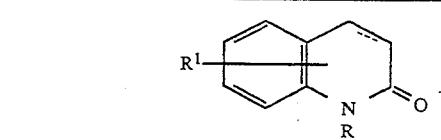

Example 185
Structure

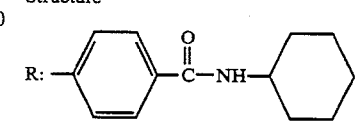

R¹: H
Bond between 3- and 4-positions in the carbostyril ring: single bond
Crystalline form: white powders
Recrystallization solvent: ethanol/diethyl ether/n-hexane
Melting point: 291–292° C.
Form: Free Example 186
Structure

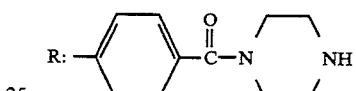

R¹: H
Bond between 3- and 4-positions in the carbostyril ring: single bond
Crystalline form: white powders
Recrystallization solvent: ethanol/diethyl ether/n-hexane
Melting point: 215–216° C.
Form: Free Example 187
Structure

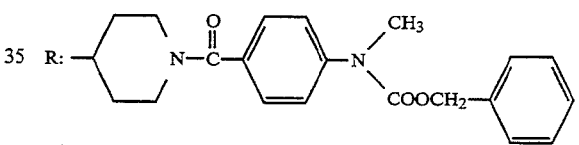

R¹: H
Bond between 3- and 4-positions in the carbostyril ring: single bond
NMR analysis: 103)
Form: Free Example 188
Structure

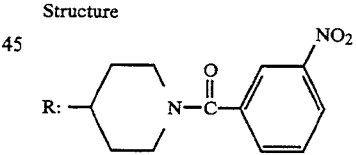

R¹: H
Bond between 3- and 4-positions in the carbostyril ring: single bond
NMR analysis: 104)
Form: Free Example 189
Structure

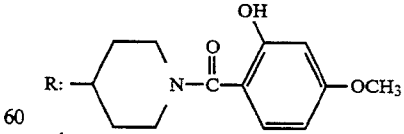

R¹: H
Bond between 3- and 4-positions in the carbostyril ring: single bond
Crystalline form: white powders
Recrystallization solvent: dichloromethane/n-hexane
Melting point: 140.5–142° C.
Form: Free Example 190
Structure

TABLE 1-continued

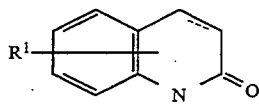

R: 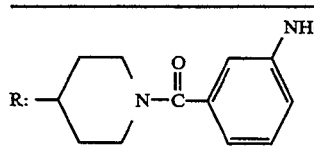

R¹: H
Bond between 3- and 4-positions in the carbostyril ring: single bond
Crystalline form: white powders
Recrystallization solvent: ethanol/n-hexane
Melting point: 164–164.5° C.
Form: Free Example 191
Structure R: 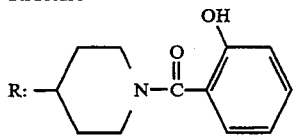

R¹: H
Bond between 3- and 4-positions in the carbostyril ring: single bond
Crystalline form: colorless needles
Recrystallization solvent: ethanol/methanol/diethyl ether
Melting point: 156–158° C.
Form: Free Example 192
Structure R: 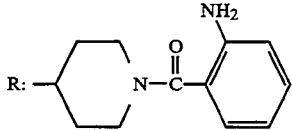

R¹: H
Bond between 3- and 4-positions in the carbostyril ring: single bond
Crystalline form: colorless needles
Recrystallization solvent: ethanol/diethyl ether
Melting point: 158–166° C.
Form: Hydrochloride Example 193
Structure R: 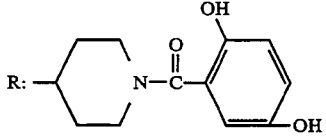

R¹: H
Bond between 3- and 4-positions in the carbostyril ring: single bond
Crystalline form: colorless prisms
Recrystallization solvent: ethanol/methanol
Melting point: 245–249° C.
Form: Free Example 194
Structure R: 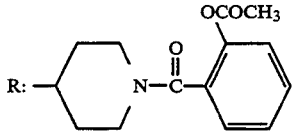

R¹: H
Bond between 3- and 4-positions in the carbostyril ring: single bond
Crystalline form: colorless prisms
Recrystallization solvent: ethanol/diethyl ether
Melting point: 159–161° C.
Form: Free

TABLE 1-continued

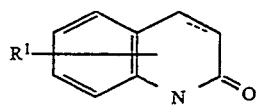

Example 195
Structure

R: 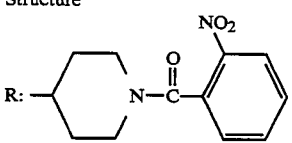

R¹: H
Bond between 3- and 4-positions in the carbostyril ring: single bond
Crystalline form: pale yellow needles
Recrystallization solvent: methanol/chloroform/diethyl ether
Melting point: 207–209° C.
Form: Free Example 196
Structure R: 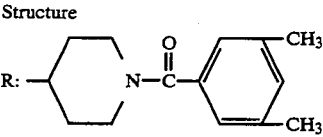

R¹: H
Bond between 3- and 4-positions in the carbostyril ring: single bond
Crystalline form: colorless needles
Recrystallization solvent: ethanol/diethyl ether/n-hexane
Melting point: 177–180° C.
Form: Free Example 197
Structure R: 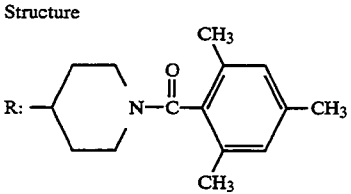

R¹: H
Bond between 3- and 4-positions in the carbostyril ring: single bond
Crystalline form: colorless needles
Recrystallization solvent: ethyl acetate/diethyl ether/n-hexane
Melting point: 145–150° C.
Form: Free Example 198
Structure R: 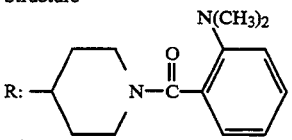

R¹: H
Bond between 3- and 4-positions in the carbostyril ring: single bond
Crystalline form: colorless flakes
Recrystallization solvent: ethyl acetate/ethanol
Melting point: 209–211° C.
Form: Free Example 199
Structure R: 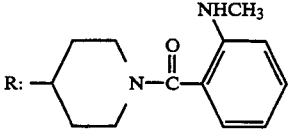

R¹: H
Bond between 3- and 4-positions in the carbostyril ring: single bond
NMR analysis: 105)
Form: Free TABLE 1-continued

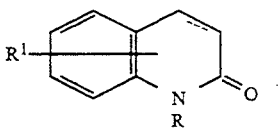

Example 200
Structure

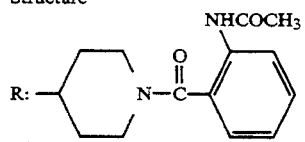

R¹: H
Bond between 3- and 4-positions in the carbostyril ring: single bond
Crystalline form: colorless needles
Recrystallization solvent: ethyl acetate/diethyl ether
Melting point: 141–143° C.
Form: Free

Example 201
Structure

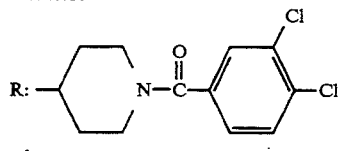

R¹: H
Bond between 3- and 4-positions in the carbostyril ring: single bond
NMR analysis: 106)
Form: Free

Example 202
Structure

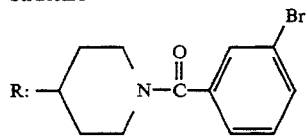

R¹: H
Bond between 3- and 4-positions in the carbostyril ring: single bond
Crystalline form: colorless prisms
Recrystallization solvent: ethyl acetate/dithyl ether/n-hexane
Melting point: 148–150° C.
Form: Free

Example 203
Structure

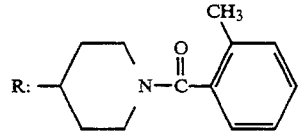

R¹: H
Bond between 3- and 4-positions in the carbostyril ring: single bond
Crystalline form: colorless prisms
Recrystallization solvent: ethanol/diethyl ether/n-hexane
Melting point: 169–172° C.
Form: Free

Example 204
Structure

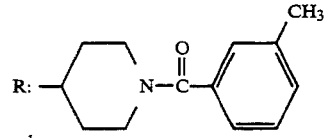

R¹: H
Bond between 3- and 4-positions in the carbostyril ring: single bond
Crystalline form: colorless prisms
Recrystallization solvent: ethyl acetate/diethyl ether/n-hexane
Melting point: 144–146° C.
Form: Free TABLE 1-continued

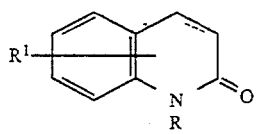

Example 205
Structure

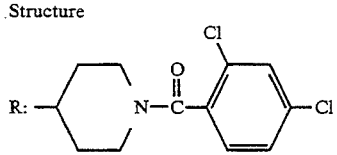

R¹: H
Bond between 3- and 4-positions in the carbostyril ring: single bond
NMR analysis: 107)
Form: Free

Example 206
Structure

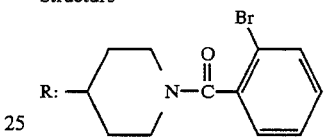

R¹: H
Bond between 3- and 4-positions in the carbostyril ring: single bond
Crystalline form: colorless flakes
Recrystallization solvent: ethyl acetate/diethyl ether/n-hexane
Melting point: 181–183° C.
Form: Free

Example 207
Structure

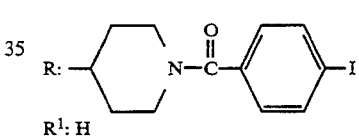

R¹: H
Bond between 3- and 4-positions in the carbostyril ring: single bond
Crystalline form: colorless needles
Recrystallization solvent: ethyl acetate/diethyl ether/n-hexane
Melting point: 141–144° C.
Form: Free

Example 208
Structure

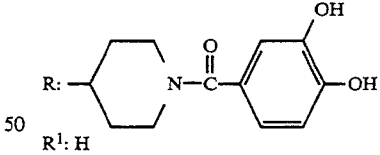

R¹: H
Bond between 3- and 4-positions in the carbostyril ring: single bond
Crystalline form: colorless prisms
Recrystallization solvent: ethanol/diethyl ether
Melting point: 234–236° C.
Form: Free

Example 209
Structure

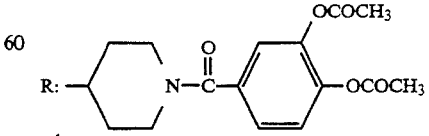

R¹: H
Bond between 3- and 4-positions in the carbostyril ring: single bond
Crystalline form: colorless needles
Recrystallization solvent: ethyl acetate/diethyl ether
Melting point: 117–119° C.
Form: Free TABLE 1-continued

[Structure: R¹-substituted carbostyril with N-R group, where the carbostyril has a C=O]

Example 210
Structure:

R: 4-piperidinyl-N-C(=O)-(2-COOH-phenyl)

R¹: H
Bond between 3- and 4-positions in the carbostyril ring: single bond
Crystalline form: white powders
Recrystallization solvent: ethanol/n-hexane
Melting point: 116–120° C.
Form: Free

Example 211
Structure:

R: 4-piperidinyl-N-C(=O)-(3-CH₂CH=CH₂, 4-OH-phenyl)

R¹: H
Bond between 3- and 4-positions in the carbostyril ring: single bond
Crystalline form: white powders
Recrystallization solvent: dichloromethane/n-hexane
Melting point: 87–90° C.
Form: Free

Example 212
Structure:

R: 4-piperidinyl-N-C(=O)-(3,4-di-OCOCH₃-phenyl)

R¹: H
Bond between 3- and 4-positions in the carbostyril ring: single bond
Crystalline form: white powders
Recrystallization solvent: dichloromethane/n-hexane
Melting point: 171.5–172.5° C.
Form: Free

Example 213
Structure:

R: 4-piperidinyl-N-C(=O)-(2-COOCH₃-phenyl)

R¹: H
Bond between 3- and 4-positions in the carbostyril ring: single bond
Crystalline form: white powders
Recrystallization solvent: dichloromethane/n-hexane
Melting point: 159.5–160° C.
Form: Free

Example 214
Structure:

R: 4-piperidinyl-N-C(=O)-(3-N(CH₃)₂-phenyl)

R¹: H
Bond between 3- and 4-positions in the carbostyril ring: single bond
Crystalline form: white powders
Recrystallization solvent: dichloromethane/n-hexane
Melting point: 168–169° C.
Form: Free

Example 215
Structure:

R: 4-piperidinyl-N-C(=O)-(3-OH-phenyl)

R¹: H
Bond between 3- and 4-positions in the carbostyril ring: single bond
Crystalline form: white powders
Recrystallization solvent: dichloromethane/n-hexane
Melting point: 188–189° C.
Form: Free

Example 216
Structure:

R: 4-piperidinyl-N-C(=O)-(3,4-di-OH-phenyl)

R¹: H
Bond between 3- and 4-positions in the carbostyril ring: single bond
Crystalline form: white powders
Recrystallization solvent: dichloromethane/n-hexane
Melting point: 295° C. (decomposition)
Form: Free

Example 217
Structure:

R: 4-piperidinyl-N-C(=O)-(3,4-di-CH₃-phenyl)

R¹: H
Bond between 3- and 4-positions in the carbostyril ring: single bond
Crystalline form: white powders
Recrystallization solvent: ethanol/n-hexane
Melting point: 131.5–132.5° C.
Form: Free

Example 218
Structure:

R: 4-piperidinyl-N-C(=O)-(2,4-di-CH₃-phenyl)

R¹: H
Bond between 3- and 4-positions in the carbostyril ring: single bond
Crystalline form: white powders
Recrystallization solvent: dichloromethane/n-hexane
Melting point: 159–160° C.
Form: Free

Example 219
Structure:

R: 4-piperidinyl-N-C(=O)-(2,5-di-CH₃-phenyl)

R¹: H
Bond between 3- and 4-positions in the carbostyril ring: single bond
Crystalline form: white powders
Recrystallization solvent: dichloromethane/n-hexane
Melting point: 172–172.5° C.
Form: Free TABLE 1-continued

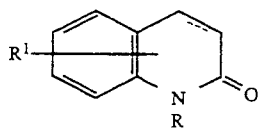

Example 220
Structure

R: 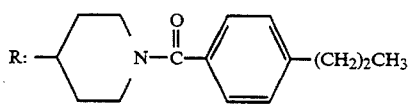

R¹: H
Bond between 3- and 4-positions in the carbostyril ring: single bond
NMR analysis: 108)
Form: Free Example 221
Structure

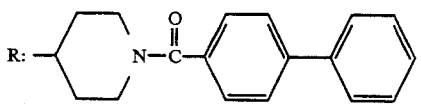

R¹: H
Bond between 3- and 4-positions in the carbostyril ring: single bond
NMR analysis: 109)
Form: Free Example 222
Structure

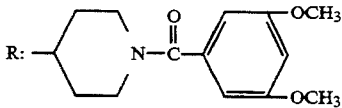

R¹: H
Bond between 3- and 4-positions in the carbostyril ring: single bond
Crystalline form: white powders
Recrystallization solvent: dichloromethane/n-hexane
Melting point: 154–154.5° C.
Form: Free Example 223
Structure

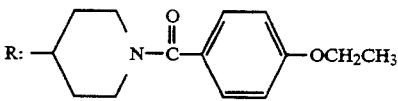

R¹: H
Bond between 3- and 4-positions in the carbostyril ring: single bond
Crystalline form: white powders
Recrystallization solvent: dichloromethane/n-hexane
Melting point: 97–99° C.
Form: Free Example 224
Structure

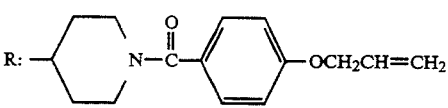

R¹: H
Bond between 3- and 4-positions in the carbostyril ring: single bond
NMR analysis: 110)
Form: Free Example 225
Structure

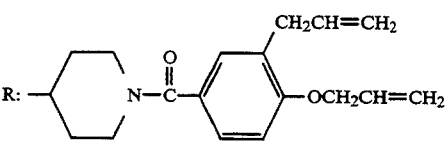

TABLE 1-continued

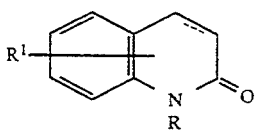

R¹: H
Bond between 3- and 4-positions in the carbostyril ring: single bond
NMR analysis: 111)
Form: Free Example 226
Structure R: 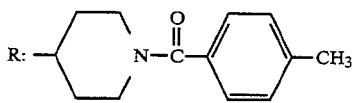

R¹: H
Bond between 3- and 4-positions in the carbostyril ring: single bond
Crystalline form: white powders
Recrystallization solvent: dichloromethane/n-hexane
Melting point: 112–113.5° C.
Form: Free Example 227
Structure R: 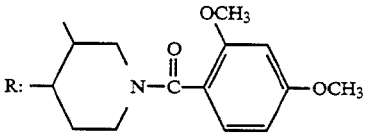

R¹: H
Bond between 3- and 4-positions in the carbostyril ring: single bond
NMR analysis: 112)
Form: Free Example 228
Structure R: 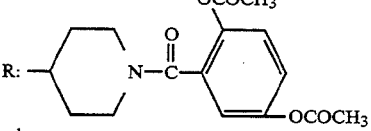

R¹: H
Bond between 3- and 4-positions in the carbostyril ring: single bond
Crystalline form: colorless needles
Recrystallization solvent: ethyl acetate/diethyl ether
Melting point: 134–137° C.
Form: Free Example 229
Structure R: 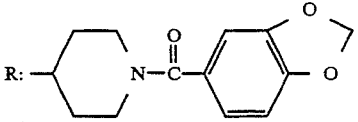

R¹: H
Bond between 3- and 4-positions in the carbostyril ring: single bond
NMR analysis: 113)
Form: Free Example 230
Structure R: 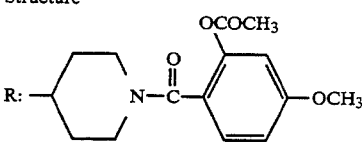

R¹: H
Bond between 3- and 4-positions in the carbostyril ring: single bond
NMR analysis: 114)
Free: Form

TABLE 1-continued

[Carbostyril structure with R¹ and R substituents]

Example 231
Structure

R: [piperidine-N-C(=O)-phenyl with NHCH₃ and OCH₃ substituents]

R¹: H
Bond between 3- and 4-positions in the carbostyril ring: single bond
NMR analysis: 115)
Form: Free

Example 232
Structure

R: [piperidine-N-C(=O)-phenyl-OCH₂CH₃]

R¹: H
Bond between 3- and 4-positions in the carbostyril ring: single bond
NMR analysis: 116)
Form: Free

Example 233
Structure

R: [phenyl-C(=O)-N-tetrahydroquinoline]

R¹: H
Bond between 3- and 4-positions in the carbostyril ring: single bond
Crystalline form: white powders
Recrystallization solvent: ethanol/diethyl ether/n-hexane
Melting point: 162–163° C.
Form: Free

Example 234
Structure

R: [piperidine-N-C(=O)-phenyl-O(CH₂)₃NH₂]

R¹: H
Bond between 3- and 4-positions in the carbostyril ring: single bond
NMR analysis: 117)
Form: Free

Example 235
Structure

R: [piperidine-N-C(=O)-phenyl-O(CH₂)₃N-phthalimide]

R¹: H
Bond between 3- and 4-positions in the carbostyril ring: single bond
NMR analysis: 118)
Form: Free

Example 236
Structure

R: [phenyl-C(=O)-N(CH₂-phenyl)(phenyl-OCH₃)]

R¹: H
Bond between 3- and 4-positions in the carbostyril ring: single bond
NMR analysis: 119)
Form: Free

Example 237
Structure

R: [phenyl-C(=O)-N(CH₂CH=CH₂)(phenyl-OCH₃)]

R¹: H
Bond between 3- and 4-positions in the carbostyril ring: single bond
NMR analysis: 120)
Form: Free

Example 238
Structure

R: [phenyl-C(=O)-N-piperazine-N-phenyl-OCH₃]

R¹: H
Bond between 3- and 4-positions in the carbostyril ring: single bond
Crystalline form: white powders
Recrystallization solvent: ethanol/diethyl ether/n-hexane
Melting point: 179–180° C.
Form: Free

Example 239
Structure

R: [phenyl-C(=O)-N-piperazine-N-C(=O)-phenyl]

R¹: H
Bond between 3- and 4-positions in the carbostyril ring: single bond
Crystalline form: white powders
Recrystallization solvent: ethanol/diethyl ether/n-hexane
Melting point: 188–189° C.
Form: Free

Example 240
Structure

R: [phenyl-C(=O)-N-piperazine-N-COCH₃]

R¹: H
Bond between 3- and 4-positions in the carbostyril ring: single bond
Crystalline form: white powders
Recrystallization solvent: ethanol/diethyl ether/n-hexane
Melting point: 217–218° C.
Form: Free

Example 241
Structure

TABLE 1-continued

[Carbostyril structure with R¹ and R substituents, N-R and C=O]

R: —[piperidine]—N—C(=O)—[phenyl]—O(CH₂)₃OSO₂CH₃

R¹: H
Bond between 3- and 4-positions in the carbostyril ring: single bond
NMR analysis: 121)
Form: Free Example 242
Structure R: —[piperidine]—N—C(=O)—[phenyl]—O(CH₂)₃N(CH₃)—CH₃

R¹: H
Bond between 3- and 4-positions in the carbostyril ring: single bond
NMR analysis: 122)
Form: Hydrochloride Example 243
Structure R: —[piperidine]—N—C(=O)—[phenyl]—O(CH₂)₃N(CH(CH₃)(CH₂)₂)—CH₃

R¹: H
Bond between 3- and 4-positions in the carbostyril ring: single bond
NMR analysis: 123)
Form: Free Example 244
Structure R: —[phenyl]—C(=O)—NH—[adamantyl]

R¹: H
Bond between 3- and 4-positions in the carbostyril ring: single bond
Crystalline form: white powders
Recrystallization solvent: ethanol/diethyl ether/n-hexane
Melting point: 279–280° C.
Form: Free Example 245
Structure R: —[phenyl]—C(=O)—N(CH₂CH₃)—[phenyl]—OCH₃

R¹: H
Bond between 3- and 4-positions in the carbostyril ring: single bond
Crystalline form: white powders
Recrystallization solvent: ethanol/diethyl ether/n-hexane
Melting point: 155–156° C.
Form: Free Example 246
Structure R: —[piperidine]—N—C(=O)—[phenyl]—O(CH₂)₃N(C(=O)phenyl)—CH₃

R¹: H
Bond between 3- and 4-positions in the carbostyril ring: single bond
NMR analysis: 124)
Form: Free Example 247
Structure R: —[piperidine]—N—C(=O)—[phenyl]—O(CH₂)₃OCH₂CH=CH₂

R¹: H
Bond between 3- and 4-positions in the carbostyril ring: single bond
NMR analysis: 125)
Form: Free Example 248
Structure R: —[piperidine]—N—C(=O)—[phenyl with NH(CH₂)₂CH₃ and OCH₃ substituents]

R¹: H
Bond between 3- and 4-positions in the carbostyril ring: single bond
NMR analysis: 126)
Form: Free Example 249
Structure R: —[piperidine]—N—C(=O)—[phenyl]—O(CH₂)₃OC(=O)—[phenyl]

R¹: H
Bond between 3- and 4-positions in the carbostyril ring: single bond
NMR analysis: 127)
Form: Free Example 250
Structure R: —[piperidine]—N—C(=O)—[phenyl]—O(CH₂)₃OCH₃

R¹: H
Bond between 3- and 4-positions in the carbostyril ring: single bond
NMR analysis: 128)
Form: Free Example 251
Structure R: —[piperidine]—N—C(=O)—[phenyl]—O(CH₂)₃C(H₅C₂OOCCH₂)(NH)(=O)

R¹: H
Bond between 3- and 4-positions in the carbostyril ring: single bond
NMR analysis: 129)
Form: Free Example 252
Structure R: —[piperidine]—N—C(=O)—[quinoline]

TABLE 1-continued

[Structure: R¹-substituted carbostyril with N-R, 3,4-position]

R¹: H
Bond between 3- and 4-positions in the carbostyril ring: single bond
NMR analysis: 130)
Form: Free Example 253
Structure R: —[piperidine]—N—C(=O)—[adamantyl]

R¹: H
Bond between 3- and 4-positions in the carbostyril ring: single bond
NMR analysis: 131)
Form: Free Example 254
Structure R: —[piperidine]—N—C(=O)—[phenyl with N((CH₂)₂CH₃)(COOCH₂-phenyl) and OCH₃ substituents]

R¹: H
Bond between 3- and 4-positions in the carbostyril ring: single bond
Crystalline form: colorless needles
Recrystallization solvent: ethanol/diethyl ether/n-hexane
Melting point: 146–148° C.
Form: Free Example 255
Structure R: —[piperidine]—N—C(=O)—[phenyl]—O(CH₂)₃N(COCH₃)—CH₃

R¹: H
Bond between 3- and 4-positions in the carbostyril ring: single bond
NMR analysis: 132)
Form: Free Example 256
Structure R: —[piperidine]—NSO₂—[phenyl]—OCH₃

R¹: H
Bond between 3- and 4-positions in the carbostyril ring: single bond
NMR analysis: 133)
Form: Free Example 257
Structure R: —[piperidine]—N—C(=O)—[quinoline-2-yl]

Bond between 3- and 4-positions in the carbostyril ring: single bond
NMR analysis: 134)
Form: Free Example 258
Structure R: —[piperidine]—N—C(=O)—[2-aminophenyl-vinyl-ketone type structure / open carbostyril]

R¹: H
Bond between 3- and 4-positions in the carbostyril ring: single bond
NMR analysis: 135)
Form: Free Example 259
Structure R: —[piperidine]—N—C(=O)CH₂C(CH₃)₃

R¹: H
Bond between 3- and 4-positions in the carbostyril ring: single bond
NMR analysis: 136)
Form: Free Example 260
Structure R: —[piperidine]—N—C(=O)—[phenyl]—O(CH₂)₃COOH R¹: H
Bond between 3- and 4-positions in the carbostyril ring: single bond
Crystalline form: white powders
Recrystallization solvent: ethanol/water
Melting point: 90–91° C.
Form: Free Example 261
Structure R: —[piperidine]—N—C(=O)—[phenyl]—OCH₂CONH—CH₂COOC₂H₅

R¹: H
Bond between 3- and 4-positions in the carbostyril ring: single bond
NMR analysis: 137)
Form: Free Example 262
Structure R: —[piperidine]—N—C(=O)—[phenyl]—OCH₂CONH—[phenyl]

R¹: H
Bond between 3- and 4-positions in the carbostyril ring: single bond
NMR analysis: 138)
Form: Free Example 263
Structure R: —[piperidine]—N—C(=O)—[phenyl]—OCH₂CON(CH₃)₂

TABLE 1-continued

R¹: H
Bond between 3- and 4-positions in the carbostyril ring: single bond
NMR analysis: 139)
Form: Free Example 264
Structure

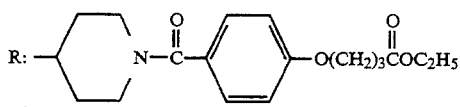

R¹: H
Bond between 3- and 4-positions in the carbostyril ring: single bond
NMR analysis: 140)
Form: Free Example 265
Structure

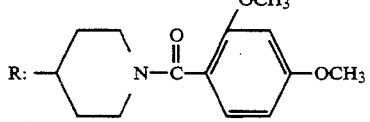

R¹: 7-N(CH₃)₂
Bond between 3- and 4-positions in the carbostyril ring: single bond
NMR analysis: 141)
Form: Free Example 266
Structure

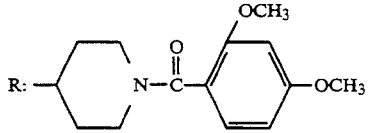

R¹: 4-CH₃
Bond between 3- and 4-positions in the carbostyril ring: single bond
NMR analysis: 142)
Form: Free Example 267
Structure

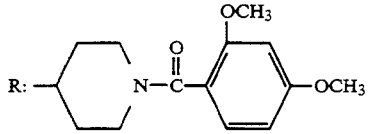

R¹: 7-NHCOCH₃
Bond between 3- and 4-positions in the carbostyril ring: single bond
Crystalline form: white powders
Recrystallization solvent: ethanol
Melting point: 176–178° C.
Form: Free Example 268
Structure

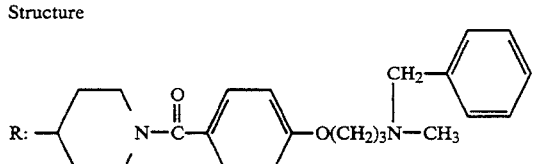

R¹: H
Bond between 3- and 4-positions in the carbostyril ring: single bond
Crystalline form: colorless needles
Recrystallization solvent: ethanol/acetone/diethyl ether
Melting point: 222–226° C.
Form: Hydrochloride TABLE 1-continued

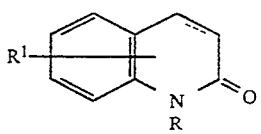

Example 269
Structure

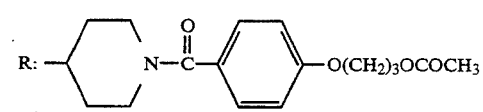

R¹: H
Bond between 3- and 4-positions in the carbostyril ring: single bond
NMR analysis: 143)
Form: Free Example 270
Structure

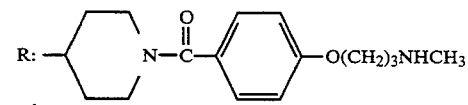

R¹: H
Bond between 3- and 4-positions in the carbostyril ring: single bond
Crystalline form: colorless needles
Recrystallization solvent: ethanol/acetone/diethyl ether
Melting point: 89–93° C.
Form: Hydrochloride Example 271
Structure

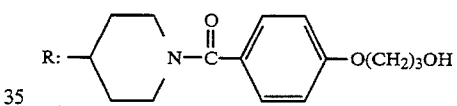

R¹: H
Bond between 3- and 4-positions in the carbostyril ring: single bond
NMR analysis: 144)
Form: Free Example 272
Structure

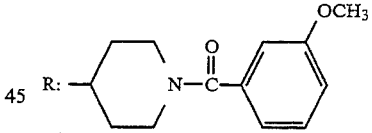

R¹: H
Bond between 3- and 4-positions in the carbostyril ring: single bond
Crystalline form: white powders
Recrystallization solvent: dichloromethane/n-hexane
Melting point: 90–92° C.
Form: Free Example 273
Structure

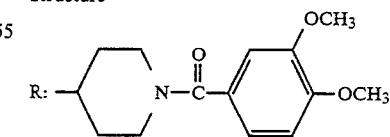

R¹: H
Bond between 3- and 4-positions in the carbostyril ring: single bond
Crystalline form: white powders
Recrystallization solvent: dichloromethane/n-hexane
Melting point: 139–139.5° C.
Form: Free Example 274
Structure

TABLE 1-continued

[Carbostyril structure with R¹ and R substituents]

R: [4-piperidinyl]-N-C(=O)-[phenyl]-OCH₂COOC₂H₅
R¹: H
Bond between 3- and 4-positions in the carbostyril ring: single bond
NMR analysis: 145)
Form: Free Example 275
Structure R: [4-piperidinyl]-N-C(=O)-[phenyl]-OCH₂COOH
R¹: H
Bond between 3- and 4-positions in the carbostyril ring: single bond
Crystalline form: white powders
Recrystallization solvent: ethanol
Melting point: 101.5–103.5° C.
Form: Free Example 276
Structure R: [4-piperidinyl]-N-C(=O)-[phenyl]-OCH₂CONH₂
R¹: H
Bond between 3- and 4-positions in the carbostyril ring: single bond
Crystallne form: white powders
Recrystallization solvent: ethanol
Melting point: 115–117° C.
Form: Free Example 277
Structure R: [4-piperidinyl]-N-C(=O)-[phenyl with OCH₃ and SCH₃]
R¹: H
Bond between 3- and 4-positions in the carbostyril ring: single bond
NMR analysis: 146)
Form: Free Example 278
Structure R: [4-piperidinyl]-N-C(=O)-[phenyl with OCH₃ and OCH₃]
R¹: 6-OCH₃
Bond between 3- and 4-positions in the carbostyril ring: single bond
NMR analysis: 147)
Form: Free Example 279
Structure R: [4-piperidinyl]-N-C(=O)-[phenyl]-OCOCH₃
R¹: H
Bond between 3- and 4-positions in the carbostyril ring: single bond
NMR analysis: 148)
Form: Free

TABLE 1-continued

[Carbostyril structure with R¹ and R substituents]

Example 280
Structure

R: [4-piperidinyl]-N-C(=O)-[phenyl with OCOCH₃ and OCOCH₃]
R¹: H
Bond between 3- and 4-positions in the carbostyril ring: single bond
NMR analysis: 149)
Form: Free Example 281
Structure R: [4-piperidinyl]-N-C(=O)-[phenyl with OH and OH]
R¹: H
Bond between 3- and 4-positions in the carbostyril ring: single bond
NMR analysis: 150)
Form: Free Example 282
Structure R: [4-piperidinyl]-N-C(=O)-[phenyl with CH₂CH=CH₂, OH, CH₂CH=CH₂]
R¹: H
Bond between 3- and 4-positions in the carbostyril ring: single bond
Crystalline form: white powders
Recrystallization solvent: dichloromethane/n-hexane
Melting point: 158–160° C.
Form: Free Example 283
Structure R: [4-piperidinyl]-N-C(=O)-[phenyl]-CON(CH₃)₂
R¹: H
Bond between 3- and 4-positions in the carbostyril ring: single bond
Crystalline form: colorless needles
Recrystallization solvent: ethyl acetate/diethyl ether
Melting point: 171–174° C.
Form: Free Example 284
Structure R: [4-piperidinyl]-N-C(=O)-[phenyl]-CONH₂
R¹: H
Bond between 3- and 4-positions in the carbostyril ring: single bond
NMR analsis: 151)
Form: Free Example 285
Structure TABLE 1-continued

[Structure: R¹-substituted carbostyril with N-R]

R: 4-piperidinyl-N-C(O)-[2-N(CH₃)₂, 4-OCH₃-phenyl]

R¹: H
Bond between 3- and 4-positions in the carbostyril ring: single bond
Crystalline form: colorless flakes
Recrystallization solvent: ethanol
Melting point: 138–140° C.
Form: Free Example 286

Structure

R: 4-piperidinyl-N-C(O)-[3-COOH-phenyl]

R¹: H
Bond between 3- and 4-positions in the carbostyril ring: single bond
Crystalline form: colorless needles
Recrystallization solvent: dichloromethane/ethanol
Melting point: 237–240° C.
Form: Free Example 287

Structure

R: 4-piperidinyl-N-C(O)-[3-CONHCH₃-phenyl]

R¹: H
Bond between 3- and 4-positions in the carbostyril ring: single bond
NMR analysis: 152)
Form: Free Example 288

Structure

R: 4-piperidinyl-N-C(O)-[2-NHCOCH₃, 4-OCH₃-phenyl]

R¹H
Bond between 3- and 4-positions in the carbostyril ring: single bond
Crystalline form: colorless flakes
Recrystallization solvent: methanol/water
Melting point: 169–171° C.
Form: Free Example 289

Structure

R: 4-piperidinyl-N-C(O)-[2-OC₂H₅, 4-OCH₃-phenyl]

R¹: H
Bond between 3- and 4-positions in the carbostyril ring: single bond
NMR analysis: 153)
Form: Free Example 290

Structure

R: 4-piperidinyl-N-C(O)-[2-OCH₂CH=CH₂, 4-OCH₃-phenyl]

R¹: H
Bond between 3- and 4-positions in the carbostyril ring: single bond
NMR analysis: 154)
Form: Free Example 291

Structure

R: 4-phenyl-NHCO-[2-OCH₃, 4-OCH₃-phenyl]

R¹: H
Bond between 3- and 4-positions in the carbostyril ring: single bond
Crystalline form: white powders
Recrystallization solvent: ethanol/diethyl ether/n-hexane
Melting point: 226–227° C.
Form: Free Example 292

Structure

R: 4-phenyl-N(CH₃)-CO-[2-OCH₃, 4-OCH₃-phenyl]

R¹: H
Bond between 3- and 4-positions in the carbostyril ring: single bond
NMR analysis: 155)
Form: Free Example 293

Structure

R: 4-phenyl-CONH-[4-OCH₃-phenyl]

R¹: H
Bond between 3- and 4-positions in the carbostyril ring: single bond
Crystalline form: white powders
Recrystallization solvent: ethanol/diethyl ether/n-hexane
Melting point: 254–255° C.
Form: Free Example 294

Structure

R: 4-piperidinyl-N-C(O)-[4-O(CH₂)₃CONH₂-phenyl]

R¹: H
Bond between 3- and 4-positions in the carbostyril ring: single bond
NMR analysis: 156)
Form: Free Example 295

Structure

R: 4-piperidinyl-N-C(O)-[quinolin-6-yl]

TABLE 1-continued

[Carbostyril structure with R¹ and R, N-R, C=O]

R¹: H
Bond between 3- and 4-positions in the carbostyril ring: single bond
NMR analysis: 157)
Form: Free Example 296
Structure R: —[piperidine]—N—C(=O)—[phenyl with O(CH₂)₃OH and OCH₃]

R¹: H
Bond between 3- and 4-positions in the carbostyril ring: single bond
NMR analysis: 158)
Form: Free Example 297
Structure R: —[piperidine]—N—C(=O)—[phenyl with OCH₂COOC₂H₅ and OCH₃]

R¹: H
Bond between 3- and 4-positions in the carbostyril ring: single bond
NMR analysis: 159)
Form: Free Example 298
Structure R: —[piperidine]—N—C(=O)—[quinoline]

R¹: H
Bond between 3- and 4-positions in the carbostyril ring: single bond
NMR analysis: 160)
Form: Free Example 299
Structure R: —[piperidine]—N—C(=O)—[phenyl with C₂H₅O and O(CH₂)₄C=O]

R¹: H
Bond between 3- and 4-positions in the carbostyril ring: single bond
NMR analysis: 161)
Form: Free Example 300
Structure R: —[piperidine]—N—C(=O)—[phenyl]—O(CH₂)₄CONH₂

R¹: H
Bond between 3- and 4-positions in the carbostyril ring: single bond
Crystalline form: colorless prisms
Recrystallization solvent: ethanol/n-hexane
Melting point: 156–157° C.
Form: Free

TABLE 1-continued

[Carbostyril structure with R¹ and R, N-R, C=O]

Example 301
Structure

R: —[piperidine]—N—C(=O)—[phenyl]—O(CH₂)₄COOH

R¹: H
Bond between 3- and 4-positions in the carbostyril ring: single bond
Crystalline form: colorless needles
Recrystallization solvent: ethanol/water
Melting point: 175–176° C.
Form: Free Example 302
Structure R: —[piperidine]—N—C(=O)—[phenyl with CH₃O and O(CH₂)₅C=O]

R¹: H
Bond between 3- and 4-positions in the carbostyril ring: single bond
NMR analysis: 162)
Form: Free Example 303
Structure R: —[piperidine]—N—C(=O)—[phenyl with OCH₂COOH and OCH₃]

R¹: H
Bond between 3- and 4-positions in the carbostyril ring: single bond
Crystalline form: white powders
Recrystallization solvent: ethanol/water
Melting point: 229.5–231° C.
Form: Free Example 304
Structure R: —[piperidine]—N—C(=O)—[phenyl]—O(CH₂)₁₀COOH R¹: H
Bond between 3- and 4-positions in the carbostyril ring: single bond
Crystalline form: white powders
Recrystallization solvent: ethanol/water
Melting point: 132–133° C.
Form: Free Example 305
Structure R: —[piperidine]—N—C(=O)—[phenyl with H₂NOCCH₂ and O(CH₂)₄CONH]

R¹: H
Bond between 3- and 4-positions in the carbostyril ring: single bond
NMR analysis: 163)
Form: Free Example 306
Structure R: —[piperidine]—N—C(=O)—[phenyl with H₅C₂OOCCH₂ and O(CH₂)₄CONH]

TABLE 1-continued

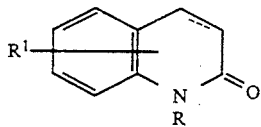

R[1]: H
Bond between 3- and 4-positions in the carbostyril ring: single bond
NMR analysis: 164)
Form: Free Example 307
Structure

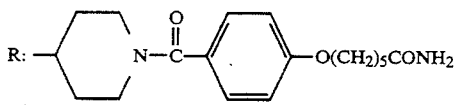

R[1]: H
Bond between 3- and 4-positions in the carbostyril ring: single bond
NMR analysis: 165)
Form: Free Example 308
Structure

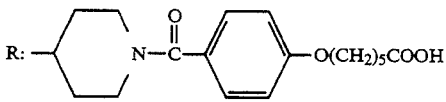

R[1]: H
Bond between 3- and 4-positions in the carbostyril ring: single bond
Crystalline form: colorless needles
Recrystallization solvent: ethanol/water
Melting point: 146–148° C.
Form: Free Example 309
Structure

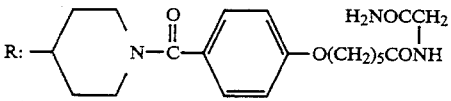

R[1]: H
Bond between 3- and 4-positions in the carbostyril ring: single bond
NMR analysis: 166)
Form: Free Example 310
Structure

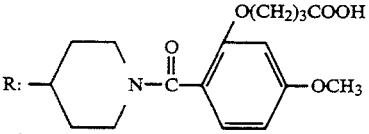

R[1]: H
Bond between 3- and 4-positions in the carbostyril ring: single bond
Crystalline form: white powders
Recrystallization solvent: ethanol/water
Melting point: 179.5–181.5° C.
Form: Free Example 311
Structure

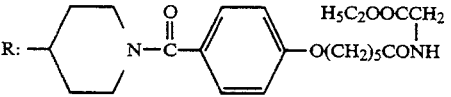

R[1]: H
Bond between 3- and 4-positions in the carbostyril ring: single bond
NMR analysis: 166A)
Form: Free Example 312
Structure

TABLE 1-continued

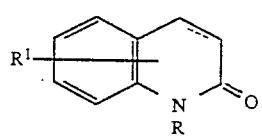

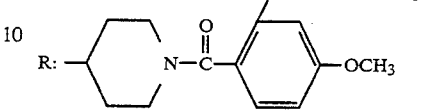

R[1]: H
Bond between 3- and 4-positions in the carbostyril ring: single bond
NMR analysis: 167)
Form: Free Example 313
Structure

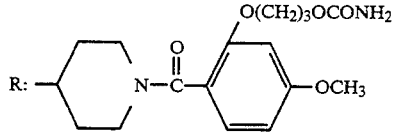

R[1]: H
Bond between 3- and 4-positions in the carbostyril ring: single bond
NMR analysis: 168)
Form: Free Example 314
Structure

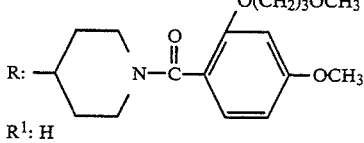

R[1]: H
Bond between 3- and 4-positions in the carbostyril ring: single bond
NMR analysis: 169)
Form: Free Example 315
Structure

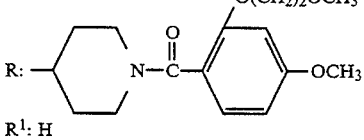

R[1]: H
Bond between 3- and 4-positions in the carbostyril ring: single bond
NMR analysis: 170)
Form: Free Example 316
Structure

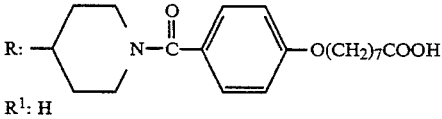

R[1]: H
Bond between 3- and 4-positions in the carbostyril ring: single bond
Crystalline form: colorless needles
Recrystallization solvent: ethanol/water
Melting point: 110–112° C.
Form: Free Example 317
Structure

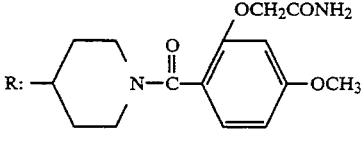

TABLE 1-continued

[Structure: carbostyril with R¹ and R substituents, 2-oxo]

R¹: H
Bond between 3- and 4-positions in the carbostyril ring: single bond
Crystalline form: white powders
Recrystallizaton solvent: ethanol/n-hexane
Melting point: 175.5–176.5° C.
Form: Free Example 318
Structure R: —[piperidine]—N—C(O)—[phenyl with O(CH₂)₃CONH₂ and OCH₃]

R¹: H
Bond between 3- and 4-positions in the carbostyril ring: single bond
NMR analysis: 171)
Form: Free Example 319
Structure R: —[piperidine]—N—C(O)—[phenyl]—O(CH₂)₇CONH₂

R¹: H
Bond between 3- and 4-positions in the carbostyril ring: single bond
NMR analysis: 172)
Form: Free Example 320
Structure R: —[piperidine]—N—C(O)—[phenyl with O(CH₂)₃COOC₂H₅ and OCH₃]

R¹: H
Bond between 3- and 4-positions in the carbostyril ring: single bond
NMR analysis: 173)
Form: Free Example 321
Structure R: —[piperidine]—N—C(O)—[phenyl]—O(CH₂)₇CONH—CH₂CONH₂

R¹: H
Bond between 3- and 4-positions in the carbostyril ring: single bond
NMR analysis: 174)
Form: Free Example 322
Structure R: —[piperidine]—N—C(O)—[phenyl]—O(CH₂)₃CONH—C(CH₃)(H)—COOC₂H₅

Bond between 3- and 4-positions in the carbostyril ring: single bond
NMR analysis: 175)
Form: Free Example 323
Structure R: —[piperidine]—N—C(O)—[phenyl]—O(CH₂)₇COOCH₃

R¹: H
Bond between 3- and 4-positions in the carbostyril ring: single bond
NMR analysis: 176)
Form: Free Example 324
Structure R: —[piperidine]—N—C(O)—[phenyl with OCH₂CH₂OH and OCH₃]

R¹: H
Bond between 3- and 4-positions in the carbostyril ring: single bond
NMR analysis: 177)
Form: Free Example 325
Structure R: —[piperidine]—N—C(O)—[phenyl with OCH₂OCOCH₃ and OCH₃]

R¹: H
Bond between 3- and 4-positions in the carbostyril ring: single bond
NMR analysis: 178)
Form: Free Example 326
Structure R: —[piperidine]—N—C(O)—[phenyl]—O(CH₂)₃CONH—CH₂CONH₂

R¹: H
Bond between 3- and 4-positions in the carbostyril ring: single bond
NMR analysis: 179)
Form: Free Example 327
Structure R: —[piperidine]—N—C(O)—[phenyl]—O(CH₂)₃CONH—C(CH₂OH)(H)—COOCH₃

R¹: H
Bond between 3- and 4-positions in the carbostyril ring: single bond
NMR analysis: 180)
Form: Free Example 328
Structure R: —[piperidine]—N—C(O)—[phenyl]—O(CH₂)₁₀C(OCH₃)=O R¹: H
Bond between 3- and 4-positions in the carbostyril ring: single bond
NMR analysis: 181)
Form: Free Example 329
Structure R: —[piperidine]—N—C(O)—[phenyl]—CONH₂

TABLE 1-continued

[Structure: carbostyril with R¹ and R substituents]

R¹: H
Bond between 3- and 4-positions in the carbostyril ring: single bond
Crystalline form: white powders
Recrystallization solvent: diethyl ether/n-hexane
Melting point: 101–104° C.
Form: Free

Example 330
Structure

R: —[piperidine]—N—C(=O)—[phenyl]—CH₂OCH₃

R¹: H
Bond between 3- and 4-positions in the carbostyril ring: single bond
Crystalline form: white powders
Recrystallization solvent: n-hexane/ethanol
Melting point: 146–147° C.
Form: Free

Example 331
Structure

R: —[piperidine]—N—C(=O)—[phenyl]—CH₂NH₂

R¹: H
Bond between 3- and 4-positions in the carbostyril ring: single bond
Crystalline form: pale yellow powders
Recrystallization solvent: ethanol/n-hexane
Melting point: 95–98° C.
Form: Free

Example 332
Structure

R: —[piperidine]—N—C(=O)—[phenyl]—O(CH₂)₃N[piperazine]N—[phenyl]

R¹: H
Bond between 3- and 4-positions in the carbostyril ring: single bond
Crystalline form: white powders
Recrystallization solvent: diethyl ether/n-hexane
Melting point: 94–97° C.
Form: (COOH)₂

Example 333
Structure

R: —[piperidine]—N—C(=O)—[phenyl]—OCH₂—[epoxide]

R¹: H
Bond between 3- and 4-positions in the carbostyril ring: single bond
Crystalline form: white powders
Recrystallization solvent: ethanol/n-hexane
Melting point: 101–102° C.
Form: Free

Example 334
Structure

R: —[piperidine]—N—C(=O)—[phenyl]—OCH₂CHCH₂N(C₂H₅)₂ with OH

R¹: H
Bond between 3- and 4-positions in the carbostyril ring: single bond
Crystalline form: white powders
Recrystallization solvent: diethyl ether
Melting point: 72–76° C.
Form:

$$CH_2COOH$$
$$OH-C-COOH$$
$$CH_2COOH$$

Example 335
Structure

R: —[piperidine]—N—C(=O)—[phenyl]—OCH₂CHCH₂N(CH₂[phenyl])([phenyl]) with OH

R¹: H
Bond between 3- and 4-positions in the carbostyril ring: single bond
Crystalline form: white powders
Recrystallization solvent: ethanol/n-hexane
Melting point: 87–89° C.
Form: Free

Example 336
Structure

R: —[piperidine]—N—C(=O)—[phenyl]—(CH₂)₂COOH

R¹: H
Bond between 3- and 4-positions in the carbostyril ring: single bond
Crystalline form: white powders
Recrystallization solvent: diethyl ether/n-hexane
Melting point: 70–72° C.
Form: Free

Example 337
Structure

R: —[piperidine]—N—C(=O)—[terpenoid/abietane structure with CH₃ groups]

R¹: H
Bond between 3- and 4-positions in the carbostyril ring: single bond
Crystalline form: white powders
Recrystallization solvent: ethanol/n-hexane
Melting point: 94–96° C.
Form: Free

Example 338
Structure

R: —[piperidine]—N—C(=O)—[phenyl]—O(CH₂)₃CH=CH₂

R¹: H
Bond between 3- and 4-positions in the carbostyril ring: single bond
Crystalline form: white powders
Recrystallization solvent: ethanol/n-hexane
Melting point: 108–109° C.
Form: Free

TABLE 1-continued

[Carbostyril structure with R¹ and R substituents]

Example 339
Structure

R: [piperidine]-N-C(=O)-[phenyl]-(CH₂)₃CH₃

R¹: H
Bond between 3- and 4-positions in the carbostyril ring: single bond
Crystalline form: white powders
Recrystallization solvent: n-hexane/ethanol
Melting point: 103–104° C.
Form: Free

Example 340
Structure

R: [piperidine]-N-C(=O)-[phenyl]-CH=CH₂

R¹: H
Bond between 3- and 4-positions in the carbostyril ring: single bond
Crystalline form: white powders
Recrystallization solvent: ethanol/n-hexane
Melting point: 114–116° C.
Form: Free

Example 341
Structure

R: [piperidine]-N-C(=O)-[phenyl]-C₂H₅

R¹: H
Bond between 3- and 4-positions in the carbostyril ring: single bond
Crystalline form: white powders
Recrystallization solvent: ethanol/n-hexane
Melting point: 133–134° C.
Form: Free

Example 342
Structure

R: [piperidine]-N-C(=O)-[phenyl]-(CH₂)₂COOCH₃

R¹: H
Bond between 3- and 4-positions in the carbostyril ring: single bond
Crystalline form: white powders
Recrystallization solvent: n-hexane
Melting point: 85–86° C.
Form: Free

Example 343
Structure

R: [piperidine]-N-C(=O)-[phenyl]-[cyclohexyl]

R¹: H
Bond between 3- and 4-positions in the carbostyril ring: single bond
Crystalline form: white powders
Recrystallization solvent: n-hexane
Melting point: 121–122° C.
Form: Free

Example 344
Structure

R: [piperidine]-N-C(=O)-[phenyl]-NH(CH₂)₃CONH₂

R¹: H
Bond between 3- and 4-positions in the carbostyril ring: single bond
Crystalline form: white powders
Recrystallization solvent: ethanol/n-hexane
Melting point: 71–73° C.
Form: Free

Example 345
Structure

R: [3-methylpiperidine]-N-C(=O)-[phenyl with 2-OCH₃, 4-OCH₃]

R¹: H
Bond between 3- and 4-positions in the carbostyril ring: single bond
NMR analysis: 182)
Form: Free

Example 346
Structure

R: [3-methylpiperidine]-N-C(=O)-[phenyl]-N(CH₃)₂

R¹: H
Bond between 3- and 4-positions in the carbostyril ring: single bond
NMR analysis: 183)
Form: Free

Example 347
Structure

R: [phenyl]-C(=O)-N(CH₃)-[adamantyl]

R¹: H
Bond between 3- and 4-positions in the carbostyril ring: single bond
NMR analysis: 184)
Form: Free

Example 348
Structure

R: [pyrrolidine]-N-C(=O)-[phenyl with 2-OCH₃, 4-OCH₃]

R¹: H
Bond between 3- and 4-positions in the carbostyril ring: single bond
NMR analysis: 185)
Form: Free

Example 349
Structure

R: [pyrrolidine]-N-C(=O)-[phenyl]-N(CH₃)₂

TABLE 1-continued

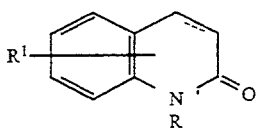

R[1]: H
Bond between 3- and 4-positions in the carbostyril ring: single bond
NMR analysis: 186)
Form: Free Example 350
Structure R: 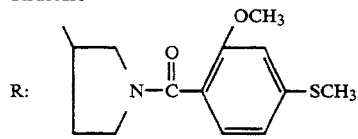

R[1]: H
Bond between 3- and 4-positions in the carbostyril ring: single bond
NMR analysis: 187)
Form: Free Example 351
Structure R: 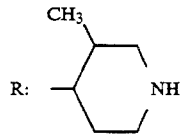

R[1]: H
Bond between 3- and 4-positions in the carbostyril ring: single bond
NMR analysis: 188)
Form: Free Example 352
Structure R: 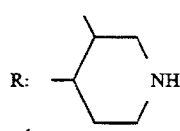

R[1]: H
Bond between 3- and 4-positions in the carbostyril ring: single bond
NMR analysis: 189)
Form: Free Example 353
Structure R: 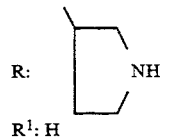

R[1]: H
Bond between 3- and 4-positions in the carbostyril ring: single bond
NMR analysis: 190)
Form: Free Example 354
Structure R: 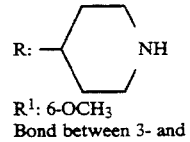

R[1]: 6-OCH3
Bond between 3- and 4-positions in the carbostyril ring: single bond
NMR analysis: 191)
Form: Free Example 355
Structure TABLE 1-continued

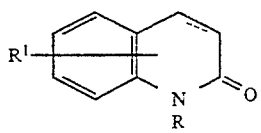

R: 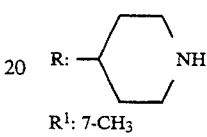

R[1]: 6-CH3
Bond between 3- and 4-positions in the carbostyril ring: single bond
NMR analysis: 192)
Form: Free Example 356
Structure R: 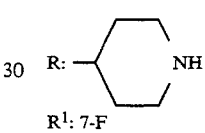

R[1]: 7-CH3
Bond between 3- and 4-positions in the carbostyril ring: single bond
NMR analysis: 193)
Form: Free Example 357
Structure R: 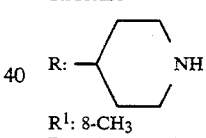

R[1]: 7-F
Bond between 3- and 4-positions in the carbostyril ring: single bond
NMR analysis: 194)
Form: Free Example 358
Structure R: 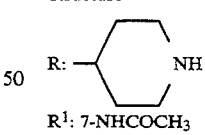

R[1]: 8-CH3
Bond between 3- and 4-positions in the carbostyril ring: single bond
NMR analysis: 195)
Form: Free Example 359
Structure R: 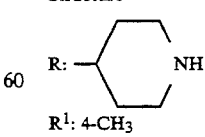

R[1]: 7-NHCOCH3
Bond between 3- and 4-positions in the carbostyril ring: single bond
NMR analysis: 196)
Form: Free Example 360
Structure R: 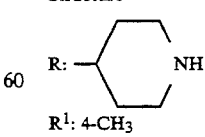

R[1]: 4-CH3
Bond between 3- and 4-positions in the carbostyril ring: single bond
NMR analysis: 197)
Form: Free Example 361
Structure TABLE 1-continued

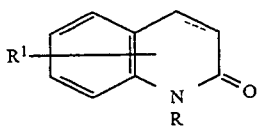

R: 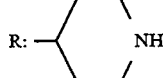

R¹: 7-N(CH₃)₂
Bond between 3- and 4-positions in the carbostyril ring: single bond
NMR analysis: 198)
Form: Free Example 362
Structure R: 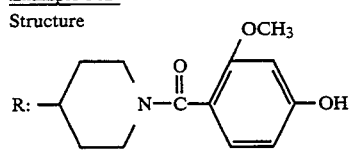

R¹: H
Bond between 3- and 4-positions in the carbostyril ring: single bond
NMR analysis: 199)
Form: Free Example 363
Structure R: 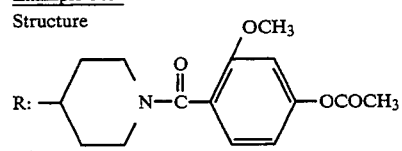

R¹: H
Bond between 3- and 4-positions in the carbostyril ring: single bond
NMR analysis: 200)
Form: Free Example 364
Structure R: 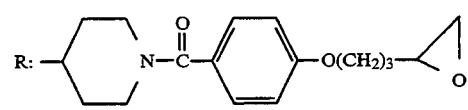

R¹: H
Bond between 3- and 4-positions in the carbostyril ring: single bond
NMR analysis: 201)
Form: Free Example 365
Structure R: 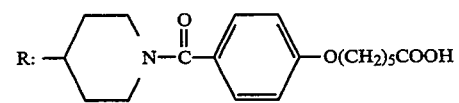

R¹: H
Bond between 3- and 4-positions in the carbostyril ring: single bond
Crystalline form: colorless needles
Recrystallization solvent: ethanol/water
Melting point: 146–148° C.
Form: Free Example 366
Structure R: 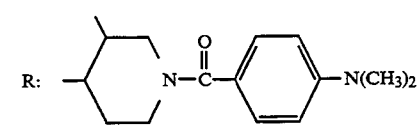

R¹: H
Bond between 3- and 4-positions in the carbostyril ring: single bond
Crystalline form: white powders
Recrystallization solvent: ethanol/diethyl ether/n-hexane
Melting point: 181–183° C.
Form: Free TABLE 1-continued

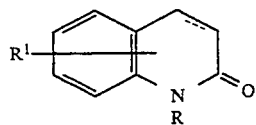

Example 367
Structure

R: 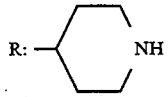

R¹: H
Bond between 3- and 4-positions in the carbostyril ring: single bond
Crystalline form: colorless prisms
Recrystallization solvent: ethanol
Melting point: 99–101° C.
Form: Free Example 368
Structure R: 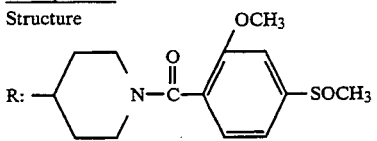

R¹: H
Bond between 3- and 4-positions in the carbostyril ring: single bond
Crystalline form: white powders
Recrystallization solvent: ethanol/n-hexane
Melting point: 83–86° C.
Form: Free Example 369
Structure R: 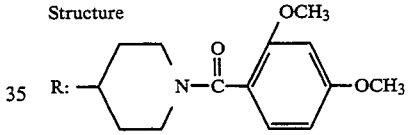

R¹: 7-C₂H₅
Bond between 3- and 4-positions in the carbostyril ring: single bond
NMR analysis: 202)
Form: Free Example 370
Structure R: 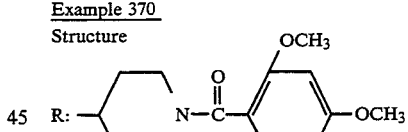

R¹: 7-OCH₃
Bond between 3- and 4-positions in the carbostyril ring: single bond
NMR analysis: 203)
Form: Free Example 371
Structure R: 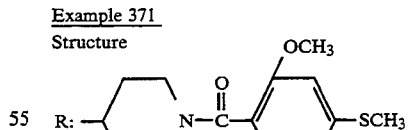

R¹: 7-F
Bond between 3- and 4-positions in the carbostyril ring: single bond
NMR analysis: 204)
Form: Free Example 372
Structure R: 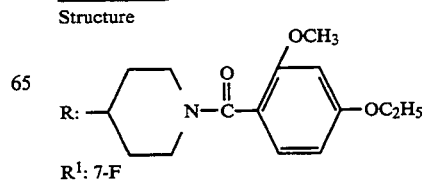

R¹: 7-F

TABLE 1-continued

[Structure: carbostyril with R¹ and N-R substituents]

Bond between 3- and 4-positions in the carbostyril ring: single bond
Crystalline form: white powders
Recrystallization solvent: ethanol/water
Melting point: 159–161° C.
Form: Free Example 373
Structure
R: –[piperidine]–N–C(=O)–[phenyl]–O(CH₂)₃Br R¹: H
Bond between 3- and 4-positions in the carbostyril ring: single bond
NMR analysis: 205)
Form: Free Example 374
Structure
R: –[piperidine]–N–C(=O)–[phenyl]–NH(CH₂)₃COOH R¹: H
Bond between 3- and 4-positions in the carbostyril ring: single bond
NMR analysis: 206)
Form: Free Example 375
Structure
R: –[piperidine]–N–C(=O)–N(H)–[phenyl]–CH₃

R¹: H
Bond between 3- and 4-positions in the carbostyril ring: single bond
Crystalline form: colorless flakes
Recrystallization solvent: diethyl ether
Melting point: 175–176° C.
Form: Free Example 376
Structure
R: –[piperidine]–N–C(=O)–N(H)–[phenyl]–Cl R¹: H
Bond between 3- and 4-positions in the carbostyril ring: single bond
Crystalline form: white powders
Recrystallization solvent: diethyl ether
Melting point: 199–200° C.
Form: Free Example 377
Structure
R: –[piperidine]–N–C(=O)–N(H)–[phenyl]–OCH₃

R¹: H
Bond between 3- and 4-positions in the carbostyril ring: single bond
Crystalline form: white powders
Recrystallization solvent: diethyl ether
Melting point: 167–168° C.
Form: Free Example 378
Structure
R: –[piperidine]–N–C(=O)–N(H)–[phenyl with OCH₃, OCH₃]

R¹: H
Bond between 3- and 4-positions in the carbostyril ring: single bond
Crystalline form: white powders
Recrystallization solvent: diethyl ether/n-hexane
Melting point: 136–137° C.
Form: Free Example 379
Structure
R: –[piperidine]–N–CO₂–[phenyl]–NO₂

R¹: H
Bond between 3- and 4-positions in the carbostyril ring: single bond
Crystalline form: white powders
Recrystallization solvent: diethyl ether/n-hexane
Melting point: 154–155° C.
Form: Free Example 380
Structure
R: –[piperidine]–N–CO₂–[phenyl]–NH₂

R¹: H
Bond between 3- and 4-positions in the carbostyril ring: single bond
Crystalline form: white powders
Recrystallization solvent: diethyl ether/n-hexane
Melting point: 167–168° C.
Form: Free Example 381
Structure
R: –[piperidine]–N–CO₂–[phenyl]–N(CH₃)₂

R¹: H
Bond between 3- and 4-positions in the carbostyril ring: single bond
Crystalline form: white powders
Recrystallization solvent: diethyl ether/n-hexane
Melting point: 189–191° C.
Form: Free Example 382
Structure
R: –[piperidine]–N–CO₂–[phenyl]–NHCOCH₃

R¹: H
Bond between 3- and 4-positions in the carbostyril ring: single bond
Crystalline form: white powders
Recrystallization solvent: diethyl ether/n-hexane
Melting point: 215–216° C.
Form: Free Example 383
Structure
R: –[piperidine]–N–CO₂–[phenyl]–NHCO–[phenyl]

R¹: H
Bond between 3- and 4-positions in the carbostyril ring: single bond
Crystalline form: white powders
Recrystallization solvent: diethyl ether/n-hexane
Melting point: 199–200° C.
Form: Free Example 383A
Structure

TABLE 1-continued

[Structure: carbostyril with R¹ on benzene ring and R on N, with C=O]

R: cyclohexyl-N(piperidine)-C(=O)-C₆H₄-O(CH₂)₅NH-SO₂CH₃

R¹: H
Bond between 3- and 4-positions in the carbostyril ring: single bond
NMR analysis: 207)
Form: Free

Example 383B
Structure

R: cyclohexyl-N(piperidine)-C(=O)-C₆H₄-O(CH₂)₅NH-C(=O)CH₃

R¹: H
Bond between 3- and 4-positions in the carbostyril ring: single bond
Crystalline form: colorless prisms
Recrystallization solvent: ethanol/ethyl acetate
Melting point: 141–142° C.
NMR analysis: 208)
Form: Free

Example 383C
Structure

R: cyclohexyl-N(piperidine)-C(=O)-C₆H₄-O(CH₂)₄NH-C(=O)CH₃

R¹: H
Bond between 3- and 4-positions in the carbostyril ring: single bond
NMR analysis: 209)
Form: Free

TABLE 2

| No. | NMR (CDCl₃) δ value |
|---|---|
| 1 | 1.55–1.82(2H, m), 2.08–2.87(7H, m), 2.95–3.17(1H, m), 3.79(2H, s), 3.90–4.08(1H, m), 4.35–4.58(1H, m), 4.73–4.92(1H, m), 6.86–7.48(9H, m) |
| 2 | 1.65–1.84(2H, m), 2.25–2.88(7H, m), 3.05–3.24(1H, m), 3.97(2H, s), 4.00–4.13(1H, m), 4.38–4.58(1H, m), 4.73–4.92(1H, m), 6.92–7.28(7H, m) |
| 3 | 1.72–2.01(2H, m), 2.53–3.01(7H, m), 3.13–3.33(1H, m), 4.09–4.23(1H, m), 4.43–4.62(1H, m), 4.87–5.04(1H, m), 6.97–7.33(4H, m), 8.55(1H, dd, J=2.5, 1.4Hz) 8.64(1H, d, J=2.5Hz), 8.99(1H, d, J=1.4Hz) |
| 4 | 0.98(3H, t, J=7.3Hz), 1.40–1.93(6H, m), 2.50–3.15(8H, m), 3.99(2H, t, J=6.4Hz), 3.13–5.10(3H, m), 6.83–7.48(4H, m) |
| 5 | 1.46–1.86(8H, m), 2.33–3.04(8H, m), 3.95–5.10(8H, m), 6.02–6.20(1H, m), 6.96–7.40(9H, m) |
| 6 | 1.65–1.93(2H, m), 2.50(3H, s), 2.52–3.24(8H, m), 3.56–5.25(3H, m), 6.95–7.46(8H, m) |
| 7 | 1.65–1.96(2H, m), 2.18(3H, s), 2.46–3.18(8H, m), 3.72–5.13(3H, m), 6.95–7.32(4H, m), 7.32–7.56(4H, m), 7.95(1H, brs) |
| 8 | 1.20–3.33(20H, m), 3.85–5.85(8H, m), 6.96–7.29(4H, m) |
| 9 | 1.12–1.93(2H, m), 2.32–3.60(8H, m), 4.00(3H, s), 3.73–5.15(3H, m) 7.00–7.34(5H, m), 7.72(1H, dd, J=8.6, 2.1Hz), 7.99(1H, d, J=2.1Hz) |
| 10 | 1.63–2.04(2H, m), 2.52–3.24(8H, m), 2.63(3H, s), 3.17–3.89(1H, m), 4.26–4.44(1H, m), 4.80–5.04(1H, m), 7.00–7.33(4H, m), 7.56(2H, d, J=8.0Hz), 8.01(2H, d, J=8.0Hz) |
| 11 | 1.33(3H, t, J=7.3Hz), 1.68–2.06(2H, m), 2.50–3.30(8H, m), 3.13(2H, q, J=7.3Hz), 3.72–5.13(3H, m), 6.97–7.34(6H, m), 7.44(2H, d, J=8.5Hz), 7.58(2H, d, J=8.5Hz) |
| 12 | 1.72–1.98(2H, m), 2.54–3.20(8H, m), 3.84–5.08(3H, m), 5.13(2H, s), 6.98–7.52(13H, m) |
| 13 | 1.58–1.73(1H, m), 1.78–1.96(1H, m), 2.50(3H, s), 2.42–3.26(8H, m), 3.56–3.73(1H, m), 3.28–3.97(3H, m), 4.20–4.73(1H, m), 4.88–5.05(1H, m) 6.78–6.92(2H, m), 6.98–7.36(4H, m) |
| 14 | 1.72–1.94(2H, m), 2.48–3.26(10H, m), 2.66(6H, s), 3.77–5.28(5H, m), 6.94–7.45(6H, m) |
| 15 | 1.03(6H, d, J=6.7Hz), 1.70–1.90(2H, m), 1.95–2.22(1H, m), 2.47–3.18(8H, m), 3.74(2H, d, J=6.5Hz), 3.66–5.10(3H, m), 6.84–7.49(8H, m) |
| 16 | 1.47(9H, s), 1.68–1.97(2H, m), 2.50–3.22(8H, m), 3.28(3H, s), 3.66–5.10(3H, m), 6.96–7.52(8H, m) |
| 17 | 1.45(9H, s), 1.55(3H, s), 1.69(3H, s), 1.60–1.94(2H, m), 2.50–3.23(8H, m), 3.72–5.14(3H, m), 4.22(2H, d, J=6.4Hz), 5.20–5.33(1H, m), 6.98–7.44(8H, m) |
| 18 | 1.68–1.93(2H, m), 2.50–3.34(16H, m), 3.90–4.97(3H, m), 6.89(2H, d, J=8.8Hz), 6.98–7.31(4H, m), 7.41(2H, d, J=8.8Hz) |
| 19 | 1.56–1.79(2H, m), 1.75(3H, s), 1.80(3H, s), 2.47–3.14(8H, m), 3.93–5.05(3H, m), 4.53(2H, d, J=6.8Hz), 5.40–5.57(1H, m), 6.83–7.53(8H, m) |
| 20 | 1.70–1.90(2H, m), 2.36(3H, s), 2.43–3.12(12H, m), 3.22–3.35(4H, m), 3.92–4.86(3H, m), 6.89(2H, d, J=8.8Hz), 6.96–7.32(4H, m), 7.41(2H, d, J=8.8Hz) |
| 21 | 1.25(6H, d, J=6.9Hz), 1.63–2.00(2H, m), 2.49–3.27(9H, m), 3.70–5.20(3H, m), 6.97–7.47(8H, m) |
| 22 | 1.68–2.07(2H, m), 2.50–3.30(8H, m), 3.70–3.93(1H, m), 4.28–4.45(1H, m), 4.83–4.58(1H, m), 7.02–7.33(4H, m), 7.62–7.69(2H, m), 7.93–8.01(2H, m), 10.08(1H, s) |
| 23 | 1.72–2.29(6H, m), 2.39–2.92(7H, m), 3.10–3.32(1H, m), 3.35–3.65(2H, m), 3.82–4.25(2H, m), 4.52–4.90(2H, m), 6.30–7.35(5H, m) |
| 24 | 1.72–1.92(2H, m), 2.52–3.12(8H, m), 3.72–3.88(2H, m), 4.07(1H, brs), 4.15–4.76(3H, m), 5.14–5.35(2H, m), 5.83–6.04(1H, m), 6.56–6.62(2H, m), 6.98–7.37(6H, m) |
| 25 | 1.72–1.90(2H, m), 2.52–3.10(8H, m), 2.99(3H, s), 3.93–4.02(2H, m), 4.23–4.68(3H, m), 5.08–5.21(2H, m), 5.72–5.94(1H, m), 6.61–6.75(2H, m), 6.96–7.32(4H, m), 7.35–7.46(2H, m) |
| 26 | 1.63–2.05(2H, m), 2.52–3.23(8H, m), 3.18(3H, s), 3.59–5.18(3H, m), 6.98–7.42(6H, m), 7.52–7.62(2H, m) |
| 27 | 1.65–1.97(2H, m), 2.48–3.22(8H, m), 3.73–5.15(3H, m), 5.20(2H, s), 6.98–7.45(13H, m) |
| 28 | 1.61–1.95(2H, m), 2.44–3.22(8H, m), 3.33(3H, s), 3.59–3.74(1H, m), 3.75–3.92(3H, m), 4.29–4.72(1H, m), 4.89–5.08(1H, m), 5.18(2H, s), 6.80–7.42(12H, m) |
| 29 | 1.56–1.95(2H, m), 2.45–3.28(8H, m), 2.85(3H, s), 3.62–4.03(5H, m), 4.32–5.12(2H, m), 6.10(1H, d, J=2.0Hz), 6.20(1H, dd, J=8.2, 2.0Hz), 6.95–7.31(4H, m) |
| 30 | 0.77–1.98(23H, m), 2.28–3.22(10H, m), 3.90–4.08(1H, m), 4.32–4.53(1H, m), 4.73–4.94(1H, m), 6.93–7.33(4H, m) |
| 31 | 1.33(9H, s), 1.58–2.01(2H, m), |

TABLE 2-continued

| No. | NMR (CDCl$_3$) δ value |
|---|---|
| | 2.48–3.21(8H, m), 3.77–5.11(3H, m), 6.99–7.31(4H, m), 7.41(4H, s) |
| 32 | 1.68–1.96(2H, m), 2.48–3.22(8H, m), 2.54(1H, s), 3.82–5.32(3H, m), 4.72(2H, d, J=2.4Hz), 6.92–7.33(6H, m), 7.38–7.52(2H, m) |
| 33 | 1.60–1.92(2H, m), 1.61(3H, s), 1.68(3H, s), 1.75(3H, s), 1.95–2.22(4H, m), 2.51–3.15(8H, m), 3.88–4.93(3H, m), 4.56(2H, d, J=6.6Hz), 5.04–5.18(1H, m), 5.42–5.56(1H, m), 6.88–7.32(6H, m), 7.38–7.48(2H, m) |
| 34 | 1.20–2.10(12H, m), 2.44–3.13(8H, m), 3.78–5.08(4H, m), 6.90(2H, d, J=8.7Hz), 6.97–7.32(4H, m), 7.40(2H, d, J=8.7Hz) |
| 35 | DMSO-d$_6$ 1.55–1.92(2H, m), 2.32–3.05(7H, m), 3.12–3.62(2H, m), 4.22–4.72(2H, m), 6.92–7.38(4H, m), 7.63(2H, d, J=8.2Hz), 7.92(2H, d, J=8.2Hz), 9.48(3H, brs) MS (m/e) = 377 (m$^+$) |
| 36 | CDCl$_3$ 0.85–1.02(3H, m), 1.25–1.60(6H, m), 1.70–1.92(4H, m), 2.52–3.16(8H, m), 3.98(2H, t, J=6.5Hz), 3.86–5.06(3H, m), 6.84–6.96(2H, m), 6.98–7.33(4H, m), 7.38–7.50(2H, m) |
| 37 | 0.80–0.96(3H, m), 1.18–1.55(18H, m), 1.68–1.92(4H, m), 2.51–3.11(8H, m), 3.78–5.05(3H, m), 3.97(2H, t, J=6.5Hz), 6.84–6.98(2H, m), 7.00–7.32(4H, m), 7.38–7.50(2H, m) |
| 38 | 1.68–1.94(2H, m), 2.08–2.26(2H, m), 2.48–3.21(10H, m), 3.81–5.10(3H, m), 4.11(2H, t, J=5.7Hz), 6.91(2H, d, J=8.8Hz), 6.98–8.30(4H, m), 7.44(2H, d, J=8.8Hz) |
| 40 | 1.26(3H, t, J=7.1Hz), 1.70–2.10(4H, m), 2.42(2H, t, J=7.0Hz), 2.49–3.31(10H, m), 4.14(2H, q, J=7.1Hz), 3.93–4.28(4H, m), 6.57(2H, d, J=8.6Hz), 6.95–7.33(4H, m), 7.34(2H, d, J=8.6Hz) |
| 41 | 1.21(3H, t, J=7.1Hz), 1.55–1.95(2H, m), 2.42–3.05(10H, m), 2.94(2H, t, J=7.3Hz), 3.70–5.02(5H, m), 4.14(2H, q, J=7.1Hz), 5.28–5.95(1H, m), 6.90–7.25(6H, m), 7.32(2H, d, J=8.1Hz) |
| 42 | 1.43–1.70(2H, m), 1.71–1.96(2H, m), 2.09–2.35(2H, m), 2.45–3.18(8H, m), 3.76–5.04(5H, m), 6.84–7.43(8H, m), 8.42–9.13(3H, m) |
| 43 | 1.56–1.83(2H, m), 2.01–2.21(2H, m), 2.43–3.11(12H, m), 3.49–3.61(4H, m), 3.70(3H, s), 3.62–4.95(7H, m), 6.71–6.90(6H, m), 6.92–7.25(4H, m), 7.30–7.45(2H, m) |
| 44 | 1.63–1.86(2H, m), 2.02–2.22(2H, m), 2.44–3.21(12H, m), 3.42–3.70(4H, m), 3.68–4.97(7H, m), 6.72–7.43(12H, m) |
| 45 | 1.65–1.98(2H, m), 2.49–3.22(8H, m), 3.78(3H, s), 3.75–5.07(3H, m), 6.96–7.32(5H, m), 7.43(4H, s) |
| 46 | 1.05–1.33(3H, m), 1.66–2.02(2H, m) 2.30–3.26(10H, m), 3.83–5.13(3H, m), 5.69–5.83, 6.35–6.75(2H, m), 7.02–7.54(8H, m) |
| 47 | 1.42–2.16(6H, m), 2.18–2.45(8H, m), 2.52–3.18(8H, m), 3.28–5.12(7H, m), 6.90(2H, d, J=8.6Hz), 6.97–7.30(4H, m), 7.42(2H, d, J=8.6Hz) |
| 48 | 1.48–2.14(6H, m), 2.35–3.18(13H, m), 3.53–5.02(8H, m), 6.90(2H, d, J=8.7Hz), 6.98–7.29(4H, m), 7.41(2H, d, J=8.7Hz) |
| 49 | 1.58–1.88(2H, m), 2.03–2.25(2H, m), 2.45–3.13(10H, m), 3.67–5.03(5H, m), 6.86–7.25(4H, m), 7.35–7.68(4H, m) |
| 50 | 1.49–1.89(16H, m), 1.90–2.07(3H, m), 2.48–3.12(8H, m), 3.79–4.99(3H, m), 4.05(2H, t, J=7.2Hz), 6.89(2H, d, J=8.7Hz), 6.97–7.31(4H, m), 7.41(2H, d, J=8.7Hz) |
| 51 | 1.27(3H, t, J=7.4Hz), 1.68–1.92(2H, m), 1.98–2.18(2H, m), 2.45–3.14(10H, m), 3.70–5.15(3H, m), 4.10(2H, t, J=6.1Hz), |

TABLE 2-continued

| No. | NMR (CDCl$_3$) δ value |
|---|---|
| | 6.91(2H, d, J=8.6Hz), 6.99–7.32(4H, m), 7.43(2H, d, J=8.6Hz) |
| 52 | 1.18–1.37(3H, m), 1.50–2.02(2H, m), 2.32–3.35(11H, m), 4.45–4.51(9H, m), 4.78–5.09(1H, m), 6.39–6.60(2H, m), 6.94–7.35(5H, m) |
| 53 | 1.65–1.97(2H, m), 2.49–3.10(11H, m), 3.78(3H, s), 3.85(2H, d, J=6.1Hz), 4.13–4.62(3H, m), 6.02(1H, t, J=6.1Hz), 6.14(1H, d, J=2.3Hz), 6.30(1H, dd, J=2.3, 8.5Hz), 6.84–7.35(6H, m) |
| 54 | 1.62–2.05(2H, m), 2.48–3.28(8H, m), 3.47(1H, d, J=5.1Hz), 3.75–4.94(6H, m), 3.83(3H, s), 6.75–7.47(7H, m) |
| 55 | 1.64–2.06(2H, m), 2.48–3.69(15H, m), 3.80(3H, m), 3.81–4.52(3H, m), 4.79–5.09(1H, m), 6.44–6.70(2H, m), 6.92–7.38(5H, m), 7.85–8.21(1H, m) |
| 56 | 1.30(3H, t, J=7.1Hz), 1.71–1.92(2H, m), 2.47–3.11(8H, m), 3.79(3H, m), 3.91(2H, d, J=5.4Hz), 4.25(2H, q, J=7.1Hz), 4.31–4.61(3H, m), 5.91(1H, t, J=5.3Hz), 6.07(1H, d, J=2.3Hz), 6.26(1H, dd, J=2.3, 8.4Hz), 6.94–7.36(5H, m) |
| 57 | 1.67–2.01(6H, m), 2.47–3.14(8H, m), 3.95–4.91(9H, m), 6.84–7.52(8H, m) |
| 58 | 1.54–2.00(6H, m), 2.45–3.36(10H, m), 3.67(3H, s), 3.84–5.08(4H, m), 4.00(2H, t, J=5.9Hz), 6.89(2H, d, J=8.7Hz), 6.94–7.48(4H, m), 7.42(2H, d, J=8.7Hz) |
| 59 | 1.55–2.00(6H, m), 2.45–3.48(10H, m), 3.76–5.10(3H, m), 3.99(2H, t, J=5.7Hz), 5.74–6.25(1H, m), 6.78–7.53(8H, m), 8.15(1H, s) |
| 60 | 1.30(3H, t, J=7.1Hz), 1.67–1.90(2H, m), 2.49–3.26(10H, m), 3.81(3H, s), 4.27–4.56(3H, m), 5.33–5.49(1H, m), 6.09–6.27(2H, m), 6.91–7.31(5H, m) |
| 61 | 0.97(3H, t, J=7.5Hz), 1.55–2.01(4H, m), 2.09–2.35(2H, m), 2.41–5.13(18H, m), 6.90(2H, d, J=8.7Hz), 6.95–7.38(4H, m), 7.42(2H, d, J=8.7Hz) |
| 62 | 1.51–2.02(8H, m), 2.48–3.20(10H, m), 3.72–5.08(3H, m), 4.01(2H, t, J=6.2Hz), 6.80–7.55(8H, m) |
| 63 | 1.55–2.20(4H, m), 2.49–3.50(10H, m), 2.96(3H, m), 3.90–5.13(4H, m), 4.09(2H, t, J=5.7Hz), 6.90(2H, d, J=8.7Hz), 6.95–7.38(4H, m), 7.43(2H, d, J=8.7Hz) |
| 64 | 1.60–2.15(5H, m), 2.47–3.18(10H, m), 3.82(2H, s), 3.95–5.11(3H, m), 4.08(2H, t, J=6.2Hz), 6.89(2H, d, J=8.5Hz), 6.95–7.50(9H, m), 7.42(2H, d, J=8.5Hz) |
| 65 | 1.59–2.20(4H, m), 2.50–3.49(10H, m), 2.96(3H, s), 3.91–5.11(4H, m), 4.09(2H, t, J=5.7Hz), 6.90(2H, d, J=8.7Hz), 6.94–7.40(4H, m), 7.43(2H, d, J=8.7Hz) |
| 66 | 1.60–2.10(4H, m), 2.45–3.49(13H, m), 3.80–5.01(7H, m), 6.88(2H, d, J=8.6Hz), 6.95–7.45(4H, m), 7.40(2H, d, J=8.6Hz) |
| 67 | 1.63–2.15(4H, m), 1.99(3H, s), 2.49–3.20(8H, m) 3.35–3.60(2H, m), 3.90–5.10(3H, m), 4.06(2H, t, J=5.9Hz), 5.89(1H, brs), 6.89(2H, d, J=8.7Hz), 6.95–7.37(4H, m), 7.43(2H, d, J=8.7Hz) |
| 68 | 1.60–2.32(4H, m), 2.41–3.27(8H, m), 3.71–5.15(5H, m), 4.07(2H, t, J=6.2Hz), 4.26(2H, t, J=6.2Hz), 6.96(2H, d, J=8.6Hz), 6.99–7.40(4H, m), 7.43(2H, d, J=8.6Hz) |
| 69 | 0.86(3H, t, J=7.3Hz), 1.35–2.04(6H, m), 2.40(2H, t, J=7Hz), 2.50–3.17(10H, m), 3.57(2H, s), 3.90–5.05(3H, m), 4.00(2H, t, J=6.5Hz), 6.85(2H, d, J=8.8Hz), 6.94–7.38(9H, m), 7.42(2H, d, J=8.8Hz) |
| 70 | 0.99–1.23(3H, m), 1.54–2.00(2H, m), 2.35–3.40(13H, m), 3.52–3.77(1H, m), 3.80(3H, s), 4.15–4.52(1H, m), 4.83–5.04(1H, m), 6.49–6.57(2H, m), 6.90–7.35(4H, m) |
| 71 | 1.50–2.12(6H, m), 2.03(3H, m), 2.45–3.44(10H, m), 3.88(2H, d, J=5.1Hz), |

TABLE 2-continued

| No. | NMR (CDCl₃) δ value |
|---|---|
|  | 3.98(2H, t, J=6.0Hz), 4.01–5.05(3H, m), 6.50–7.52(10H, m) |
| 72 | 1.45–2.01(8H, m), 2.06(3H, s), 2.48–3.25(8H, m), 3.70–5.12(3H, m), 3.99(2H, t, J=6.3Hz), 4.10(2H, t, J=6.3Hz), 6.89(2H, d, J=8.8Hz), 6.97–7.35(4H, m), 7.43(2H, d, J=8.8Hz) |
| 73 | 1.40–2.02(8H, m), 2.48–3.15(8H, m), 3.60–5.12(3H, m), 3.72(2H, t, J=7.0Hz), 3.97(2H, t, J=6.3Hz), 6.87(2H, d, J=8.7Hz), 6.92–7.32(4H, m), 7.41(2H, d, J=8.7Hz), 7.61–7.93(4H, m) |
| 74 | 1.35–2.02(10H, m), 2.47–3.25(10H, m), 3.71–5.16(3H, m), 3.99(2H, t, J=6.4Hz), 6.89(2H, d, J=8.7Hz), 6.93–7.35(4H, m), 7.42(2H, d, J=8.7Hz) |
| 75 | 1.01–5.60(20H, m), 3.82(3H, s), 6.55–7.60(12H, m) |
| 76 | 1.52–5.51(17H, m), 3.83(3H, s), 6.75–7.55(12H, m) |
| 77 | 1.50–5.52(20H, m), 3.82(3H, s), 6.69–7.55(12H, m), 9.20–9.75(1H, m) |
| 78 | 1.09–5.45(25H, m), 6.77–7.48(12H, m) |
| 79 | 1.65–1.97(2H, m), 2.10–2.30(2H, m), 2.48–3.01(8H, m), 3.82–4.78(7H, m), 6.62–6.93(4H, m), 7.11(1H, dd, J=6.2, 7.3Hz), 7.38(2H, d, J=8.5Hz), 7.66–7.86(4H, m) |
| 80 | 1.55–2.10(4H, m), 2.43–3.18(10H, m), 3.74–5.18(5H, m), 6.65–7.00(4H, m), 7.10(1H, dd, J=6.4, 7.3Hz), 7.41(2H, d, J=8.7Hz) |
| 81 | 1.60–1.90(2H, m), 1.98(3H, s), 1.90–2.10(2H, m), 2.43–3.10(8H, m), 3.45(2H, q, J=6.4Hz), 4.05(2H, t, J=5.9Hz), 3.82–5.04(3H, m), 5.92(1H, brs), 6.65–6.97(4H, m), 7.11(1H, dd, J=6.4, 7.3Hz), 7.43(2H, d, J=8.7Hz) |
| 82 | 1.25(3H, t, J=7.5Hz), 1.64–1.82(2H, m), 1.91(1H, brs), 2.35–2.87(10H, m), 3.15–3.35(2H, m), 4.16–4.50(1H, m), 6.85(1H, d, J=7.7Hz), 7.00(1H, s), 7.10(1H, d, J=7.7Hz) |
| 83 | 1.26(3H, t, J=7.5Hz), 1.58–1.98(2H, m), 2.45–3.22(10H, m), 3.58–3.98(7H, m), 4.23–4.61(1H, m), 4.87–5.05(1H, m), 6.40–6.57(1H, m), 6.80–7.38(3H, m) |
| 84 | 1.62–1.95(2H, m), 2.50–2.93(9H, m), 3.15–3.50(2H, m), 3.84(3H, s), 4.15–4.48(1H, m), 6.50–6.60(1H, m), 6.70–6.82(1H, m), 7.06(1H, d, J=8.2Hz) |
| 85 | 1.55–1.98(2H, m), 2.44–3.25(8H, m), 3.60–4.10(10H, m), 4.20–4.75(1H, m), 4.86–5.05(1H, m), 6.44–6.85(4H, m), 7.07(1H, d, J=8.2Hz), 7.17–7.36(1H, m) |
| 86 | 1.54–1.92(2H, m), 2.32–3.22(8H, m), 3.50–3.90(7H, m), 4.23–4.71(1H, m), 4.82–5.00(1H, m), 6.34–6.60(2H, m), 6.95–7.72(5H, m), 7.90(2H, d, J=7.0Hz), 8.40–8.65(1H, m) |
| 87 | 1.50–1.93(2H, m), 2.34–3.20(8H, m), 3.30–4.15(9H, m), 4.22–4.75(1H, m), 4.85–5.03(1H, m), 6.42–6.63(4H, m), 6.82–7.33(2H, m) |
| 88 | 1.60–2.02(2H, m), 2.62–3.41(4H, m), 3.73–4.26(1H, m), 4.50–5.72(2H, m), 6.64(1H, d, J=9.4Hz), 7.15–7.70(10H, m) |
| 89 | 1.55–1.96(2H, m), 2.72–3.30(4H, m), 3.84(3H, s), 3.82–5.55(3H, m), 6.65(1H, d, J=9.4Hz), 6.93(2H, d, J=8.7Hz), 7.23(1H, t, J=7.6Hz), 7.48–7.75(6H, m) |
| 90 | 1.55–1.95(2H, m), 2.63–3.34(4H, m), 3.66–4.00(7H, m), 4.95–5.16(1H, m), 6.42–6.77(3H, m), 7.13–7.40(2H, m), 7.45–7.86(4H, m) |
| 91 | 1.62–2.03(3H, m), 2.55–3.03(4H, m), 3.14–3.50(2H, m), 4.68–5.85(1H, br), 6.65(1H, d, J=6.4Hz), 7.19(1H, t, J=7.4Hz) |
| 92 | 1.55–1.98(2H, m), 2.38–3.26(8H, m), 3.57–4.00(7H, m), 4.24–4.71(1H, m), 4.85–5.07(1H, m), 6.50–6.61(2H, m), 6.83–7.39(4H, m) |
| 93 | 1.60–2.05(3H, m), 2.31–3.00(8H, m), 3.10–3.48(2H, m), 4.21–4.52(1H, m), 6.76–7.38(3H, m) |
| 94 | 2.76(3H, t, J=8.1Hz), 3.0(3H, t, J=8Hz), 3.48(3H, s), 3.75(3H, s), 6.19(1H, dd, J=3.1, 6Hz), 6.78(2H, d, J=8.3Hz), 6.9–7.2(7H, m), 7.43(2H, d, J=8.4Hz) |
| 95 | 1.57–1.95(2H, m), 2.50(3H, s), 2.45–3.25(7H, m), 3.57–4.00(4H, m), 4.15–4.77(1H, m), 4.88–5.07(1H, m), 6.63–7.36(6H, m) |
| 96 | 1.73–1.95(2H, m), 2.49–3.11(8H, m), 3.84(3H, s), 4.24–4.58(3H, m), 5.21(2H, s), 6.57(1H, dd, J=2.5, 8.5Hz), 6.96–7.52(10H, m), 7.87(1H, d, J=2.5Hz), 8.81(1H, s) |
| 97 | 1.54–1.72(1H, m), 1.77–1.92(1H, m), 2.40–3.23(8H, m), 3.58–3.73(1H, m), 3.73–3.95(6H, m), 4.20–4.77(1H, m), 4.88–5.07(1H, m), 6.43–6.60(2H, m), 6.65–7.00(2H, m), 7.05–7.37(2H, m) |
| 98 | 1.55–1.93(2H, m), 2.30(3H, s), 2.40–3.24(8H, m), 3.56–3.72(1H, m), 3.73–3.85(6H, m), 4.27–4.73(1H, m), 4.85–5.02(1H, m), 6.41–6.57(2H, m), 6.90–7.37(4H, m) |
| 99 | 1.58–2.00(2H, m), 2.35(3H, s), 2.32–3.14(8H, m), 3.27–3.48(1H, m), 3.53–4.00(7H, m), 4.78–5.01(1H, m), 6.37–6.64(2H, m), 6.87–7.48(4H, m) |
| 100 | 1.57–1.97(2H, m), 2.37(3H, s), 2.43–3.26(8H, m), 3.48–3.98(7H, m), 4.21–4.63(1H, m), 4.84–5.07(1H, m), 6.42–6.60(2H, m), 6.78–7.37(4H, m) |
| 101 | 1.40(3H, t, J=7.1Hz), 1.55–2.09(2H, m), 2.43–3.34(8H, m), 3.66–4.07(1H, m), 4.25–4.58(1H, m), 4.39(2H, q, J=7.1Hz), 4.75–5.12(1H, m), 6.96–7.74(6H, m), 8.01–8.23(2H, m) |
| 102 | 2.3–2.7(4H, br), 2.8(2H, t, J=8Hz), 3.1(2H, t, J=8Hz), 3.4–3.9(4H, m), 3.55(2H, s), 6.36(1H, dd, J=2.2, 6.9Hz), 6.9–7.1(2H, m), 7.1–7.4(8H, m), 7.54(2H, d, J=8.4Hz) |
| 103 | 1.60–2.08(2H, m), 2.45–3.10(8H, m), 3.35(3H, s), 3.62–4.05(1H, br), 4.34(1H, m), 4.60–5.07(1H, br), 5.16(2H, s), 6.76–7.53(13H, m) |
| 104 | 1.82(2H, m), 2.54–3.32(8H, m), 3.77(1H, brs), 4.35(1H, m), 4.89(1H, brs), 7.00–7.30(4H, m), 7.59–7.67(1H, m), 7.80–7.84(1H, m), 8.27–8.33(1H, m) |
| 105 | 1.68–2.01(2H, m), 2.50–3.09(11H, m), 4.19–4.73(3H, m), 4.88–5.33(1H, m), 6.60–6.75(2H, m), 4.96–7.39(6H, m) |
| 106 | 1.60–2.03(2H, m), 2.45–3.32(8H, m), 3.67–4.07(1H, m), 4.15–4.44(1H, m), 4.61–5.04(1H, m), 6.96–7.68(7H, m) |
| 107 | 1.51–2.08(2H, m), 2.42–3.67(9H, m), 4.15–5.09(2H, m), 6.90–7.62(7H, m) |
| 108 | 0.94(3H, t, J=7.3Hz), 1.50–1.97(4H, m), 2.50–3.20(10H, m), 3.74–4.20(1H, br), 4.41(1H, m), 4.50–5.08(1H, br), 6.98–7.34(6H, m), 7.38(2H, d, J=8.1Hz) |
| 109 | 1.85(2H, m), 2.55–3.30(8H, m), 3.78–4.38(1H, br), 4.41(1H, m), 4.66–5.17(1H, br), 6.99–7.66(13H, m) |
| 110 | 1.84(2H, m), 2.55–3.10(8H, m), 4.00–5.00(2H, m), 4.40(1H, m), 4.57(2H, d, J=5.3Hz), 5.31(1H, d, J=10.5Hz), 5.42(1H, d, J=16.6Hz), 6.06(1H, ddt, J=16.6, 10.5, 5.3Hz), 6.93(2H, d, J=8.7Hz), 6.99–7.32(4H, m), 7.43(2H, d, J=8.7Hz) |
| 111 | 1.82(2H, m), 2.51–3.12(8H, m), 3.43(2H, d, J=6.8Hz), 4.12–4.70(2H, m), 4.43(1H, m), 4.58(2H, d, J=5.0Hz), 5.06(1H, d, J=10.0Hz), 5.08(1H, d, J=17.0Hz), 5.29(1H, d, J=9.0Hz), 5.43(1H, d, J=18.9Hz), 5.92–6.16(2H, m), 6.84(1H, d, J=8.5Hz), |

TABLE 2-continued

| No. | NMR (CDCl₃) δ value |
|---|---|
| | 7.00–7.37(6H, m) |
| 112 | 1.6–2.1(3H, m), 2.4–2.7(2H, m), 2.7–3.2(4H, m), 3.4–4.2(3H, m), 3.8(6H, s), 4.7–5.0(1H, br), 6.4–6.6(2H, m), 6.9–7.4(5H, m) |
| 113 | 1.66–1.97(2H, m), 2.44–3.10(8H, m), 3.90–5.00(2H, m), 4.39(1H, m), 6.00(2H, s), 6.83(1H, d, J=8.2Hz), 6.96–7.32(6H, m) |
| 114 | 1.83(2H, m), 2.31(3H, s), 2.48–3.17(8H, m), 3.82(3H, s), 4.13–4.63(2H, m), 4.70–5.02(1H, m), 6.67–6.88(2H, m), 6.97–7.49(5H, m) |
| 115 | 1.70–1.92(2H, m), 2.47–3.08(11H, m), 3.82(3H, s), 4.26–4.61(3H, m), 5.55(1H, brs), 6.12–6.29(2H, m), 6.95–7.36(5H, m) |
| 116 | 1.42(3H, t, J=6.9Hz), 1.64–1.90(2H, m), 2.44–3.17(8H, m), 4.05(2H, q, J=6.9Hz), 3.90–5.00(3H, m), 6.65–6.98(4H, m), 7.03–7.17(1H, m), 7.41(2H, d, J=8.7Hz) |
| 117 | 1.64–2.10(4H, m), 2.97–3.18(8H, m), 2.92(2H, t, J=6.8Hz), 4.08(1H, t, J=6.1Hz), 4.10–5.15(3H, m), 6.82–7.58(8H, m) MS (m/e): 407(m⁺), 333, 260, 229, 121, 82 |
| 118 | 1.62–1.95(2H, m), 2.07–2.33(2H, m), 2.43–3.16(8H, m), 3.92(2H, t, J=6.8Hz), 4.06(2H, t, J=6.1Hz), 3.95–5.05(3H, m), 6.80(2H, d, J=8.7Hz), 6.95–7.39(4H, m), 7.38(2H, d, J=8.7Hz), 7.65–8.00(4H, m) |
| 119 | 2.76(2H, t, J=8.1Hz), 3.02(2H, t, J=7.8Hz), 3.72(3H, s), 5.10(2H, s), 6.17(1H, dd, J=2.6, 6.5Hz), 6.68(2H, d, J=9.0Hz), 6.85(2H, d, J=8.8Hz), 6.9–7.4(10H, m), 7.46(2H, d, J=8.5Hz) |
| 120 | 2.76(2H, t, J=8.1), 3.02(2H, t, J=7.9Hz), 3.75(3H, s), 4.50(2H, d, J=6Hz), 5.20(1H, d, J=1.62Hz), 5.19(1H, d, J=11.0Hz), 5.9–6.1(1H, m), 6.18(1H, dd, J=2.6, 6.5Hz), 6.76(2H, d, J=8.9Hz), 6.9–7.3(7H, m), 7.45(2H, d, J=8.3Hz) |
| 121 | 1.64–1.96(2H, m), 2.15–2.87(2H, m), 2.49–3.20(8H, m), 3.01(3H, s), 4.02–5.03(3H, m), 4.12(2H, t, J=5.9Hz), 4.53(2H, t, J=6.1Hz), 6.91(2H, d, J=8.7Hz), 6.95–7.46(4H, m), 7.44(2H, d, J=8.7Hz) |
| 121 | 1.55–3.26(14H, m), 2.72(6H, s), 3.90–5.18(3H, m), 4.05(2H, t, J=5.7Hz), 6.90(2H, d, J=8.7Hz), 6.93–7.38(4H, m), 7.43(2H, d, J=8.7Hz) |
| 123 | 0.91(3H, t, J=5.8Hz), 1.42–3.31(21H, m), 2.33(3H, s), 3.88–5.15(3H, m), 4.05(2H, t, J=5Hz), 6.91(2H, d, J=7Hz), 6.95–7.38(4H, m), 7.42(2H, d, J=7Hz) |
| 124 | 1.65–5.12(22H, m), 6.67–7.60(13H, m) |
| 125 | 1.65–1.99(2H, m), 2.07(2H, quint, J=6.2Hz), 2.49–3.24(8H, m), 3.62(2H, t, J=6.2Hz), 3.87–4.93(5H, m), 4.10(2H, t, J=6.2Hz), 5.11–5.38(2H, m), 5.80–6.07(1H, m), 6.80–7.53(8H, m) |
| 126 | 1.02(3H, t, J=7.3Hz), 1.60–2.07(4H, m), 2.47–3.18(10H, m), 3.80(3H, s), 4.30–4.58(5H, m), 5.53(1H, t, J=5.2Hz), 6.07–6.28(2H, m), 6.94–7.34(5H, m) |
| 127 | 1.64–1.92(2H, m), 2.28(2H, quint, J=6.1Hz), 2.45–3.27(8H, m), 4.02–5.22(3H, m), 4.16(2H, t, J=6.1Hz), 4.53(2H, t, J=6.1Hz), 6.83–7.69(11H, m), 7.98–8.18(2H, m) |
| 128 | 1.69–1.97(2H, m), 2.06(2H, quint, J=6.2Hz), 2.48–3.16(8H, m), 3.36(3H, s), 3.56(2H, t, J=6.2Hz), 4.09(2H, t, J=6.2Hz), 4.12–5.04(3H, m), 6.91(2H, t, J=8.7Hz), 6.94–7.35(4H, m), 7.43(2H, d, J=8.7Hz) |
| 129 | 1.28(3H, t, J=7.1Hz), 1.83(2H, m), 2.15(2H, quint, J=6.7Hz), 2.47(2H, t, J=6.7Hz), 2.50–3.20(8H, m), 3.60–5.10(2H, m), 4.02(2H, s), 4.05(2H, t, J=6.7Hz), 4.21(2H, q, J=7.1Hz), 4.39(1H, m), 6.12(1H, brs), 6.91(2H, d, J=8.6Hz), 6.99–7.29(2H, m), 7.42(2H, d, J=8.6Hz) |
| 130 | 1.87(2H, m), 2.50–3.43(8H, m), 3.94(1H, m), 4.38(1H, m), 4.96(1H, m), 6.99–7.30(4H, m), 7.58–7.65(1H, m), 7.75–7.98(2H, m), 8.12–8.16(1H, m), 8.31(1H, m), 9.01(1H, m) |
| 131 | 1.73(6H, m), 1.82(2H, m), 2.04(9H, m), 2.43–3.00(8H, m), 4.46(1H, m), 4.67(1H, m), 4.73(1H, m), 6.98–7.30(4H, m) |
| 132 | 1.65–2.28(7H, m), 2.44–3.20(11H, m), 3.42–5.11(7H, m), 6.83–7.60(8H, m) |
| 133 | 1.40–1.90(2H, m), 2.30–2.95(8H, m), 3.90(3H, s), 3.98(2H, m), 4.32(1H, m), 6.90–7.27(6H, m), 7.73(2H, m) |
| 134 | 1.55–2.05(2H, m), 2.54–3.33(8H, m), 4.05–4.24(1H, m), 4.47–4.65(1H, m), 4.93–5.10(1H, m), 6.98–7.31(4H, m), 7.64(1H, m), 7.71–7.80(2H, m), 7.86(1H, m), 8.11(1H, d, J=8.4Hz), 8.28(1H, d, J=8.4Hz) |
| 135 | 1.56–1.86(1H, m), 1.86–2.30(1H, m), 2.44–3.35(8H, m), 3.60–3.86(1H, m), 4.12–4.62(1H, m), 4.91–5.20(1H, m), 6.63–7.78(9H, m) |
| 136 | 1.08(9H, s), 1.80(2H, m), 2.32(2H, s), 2.45–2.76(5H, m), 2.76–2.92(2H, m), 3.05–3.18(1H, m), 4.03–4.18(1H, m), 4.40(1H, m), 4.78–4.98(1H, m), 6.97–7.28(4H, m) |
| 137 | 1.30(3H, t, J=7.1Hz), 1.84(2H, m), 1.50–3.22(8H, m), 3.90(1H, t, J=5.4Hz), 3.43–5.20(2H, m), 4.13(2H, d, J=5.4Hz), 4.24(2H, q, J=7.1Hz), 4.57(2H, s), 4.38(1H, m), 6.97(2H, d, J=8.7Hz), 7.03–7.32(4H, m), 7.47(2H, d, J=8.7Hz) |
| 138 | 1.75(2H, m), 2.51–3.31(8H, m), 3.80–5.28(2H, m), 4.37(1H, m), 4.64(2H, s), 6.90–7.67(13H, m) |
| 139 | 1.83(2H, m), 2.54–3.23(8H, m), 2.94(3H, s), 3.09(3H, s), 3.76–5.17(2H, m), 4.39(1H, m), 4.73(2H, s), 6.97(2H, d, J=8.6Hz), 7.02–7.27(4H, m), 7.43(2H, d, J=8.6Hz) |
| 140 | 1.26(3H, t, J=7.1Hz), 1.83(2H, m), 2.12(2H, quint, J=6.2Hz), 2.40–3.20(10H, m), 3.40–5.10(2H, m), 4.04(2H, t, J=6.21Hz), 4.15(2H, q, J=7.1Hz), 4.39(1H, m), 6.90(2H, d, J=8.6Hz), 6.98–7.28(4H, m), 7.43(2H, d, J=8.6Hz) |
| 141 | 1.54–1.98(2H, m), 2.40–3.22(9H, m), 2.95(6H, s), 3.58–3.90(7H, m), 4.85–5.06(1H, m), 6.33–6.62(4H, m), 6.70(1H, d, J=8.2Hz), 7.12–7.30(1H, m) |
| 153 | 1.31–1.78(5H, m), 2.32–3.28(8H, m), 3.68(1H, m), 3.81(3H, s), 4.06(2H, m), 4.43(1H, m), 4.96(1H, m), 6.49–6.62(2H, m), 6.97–7.44(5H, m) |
| 154 | 1.53–1.90(2H, m), 2.35–3.27(8H, m), 3.60–3.77(1H, m), 3.81(3H, s), 4.29–4.60(1H, br), 4.58(2H, m), 4.88–5.06(1H, m), 5.18–5.51(2H, m), 6.08–(1H, m), 6.42–6.60(2H, m), 6.93–7.48(5H, m) |
| 155 | 2.78(3H, t, J=8Hz), 3.04(3H, t, J=8Hz), 3.50(3H, s), 3.59(3H, s), 3.76(3H, s), 6.0–6.1(1H, br), 6.2(1H, brs), 6.41(1H, dd, J=2.3, 8.4Hz), 6.9–7.1(4H, m), 7.1–7.3(4H, m) |
| 156 | 1.66–2.03(2H, m), 2.14(2H, m), 2.44(2H, t, J=7.2Hz), 2.51–3.32(8H, m), 3.70–5.30(2H, m), 4.04(2H, t, J=6.0Hz), 4.38(1H, m), 5.75(1H, brs), 5.90(1H, brs), 6.90(2H, d, J=8.6Hz), 6.99–7.29(4H, m), 7.42(2H, d, J=8.6Hz) |
| 157 | 1.55–2.10(2H, m), 2.22–3.36(8H, m), 3.78–4.20(1H, m), 4.23–4.56(1H, m), 4.70–5.18(1H, m), 6.95–7.34(4H, m), 7.46(1H, dd, J=8.3, 4.2Hz), 7.67(1H, dd, J=8.3, 1.3Hz), 7.90(1H, d, J=8.3Hz), 8.20(2H, m), 8.96(1H, dd, J=4.2, 1.3Hz) |
| 158 | 1.58–2.31(4H, m), 2.44–3.30(8H, m), 3.60–4.50(6H, m), 3.81(3H, s), 4.70–5.15(1H, m), 6.43–6.60(2H, m), 6.99–7.33(5H, m) |

TABLE 2-continued

| No. | NMR (CDCl$_3$) δ value |
|---|---|
| 159 | 1.29(3H, t, J=7.1Hz), 1.58–1.98(2H, m), 2.53–3.37(8H, m), 3.80(3H, s), 4.21(2H, q, J=7.1Hz), 4.22–4.47(1H, m), 4.62(2H, s), 4.63–4.80(1H, m), 4.87–5.07(1H, m), 6.28–6.37(1H, m), 6.52–6.66(1H, m), 6.95–7.46(5H, m) |
| 160 | 1.46–2.12(2H, m), 2.45–3.22(8H, m), 3.36–3.55(1H, m), 4.22–4.53(1H, m), 5.02–5.17(1H, m), 6.98–7.74(7H, m), 8.03–8.26(2H, m), 8.94–9.05(1H, m) |
| 161 | 1.26(3H, t, J=7.1Hz), 1.63–2.00(6H, m), 2.32–2.44(2H, m), 2.54–3.03(8H, m), 3.75–5.03(2H, m), 3.95–4.09(2H, m), 4.14(2H, q, J=7.1Hz), 4.40(1H, m), 6.90(2H, d, J=8.7Hz), 6.98–7.27(4H, m), 7.43(2H, d, J=8.7Hz) |
| 162 | 1.42–1.62(2H, m), 1.62–1.93(6H, m), 2.36(2H, t, J=7.1Hz), 2.45–3.12(8H, m), 3.67(3H, s), 3.74–5.03(2H, m), 3.98(2H, t, J=6.3Hz), 4.39(1H, m), 6.90(2H, d, J=8.7Hz), 6.99–7.28(4H, m), 7.43(2H, d, J=8.7Hz) |
| 163 | 1.63–2.10(6H, m), 2.33(2H, m), 2.46–3.18(8H, m), 3.50–5.00(2H, m), 3.89(2H, d, J=4.8Hz), 4.00(2H, m), 4.37(1H, m), 5.76(1H, brs), 6.50(1H, brs), 6.74(1H, brs), 6.89(2H, d, J=8.6Hz), 6.99–7.27(4H, m), 7.41(2H, d, J=8.6Hz) |
| 164 | 1.28(3H, t, J=7.1Hz), 1.83(6H, m), 2.17(2H, m), 2.43–3.18(8H, m), 3.55–5.00(2H, m), 3.98(2H, m), 3.99(2H, d, J=5.1Hz), 4.20(2H, q, J=7.1Hz), 4.37(1H, m), 6.66(1H, brs), 6.89(2H, d, J=8.6Hz), 6.99–7.32(4H, m), 7.42(2H, d, J=8.6Hz) |
| 165 | 1.41–2.10(8H, m), 2.26(2H, t, J=7.3Hz), 2.54–3.24(8H, m), 3.80–5.10(2H, m), 3.99(2H, t, J=6.3Hz), 4.39(1H, m), 5.22–5.86(2H, m), 6.89(2H, d, J=8.7Hz), 6.99–7.29(4H, m), 7.42(2H, d, J=8.7Hz) |
| 166 | 1.48–1.62(2H, m), 1.62–2.17(6H, m), 2.27(2H, t, J=7.3Hz), 2.54–3.30(8H, m), 3.30–5.10(2H, m), 3.91(2H, d, J=5.0Hz), 3.98(2H, t, J=6.3Hz), 4.37(1H, m), 5.75(1H, brs), 6.51(1H, brs), 6.66(1H, brs), 6.89(2H, d, J=8.7Hz), 6.99–7.27(4H, m), 7.41(2H, d, J=8.7Hz) |
| 166A | 1.28(3H, t, J=7.1Hz), 1.46–1.63(2H, m), 1.63–1.96(6H, m), 2.28(2H, t, J=7.3Hz), 2.54–3.12(8H, m), 3.62–5.07(2H, m), 3.98(2H, t, J=6.4Hz), 4.01(2H, d, J=5.3Hz), 4.20(2H, q, J=7.1Hz), 4.48(1H, m), 6.45(1H, brs), 6.89(2H, d, J=8.7Hz), 6.99–7.31(4H, m), 7.42(2H, d, J=8.7Hz) |
| 167 | 1.57–1.94(2H, m), 2.02–2.35(2H, m), 2.06(3H, s), 2.45–3.24(8H, m), 3.64(1H, m), 3.82(3H, s), 3.98–4.50(5H, m), 4.85–5.06(1H, m), 6.38–6.63(2H, m), 6.97–7.33(5H, m) |
| 168 | 1.67(1H, m), 1.75–1.94(1H, m), 2.00–2.37(2H, m), 2.45–3.26(8H, m), 3.56–3.80(1H, m), 3.81(3H, m), 3.94–4.47(5H, m), 4.66–5.27(3H, m), 6.44–6.55(2H, m), 6.98–7.32(5H, m) |
| 169 | 1.55–1.77(1H, m), 1.77–1.94(1H, m), 1.94–2.33(2H, m), 2.33–3.24(8H, m), 3.35(3H, s), 3.42–3.77(3H, m), 3.81(3H, m), 3.95–4.27(2H, m), 4.40(1H, m), 4.87–5.07(1H, m), 6.42–6.62(2H, m), 6.98–7.32(5H, m) |
| 170 | 1.53–1.77(1H, m), 1.77–1.98(1H, m), 2.32–3.33(8H, m), 3.43(3H, s), 3.56–3.99(3H, m), 3.81(3H, s), 3.99–4.30(2H, m), 4.40(1H, m), 4.85–5.06(1H, m), 6.49–6.66(2H, m), 6.97–7.43(5H, m) |
| 171 | 1.62–1.82(1H, m), 1.82–2.02(1H, m), 2.03–2.40(2H, m), 2.40–3.26(10H, m), 3.68–3.90(1H, m), 3.81(3H, s), 3.97(1H, m), 4.02–4.26(2H, m), 4.36–5.10(1H, m), 6.43–6.57(2H, m), 7.00–7.29(5H, m) |
| 172 | 1.26–1.98(12H, m), 2.20(2H, t, J=7.5Hz), 2.53–3.27(8H, m), 3.77–5.05(2H, m), 3.97(2H, t, J=6.4Hz), 4.37(1H, m), 6.01(1H, brs), 6.05(1H, brs), 6.90(2H, d, J=8.6Hz), 6.99–7.29(4H, m), 7.42(2H, d, J=8.6Hz) |
| 173 | 1.26(3H, t, J=7.1Hz), 1.54–1.75(1H, m), 175–1.96(1H, m), 2.03–2.33(2H, m), 2.44–3.24(10H, m), 3.57–3.78(1H, m), 3.80(3H, s), 4.01(2H, t, J=6.3Hz), 4.14(2H, q, J=7.1Hz), 4.39(1H, m), 4.82–5.04(1H, m), 6.40–6.59(2H, m), 6.98–7.33(5H, m) |
| 174 | 1.10–2.06(12H, m), 2.23(2H, t, J=7.5Hz), 2.42–3.24(8H, m), 3.67–5.15(2H, m), 3.90(2H, d, J=5.2Hz), 3.97(2H, t, J=6.4Hz), 4.37(1H, m), 6.09(1H, brs), 6.90(2H, d, J=8.6Hz), 6.97–7.30(4H, m), 7.41(2H, d, J=8.6Hz) |
| 175 | 1.27(3H, t, J=7.1Hz), 1.39(3H, d, J=7.2Hz), 1.63–1.95(2H, m), 2.14(2H, quint, J=6.5Hz), 2.43(2H, t, J=6.5Hz), 2.54–3.10(8H, m), 3.80–5.15(2H, m), 4.04(2H, t, J=6.5Hz), 4.19(2H, q, J=7.1Hz), 4.39(1H, m), 4.57(1H, quint, J=7.2Hz), 6.29(1H, d, J=7.2Hz), 6.90(2H, d, J=8.7Hz), 6.99–7.29(4H, m), 7.42(2H, d, J=8.7Hz) |
| 176 | 1.18–1.54(6H, m), 1.54–1.93(6H, m), 2.32(2H, t, J=7.4Hz), 2.54–3.10(8H, m), 3.67(3H, s), 3.80–5.05(2H, m), 3.97(2H, t, J=6.5Hz), 4.40(1H, m), 6.70(2H, d, J=8.6Hz), 6.99–7.27(4H, m), 7.43(2H, d, J=8.6Hz) |
| 177 | 1.62–1.96(2H, m), 2.52–3.18(8H, m), 3.68–4.42(6H, m), 3.81(3H, m), 4.80–5.05(1H, m), 6.47–6.64(2H, m), 6.99–7.29(5H, m) |
| 178 | 1.54–1.93(2H, m), 2.04(3H, s), 2.27–3.28(8H, m), 3.56–3.80(1H, m), 3.81(3H, s), 4.00–4.73(5H, m), 4.83–5.05(1H, m), 6.49–6.65(2H, m), 6.98–7.36(4H, m) |
| 179 | 1.52–1.98(2H, m), 2.12(2H, quint, J=6.5Hz), 2.45(2H, t, J=6.5Hz), 2.54–3.24(8H, m), 3.65–5.18(2H, m), 3.89(2H, d, J=5.2Hz), 4.02(2H, t, J=6.5Hz), 4.36(1H, m), 6.00(1H, brs), 6.61(1H, brs), 6.89(2H, d, J=8.6Hz), 6.99–7.29(5H, m), 7.40(2H, d, J=8.6Hz) |
| 180 | 1.57–1.94(2H, m), 2.12(2H, quint, J=6.6Hz), 2.43(2H, t, J=6.6Hz), 2.54–3.14(8H, m), 3.28(1H, m), 3.76(3H, m), 4.00(2H, d, J=3.8Hz), 4.01(2H, t, J=6.6Hz), 4.10–5.00(1H, m), 4.37(1H, m), 4.65(1H, dt, J=7.6, 3.8Hz), 6.74(1H, d, J=7.6Hz), 6.91(2H, d, J=8.7Hz), 6.99–7.29(4H, m), 7.42(2H, d, J=8.7Hz) |
| 181 | 1.22–1.94(18H, m), 2.31(2H, t, J=7.5Hz), 2.42–3.17(8H, m), 3.66(3H, s), 3.80–5.10(2H, m), 3.97(2H, t, J=6.5Hz), 4.40(1H, m), 6.90(2H, d, J=8.6Hz), 6.99–7.28(4H, m), 7.43(2H, d, J=8.6Hz) |
| 182 | 0.9–1.4(3H, s), 1.5–1.8(1H, m), 2.3–2.7(3H, m), 2.8–3.3(4H, m), 3.3–4.0(8H, m), 4.2–4.5(1H, m), 4.6–4.9(1H, br), 6.4–6.6(2H, m), 7.0–7.4(5H, m) |
| 183 | 1.12(3H, d, J=6.9Hz), 1.6–1.8(1H, m), 2.4–2.7(3H, m), 2.8–2.9(2H, m), 3.00(6H, s), 2.9–3.4(3H, m), 4.1–4.5(3H, m), 6.68(2H, d, J=8.8Hz), 7.0–7.3(4H, m), 7.40(2H, d, J=8.8Hz) |
| 184 | 1.6–1.8(6H, m), 2.1–2.3(3H, br), 2.3–2.4(6H, br), 2.7–2.9(2H, m), 2.92(3H, s), 3.0–3.2(2H, m), 6.3–6.5(1H, m), 6.9–7.1(2H, m), 7.2–7.3(1H, m), 7.25(2H, d, J=8.5Hz), 7.56(2H, d, J=8.5Hz) |
| 185 | 2.1–2.3(1H, m), 2.5–2.9(5H, m), 3.3–4.2(10H, m), 5.0–5.2(1H, m), 6.4–6.6(2H, m), 7.0–7.2(2H, m) |
| 186 | 2.1–2.3(1H, m), 2.5–2.9(5H, m), 2.99(6H, s), 3.6–4.3(4H, m), |

TABLE 2-continued

| No. | NMR (CDCl₃) δ value |
|---|---|
| 187 | 4.8–5.0(1H, br), 6.6–6.7(2H, m)<br>2.1–2.4(1H, m), 2.5–3.0(8H, m),<br>3.3–4.2(7H, m), 5.0–5.2(1H, m),<br>6.7–7.1(4H, m), 7.1–7.3(3H, m) |
| 188 | 1.22(3H, d, J=7.1Hz), 1.5–1.7(1H, m),<br>2.3–2.5(1H, m), 2.5–3.3(9H, m),<br>4.1–4.3(1H, m), 6.9–7.1(1H, m),<br>7.1–7.3(3H, m) |
| 189 | 1.6–2.0(3H, m), 2.5–2.6(8H, m),<br>3.6–3.9(2H, m), 4.0–4.3(1H, m),<br>6.9–7.1(1H, m), 7.1–7.3(3H, m) |
| 190 | 2.1–2.4(2H, m), 2.5–2.7(2H, m),<br>2.7–3.1(3H, m), 3.1–3.3(1H, m),<br>3.3–3.6(2H, m), 3.9(1H, s),<br>4.6–4.8(1H, m), 7.0–7.3(4H, m) |
| 191 | 1.65–1.97(2H, m), 2.40–2.92(9H, m),<br>3.15–3.34(2H, m), 3.78(3H, s),<br>4.25–4.49(1H, m), 6.67–6.72(2H, m),<br>7.16(1H, d, J=8.9Hz) |
| 192 | 1.55–1.85(3H, m), 2.30(3H, s),<br>2.36–2.90(8H, m), 3.15–3.32(2H, m),<br>4.23–4.48(1H, m), 6.90–7.06(2H, m),<br>7.11(1H, d, J=8.1Hz) |
| 193 | 1.63–1.95(3H, m), 2.36(3H, s),<br>2.43–2.90(8H, m), 3.13–3.31(2H, m),<br>4.18–4.40(1H, m), 6.81(1H, d, J=7.5Hz),<br>6.95–7.10(2H, m) |
| 194 | 1.65–1.86(2H, m), 1.98(2H, brs),<br>2.40–2.90(8H, m), 3.15–3.38(2H, m),<br>4.14–4.48(1H, m), 6.70(1H, dt, J=8.2, 2.3Hz),<br>6.94(1H, dd, J=11.0, 2.3Hz),<br>7.09(1H, t, J=8.1Hz) |
| 195 | 1.62–1.95(3H, m), 2.35(3H, s),<br>2.38–2.90(8H, m), 3.10–3.48(3H, m),<br>6.88–7.20(3H, m) |
| 196 | 1.64–1.83(2H, m), 2.19(3H, s),<br>2.40–2.86(8H, m), 4.42–4.62(1H, m),<br>7.08(2H, s), 7.67(1H, s), 7.81(1H, brs) |
| 197 | 1.27(3H, t, J=7.0Hz), 1.62–1.83(2H, m),<br>1.91(1H, brs), 2.30–3.32(9H, m),<br>4.23–4.45(1H, m), 6.96–7.30(4H, m) |
| 198 | 1.67–1.86(2H, m), 2.21(1H, brs),<br>2.43–2.83(8H, m), 2.95(6H, s),<br>3.15–3.32(2H, m), 4.16–4.40(1H, m),<br>6.41(1H, dd, J=8.3, 2.3Hz),<br>6.57(1H, d, J=2.3Hz), 7.01(1H, d, J=8.3Hz) |
| 199 | 1.56–1.95(2H, m), 2.43–3.23(8H, m),<br>3.56–3.83(1H, m), 3.67(3H, d, J=9.3Hz),<br>4.23–4.67(1H, m), 4.86–5.05(1H, m),<br>6.26–6.42(2H, m), 6.96–7.35(5H, m),<br>8.57–8.73(1H, m) |
| 200 | 1.60–1.74(1H, m), 1.80–1.93(1H, m),<br>2.31(3H, s), 2.47–3.38(8H, m),<br>3.58–3.75(1H, m), 3.91(3H, d, J=8.9Hz),<br>4.27–4.69(1H, m), 4.88–5.03(1H, m),<br>6.67–6.91(2H, m), 6.96–7.30(5H, m) |
| 201 | 1.52–2.10(6H, m), 2.45–3.10(11H, m),<br>3.72–5.10(5H, m), 6.90(2H, d, J=8.7Hz),<br>6.97–7.32(4H, m), 7.43(2H, d, J=8.7Hz) |
| 202 | 1.26(3H, t, J=7.5Hz), 1.62–1.98(2H, m),<br>2.35–3.28(10H, m), 3.57–3.98(7H, m),<br>4.41(1H, brs), 4.85–5.05(1H, m),<br>6.40–6.60(2H, m), 6.82–7.00(2H, m),<br>7.08(1H, d, J=7.5Hz), 7.16–7.35(1H, m) |
| 203 | 1.58–2.00(2H, m), 2.42–3.25(8H, m),<br>3.60–4.02(10H, m), 4.20–4.70(1H, m),<br>4.86–5.05(1H, m), 6.42–6.80(4H, m),<br>7.07(1H, d, J=8.2Hz), 7.13–7.38(1H, m) |
| 204 | 1.58–2.02(2H, m), 2.50(3H, s),<br>2.40–3.28(8H, m), 3.57–4.00(4H, m),<br>4.15–4.78(1H, m), 4.87–5.08(1H, m),<br>6.65–7.38(6H, m) |
| 205 | 1.67–1.93(2H, m), 2.33(2H, quint, J=6.1Hz),<br>2.48–3.15(8H, m), 3.61(2H, t, J=6.4Hz),<br>3.78–5.28(3H, m), 4.14(2H, t, J=5.8Hz),<br>6.92(2H, d, J=8.7Hz), 6.98–7.32(4H, m),<br>7.44(2H, d, J=8.7Hz) |
| 206 | 1.72–2.13(4H, m), 2.45(2H, t, J=7.0Hz),<br>2.47–3.35(10H, m), 3.90–4.35(4H, m),<br>6.55(2H, d, J=8.6Hz), 6.93–7.30(6H, m),<br>7.33(2H, d, J=8.6Hz), 8.95(1H, brs) |
| 207 | 1.44–1.97(8H, m), 2.48–3.30(10H, m),<br>2.96(3H, s), 3.83–5.02(4H, m),<br>3.98(2H, t, J=6.1Hz), 6.89(2H, d, J=8.7Hz),<br>6.98–7.35(4H, m), 7.42(2H, d, J=8.7Hz) |
| 208 | 1.46–2.02(8H, m), 1.97(3H, s),<br>2.48–3.37(10H, m), 3.80–5.09(3H, m),<br>3.97(2H, t, J=6.2Hz), 5.87(1H, brs),<br>6.89(2H, d, J=8.8Hz), 6.95–7.39(4H, m),<br>7.42(2H, d, J=8.8Hz) |
| 209 | 1.52–2.03(6H, m), 1.97(3H, s),<br>2.47–3.40(10H, m), 3.81–4.96(3H, m),<br>3.99(2H, t, J=6.1Hz), 5.86(1H, brs),<br>6.88(2H, d, J=8.7Hz), 6.94–7.38(4H, m),<br>7.42(2H, d, J=8.7Hz) |

Example 384

Acetic acid (30 ml) and 1-(1-benzyl-3-methyl-4-piperidinyl)carbostyril (2.1 g) are added to 10% palladium-carbon (0.5 g) and the mixture is subjected to catalytic reduction at 80° C. under atmospheric pressure. After the catalytic reduction, 10% palladium-carbon is filtered off and the filtrate is concentrated under reduced pressure. Water is added to the residue and the mixture is basified with aqueous sodium hydroxide solution and then extracted with dichloromethane. After washed with water, the extract is dried with magnesium sulfate and the solvent is distilled off under reduced pressure to give 1-(3-methyl-4-piperidinyl)-3,4-dihydrocarbostyril (1.01 g).

NMR (CDCl₃) δ ppm: 1.22 (3H, d, J=7.1 Hz), 1.5–1.7 (1H, m), 2.3–2.5 (1H, m), 2.5–3.3 (9H, m), 4.1–4.3 (1H, m), 6.9–7.1 (1H, m), 7.1–7.3 (3H, m)

The compounds of the above Examples 1–9, 11–164, 169–350, 352–383C are obtained in the same manners as in Example 384.

Example 385

Conc. sulfuric acid (8 ml) is added to N-(β-ethoxyaryloyl)-N-(1-benzoyl-4-piperidinyl)aniline (0.8 g) and the mixture is reacted at 60° C. for 30 minutes. The reaction mixture is poured into ice-water and then extracted with dichloromethane. The solvent is concentrated and the resulting residue is purified by silica gel column chromatography (solvent; dichloromethane:methanol=50:1) to give 1-(1-benzoyl-4-piperidinyl)carbostyril (0.53 g).

NMR (CDCl₃) δ ppm: 1.60–2.02 (2H, m), 2.62–3.41 (4H, m), 3.73–4.26 (1H, m), 4.50–5.72 (2H, m), 6.64 (1H, d, J=9.4 Hz), 7.15–7.70 (10H, m)

The compounds of the above Examples 10 and 166–168 are obtained in the same manners as in Example 385.

Example 386

Ethanol (10 ml) and 10% aqueous sodium hydroxide solution (12 ml) are added to 1-(1-benzoyl-4-piperidinyl)carbostyril (1.0 g) and the mixture is refluxed with heating for 7 hours. After concentration, water is added thereto and the mixture is extracted with dichloromethane. The dichloromethane layer is collected by filtration and water is added thereto. The mixture is acidified with diluted hydrochloric acid. The aqueous layer is basified with diluted aqueous sodium hydroxide solution, extracted with dichloromethane and then concentrated to give 1-(4-piperidinyl)carbostyril (0.58 g).

NMR (CDCl₃) δ ppm: 1.62–2.03 (3H, m), 2.55–3.03 (4H, m), 3.14–3.50 (2H, m), 4.68–5.85 (1H, br), 6.65 (1H, d, J=9.4 Hz), 7.19 (1H, t, J=7.4 Hz), 7.35–8.00 (4H, m)

Using the suitable starting materials, the compounds of the above Examples 156, 158, 171, 186, 351–361 and the following Examples 580, 581 and 577A are obtained in the same manners as in Example 386.

Example 387

1-(4-Piperidinyl)-3,4-dihydrocarbostyril (0.2 g) is added to conc. sulfuric acid (5 ml) and thereto is added fuming nitric acid (0.1 ml) under ice cooling. The mixture is stirred at room temperature for 30 minutes, and then the reaction mixture is poured into ice-water. The mixture is basified and extracted with dichloromethane. The solvent is concentrated to give 6-nitro-1-(4-piperidinyl)-3,4-dihydrocarbostyril (0.2 g).

NMR (CDCl₃) δ ppm: 1.65–2.10 (3H, m), 2.44–3.45 (10H, m), 4.26–4.55 (1H, m), 7.34 (1H, d, J=8.9 Hz), 8.00–8.22 (2H, m)

Using the suitable starting materials, the compounds of the above Examples 3, 38, 43, 163, 175, 188, 195, 379 and the following Example 510 are obtained in the same manners as in Example 387.

Example 388

A mixture of 10% palladium-carbon (0.4 g) and acetic acid (50 ml) is added to 6-nitro-1-[1-(2,4-dimethoxybenzoyl)-4-piperidinyl]-3,4-dihydrocarbostyril (4.0 g) and the mixture is subjected to catalytic reduction at 70° C. for 1 hour. The catalyst is filtered off and the filtrate is concentrated. The resulting residue is basified with 10% aqueous sodium hydroxide solution and extracted with dichloromethane. The solvent is concentrated and the resulting residue is purified by silica gel column chromatography (solvent; dichloromethane:methanol=20:1) to give 6-amino-1-[1-(2,4-dimethoxybenzoyl)-4-piperidinyl]-3,4-dihydrocarbostyril (1.9 g).

NMR (CDCl₃) δ ppm: 1.50–1.93 (2H, m), 2.34–3.20 (8H, m), 3.30–4.15 (9H, m), 4.22–4.75 (1H, m), 4.85–5.03 (1H, m), 6.42–6.63 (4H, m), 6.82–7.33 (2H, m)

Using the suitable starting materials, the compounds of the above Examples 48, 80, 182, 176, 192, 380 and the following Examples 485, 511 are obtained in the same manners as in Example 388 and in following Example 401.

Example 389

Dichloromethane (10 ml) and triethylamine (0.15 ml) are added to 6-amino-1-[1-(2,4-dimethoxybenzoyl)-4-piperidinyl]-3,4-dihydrocarbostyril (0.3 g). Acetic anhydride (0.2 ml) is added thereto and the mixture is stirred at room temperature for 1 hour. Water is added to the reaction mixture and extracted with dichloromethane. After concentration, the residue is purified by silica gel column chromatography (solvent; chloroform:methanol=20:1) and further recrystallized from ethanol to give 6-acetylamino-1-[1-(2,4-dimethoxybenzoyl)-4-piperidinyl]-3,4-dihydrocarbostyril (0.25 g) as white powder, m.p. 271°–272° C.

The compounds of the above Examples 160, 267, 359 and the following Examples 484 and 486 are obtained in the same manners as in Example 389.

Example 390

7-Fluoro-1-(4-piperidinyl)-3,4-dihydrocarbostyril (2.37 g), 2-methoxy-4-ethoxybenzoic acid (2.43 g) and bis(2-oxo-oxazolydinyl)phosphinyl chloride (3.65 g) are dissolved in dichloromethane (50 ml) and thereto is added dropwise triethylamine (4 ml). The mixture is stirred at room temperature overnight and poured into water. The mixture is extracted with dichloromethane, dried with sodium carbonate and then purified by silica gel column chromatography (solvent; n-hexane:ethyl acetate=1:1). The resultant is recrystallized from ethanol/water to give 7-fluoro-1-[1-(2-methoxy-4-ethoxybenzoyl)-4-piperidinyl]-3,4-dihydrocarbostyril (2.5 g) as white powder, m.p. 159°–161° C.

Example 391

1-(4-Piperidinyl)-3,4-dihydrocarbostyril (500 mg) and triethylamine (0.6 ml) are dissolved in dichloromethane (10 ml) and thereto is added dropwise ethyl chlorocarbonate (0.31 ml) gradually. The mixture is stirred at room temperature for 2 hours and poured into water. The mixture is extracted with chloroform, dried with sodium carbonate and purified by silica gel column chromatography (solvent; n-hexane:ethyl acetate=3:1). The resultant is recrystallized from ethanol/n-hexane to give 1-(1-ethoxycarbonyl-4-piperidinyl)-3,4-dihydrocarbostyril (0.1 g) as white powder, m.p. 82°–83° C.

Example 392

1-(4-Piperidinyl)-3,4-dihydrocarbostyril (500 mg), triethylamine (1.2 ml) and pyrrole-2-carboxylic acid (314 mg) are dissolved in dichloromethane (10 ml) and thereto is added dropwise diethyl cyanophosphate (0.82 ml) under ice cooling. The mixture is stirred with ice cooling for 1 hour and then stirred at room temperature for 2 hours. The mixture is poured into water, extracted with chloroform, dried with sodium carbonate and purified by silica gel column chromatography (solvent; dichloromethane:methanol=20:1). The resultant is recrystallized from n-hexane/diethyl ether to give 1-[1-(2-pyrrolylcarbonyl)-4-piperidinyl]-3,4-dihydrocarbostyril (0.2 g), as white powder, m.p. 161°–162° C. (decomposed).

Example 393

1-(4-Piperidinyl)-3,4-dihydrocarbostyril (0.8 g) is dissolved in dichloromethane (20 ml) and thereto is added phenylisocyanate (0.57 ml) and the mixture is stirred at room temperature for 4 hours. The solvent is concentrated and the residue is purified by silica gel column chromatography (solvent; n-hexane:ethyl acetate=5:1) and recrystallized from n-hexane/ethanol to give 1-(1-anilinocarbonyl-4-piperidinyl)-3,4-dihydrocarbostyril (0.8 g), as white powder, m.p. 194°–196° C.

The compounds of the above Examples 1–155, 157, 159–167, 169–170, 173–182, 187–232, 234–235, 241–243, 246–290, 294–346, 348–350, 362–383C and the following Examples 436, 438, 440, 442, 443–460, 465–475, 482–579 and 582–587 are obtained in the same manners as in Examples 390–393.

Example 394

1-[1-(4-α-t-Butoxycarbonylaminophenylacetyl)-4-piperidinyl]-3,4-dihydrocarbostyril (400 mg) is dissolved in formic acid (5 ml) and the mixture is stirred at room temperature overnight. The solvent is distilled off under reduced pressure and the resulting oily product is purified by silica gel column chromatography (solvent; dichloromethane:methanol=8:1). The resultant is recrystallized from diethyl ether to give 1-[1-(4-α-aminophenylacetyl)-4-piperidinyl]-3,4-dihydrocarbostyril (0.22 g), as white powder, m.p. 116°–120° C.

Example 395

A mixture (5 ml) of hydrobromic acid and acetic acid (35% solution) is added to 1-{1-[4-(N-t-butoxycarbonyl-N-methylamino)benzoyl]-4-piperidinyl}-3,4-dihydrocarbostyril (1.8 g) and the mixture is stirred at room temperature overnight. The reaction mixture is poured into water and the pH value thereof is adjusted to pH 12-14 by adding potassium carbonate. The mixture is extracted with chloroform, dried with sodium carbonate and then purified by silica gel column chromatography (solvent; n-hexane:ethyl acetate=1:1). The resultant is crystallized from n-hexane/ethanol to give 1-{1-[4-(N-methylamino)benzoyl]-4-piperidinyl}-3,4-dihydrocarbostyril (1.2 g), as white powder, m.p. 184°-186° C.

Example 396

1-[1-(1-Benzyloxycarbonyl-2-pyrrolidinylcarbonyl)-4-piperidinyl]-3,4-dihydrocarbostyril (0.87 g) is dissolved in ethanol (20 ml) and thereto is added 5% palladium-carbon (0.1 g). The mixture is stirred at room temperature under 1 atm. under hydrogen atmosphere. After the completion of the reaction, the catalyst is filtered off and the filtrate is concentrated. The resultant is purified by silica gel column chromatography (solvent; dichloromethane:methanol=8:1) to give 1-[1-(2-pyrrolidinylcarbonyl)-4-piperidinyl]-3,4-dihydrocarbostyril (205 mg).

NMR (CDCl$_3$) δ ppm: 1.72-2.29 (6H, m), 2.39-2.92 (7H, m), 3.10-3.32 (1H, m), 3.35-3.65 (2H, m), 3.82-4.25 (2H, m), 4.52-4.90 (2H, m), 6.30-7.35 (5H, m)

Example 397

1-[1-(4-Benzyloxybenzoyl)-4-piperidinyl]-3,4-dihydrocarbostyril (4.76 g) is dissolved in methanol (100 ml) and thereto is added 5% palladium-carbon (1 g). The mixture is stirred at room temperature under 1 atm. under hydrogen atmosphere. After the completion of the reaction, the catalyst is filtered off and the filtrate is concentrated. The resultant is purified by silica gel column chromatography (solvent; n-hexane:ethyl acetate=1:1) and further recrystallized from n-hexane/ethanol to give 1-[1-(4-hydroxybenzoyl)-4-piperidinyl]-3,4-dihydro carbostyril (2.5 g) as white powder, m.p. 182°-183° C.

Example 398

60% Sodium hydride (0.34 g) is washed with n-hexane and thereto is added dimethylformamide (20 ml). Thereto are added 1-[2-94-hydroxybenzoyl)-4-piperidinyl]-3,4-dihydrocarbostyril (1 g), 2-chloroethyl-dimethylamine hydrochloride (0.66 g) and sodium iodide (1.7 g) and the mixture is stirred at 50°-60° C. under argon atmosphere for 2 hours. Then, the mixture is further stirred at room temperature overnight. The reaction mixture is poured into water and extracted with ethyl acetate/toluene, dried with sodium carbonate. The resultant is purified by silica gel column chromatography (solvent; n-hexane:ethyl acetate=1:1) to give 1-{1-[1-(2-dimethylaminoethoxy)benzoyl]-4-piperidinyl}-3,4-dihydrocarbostyril (0.362 g).

NMR (DMSO-d$_6$) δ ppm: 1.72-1.94 (2H, m), 2.48-3.26 (10H, m), 2.66 (6H, s), 3.77-5.28 (5H, m), 6.94-7.45 (6H, m)

Example 399

1-[1-(4-Hydroxybenzoyl)-4-piperidinyl]-3,4-dihydrocarbostyril (500 mg), prenyl bromide (0.5 ml) and 1,8-diazabicyclo[5.4.0]-undecene-7 (0.65 ml) are dissolved in isopropanol (10 ml) and the mixture is refluxed with heating for 4 hours. The solvent is distilled off under reduced pressure and the residue is purified by silica gel column chromatography (solvent; n-hexane:ethyl acetate=2:1) to give 1-{1-[4-(2-isopentenyloxy)benzoyl]-4-piperidinyl}-3,4-dihydrocarbostyril (0.159 g).

NMR (CDCl$_3$) δ ppm: 1.56-1.79 (2H, m), 1.75 (3H, s), 1.80 (3H, s), 2.47-3.14 (8H, m), 3.93-5.05 (3H, m), 4.53 (2H, d, J=6.8 Hz), 5.40-5.57 (1H, m), 6.83-7.53 (8H, m)

The compounds of the above Examples 10, 19, 23, 26, 30, 31, 33, 38, 44, 45, 47, 50, 54, 55, 56, 61, 66, 72, 74, 76, 84, 89, 91, 94, 95, 98, 99, 102, 106, 108-110, 113-115, 118-119, 121-155, 157, 159-164, 166, 167, 170, 172-180, 189, 194, 209, 212, 222-225, 227, 228, 230-232, 234-235, 241-243, 246-251, 254-256, 260-280, 285, 288-294, 296, 297, 299-328, 332-335, 338, 345, 348, 350, 362-365, 367-373, 377-378, 383A-383C and the following Examples 436, 438, 440, 442, 445, 472, 475, 482-577, 582-587 are obtained in the same manner as in Examples 398 and 399.

Example 400

Trifluoroacetic acid (0.21 ml) is added dropwise with stirring to a mixture of 1-{1-[4-(3-hydroxypropoxy)benzoyl]-4-piperidinyl}-3,4-dihydrocarbostyril (0.51 g), NaOCN (0.16 g), toluene (5 ml) and chloroform (5 ml) at room temperature. After adding, the mixture is stirred at room temperature overnight. Ethyl acetate is added to the reaction mixture and the mixture is washed with saturated aqueous sodium hydrogen carbonate solution, water and saline solution successively and then dried with sodium sulfate. The solvent is distilled off and the resulting residue is purified by silica gel column chromatography (solvent; dichloromethane:methanol=100:1) to give 1-{1-[4-(3-carbamoyloxypropoxy)benzoyl-4-piperidinyl}-3,4-dihydrocarbostyril (0.15 g).

NMR (CDCl$_3$) δ ppm: 1.60-2.32 (4H, m), 2.41-3.27 (8H, m), 3.71-5.15 (5H, m), 4.07 (2H, t, J=6.2 Hz), 4.26 (2H, t, J=6.2 Hz), 6.98 (2H, d, J=8.6 Hz), 6.99-7.40 (4H, m), 7.43 (2H, d, J=8.6 Hz)

The compounds of the above Examples 128, 313 and the following Examples 470, 569 are obtained in the same manners as in Example 400.

Example 401

1-[1-(4-Nitrobenzoyl)-4-piperidinyl-3,4-dihydrocarbostyril (4.21 g) is dissolved in ethanol (100 ml) and thereto is added 5% palladium-carbon (1 g) and the mixture is stirred at room temperature under 1 atm. under hydrogen atmosphere. After the reaction, the catalyst is removed by fileration. The filtrate is concentrated and the residue is purified by silica gel column chromatography (solvent: dichloromethane:methanol=20:1) and recrystallized from n-hexane/ethanol to give 1-[1-(4-aminobenzoyl)-4-piperidinyl]-3,4-dihydrocarbostyril (2.1 g) as white powder, m.p.: 198°-199° C.

Example 402

1-[1-(4-Methoxycarbonylbenzoyl)-4-piperidinyl]-3,4-dihydrocarbostyril (6.33 g) and sodium hydroxide (1.94 g) are dissolved in methanol (100 ml) and the mixture is stirred at room temperature overnight. After the solvent is concentrated, water is added to the residue and the mixture is extracted with diethyl ether. The aqueous layer is adjusted to pH 1 by adding conc. hydrochloric acid and extracted with ethyl acetate. The extract is dried with magnesium sulfate, concentrated and recrystallized from n-hexane/ethanol to give 1-[1-(4-carboxybenzoyl)-4-piperidinyl]-3,4-dihydrocarbostyril (4.5 g ) as white powder, m.p.: 232°–235° C.

Using the suitable starting materials, the compounds of the above Examples 260, 275, 301, 303, 304, 308, 310, 316, 336, 365, 374 and the following Example 482 are obtained in the same manners as in Example 402.

Example 403

1-{1-[4-(N-methylamino)benzoyl]-4-piperidinyl}-3,4-dihydrocarbostyril (200 mg) is dissolved in dichloromethane (5 ml) and thereto is added α-chloroacetyl chloride (55 μl) under ice cooling. Continually thereto is added triethylamine (0.23 ml) and the mixture is stirred at room temperature overnight. After the solvent is concentrated, the residue is purified by silica gel column chromatography (solvent: n-hexane:ethyl acetate=1:1) and recrystallized from n-hexane/ethanol to give 1-{1-[4-(N-α-chloroacetyl-N-methylamino)benzoyl)-4-piperidinyl]-3,4-dihydrocarbostyril (0.18 g) as white powder, m.p.: 220°–222° C. (decomposed).

Example 404

1-[1-(4-Aminobenzoyl)-1-piperidinyl]-3,4-dihydrocarbostyril (4 g) is dissolved in dichloromethane (100 ml) and thereto is added trifluoroacetic anhydride (2.1 ml). Under ice cooling, thereto is added dropwise triethylamine (4.78 ml) and the mixture is stirred at the same temperature for 2 hours and then at room temperature overnight. The reaction mixture is poured into water and extracted with chloroform and dried with magnesium sulfate. The resulting residue is purified by silica gel column chromatography (solvent: n-hexane:ethyl acetate=1:1) and recrystallized from n-hexane to give 1-[1-(4-trifluoroacetylamino)-4-piperidinyl]-3,4-dihydrocarbostyril (3.8 g) as light red powder, m.p.: 104°–107° C.

Example 405

A mixture of 1-[1-(2-aminobenzoyl)-4-piperidinyl]-3,4-dihydrocarbostyril (0.96 g), acetic anhydride (10 ml) and conc. sulfuric acid (0.1 ml) is stirred at room temperature for 2 hours. The reaction mixture is basified with 1N aqueous sodium hydroxide solution and extracted with ethyl acetate. The extract is washed successively with saturated aqueous sodium hydrogen carbonate solution, 1N hydrochloric acid and saturated saline solution and dried with sodium sulfate. After the solvent is distilled off, the residue is recrystallized from ethyl acetate/diethyl ether to give 1-[1-(2-acetylaminobenzoly)-4-piperidinyl]-3,4-dihydrocarbostyril (0.55 g) as colorless needles, m.p.: 141°–143° C.

Using the suitable starting materials, the compounds of the above Example 32, 57–59, 67, 78, 87, 88, 116, 129, 130, 137, 140–141, 145, 149–152, 155, 174, 187, 200, 246, 254, 255, 288, 291, 292, 382, 383, 383B, 383C and the following Examples 451, 452, 463, 467, 468, 469, 488, 500–503, 506–508, 510, 511, 513–515, 519–521, 523, 536, 537, 587 are obtained in the same manners as in Examples 403–405.

Example 406

1-[1-(3-Ethoxycarbonylbenzoyl)-4-piperidinyl]-3,4-dihydrocarbostyril (0.5 g), aqueous ammonia (10 ml) and ammonium chloride (the affective amount as a catalyst) are dissolved in ethanol (10 ml) and the mixture is stirred at 110°–130° C. for 10 hours in an autoclave. Ethanol is distilled off under reduced pressure and the residue is extracted with methylene chloride. The organic layer is washed with water and saturated saline solution, dried with sodium sulfate and concentrated. The solvent is distilled off and the resulting residue is purified by silica gel column chromatography (solvent: methylene chloride:methanol=10:1) to give 1-[1-(3-carbamoylbenzoyl)-4-piperidinyl]-3,4-dihydrocarbostyril (0.15 g).

NMR (CDCl$_3$) δ ppm: 1.59–2.11 (2H, m), 2.48–3.33 (8H, m), 3.70–5.15 (3H, m), 5.58–6.60 (2H, m), 6.97–8.05 (8H, m)

Using the suitable starting materials, the compounds of the above Examples 276, 294, 300, 305, 307, 309, 313, 317–319, 321, 326, 329 and 344 are obtained in the same manners as in Example 406.

Example 407

A mixture of 1-{1-[4-3-methylaminopropoxy)benzoyl]-4-piperidinyl}-3,4-dihydrocarbostyril (0.5 g), propyl bromide (0.13 ml), sodium hydrogen carbonate (0.15 g) and acetonitrile (10 ml) is stirred at room temperature for 8 hours. Further thereto are added propyl bromide (0.13 ml) and sodium hydrogen carbonate (0.15 g) and the mixture is stirred with heating at 60° C. for 8 hours. The solvent is distilled off and the resulting residue is extracted with ethyl acetate. The extract is washed successively with saturated sodium hydrogen carbonate, water and saline solution and dried with sodium sulfate. The solvent is distilled off and the resulting residue is purified by silica gel column chromatography (solvent: dichloromethane:methanol=20:1) to give 1-[4-{4-[3-(N-methyl-N-propylamino)propoxy]benzoyl}-4-piperidinyl]-3,4-dihydrocarbostyril (0.15 g).

NMR (CDCl$_3$) δ ppm: 0.91 (3H, t, J=5.8 Hz), 1.42–3.31 (2H, m), 2.33 (3H, s), 3.88–5.15 (3H, m), 4.05 (2H, t, J=5 Hz), 6.91 (2H, d, J=7 Hz), 6.95–7.38 (4H, m), 7.42 (2H, d, J=7 Hz)

Example 408

A mixture of 1-{1-[4-(3-aminopropoxy)benzoyl]-4-piperidinyl}-3,4-dihydrocarbostyril (1.4 g), benzaldehyde (0.42 ml) and methanol (15 ml) is stirred at room temperature for 3 hours and cooled with ice. Thereto is added sodium boron hydride (0.21 g) and the mixture is stirred under ice cooling for 2 hours and then allowed to stand a room temperature overnight. The solvent is distilled off and water is added to the resulting residue and the mixture is extracted with ethyl acetate. The extract is washed successively with saturated sodium hydrogen carbonate, water and saline solution, dried with sodium sulfate and then the solvent is distilled off. The resulting residue is purified by silica gel column chromatography (solvent: methanol:dichloromethane=1:100) to give 1-{1-[4-benzylaminopropoxy)-benzoyl]-4-piperidinyl}-3,4-dihydrocarbostyril (1.02 g).

NMR (CDCl$_3$) δ ppm: 1.60–2.15 (5H, m), 2.47–3.18 (10H, m), 3.82 (2H, s), 3.95–5.11 (3H, m), 4.08 (3H, t, J=6.2 Hz), 6.89 (2H, d, J=8.5 Hz), 6.95–7.50 (9H, m), 7.42 (2H, d, J=8.5 Hz)

Example 409

1-[1-(2-Methoxy-4-methylaminobenzoyl)-4-piperidinyl]-3,4-dihydrocarbostyril (500 mg) is dissolved in methanol (10 ml) and thereto is added formaldehyde (0.54 ml) and then thereto is added NaBH₃CN (86.4 mg) under ice cooling. The mixture is stirred under ice cooling for 2 hours and further stirred at room temperature. The reaction mixture is concentrated and to the residue is added saturated aqueous sodium hydrogen carbonate solution. The mixture is extracted with chloroform and dried with sodium sulfate. The solvent is distilled off and the resulting residue is purified by silica gel column chromatography (solvent: n-hexane:ethyl acetate=1:1) and recrystallized from n-hexane/ethanol to give 1-[1-(2-methoxy-4-dimethylaminobenzoyl)-4-piperazinyl]-3,4-dihydrocarbostyril (0.263 g) as white powder, m.p.: 93°–96° C.

Using the suitable starting materials, the compounds of the above Examples 27, 40, 55, 57, 59, 62, 63, 65, 67, 68, 76, 79, 81, 82, 88, 89, 92, 114, 115, 118, 119, 123, 124, 126, 127, 131, 133, 138, 139, 143, 144, 149, 150–152, 169, 184, 185, 187, 190, 198, 199, 214, 231, 236–238, 242–246, 248, 251, 254, 255, 261–263, 265, 268, 270, 283, 285, 287, 291–293, 305, 306, 309, 311, 321, 322, 326, 327, 332, 334, 335, 344, 346, 439, 361, 366, 367, 374, 381, 383A and the following Examples 448, 449, 454, 455, 456, 458, 459, 464, 466, 474A, 489–496, 498, 499, 504, 505, 509, 516–518, 522, 532, 539–546, 550–552, 554–556, 559, 562–565 and 567 are obtained in the same manners as in Examples 407–409.

Example 410

A mixture of 1-[1-{4-[3-(N-benzyl-N-methylamino)propoxy]benzoyl}-4-piperidinyl]-3,4-dihydrocarbostyril (5.3 g), 5% palladium-carbon (0.8 g), ammonium formate (2.6 g) and ethanol (300 ml) is refluxed with heating for 2 hours. The catalyst is filtered off and ethanol is distilled off under reduced pressure. To the residue is added chloroform and the mixture is washed successively with saturated sodium hydrogen carbonate, water and saline solution. Further the mixture is dried with sodium sulfate and the solvent is distilled off. The resulting residue is purified by silica gel column chromatography (solvent: dichloromethane:methanol=20:1→5:1) to give 1-[1-{4-[3-(N-methylamino)propoxy]benzoyl}-4-piperidinyl]-3,4-dihydrocarbostyril (4.37 g).

This product is dissolved in acetone and converted into hydrochloride salt thereof in hydrochloric acid/ethanol. The precipitated crystal is collected by filtration and recrystallized from ethanol/acetone/diethyl ether to give 1-[1-{4-[3-(N-methylamino)propoxy]benzoyl}-4-piperidinyl]-3,4-dihydrocarbostyril hydrochloride as colorless needles, m.p.: 89°–93° C.

Example 411

1-[1-{4-[3-(Phthalimido-1-yl)propoxy]benzoyl}-4-piperidinyl]-3,4-dihydrocarbostyril (9.5 g), hydrazine hydrate (1.03 ml) and ethanol (100 ml) are refluxed with heating for 2.5 hours. After cooling, the mixture is adjusted to pH 1 by adding conc. hydrochloric acid and the precipitated materials are filtered off. Most of ethanol is distilled off from the filtrate and water is added to the residue. The insoluble materials are filtered off and the mother liquid is basified with 5N sodium hydroxide, extracted with ethyl acetate. The organic layer is washed with saturated saline solution and dried with sodium sulfate, concentrated. The residue is purified by silica gel column chromatography (solvent: methylene chloride: methanol=15:1) to give 1-{1-[4-(3-aminopropoxy)benzoyl]-4-piperidinyl}-3,4-dihydrocarbostyril (5.18 g).

NMR (CDCl₃) δ ppm: 1.64–2.10 (4H, m), 2.97–3.18 (8H, m), 2.92 (2H, t, J=6.8 Hz), 4.08 (2H, t, j=6.1 Hz), 4.10–5.15 (3H, m), 6.82–7.58 (8H, m)

Using the suitable starting materials, the compounds of the above Examples 136, 148, 154 and the following Examples 473 and 586 are obtained in the same manner as in Example 411.

Example 412

1-{1-[4-(3-Aminopropoxy)benzoyl]-4-piperidinyl}-3,4-dihydrocarbostyril (0.5 g), methylisocyanate (0.15 ml) and acetone (10 ml) are heated at 100° C. for 18 hours in an autoclave. Acetone is distilled off and the residue is purified by silica gel column chromatography (solvent: methylene chloride:methanol=100-50:1) to give 1-{1-[4-(3-(3-methylureido)propoxy)benzoyl]-4-piperidinyl}-3,4-dihydrocarbostyril (0.19 g).

NMR (CDCl₃) δ ppm: 1.55–2.20 (4H, m), 2.49–3.50 (10H, m), 2.96 (3H, m), 3.90–5.13 (4H, m), 4.09 (2H, t, J=5.7 Hz), 6.90 (2H, d, J=8.7 Hz), 6.95–7.38 (4H, m), 7.43 (2H, d, J=8.7 Hz)

Example 413

A mixture of formic acid (0.19 ml) and acetic anhydride (0.4 ml) is stirred with heating at 50°–60° C. for 1.5 hour. Thereto is added 1-{1-[4-(4-aminobutoxy)benzoyl]-4-piperidinyl}-3,4-dihydrocarbostyril (0.6 g) at room temperature and the mixture is stirred at room temperature for 13 hours. The reaction mixture is poured into ice-water and extracted with ethyl acetate. The extract is washed with aqueous sodium hydrogen carbonate, water and saline solution and dried with sodium sulfate. The solvent is distilled off and the resulting residue is purified by silica gel column chromatography (solvent: dichloromethane:methanol=50:1→25:1) to give 1-{1-[4-(4-formylaminobutoxy)benzoyl]-4-piperidinyl}-3,4-dihydrocarbostyril (0.49 g).

NMR (CDCl₃) δ ppm: 1.55–2.00 (6H, m), 2.45–3.48 (10H, m), 3.76–5.10 (3H, m), 3.99 (2H, t, J=5.7 Hz), 5.74–6.25 (1H, m), 6.78–7.53 (8H, m), 8.15 (1H, s)

Using the suitable starting materials, the compounds of the above Example 130 and the following Examples 488 and 508 are obtained in the same manners as in Example 413.

Example 414

1-[1-(4-Formylbenzoyl)-4-piperidinyl]-3,4-dihydrocarbostyril (500 mg) is dissolved in methanol (10 ml) and thereto is added sodium boron hydride (63 mg) under ice cooling and the mixture is stirred for 2 hours. The solvent is concentrated and the resulting residue is purified by silica gel column chromatography (solvent: n-hexane:ethyl acetate=2:1) and recrystallized from n-hexane/ethanol to give 1-[1-(4-hydroxymethylbenzoyl)-4-piperidinyl]-3,4-dihydrocarbostyril (390 mg) as white powder, m.p.: 138°–139° C.

Using the suitable starting materials, the compounds of the above Examples 83, 85 and the following Examples 444 and 456 are obtained in the same manners as in Example 414.

Example 415

60% Sodium hydride (147 mg) is washed with n-hexane and thereto is added dimethylformamide (10 ml) under argon atmosphere. To the mixture is added 1-[1-(4-trifluoroacetylaminobenzoyl)-4-piperidinyl]-3,4-dihydrocarbostyril (1 g) under ice cooling, and the mixture is stirred for a while and then thereto is added dropwise allyl bromide (0.32 ml). The mixture is stirred under ice cooling for 1 hour and then at room temperature overnight to give 1-{1-[4-(N-trifluoroacetyl-N-allylamino)benzoyl]-4-piperidinyl}-3,4-dihydrocarbostyril. To this product are added water (20 ml) and sodium hydroxide (0.1 g) and the mixture is stirred for 4 hours. The reaction mixture is poured into water and extracted with ethyl acetate/toluene (1:1), dried with sodium carbonate. The solvent is distilled off and the resulting residue is purified by silica gel column chromatography (solvent: n-hexane:ethyl acetate=1:1) to give 1-[1-(4-allylaminobenzoyl)-4-piperidinyl]-3,4-dihydrocarbostyril (0.5 g).

NMR (CDCl$_3$) δ ppm: 1.72–1.92 (2H, m), 2.52–3.12 (8H, m), 3.72–3.88 (2H, m), 4.07 (1H, brs), 4.15–4.76 (3H, m), 5.14–5.35 (2H, m), 5.83–6.04 (1H, m), 6.56–6.62 (2H, m), 6.98–7.37 (6H, m)

Example 416

1-[1-(2-Methoxy-4-methylthiobenzoyl)-4-piperidinyl]-3,4-dihydrocarbostyril (500 mg) is dissolved in methanol (10 ml) and thereto is added a solution of NaIO$_4$ (391 mg) in water (4 ml) and the mixture is stirred at room temperature overnight. The solvent is distilled off under reduced pressure, and water is added to the resulting residue. The mixture is extracted with chloroform, dried with magnesium sulfate. The solvent is distilled off and the resulting residue is purified by silica gel column chromatography (solvent: n-hexane:ethyl acetate=2:1) and recrystallized from n-hexane/ethanol to give 1-[1-(2-methoxy-4-methylsulfinylbenzoyl)-4-piperidinyl]-3,4-dihydrocarbostyril (0.31 g) as white powder, m.p.: 95°–98° C.

Using the suitable starting materials, the compounds of the above Examples 51, 368 and the following Example 570 are obtained in the same manners as in Example 416.

Example 417

1-[1-(2-Methoxy-4-acetyloxybenzoyl)-4-piperidinyl]-3,4-dihydrocarbostyril (0.4 g) and sodium hydroxide (0.5 g) are dissolved in methanol (20 ml) and the mixture is stirred at room temperature for 1 hour. The solvent is concentrated and water is added to the residue, then the mixture is extracted with chloroform, dried with magnesium sulfate. The solvent is distilled off and the resulting residue is purified by silica gel column chromatography (solvent: n-hexane:ethyl acetate=1:1) to give 1-[1-(2-methoxy-4-hydroxybenzoyl)-4-piperidinyl]-3,4-dihydrocarbostyril (0.3 g).

NMR (CDCl$_3$) δ ppm: 1.56–1.95 (2H, m), 2.43–3.23 (8H, m), 3.56–3.83 (1H, m), 3.67 (3H, d, J=9.3 Hz), 4.23–4.67 (1H, m), 4.86–5.05 (1H, m), 6.26–6.42 (2H, m), 6.96–7.35 (5H, m), 8.57–8.73 (1H, m)

Example 418

1-{1-[4-(2-Cyclohexenyloxy)benzoyl]-4-piperidinyl}-3,4-dihydrocarbostyril (200 mg) is dissolved in ethanol (5 ml) and thereto is added 10% palladium-carbon (50 mg). The mixture is stirred at room temperature under atmospheric pressure under hydrogen atmosphere. After the completion of the reaction, the catalyst is removed by filtration. The resulting filtrate is concentrated and purified by silica gel column chromatography (solvent: n-hexane:ethyl acetate=1:1) to give 1-[1-(4-cyclohexyloxybenzoyl)-4-piperidinyl]-3,4-dihydrocarbostyril (174 mg).

NMR (CDCl$_3$) δ ppm: 1.20–2.10 (12H, m), 2.44–3.13 (8H, m), 3.78–5.08 (4H, m), 6.90 (2H, d, J=8.7 Hz), 6.97–7.32 (4H, m), 7.40 (2H, d, J=8.7 Hz)

Example 419

1-[1-(4-Formylbenzoyl)-4-piperidinyl]-3,4-dihydrocarbostyril (1 g), hydroxylamine hydrochloride (580 mg) and sodium acetate (1.6 g) are dissolved in ethanol (20 ml) and water (10 ml) and the mixture is stirred at room temperature overnight. The solvent is concentrated and water is added to the residue. The mixture is extracted with chloroform, dried with sodium carbonate. The solvent is distilled off and the resulting residue is purified by silica gel column chromatography (solvent: n-hexane:ethyl acetate=1:2) and recrystallized from n-hexane/ethanol to give 1-[1-(4-hydroxyiminomethylbenzoyl)-4-piperidinyl]-3,4-dihydrocarbostyril (1 g) as white powder, m.p.: 222°–224° C.

Example 420

1-[1-(4-Aminobenzoyl)-4-piperidinyl]-3,4-dihydrocarbostyril (500 mg) and 2,5-dimethoxytetrahydrofuran (0.19 ml) are refluxed with heating for 2 hours in acetic acid. The solvent is concentrated and the residue is purified by silica gel column chromatography (solvent: n-hexane:ethyl acetate=1:1) and recrystallized from n-hexane to give 1-{1-[4-(1-pyrrolyl)benzoyl]-4-piperidinyl}-3,4-dihydrocarbostyril (228 mg) as light gray powder, m.p.: 153°–156° C.

Example 421

1-[1-(4-Glycidoxybenzoyl)-4-piperidinyl]-3,4-dihydrocarbostyril (200 mg) is dissolved in methanol (4 ml) and thereto is added diethylamine (0.26 ml) and the mixture is stirred at room temperature overnight, and then refluxed with heating for 3 hours. The solvent is concentrated and the residue is purified by silica gel column chromatography (solvent: n-hexane:ethyl acetate=1:1→dichloromethane: methanol=10:1) to give 1-{1-[4-(3-diethylamino-2-hydroxypropoxy)benzoyl]-4-piperidinyl}-3,4-dihydrocarbostyril (0.18 g).

This product is stirred with the equivalent amount of citric acid in diethyl ether to give citrate salt thereof as white powder, m.p.: 72°–76° C. (recrystallized from diethyl ether).

Using the suitable starting materials, the compounds of the above Examples 118, 119, 335 and the following Examples 448, 474A, 489, 532–535, 537, 538, 541–558, 562–587 are obtained in the same manners as in Example 421.

Example 422

1-[1-(4-Cyanobenzoyl)-4-piperidinyl]-3,4-dihydrocarbostyril (1 g) is dissolved in chloroform (10 ml) and thereto is added ethanol (0.18 ml). Under ice cooling, hydrochloric acid gas is passed through the mixture to saturate and further the mixture is stirred at 5°–7° C. for 4 days. After the reaction, the solvent is concentrated to give 1-{1-[4-(1-ethoxy-1-iminomethyl)benzoyl]-4-piperidinyl}-3,4-dihydrocarbostyril (1 g). The product is used for the subsequent reaction.

1-{1-[4-(1-Ethoxy-1-iminomethyl)benzoyl]-4-piperidinyl}-3,4-dihydrocarbostyril (1 g) is dissolved in methanol (10 ml) and thereto is added aqueous ammonia (10 ml) and the mixture is stirred at room temperature overnight. The solvent is concentrated and water is added to the residue. The mixture is extracted with chloroform, dried with sodium carbonate, concentrated and then purified by silica gel column chromatography (solvent: chloroform: methanol=10:1) and recrystallized from ethanol/n-hexane to give 1-[1-(4-carbamoyl-4-piperidinyl]-3,4-dihydrocarbostyril (0.2 g) as white powder, m.p.: 101°–104° C.

Further, the aqueous layer is concentrated and the resulting residue is recrystallized from water to give 1-[1-(4-amidinobenzoyl)-4-piperidinyl]-3,4-dihydrocarbostyril (0.4 g) as white powder, m.p.: 92°–97° C.

NMR (CDCl$_3$) δ ppm: 1.55–1.92 (2H, m), 2.32–3.05 (7H, m), 3.12–3.62 (2H, m), 4.22–4.72 (2H, m), 6.92–7.38 (4H, m), 7.63 (2H, d, J=8.2 Hz), 7.92 (2H, d, J=8.2 Hz), 9.48 (3H, brs)

Using the suitable starting materials, the compound of the above Example 113 is obtained in the same manners as in Example 422.

Example 423

1-{1-[4-(4-Pentenyloxy)benzoyl]-4-piperidinyl}-3,4-dihydrocarbostyril (2 g) is dissolved in dichloromethane (50 ml) and thereto is added gradually m-chloroperbenzoic acid (1.6 g) at room temperature. The mixture is stirred under the same conditions overnight and the reaction mixture is poured into aqueous sodium hydrogen carbonate solution and the mixture is extracted with chloroform and dried with magnesium sulfate. The solvent is distilled off and the resulting residue is purified by silica gel column chromatography (solvent: n-hexane:ethyl acetate=1:1) to give 1-{1-[4-(3-oxiranylpropoxy)benzoyl]-4-piperidinyl}-3,4-dihydrocarbostyril (1.5 g).

NMR (CDCl$_3$) δ ppm: 1.52–2.10 (6H, m), 2.45–3.10 (11H, m), 3.72–5.10 (5H, m), 6.90 (2H, d, J=8.7 Hz), 6.97–7.32 (4H, m), 7.43 (2H, d, J=8.7 Hz)

Using the suitable starting materials, the compounds of the above Example 333 and the following Example 572 are obtained in the same manner as in Example 423.

Example 424

1-[1-(4-Formylbenzoyl)-4-piperidinyl]-3,4-dihydrocarbostyril (4.77 g) is dissolved in methanol (100 ml) and thereto is added carbomethoxymethylenetriphenylphosphorane (5.3 g) and the mixture is stirred at room temperature for 1 hour. The solvent is concentrated and the residue is purified roughly by silica gel column chromatography (solvent: n-hexane:ethyl acetate=1:1) to give a mixture (8 g) of 1-{1-[4-(2-methoxycarbonylvinyl)benzoyl]4-piperidinyl}-3,4-dihydrocarbostyril and triphenylphosphineoxide.

This mixture is dissolved in ethanol (100 ml) and thereto is added 10% palladium-carbon (1 g). The mixture is stirred at room temperature under 1 atm. under hydrogen atmosphere. After the reaction, the catalyst is removed by filtration and the resulting filtrate is concentrated. The resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl]-3,4-dihydrocarbostyril (3 g) as white powder, m.p.: 85°–86° C.

Using the suitable starting materials, the compounds of the above Examples 220, 336 and 339 are obtained in the same manners as in Example 424.

Example 425

To a mixture of propyltriphenylphosphonium bromide (2.34 g), potassium-t-butoxide (62 mg) and sodium amide powder (0.3 g) is added tetrahydrofuran (110 ml) under argon atmosphere and the mixture is stirred at room temperature for 3 hours. To the resulting yellowish red solution is added 1-[1-(4-formylbenzoyl)-4-piperidinyl]-3,4-dihydrocarbostyril (2 g) gradually under ice cooling and the mixture is stirred under the same conditions for 3 hours. The reaction mixture is poured into water and extracted with ethyl acetate/toluene and then dried over sodium carbonate. The resultant is purified by silica gel column chromatography (solvent: n-hexane:ethyl acetate=1:1) to give 1-{1-[4-(1-butenyl)benzoyl]-4-piperidinyl}-3,4-dihydrocarbostyril (2 g).

NMR (CDCl$_3$) δ ppm: 1.05–1.33 (3H, m), 1.66–2.02 (2H, m), 2.30–3.26 (10H, m), 3.85–5.13 (3H, m), 5.69–5.83, 6.35–6.75 (2H, m), 7.02–7.54 (8H, m)

Example 426

Ethanethiol (0.125 ml) is dissolved in methanol (10 ml) and thereto is added sodium methoxide (0.11 g). The mixture is stirred at room temperature for 30 minutes. Thereto is added a solution of 1-{1-[4-(3-bromopropoxy)benzoyl]-4-piperidinyl}-3,4-dihydrocarbostyril (0.59 g) in methanol (2 ml) and the mixture is stirred at room temperature overnight. The solvent is concentrated and water is added to the residue, extracted with chloroform, dried with sodium carbonate. The solvent is distilled off and the resulting residue is purified by silica gel column chromatography (solvent: n-hexane:ethyl acetate=1:1) to give 1-{1-[4-(3-ethylthiopropoxy)benzoyl]-4-piperidinyl}-3,4-dihydrocarbostyril (0.2 g).

NMR (CDCl$_3$) δ ppm: 1.27 (3H, t, J=7.4 Hz), 1.68–1.92 (2H, m), 1.98–2.18 (2H, m), 2.45–3.14 (10H, m), 3.70–5.15 (3H, m), 4.10 (2H, t, J=6.1 Hz), 6.91 (2H, d, J=8.6 Hz), 6.99–7.32 (4H, m), 7.43 (2H, d, J=8.6 Hz)

Using the suitable starting materials, the compounds of the above Example 40, 55, 56, 66, 114, 115, 129, 132, 133, 135, 136, 137–141, 143, 145, 146, 147, 148, 153–155, 234, 235, 241–243, 246, 249, 250, 251, 255, 261, 262, 268–270, 276, 294, 300, 305–307, 309, 311, 317–319, 321, 322, 325–327, 332, 367, 383A–383C and the following Examples 445, 449–459, 466–469, 471–473, 488–496, 498–531, 539–540, 559–560, 569, 585–587 are obtained in the same manners as in Example 426.

Example 427

1-[1-(4-Vinylbenzoyl)-4-piperidinyl]-3,4-dihydrocarbostyril (0.6 g) is dissolved in ethanol (10 ml) and thereto is added 10% palladium-carbon (0.1 g) and the mixture is stirred under hydrogen atmosphere. After the reaction, the catalyst is removed by filtration and the filtrate is concentrated. The resultant is purified by silica gel column chromatography (solvent: n-hexane:ethyl acetate=1:1) and recrystallized from n-hexane/ethanol to give 1-[1-(4-ethylbenzoyl)-4-piperidinyl]-3,4-dihydrocarbostyril (0.5 g) as white powder, m.p.: 133°–134° C.

Using the suitable starting materials, the compounds of the above Examples 69, 220 and 339 are obtained in the same manners as in Example 427.

Example 428

1-[1-(4-Allyloxybenzoyl)-4-piperidinyl]-3,4-dihydrocarbostyril (1.15 g) is dissolved in N,N-dimethylaniline (5 ml) and the mixture is heated at 180°–190° C. for 8 hours. After cooling, the reaction mixture is adjusted to around pH 4 by adding hydrochloric acid thereto. The mixture is extracted with dichloromethane and dried with magnesium sulfate. The solvent is distilled off and the residue is purified by silica gel column chromatography (solvent: n-hexane:ethyl acetate=3:1→1:3) and further purified by silica gel column chromatography (solvent: dichloromethane:methanol=100:1) and recrystallized from dichloromethane/n-hexane to give 1-[1-(4-hydroxy-3-allylbenzoyl)-4-piperidinyl]-3,4-dihydrocarbostyril (0.22 g) as white powder, m.p.: 87°–90° C.

Using the suitable starting materials, the compound of the above Example 282 is obtained in the same manners as in Example 428.

Example 429

To a solution of 1-(4-aminophenyl)-3,4-dihydrocarbostyril (0.45 g) in dichloromethane (15 ml) is added triethylamine (0.29 g). Thereto is added 2,4-dimethoxybenzoyl chloride (0.42 g) with stirring under ice cooling. The mixture is refluxed with heating for 0.5 hour. After cooling, water is added thereto and the mixture is extracted with dichloromethane, washed with water and then dried with magnesium sulfate. The solvent is distilled off under reduced pressure and the residue is purified by silica gel column chromatography and recrystallized from ethanol/diethyl ether/n-hexane to give 1-[4-(2,4-dimethoxybenzoylamino)phenyl]-3,4-dihydrocarbostyril (0.44 g) as white powder, m.p.: 226°–227° C.

Using the suitable starting materials, the compound of the above Example 292 is obtained in the same manners as in Example 429.

Example 430

To a solution of 1-[4-(4-methoxyanilinocarbonyl)phenyl]-3,4-dihydrocarbostyril (0.2 g) in dimethylformamide (15 ml) is added 60% sodium hydride (24 mg) with stirring under ice cooling and the mixture is stirred at room temperature for 0.5 hour. Then, thereto is added a solution of ethyl bromide (64 mg) in dimethylformamide (DMF, 1 ml) and the mixture is refluxed with heating for 1 hour. DMF is distilled off under reduced pressure and water is added to the residue and the mixture is extracted with dichloromethane. The extract is washed with water and dried with magnesium sulfate. The solvent is distilled off under reduced pressure and the resulting residue is purified by silica gel column chromatography to give 1-[4-(N-ethyl-4-methoxyanilinocarbonyl)phenyl]-3,4-dihydrocarbostyril (0.12 g).

NMR (CDCl$_3$) δ ppm: 2.76 (3H, t, J=8.1 Hz), 3.0 (3H, t, J=8 Hz), 3.48 (3H, s), 3.75 (3H, s), 6.19 (1H, dd, J=3.1 Hz, 6 Hz), 6.78 (2H, d, J=8.3 Hz), 6.9–7.2 (7H, m), 7.43 (2H, d, J=8.4 Hz)

Example 431

To a solution of 1-[4-(2,4-dimethoxybenzoylamino)phenyl]-3,4-dihydrocarbostyril (0.19 g) in dimethylformamide (8 ml) is added with stirring 60% sodium hydride (0.02 g) under ice cooling. The mixture is stirred at room temperature for 0.5 hour and thereto is added a solution of methyl iodide (0.08 g) in dimethylformamide (6 ml). The mixture is stirred at room temperature for 3 hours. The solvent is distilled off under reduced pressure and water is added to the residue. The mixture is extracted with dichloromethane, washed with water and dried with magnesium sulfate. The solvent is distilled off under reduced pressure and the resulting residue is purified by silica gel column chromatography to give 1-{4-[N-(2,4-dimethoxybenzoyl)-N-methylamino]phenyl}-3,4-dihydrocarbostyril (70 mg).

NMR (CDCl$_3$) δ ppm: 2.78 (3H, t, J=8 Hz), 3.04 (3H, t, J=8 Hz), 3.50 (3H, s), 3.59 (3H, s), 3.76 (3H, s), 6.0–6.1 (1H, m), 6.2 (1H, brs), 6.41 (1H, dd, J=2.3 Hz, 8.4 Hz), 6.9–7.1 (4H, m), 7.1–7.3 (4H, m)

Using the suitable starting materials, the compounds of the above Examples 245, 236, 237, 172, 292 and 347 are obtained in the same manners as in Examples 430 and 431.

Example 432

To a solution of 1-(4-carboxyphenyl)-3,4-dihydrocarbostyril (0.2 g) in chloroform (5 ml) is added thionyl chloride (0.8 ml) and the mixture is refluxed with h eating for 1 hour. Then, chloroform and thionyl chloride are distilled off under reduced pressure to give 4-(3,4-dihydrocarbostyril-1-yl)benzoic acid chloride.

To a solution of p-anisidine (0.11 g) in chloroform (5 ml) is added triethylamine (0.15 g) and thereto is added with stirring a solution of 4-(3,4-dihydrocarbostryil-1-yl)benzoic acid chloride obtained above in chloroform (2 ml) under ice cooling. The mixture is stirred at room temperature overnight. Water is added to the reaction mixture and the mixture is extracted with dichloromethane, washed with water and dried with magnesium sulfate. The solvent is distilled off under reduced pressure and the resulting residue is crystallized from diethyl ether and further recrystallized from ethanol/diethyl ether/n-hexane to give 1-[4-(4-methoxyanilinocarbonyl)phenyl]-3,4-dihydrocarbostyril (240 mg) as white powder, m.p.: 254°–255° C.

Using the suitable starting materials, the compounds of the above Examples 172, 183–186, 223, 236–240, 244, 245 and 347 are obtained in the same manners as in Example 432.

Example 433

To a solution of 1-[4-(1-piperazinylcarbonyl)phenyl]-3,4-dihydrocarbostryil (0.15 g) in dichloromethane (20 ml) is added triethylamine (91 mg), and further thereto is added with stirring a solution of benzoyl chloride (69 mg) in dichloromethane (2 ml) under ice cooling and the mixture is stirred at room temperature for 1 hour. Water is added thereto and the mixture is extracted with dichloromethane, dried with magnesium sulfate. The solvent is distilled off under reduced pressure and the resulting residue is crystallized by adding diethyl ether and n-hexane. The precipitated crystal is recrystallized from ethanol/diethyl ether/n-hexane to give 1-[4-(4-benzoyl-1-piperazinyl)phenyl]-3,4-dihydrocarbostyril (0.16 g) as white powder, m.p.: 188°–189° C.

Using the suitable starting materials, the compound of the above Example 240 is obtained in the same manners as in Example 433.

Example 434

1-{1-[4-(2-Carboxyethyl)benzoyl]-4-piperidinyl}-3,4-dihydrocarbostyril (2 g) is dissolved in methanol (50 ml) and thereto is added dropwise thionyl chloride (1.1 ml)

under ice cooling. After adding, the mixture is stirred at 0°–5° C. for 1 hour and further at room temperature overnight. The solvent is concentrated and the resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl}-3,4-dihydrocarbostyril (1.46 g) as white powder, m.p.: 85°–86° C.

Using the suitable starting materials, the compounds of the above Examples 49, 111, 112, 123, 127, 181, 213, 264, 274, 297, 299, 302, 206, 311, 320, 322, 323, 327, 328 and 342 are obtained in the same manners as in Example 434.

Using the suitable starting materials, the following compounds are obtained in the same manners as in Examples 1 and 384.

TABLE 3

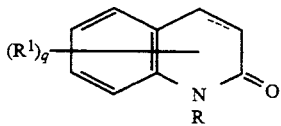

Example 435
Structure

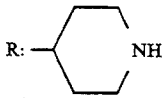

R¹: F (6-, 7-positions), q: 2
Bond between 3- and 4-positions in the carbostyril ring:
Single bond
NMR analysis: 210)
Form: Free Example 436
Structure

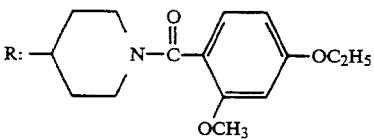

R¹: F (6-, 7-positions), q: 2
Bond between 3- and 4-positions in the carbostyril ring:
Single bond
Crystalline form: White powders
Recrystallization solvent: Ethanol
Melting point: 135–136° C.
Form: Free Example 437
Structure

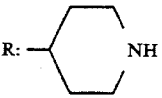

R¹: F (5-, 7-positions), q: 2
Bond between 3- and 4-positions in the carbostyril ring:
Single bond
Crystalline form: White powders
Recrystallization solvent: Ethanol
Melting point: 137–140° C.
Form: Free Example 438
Structure

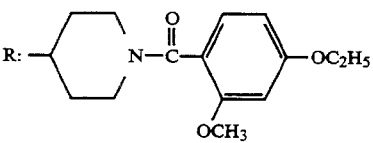

R¹: F (5-, 7-positions), q: 2

TABLE 3-continued

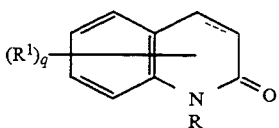

Bond between 3- and 4-positions in the carbostyril ring:
Single bond
Crystalline form: White powders
Recrystallization solvent: Ethanol
Melting point: 178–180° C.
Form: Free Example 439
Structure

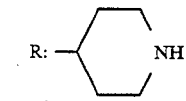

R¹: CH₃ (3-position), q: 1
Bond between 3- and 4-positions in the carbostyril ring:
Single bond
NMR analysis: 211)
Form: Free Example 440
Structure

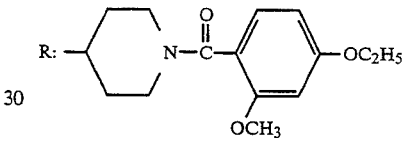

R¹: CH₃ (3-position), q: 1
Bond between 3- and 4-positions in the carbostyril ring:
Single bond
NMR analysis: 212)
Form: Free Example 441
Structure

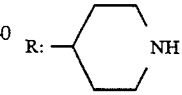

R¹: CO₂C₂H₅ (3-position), q: 1
Bond between 3- and 4-positions in the carbostyril ring:
Single bond
NMR analysis: 213)
Form: Free Example 442
Structure

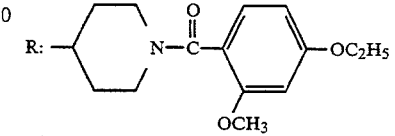

R¹: CO₂C₂H₅ (3-position), q: 1
Bond between 3- and 4-positions in the carbostyril ring:
Single bond
NMR analysis: 214)
Form: Free Example 443
Structure

R¹: H, q: 1
Bond between 3- and 4-positions in the carbostyril ring:
Double bond
NMR analysis: 215)

TABLE 3-continued

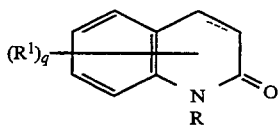

Form: Free

Example 444
Structure

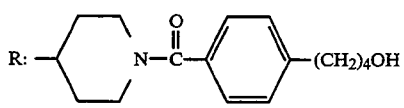

R[1]: H, q: 1
Bond between 3- and 4-positions in the carbostyril ring:
Single bond
Crystalline form: White powders
Recrystallization solvent: Ethanol/n-hexane
Melting point: 140–143° C.
Form: Free Example 445
Structure

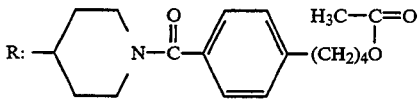

R[1]: H, q: 1
Bond between 3- and 4-positions in the carbostyril ring:
Single bond
NMR analysis: 216)
Form: Free Example 446
Structure

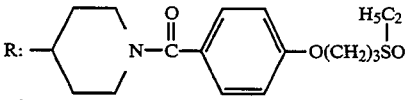

R[1]: H, q: 1
Bond between 3- and 4-positions in the carbostyril ring:
Single bond
NMR analysis: 217)
Form: Free Example 447
Structure

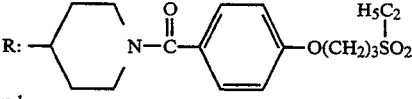

R[1]: H, q: 1
Bond between 3- and 4-positions in the carbostyril ring:
Single bond
NMR analysis: 218)
Form: Free Example 448
Structure

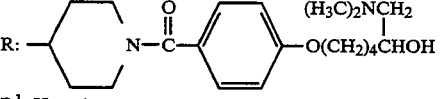

R[1]: H, q: 1
Bond between 3- and 4-positions in the carbostyril ring:
Single bond
NMR analysis: 219)
Form: Free Example 449
Structure TABLE 3-continued

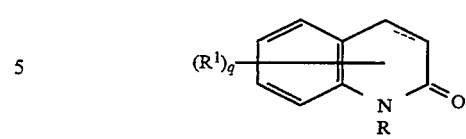

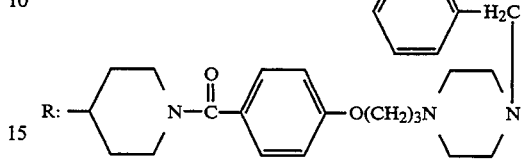

R[1]: H, q: 1
Bond between 3- and 4-positions in the carbostyril ring:
Single bond
Crystalline form: White powders
Recrystallization solvent: Ethanol/water
Melting point: 208–210° C.
Form: Dioxalate Example 450
Structure

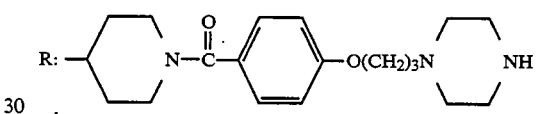

R[1]: H, q: 1
Bond between 3- and 4-positions in the carbostyril ring:
Single bond
Crystalline form: Light yellow powders
Recrystallization solvent: n-Hexane/diethyl ether
Melting point: 64–68° C.
Form: Dihydrochloride.trihydrate Example 451
Structure

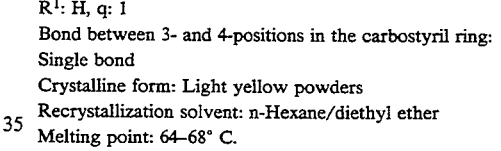

R[1]: H, q: 1
Bond between 3- and 4-positions in the carbostyril ring:
Single bond
NMR analysis: 220)
Form: Free Example 452
Structure

R[1]: H, q: 1
Bond between 3- and 4-positions in the carbostyril ring:
Single bond
NMR analysis: 221)
Form: Free Example 453
Structure TABLE 3-continued

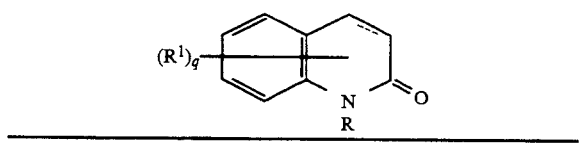

R:  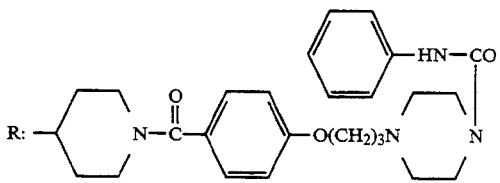

R¹: H, q: 1
Bond between 3- and 4-positions in the carbostyril ring:
Single bond
NMR analysis: 222)
Form: Free Example 454
Structure R:  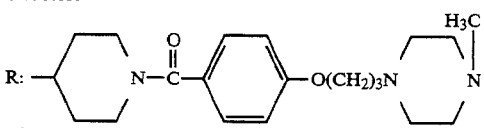

R¹: H, q: 1
Bond between 3- and 4-positions in the carbostyril ring:
Single bond
Crystalline form: White powders
Recrystallization solvent: Ethanol/water
Melting point: 214–217° C.
Form: Dioxalate Example 455
Structure

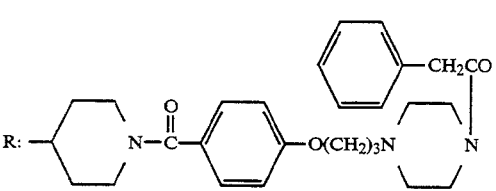

R¹: H, q: 1
Bond between 3- and 4-positions in the carbostyril ring:
Single bond
Crystalline form: White powders
Recrystallization solvent: Ethanol/water
Melting point: 208–211° C. (decomposed)
Form: Dioxalate Example 456
Structure

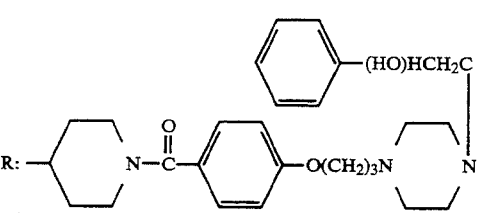

R¹: H, q: 1
Bond between 3- and 4-positions in the carbostyril ring:
Single bond
Crystalline form: White powders
Recrystallization solvent: Ethanol/water
Melting point: 206–210° C.
Form: Dioxalate Example 457
Structure TABLE 3-continued

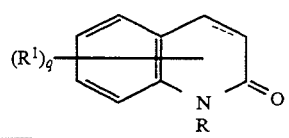

R:  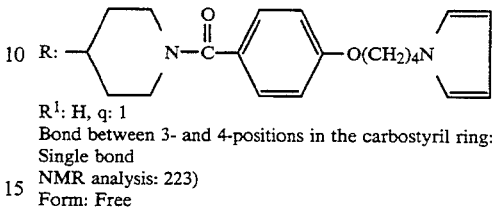

R¹: H, q: 1
Bond between 3- and 4-positions in the carbostyril ring:
Single bond
NMR analysis: 223)
Form: Free Example 458
Structure R:  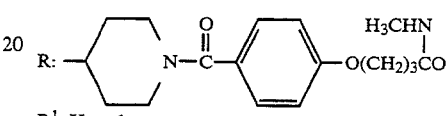

R¹: H, q: 1
Bond between 3- and 4-positions in the carbostyril ring:
Single bond
NMR analysis: 224)
Form: Free Example 459
Structure R:  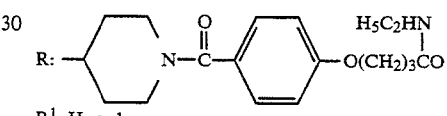

R¹: H, q: 1
Bond between 3- and 4-positions in the carbostyril ring:
Single bond
NMR analysis: 225)
Form: Free Example 460
Structure R:  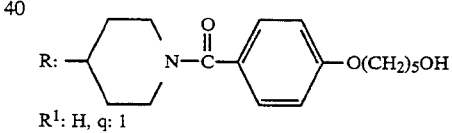

R¹: H, q: 1
Bond between 3- and 4-positions in the carbostyril ring:
Single bond
Crystalline form: Colorless needles
Recrystallization solvent: Ethanol/diethyl ether
Melting point: 123–125° C.
Form: Free Example 461
Structure R:  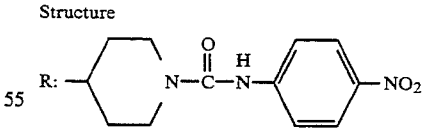

R¹: H, q: 1
Bond between 3- and 4-positions in the carbostyril ring:
Single bond
Crystalline form: Light yellow needles
Recrystallization solvent: Ethanol/chloroform
Melting point: 194–196° C.
Form: Free Example 462
Structure R:  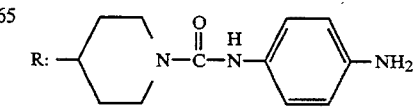

TABLE 3-continued

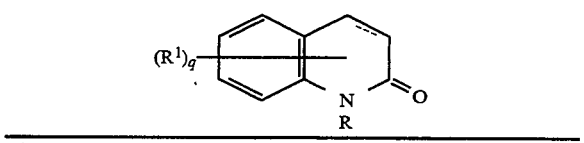

R¹: H, q: 1
Bond between 3- and 4-positions in the carbostyril ring:
Single bond
NMR analysis: 226)
Form: Free Example 463
Structure

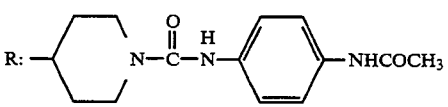

R¹: H, q: 1
Bond between 3- and 4-positions in the carbostyril ring:
Single bond
Crystalline form: Colorless prisms
Recrystallization solvent: Ethanol
Melting point: 249–252° C.
Form: Free Example 464
Structure

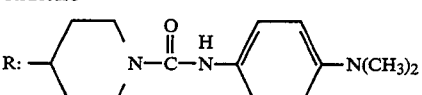

R¹: H, q: 1
Bond between 3- and 4-positions in the carbostyril ring:
Single bond
Crystalline form: Colorless prisms
Recrystallization solvent: Methanol
Melting point: 107–110° C.
Form: Free Example 465
Structure

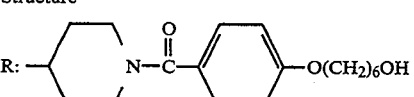

R¹: H, q: 1
Bond between 3- and 4-positions in the carbostyril ring:
Single bond
Crystalline form: Colorless needles
Recrystallization solvent: Ethanol/diethyl ether
Melting point: 120–122° C.
Form: Free Example 466
Structure

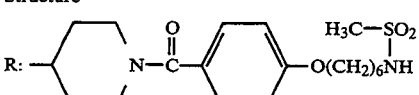

R¹: H, q: 1
Bond between 3- and 4-positions in the carbostyril ring:
Single bond
NMR analysis: 227)
Form: Free Example 467
Structure

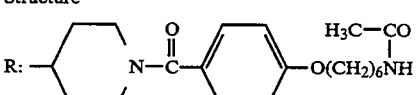

R¹: H, q: 1
Bond between 3- and 4-positions in the carbostyril ring:
Single bond TABLE 3-continued

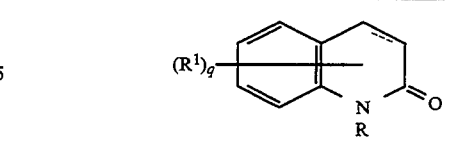

NMR analysis: 228)
Form: Free

Example 468
Structure

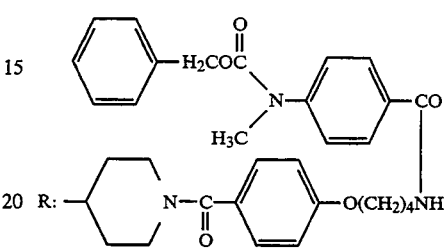

R¹: H, q: 1
Bond between 3- and 4-positions in the carbostyril ring:
Single bond
NMR analysis: 229)
Form: Free Example 469
Structure

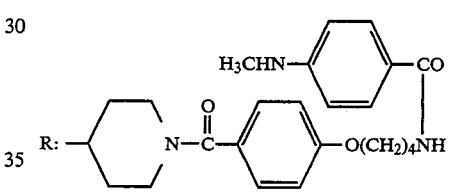

R¹: H, q: 1
Bond between 3- and 4-positions in the carbostyril ring:
Single bond
NMR analysis: 230)
Form: Free Example 470
Structure

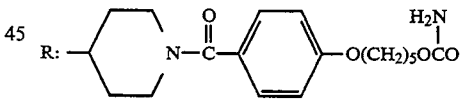

R¹: H, q: 1
Bond between 3- and 4-positions in the carbostyril ring:
Single bond
NMR analysis: 231)
Form: Free Example 471
Structure

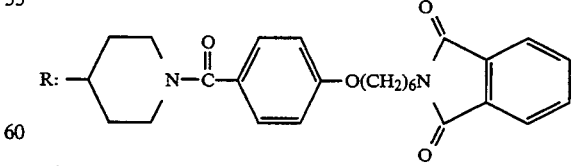

R¹: H, q: 1
Bond between 3- and 4-positions in the carbostyril ring:
Single bond
NMR analysis: 232)
Form: Free Example 472
Structure

TABLE 3-continued

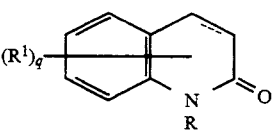

R:

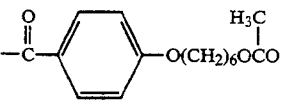

R¹: H, q: 1
Bond between 3- and 4-positions in the carbostyril ring:
Single bond
NMR analysis: 233)
Form: Free Example 473
Structure

R:

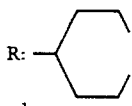

R¹: H, q: 1
Bond between 3- and 4-positions in the carbostyril ring:
Single bond
NMR analysis: 234)
Form: Free Example 474
Structure

R:

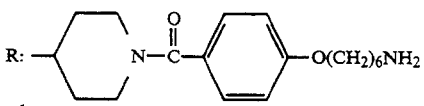

R¹: H, q: 1
Bond between 3- and 4-positions in the carbostyril ring:
Single bond
NMR analysis: 235)
Form: Free Example 474A
Structure

R:

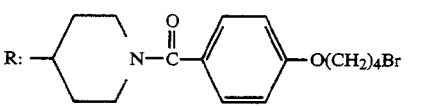

R¹: H, q: 1
Bond between 3- and 4-positions in the carbostyril ring:
Single bond
NMR analysis: 236)
Form: Free

TABLE 4

| No. | NMR (CDCl$_3$) δ value |
|---|---|
| 210 | 1.60(1H, s), 1.68–1.85(2H, m), 2.35–2.92(8H, m) 3.15–3.32(2H, m), 4.18–4.40(1H, m), 6.86–7.18 (2H, m) |
| 211 | 1.21(3H, d, J=6.5Hz), 1.60–2.00(3H, m), 2,35– 2.95(8H, m), 3.14–3.37(2H, m), 4.28–4.50(1H, m) 6.95–7.32(4H, m) |
| 212 | 1.21(3H, d, J=6.5Hz), 1.42(3H, t, J=7.0Hz), 1.62–2.04(2H, m), 2.30–3.28(7H, m), 3.55–3.95 (4H, m), 4.04(2H, q, J=7.0Hz), 4.25–5.10(2H, m) 6.38–6.60(2H, m), 6.98–7.40(5H, m) |
| 213 | 1.18 (3H, t, J=7.1Hz), 1.50–1.88(3H, m), 2.50– 3.46(9H, m), 3.60–3.62(2H, m), 4.03–4.28(2H, m), 4.47–4.60(1H, m), 6.95–7.30(4H, m) |
| 214 | 1.17(3H, t, J=7.1Hz), 1.42(3H, t, J=7.0Hz), 1.56–2.00(3H, m), 2.38–3.35(6H, m), 3.42–5.10 (11H, m), 6.37–6.60(2H, m), 6.95–7.40(5H, m) |
| 215 | 1.58–1.97(2H, m), 2,43–3.22(10H, m), 3.65–5.12 (5H, m), 5.68–5.84, 6.18–6.36(total: 1H, m), 6.51(1H, d, J=15.9Hz), 6.46–7.49(8H, m) |
| 216 | 1.56–1.98(6H, m), 2.05(3H, s), 2.52–3.21(10H, m) 3.76–5.08(5H, m), 6.98–7.43(8H, m) |
| 217 | 1.44(3H, t, J=7.5Hz), 1.68–1.97(2H, m), 2.28– 3.17(10H, m), 3.05(2H, q, J=7.5Hz), 3.20(2H, t, J=7.4Hz), 3.78–5.13(3H, m), 4.15(2H, t, J=5.7 Hz), 6.86–7.49(8H, m) |
| 218 | 1.44(3H, t, J=7.5Hz), 1.68–1.97(2H, m), 2.28– 3.17(10H, m), 3.05(2H, q, J=7.5Hz), 3.20(2H, t, J=7.4Hz), 3.78–5.13(3H, m), 4.15(2H, t, J=5.7 Hz), 6.86–7.49(8H, m) |
| 219 | 1.34–1.93(8H, m), 2.17–2.42(2H, m), 2.31(6H, s), 2.51–3.04(9H, m), 3.62–5.07(6H, m), 6.86–6.95 (2H, m), 6.97–7.32(4H, m), 7.36–7.48(2H, m) |
| 220 | 1.68–2.18(4H, m), 2.09(3H, s), 3.28–3.13(14H, m), 3.43–3.72(4H, m), 3.86–5.08(5H, m), 6.85–7.50 (8H, m) |
| 221 | 1.70–2.08(4H, m), 2.34–3.12(14H, m), 3.34–5.04 (9H, m), 6.88–7.52(8H, m), 7.40(5H, s) |
| 222 | 1.72–2.14(4H, m), 2.40–3.14(14H, m), 3.43–3.60 (4H, m), 3.73–5.13(5H, m), 6.47(1H, brs), 6.88– 7.48(13H, m) |
| 223 | 1.71–2.15(6H, m), 2.46–3.20(8H, m), 3.80–5.15 (2H, m), 3.96(4H, t, J=6.8Hz), 4.39(1H, m), 6.15 (2H, t, J=2.1Hz), 6.67(2H, t, J=2.1Hz), 6.88 (2H, d, J=8.7Hz), 6.99–7.28(4H, m), 7,42(2H, d, J=8.7Hz) |
| 224 | 1.60–1.98(2H, m), 2.11(2H, quint, J=6.5Hz), 2.36 (2H, t, J=6.5Hz), 2.53–3.15(8H, m), 2,78(3H, d, J=4.8Hz), 3.60–5.10(2H, brs), 4.00(2H, t, J=6.5 Hz), 4.36(1H, m), 6.16(1H, brs), 6.88(2H, d, J= 8.7Hz), 6.99–7.29(4H, m), 7.41(2H, d, J=8.7Hz) |
| 225 | 1.33(3H, t, J=6.8Hz), 1.65–1.94(2H, m), 2.14 (2H, quint, J=6.6Hz), 2.37(2H, t, J=6.6Hz), 2.46–3.12(8H, m), 3.80–5.00(2H, m), 4.03(2H, t, J=6.6Hz), 4.05(2H, q, J=6.8Hz), 4.38(1H, m), 5.69(1H, brs), 6.90(2H, d, J=8.6Hz), 6.98–7.30 (4H, m), 7.42(2H, d, J=8.6Hz) |
| 226 | 1.63–1.92(2H, m), 2.40–3.80(10H, m), 4.08–4.55 (3H, m), 6.41(1H, brs), 6.52–6.75(2H, m), 6.92– 7.35(6H, m), |
| 227 | 1.31–2.02(10H, m), 2.47–3.25(10H, m), 2.95(3H, s), 3.98(2H, t, J=6.3Hz), 4.04–5.05(4H, m), 6.89 (2H, d, J=8.8Hz), 6.95–7.37(4H, m), 7.42(2H, d, J=8.8Hz), |
| 228 | 1.25–2.18(13H, m), 2.45–3.40(10H, m), 3.97(2H, t, J=6.4Hz), 4.05–5.07(3H, m), 5.79(1H, brs), 6.89(2H, d, J=8.7Hz), 6.95–7.37(4H, m), 7.42 (2H, d, J=8.7Hz) |
| 229 | 1.60–2.05(6H, m), 2.43–3.15(8H, m), 3.34(3H, s), 3.49–3.63(2H, m), 3.82–5.05(5H, m), 5.17(2H, s), 6.50(1H, brs), 6.88(2H, d, J=8.6Hz), 6.94–7.49 (13H, m), 7.74(2H, d, J=8.6Hz) |
| 230 | 1.60–2.07(6H, m), 2.42–3.18(11H, m), 3.35–3.62 (2H, m), 3.80–5.09(6H, m), 6.20–6.45(1H, m), 6.54 (2H, d, J=8.7Hz), 6.88(2H, d, J=8.7Hz), 6.94– 7.35(4H, m), 7.40(2H, d, J=8.7Hz), 7.63(2H, d, J=8.7Hz) |
| 231 | 1.45–1.99(8H, m), 2.48–3.18(8H, m), 3.99(2H, t, J=6.3Hz), 4.10(2H, t, J=6.3Hz), 4.17–5.08(5H, m), 6.82–7.54(8H, m) |
| 232 | 1.27–1.99(10H, m), 2.40–3.15(8H, m), 3.70(2H, J=7Hz), 3.97(2H, t, J=6.3Hz), 4.08–5.10(3H, m), 6.29–7.96(12H, m) |
| 233 | 1.26–1.95(10H, m), 2.05(3H, s), 2.45–3.18(8H, m), 3.87–5.08(7H, m), 6,82–7.52(8H, m) |
| 234 | 1.25–2.03(10H, m), 2.45–3.26(10H, m), 3.98(2H, t, J=6.4Hz), 4.08–5.11(3H, m), 6.90(2H, d, J=8.8 Hz), 6.90–7.39(4H, m), 7.42(2H, d, J=8.8Hz) |
| 235 | 1.63–2.22(6H, m), 2.47–3.18(8H, m), 3.63(2H, t, J=6.6Hz), 3.94–5.04(5H, m), 6.82–7.52 (8H, m) |
| 236 | 1.11(6H, t, J=7.2Hz), 1.35–1.96(8H, m), 2.32– 3.13(14H, m), 3.58–5.07(5H, m), 4.00(2H, t, J=6.3Hz), 6.83–6.95(2H, m), 6.98–7.32(4H, m), 7.35–7.48(2H, m), |

TABLE 5

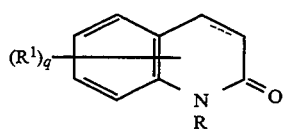

Example 475
Structure

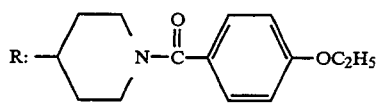

$R^1$: H, q: 1
Bond between 3- and 4-positions in the carbostyril ring: Double bond
Crystalline form: Colorless needles
Recrystallization solvent: Ethanol/diethyl ether
Melting point: 144–148° C.
Form: Free

Example 476

To a solution of 1-{1-[4-(3-ethylthiopropoxy)benzoyl]-4-piperidinyl}-3,4-dihydrocarbostyril (0.44 g) in dichloromethane (10 ml) is added m-chloroperbenzoic acid (0.52 g) under ice cooling. The mixture is stirred at room temperature overnight, and the reaction mixture is poured into aqueous sodium carbonate solution. The mixture is extracted with chloroform and dried with sodium carbonate. The solvent is distilled off and the resulting residue is purified by silica gel column chromatography (solvent: n-hexane:ethyl acetate=1:2) to give 1-{1-[4-(3-ethyl sulfonylpropoxy)benzoyl]-4-piperidinyl}-3,4-dihydrocarbostyril (0.19 g).

NMR (CDCl₃) δ ppm: 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

Example 478

A mixture of 1-{1-[4-(4-aminobutoxy)benzoyl]-4-piperidinyl}-3,4-dihydrocarbostyril (0.50 g), acetic acid (10 ml) and 2,5-dimethoxytetrahydrofuran (0.17 ml) is refluxed with stirring under heating for 1 hour. The reaction solution is concentrated under reduced pressure and the resulting residue is purified by silica gel column chromatography (solvent: dichloromethane:methanol=100:1) to give 1-[1-{4-[4-(1-pyrrolyl)butoxy]benzoyl}-4-piperidinyl]-3,4-dihydrocarbostyril (0.30 g).

NMR (CDCl₃) δ ppm: 1.71–2.15 (6H, m), 2.46–3.20 (8H, m), 3.80–5.15 (2H, m), 3.96 (4H, t, J=6.8 Hz), 4.39 (1H, m), 6.15 (2H, t, J=2.1 Hz), 6.67 (2H, t, J=2.1 Hz), 6.88 (2H, d, J=8.7 Hz), 6.99–7.28 (4H, m), 7.42 (2H, d, J=8.7 Hz)

Example 479

Sodium metaperiodate (0.28 g) is dissolved in water (4 ml) and thereto is added a solution of 1-{1-[4-(3-ethylthiopropoxy)benzoyl]-4-piperidinyl}-3,4-dihydrocarbostyril (0.4 g) in methanol (15 ml) and the mixture is stirred at room temperature overnight. The reaction mixture is concentrated and the residue is extracted with chloroform. The extract is dried with magnesium sulfate and the solvent is distilled off. The resulting residue is purified by silica gel column chromatography (solvent: n-hexane:ethyl acetate=1:2→ethyl acetate:methanol=20:1) to give 1-{1-[4-(3-ethylsulfinylpropoxy)benzoyl]-4-piperidinyl]-3,4-dihydrocarbostyril (0.12 g).

MNR (CDCl₃) δ ppm: 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

Example 480

4-Hydroxypropyltriphenylphosphonium bromide (2.4 g) is dispersed into tetrahydrofuran (50 ml) and thereto is added dropwise lithium diisopropylamide (a solution in 1.99N tetrahydrofuran) (6.1 ml) at 0°–5° C. After adding, the mixture is stirred at 0°–5° C. for 1 hour and thereto is added 1-[1-(4-formylbenzoyl)-4-piperidinyl]-3,4-dihydrocarbostyril (2 g). The mixture is stirred at room temperature overnight. The reaction mixture is poured into ice-water and adjusted to pH 4–5 by adding conc. hydrochloric acid. The mixture is extracted with ethyl acetate and dried with magnesium sulfate. The solvent is distilled off and the resulting residue is purified by silica gel column chromatography (solvent: n-hexane:ethyl acetate=1:1→ethyl acetate:methanol=20:1) to give 1-{1-[4-(4-hydroxy-1-butenyl)benzoyl]-4-piperidinyl}-3,4-dihydrocarbostyril (1 g).

NMR (CDCl₃) δ ppm: 1.58–1.97 (2H, m), 2.43–3.22 (10H, m), 3.65–5.12 (5H, m), 5.68–5.84, 6.18–6.36 (total; 1H, m), 6.51 (1H, d, J=15.9 Hz), 6.96–7.49 (8H, m)

Example 481

To crushed aluminum chloride (26 g) are added chlorobenzene (26 ml) and N-cinnamoyl-N-(1-benzoyl-4-piperidinyl)aniline (8.7 g) and the mixture is reacted at 110° C. for 1 hour. After cooling, the reaction mixture is poured into ice-water and the mixture is basified with aqueous sodium hydroxide solution. The mixture is extracted with dichloromethane and the solvent is concentrated. The residue is purified by silica gel column chromatography (solvent: methylene chloride) to give 1-(1-benzoyl-4-piperidinyl)carbostyril (5.9 g).

Using the suitable starting materials, the compounds of the above Examples 10, 166–168, 475 and the following Examples 578–587 are obtained in the same manners as in Example 481.

Using the suitable materials, the following compounds are obtained in the same manners as in Exampels 1 and 384.

TABLE 6

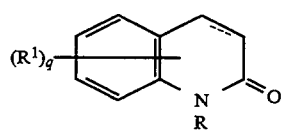

Example 482

TABLE 6-continued

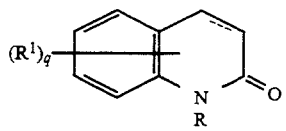

Structure

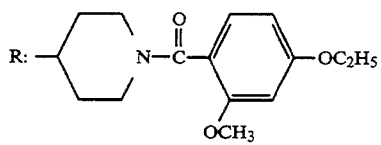

R¹: —COOH (3-position), q: 1
Bond between 3- and 4-positions in the carbostyril ring: Single bond
Crystalline form: White amorphous form
NMR analysis: 237)
Form: Free Example 483
Structure

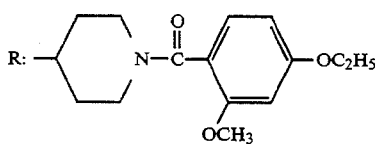

R¹: —CONHNH₂ (3-position), q: 1
Bond between 3- and 4-positions in the carbostyril ring: Single bond
Crystalline form: White amorphous form
NMR analysis: 238)
Form: Free Example 484
Structure

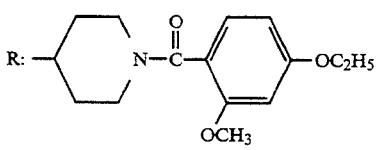

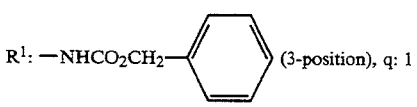

R¹: —NHCO₂CH₂— (3-position), q: 1

Bond between 3- and 4-positions in the carbostyril ring: Single bond
Crystalline form: White amorphous form
NMR analysis: 239)
Form: Free Example 485
Structure

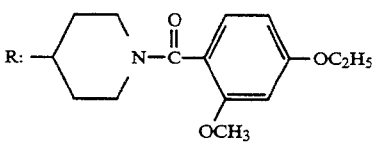

R¹: —NH₂ (3-Position), q: 1
Bond between 3- and 4-positions in the carbostyril ring: Single bond
Crystalline form: White powders
Recrystallization solvent: Ethanol
Melting point 257–260° C.
Form: Hydrochloride Example 486
Structure

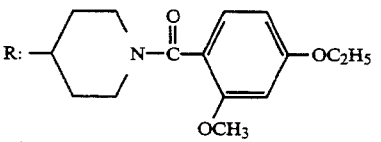

R¹: —NHCOCH₃ (3-position), q: 1
Bond between 3- and 4-positions in the carbostyril ring: Single bond TABLE 6-continued

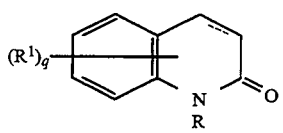

Crystalline form: White amorphous form
NMR analysis: 240)
Form: Free

Example 487
Structure

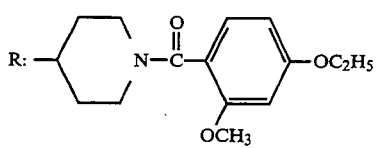

R$^1$: —N(CH$_3$)$_2$ (3-Position), q: 1
Bond between 3- and 4-positions in the carbostyril ring: Single bond
Crystalline form: white amorphous form
NMR analysis: 241)
Form: Free Example 488
Structure

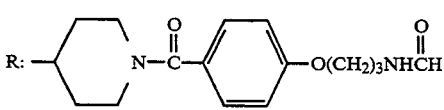

R$^1$: F (7-position), q: 1
Bond between 3- and 4-positions in the carbostyril ring: Single bond
Crystalline form: white amorphous form
NMR analysis: 242)
Form: Free Example 489
Structure

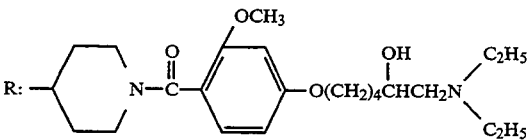

R$^1$: F (5-, 7-positions), q: 2
Bond between 3- and 4-positions in the carbostyril ring: Single bond
Crystalline form: White amorphous form
NMR analysis: 245)
Form: Free Example 490
Structure

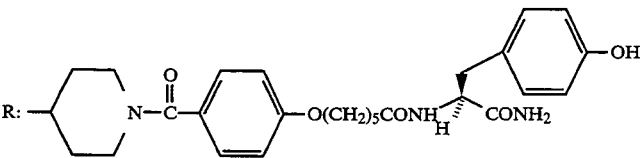

R$^1$: H, q: 1
Bond between 3- and 4-positions in the carbostyril ring: Single bond
Crystalline form: White amorphous form
NMR analysis: 246)
Form: Free Example 491
Structure

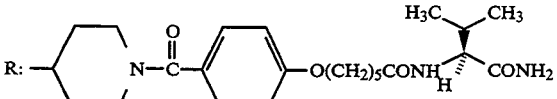

R$^1$: H, q: 1
Bond between 3- and 4-positions in the carbostyril ring: Single bond
Crystalline form: White amorphous form
NMR analysis: 247)

TABLE 6-continued

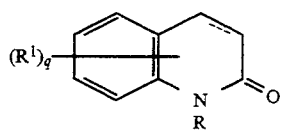

Form: Free

Example 492
Structure

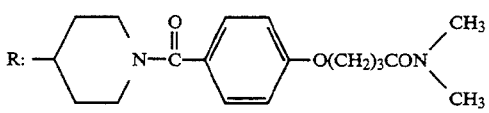

R¹: H, q: 1
Bond between 3- and 4-positions in the carbostyril ring: Single bond
NMR analysis: 248)
Form; Free Example 493
Structure

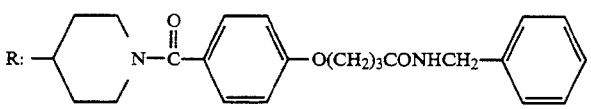

R¹: H, q: 1
Bond between 3- and 4-positions in the carbostyril ring: Single bond
NMR analysis: 249)
Form: Free Example 494
Structure

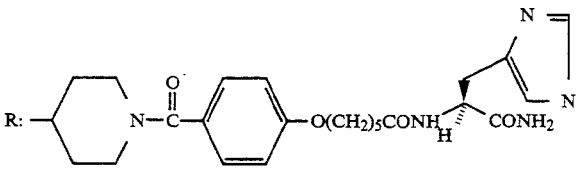

R¹: H, q: 1
Bond between 3- and 4-positions in the carbostyril ring: Single bond
Crystalline form: White amorphous form
NMR analysis: 250)
Form: Free Example 495
Structure

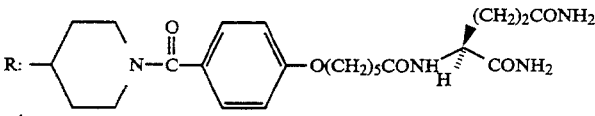

R¹: H, q: 1
Bond between 3- and 4-positions in the carbostyril ring: Single bond
Crystalline form: White amorphous form
NMR analysis: 251)
Form: Free Example 496
Structure

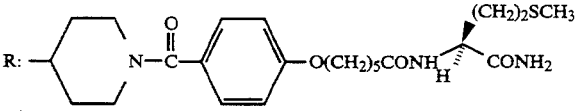

R¹: H, q: 1
Bond between 3- and 4-positions in the carbostyril ring: Single bond
Crystalline form: White amorphous form
NMR analysis: 252)
Form: Free Example 497
Structure TABLE 6-continued

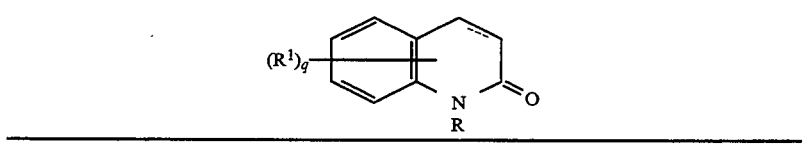

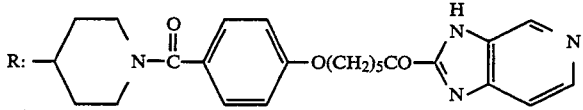

R¹: H, q: 1
Bond between 3- and 4-positions in the carbostyril ring: Single bond
Crystalline form: White amorphous form
NMR analysis: 253)
Form: Free Example 498
Structure

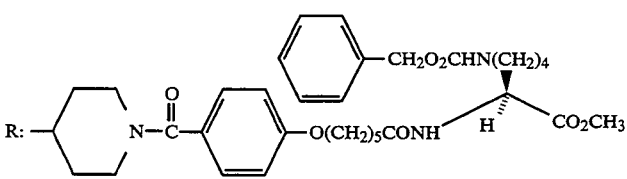

R¹: H, q: 1
Bond between 3- and 4-positions in the carbostyril ring: Single bond
NMR analysis: 254)
Form: Free Example 499
Structure

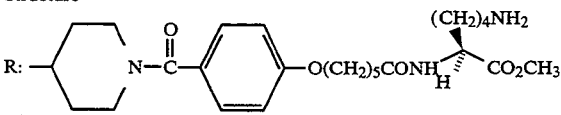

R¹: H, q: 1
Bond between 3- and 4-positions in the carbostyril ring: Single bond
NMR analysis: 255)
Form: Free Example 500
Structure

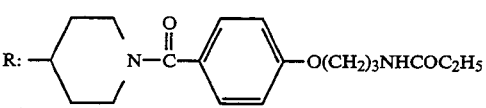

R¹: H, q: 1
Bond between 3- and 4-positions in the carbostyril ring: Single bond
NMR analysis: 256)
Form: Free Example 501
Structure

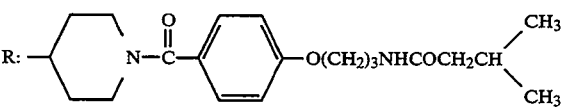

R¹: H, q: 1
Bond between 3- and 4-positions in the carbostyril ring: Single bond
NMR analysis 257)
Form: Free Example 502
Structure

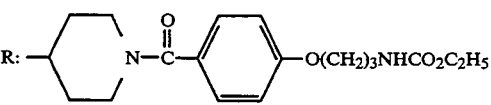

R¹: H, q: 1
Bond between 3- and 4-positions in the carbostyril ring: Single bond
Crystalline form: White amorphous form
NMR analysis: 258)

TABLE 6-continued

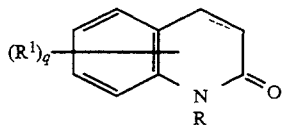

Form: Free

Example 503
Structure

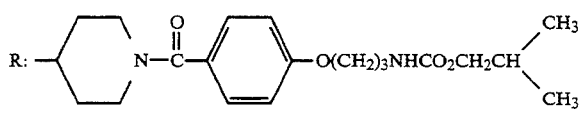

$R^1$: H, q: 1
Bond between 3- and 4-positions in the carbostyril ring: Single bond
Crystalline form: White amorphous form
NMR analysis: 259)
Form: Free Example 504
Structure

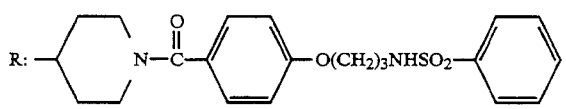

$R^1$: H, q: 1
Bond between 3- and 4-positions in the carbostyril ring: Single bond
Crystalline form: White amorphous form
NMR analysis: 260)
Form: Free Example 505
Structure

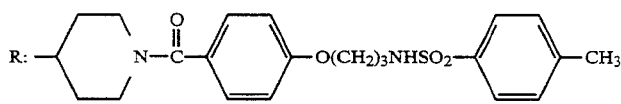

$R^1$: H, q: 1
Bond between 3- and 4-positions in the carbostyril ring: Single bond
Crystalline form: White amorphous form
NMR analysis: 261)
Form: Free Example 506
Structure

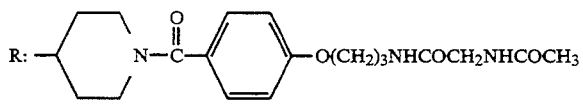

$R^1$: H, q: 1
Bond between 3- and 4-positions in the carbostyril ring: Single bond
Crystalline form: White amorphous form
NMR analysis: 262)
Form: Free Example 507
Structure

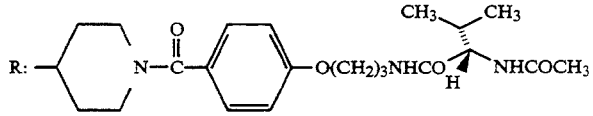

$R^1$: H, q: 1
Bond between 3- and 4-positions in the carbostyril ring: Single bond
Crystalline form: White amorphous form
NMR analysis: 263)
Form: Free Example 508
Structure TABLE 6-continued

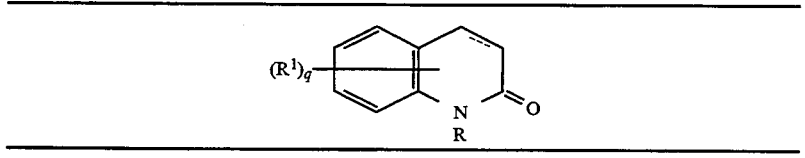

R: 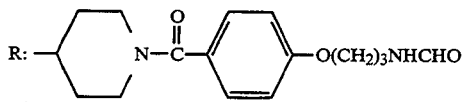—O(CH₂)₃NHCHO

R¹: H, q: 1
Bond between 3- and 4-positions in the carbostyril ring: Single bond
Crystalline form: White amorphous form
NMR analysis: 264)
Form: Free Example 509
Structure R: 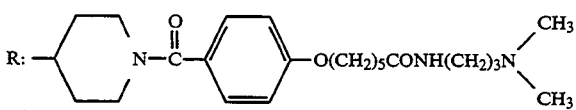—O(CH₂)₅CONH(CH₂)₃N(CH₃)₂

R¹: H, q: 1
Bond between 3- and 4-positions in the carbostyril ring: Single bond
Crystalline form: White amorphous form
NMR analysis: 265)
Form: Free Example 510
Structure:

R: 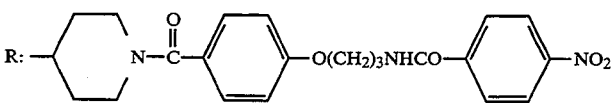—O(CH₂)₃NHCO—⟨⟩—NO₂

R¹: H, q: 1
Bond between 3- and 4-positions in the carbostyril ring: Single bond
Crystalline form: White Amorphous form
NMR analysis: 266)
Form: Free Example 511
Structure R: 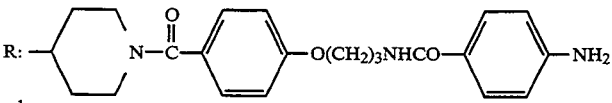—O(CH₂)₃NHCO—⟨⟩—NH₂

R¹: H, q: 1
Bond between 3- and 4-positions in the carbostyril ring: Single bond
Crystalline form: White amorphous form
NMR analysis: 267)
Form: Free Example 512
Structure R: 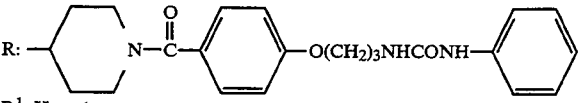—O(CH₂)₃NHCONH—⟨⟩

R¹: H, q: 1
Bond between 3- and 4-positions in the carbostyrile ring: Single bond
Crystalline form: White powders
NMR analysis: 268)
Recrystallization solvent: Ethyl acetate/n-hexane
Melting point: 121–126° C.
Form: Free Example 513
Structure R: 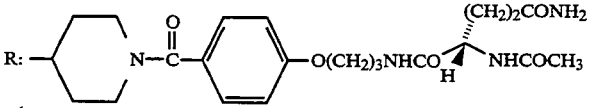—O(CH₂)₃NHCO—CH(NHCOCH₃)(CH₂)₂CONH₂

R¹: H, q: 1
Bond between 3- and 4-positions in the carbostyril ring: Single bond TABLE 6-continued

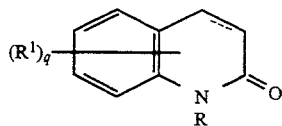

Crystalline form: White amorphous form
NMR analysis: 269)
Form: Free

Example 514
Structure

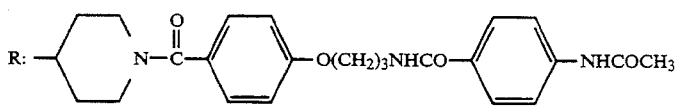

R¹: H, q, 1
Bond between 3- and 4-positions in the carbostyril ring: Single bond
Crystalline form: White amorphous form
NMR analysis: 270)
Form: Free Example 515
Structure

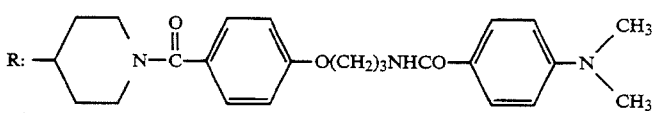

R¹: H, q: 1
Bond between 3- and 4-positions in the carbostyril ring: Single bond
Crystalline form: White powder
Recrystallization solvent: Ethyl acetate/n-hexane
Meting point: 175.5–177° C.
Form: Free Example 516
Structure

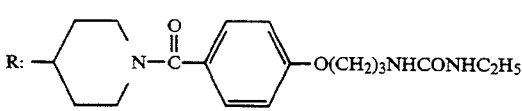

R¹: H, q: 1
Bond between 3- and 4-positions in the carbostyril ring: Single bond
Crystalline form: White amorphous form
NMR analysis: 271)
Form: Free Example 517
Structure

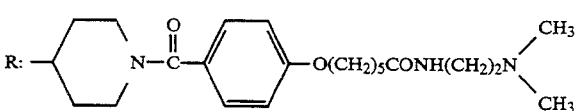

R¹: H, q: 1
Bond between 3- and 4-positions in the carbostyril ring: Single bond
NMR analysis: 272)
Form: Free Example 518
Structure

R¹: H, q: 1
Bond between 3- and 4-positions in the carbostyril ring: Single bond
Crystalline form: White amorphous form
NMR analysis: 273)
Form: Free Example 519
Structure TABLE 6-continued

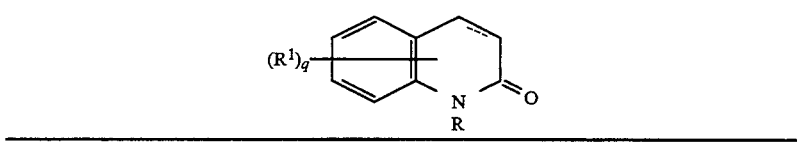

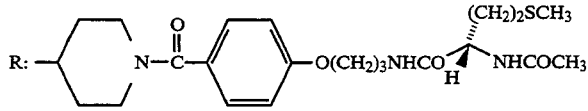

R[1]: H, q: 1
Bond between 3- and 4-positions in the carbostyril ring: Single bond
Crystalline form: White amorphous form
NMR analysis: 274)
Form: Free Example 520
Structure

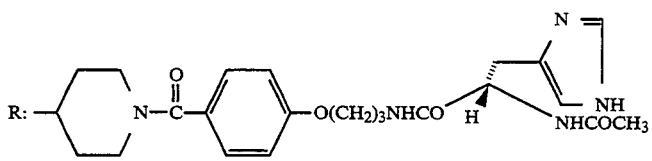

R[1]: H, q: 1
Bond between 3- and 4-positions in the carbostyril ring: Single bond
Crystalline form: White amorphous form
NMR analysis: 275)
Form: Free Example 521
Structure

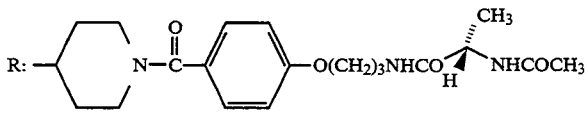

R[1]: H, q: 1
Bond between 3- and 4-positions in the carbostyril ring: Single bond
Crystalline form: White amorphous form
NMR analysis: 276)
Form: Free Example 522
Structure

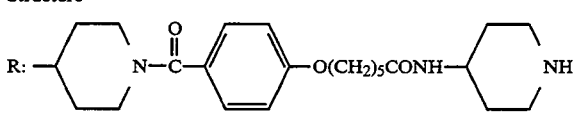

R[1]: H, q: 1
Bond between 3- and 4-positions in the carbostyril ring: Single bond
Crystalune form: White amorphous form
NMR analysis: 277)
Form: Free Example 523
Structure

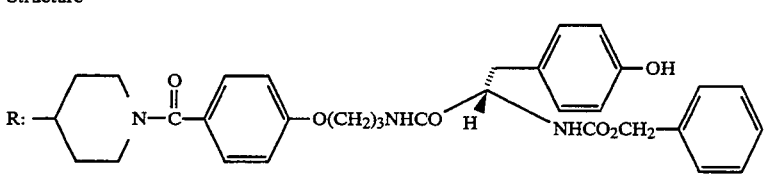

R[1]: H, q: 1
Bond between 3- and 4-positions in the carbostyril ring: Single bond
Crystalline form: White amorphous form
NMR analysis: 278)
Form: Free Example 524
Structure TABLE 6-continued

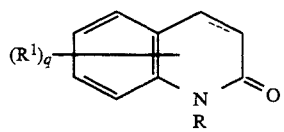

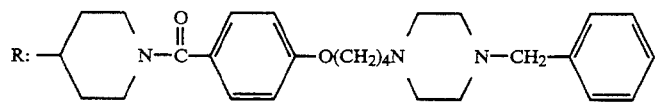

R¹: H, q: 1
Bond between 3- and 4-positions in the carbostyril ring: Single bond
NMR analysis: 279)
Form: Free Example 525

Structure

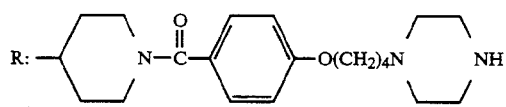

R¹: H, q: 1
Bond between 3- and 4-positions in the carbostyril ring: Single bond
Crystalline form: White powders
Recrystallization solvent: Ethanol/water
Melting point: 196–198° C.
Form: Dioxalate Example 526

Structure

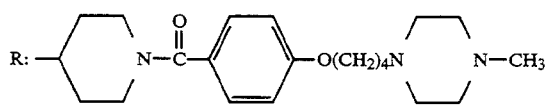

R¹: H, q: 1
Bond between 3- and 4-positions in the carbostyril ring: Single bond
Crystalline form: White powder
Recrystallization solvent: Ethanol/water
Melting point: 214–215° C.
Form: Dioxalate Example 527

Structure

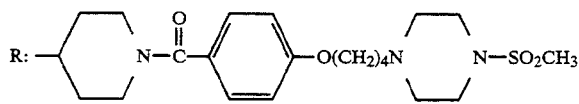

R¹: H, q: 1
Bond between 3- and 4-positions in the carbostyril ring: Single bond
NMR analysis: 280)
Form: Free Example 528

Structure

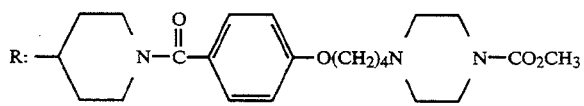

R¹: H, q: 1
Bond between 3- and 4-positions in the carbostyril ring: Single bond
NMR analysis: 281)
Form: Free Example 529

Structure

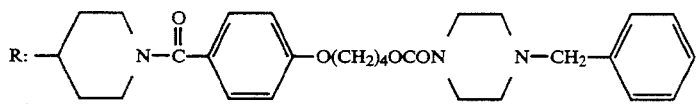

R¹: H, q: 1
Bond between 3- and 4-positions in the carbostyril ring: Single bond
NMR analysis: 282)
Form: Free TABLE 6-continued

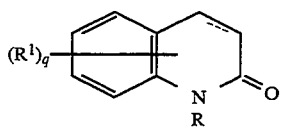

Example 530
Structure

R: 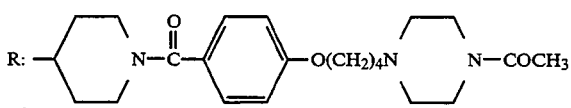

$R^1$: H, q: 1
Bond between 3- and 4-positions in the carbostyril ring: Single bond
NMR analysis: 283)
Form: Free Example 531
Structure R: 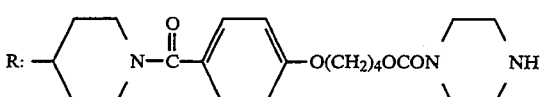

$R^1$: H, q: 1
Bond between 3- and 4-positions in the carbostyril ring: Single bond
NMR analysis: 284)
Form: Free Example 532
Structure R: 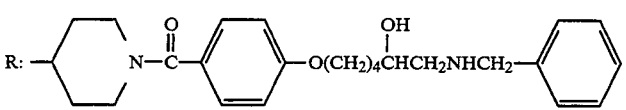

$R^1$: H, q: 1
Bond between 3- and 4-positions in the carbostyril ring: Single bond
NMR analysis: 285)
Form: Free Example 533
Structure R: 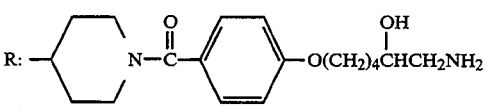

$R^1$: H, q: 1
Bond between 3- and 4-positions in the carbostyril ring: Single bond
NMR analysis: 286)
Form: Free Example 534
Structure R: 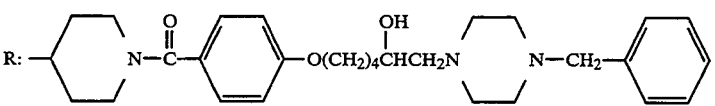

$R^1$: H, q: 1
Bond between 3- and 4-positions in the carbostyril ring: Single bond
Crystalline form: White powders
Recrystallization solvent: Ethanol/water
Melting point: 196–198° C.
Form: Dioxalate Example 535
Structure R: 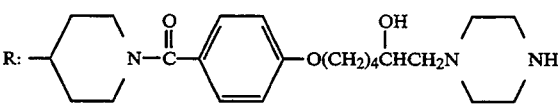

$R^1$: H, q: 1
Bond between 3- and 4-positions in the carbostyril ring: Single bond
Crystalline form: White powders
Recrystallization solvent: Ethanol/water
Melting point: 198–199° C.

TABLE 6-continued

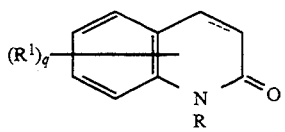

Form: Dioxalate

Example 536
Structure

R: 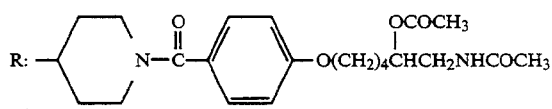

R¹: H, q: 1
Bond between 3- and 4-positions in the carbostyril ring: Single bond
NMR analysis: 287)
Form: Free Example 537
Structure R: 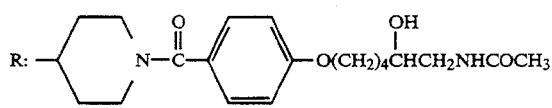

R¹: H, q: 1
Bond between 3- and 4-positions in the carbostyril ring: Single bond
NMR analysis: 288)
Form: Free Example 538
Structure R: 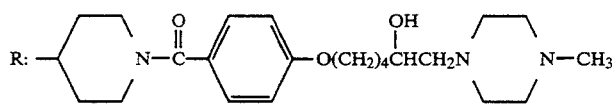

R¹: H, q: 1
Bond between 3- and 4-positions in the carbostyril ring: Single bond
NMR analysis: 289)
Form: Free Example 539
Structure R: 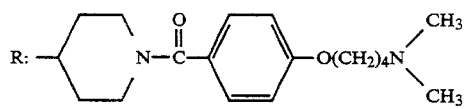

R¹: H, q: 1
Bond between 3- and 4-positions in the carbostyril ring: Single bond
NMR analysis: 290)
Form: Free Example 540
Structure R: 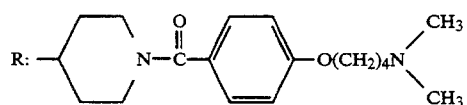

R¹: H, q: 1
Bond between 3- and 4-positions in the carbostyril ring: Single bond
NMR analysis: 291)
Form: Free Example 541
Structure R: 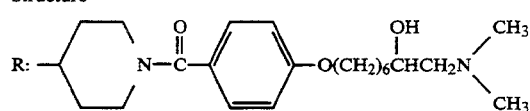

R¹: H, q: 1
Bond between 3- and 4-positions in the carbostyril ring: Single bond
NMR analysis: 292)
Form: Free TABLE 6-continued

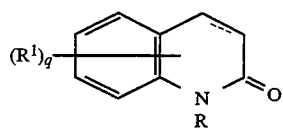

Example 542
Structure

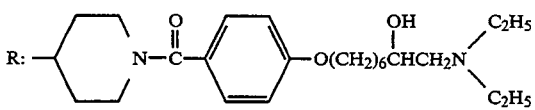

R[1]: H, q: 1
Bond between 3- and 4-positions in the carbostyril ring: Single bond
NMR analysis: 293)
Form: Free Example 543
Structure

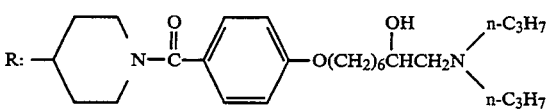

R[1]: H, q: 1
Bond between 3- and 4-positions in the carbostyril ring: Single bond
NMR analysis: 294)
Form: Free Example 544
Structure

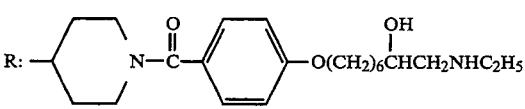

R[1]: H, q: 1
Bond between 3- and 4-positions in the carbostyril ring: Single bond
NMR analysis: 295)
Form: Free Example 545
Structure

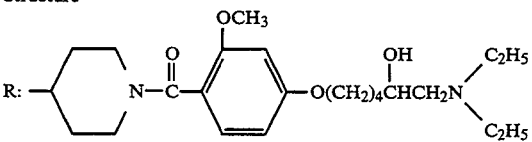

R[1]: F (7-position), q: 1
Bond between 3- and 4-positions in the carbostyril ring: Single bond
NMR analysis: 296)
Form: Free Example 546
Structure

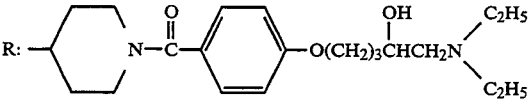

R[1]: H, q: 1
Bond between 3- and 4-positions in the carbostyril ring: Single bond
NMR analysis: 297)
Form: Free Example 547
Structure

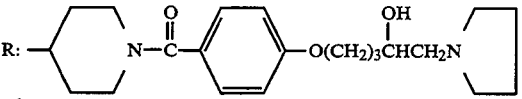

R[1]: H, q: 1
Bond between 3- and 4-positions in the carbostyril ring: Single bond
NMR analysis, 298)
Form: Free TABLE 6-continued

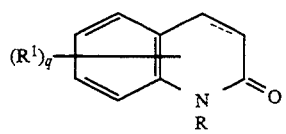

Example 548
Structure

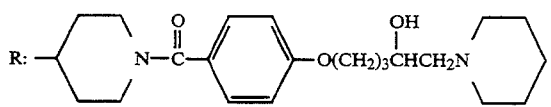

R¹: H, q: 1
Bond between 3- and 4-positions in the carbostyril ring: Single bond
NMR analysis: 299)
Form: Free Example 549
Structure

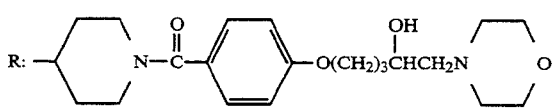

R¹: H, q: 1
Bond between 3- and 4-positions in the carbostyril ring: Single bond
NMR analysis: 300)
Form: Free Example 550
Structure

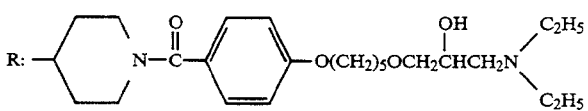

R¹: H, q: 1
Bond between 3- and 4-positions in the carbostyril ring: Single bond
NMR analysis: 301)
Form: Free Example 551
Structure

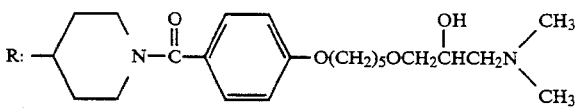

R¹: H, q: 1
Bond between 3- and 4-positions in the carbostyril ring: Single bond
NMR analysis: 302)
Form: Free Example 552
Structure

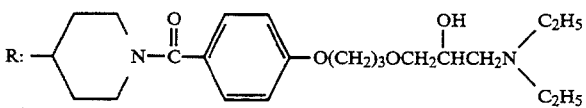

R¹: H, q: 1
Bond between 3- and 4-positions in the carbostyril ring: Single bond
NMR analysis: 303)
Form: Free Example 553
Structure

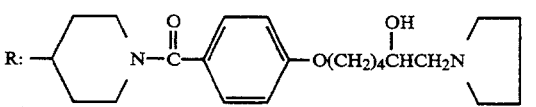

R¹: H, q: 1
Bond between 3- and 4-positions in the carbostyril ring: Single bond
NMR analysis: 304)
Form: Free Example 554

TABLE 6-continued

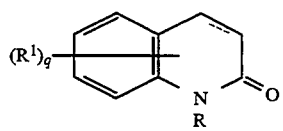

Structure

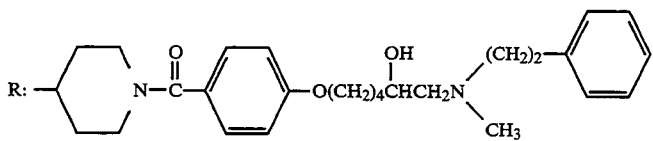

R¹: H, q: 1
Bond between 3- and 4-positions in the carbostyril ring: Single bond
NMR analysis: 305)
Form: Free Example 555
Structure

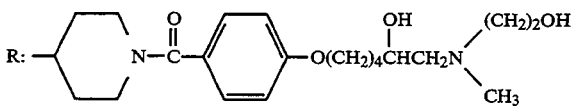

R¹: H, q: 1
Bond between 3- and 4-positions in the carbostyril ring: Single bond
NMR analysis: 306)
Form: Free Example 556
Structure

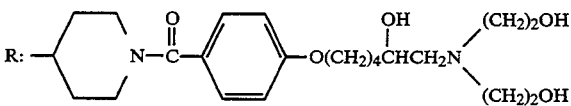

R¹: H, q: 1
Bond between 3- and 4-positions in the carbostyril ring: Single bond
NMR analysis: 307)
Form: Free Example 557
Structure

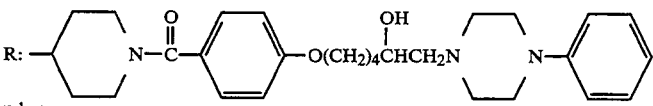

R¹: H, q: 1
Bond between 3- and 4-positions in the carbostyril ring: Single bond
NMR analysis. 308)
Form: Free Example 558
Structure

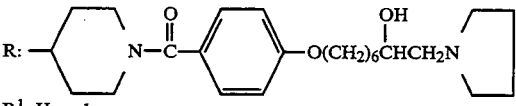

R¹: H, q: 1
Bond between 3- and 4-positions in the carbostyril ring: Single bond
NMR analysis: 309)
Form: Free Example 559
Structure

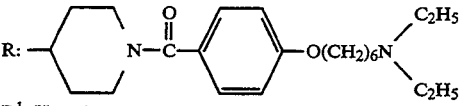

R¹: H, q: 1
Bond between 3- and 4-positions in the carbostyril ring: Single bond
NMR analysis: 310)
Form: Free Example 560

TABLE 6-continued

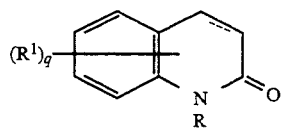

Structure

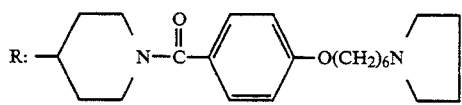

$R^1$: H, q: 1
Bond between 3- and 4-positions in the carbostyril ring: Single bond
NMR analysis: 311)
Form: Free Example 561
Structure

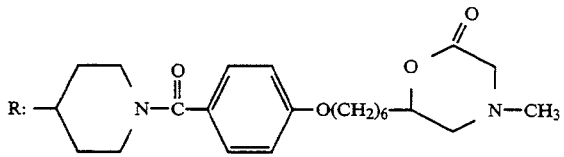

$R^1$: H, q: 1
Bond between 3- and 4-positions in the carbostyril ring: Single bond
NMR analysis: 312)
Form: Free Example 562
Structure

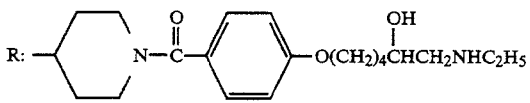

$R^1$: H, q: 1
Bond between 3- and 4-positions in the carbostyril ring. Single bond
NMR analysis: 313)
Form: Free Example 563
Structure

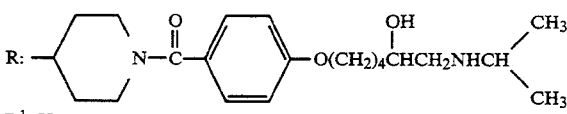

$R^1$: H, q: 1
Bond between 3- and 4-positions in the carbostyril ring: Single bond
NMR analysis: 314)
Form: Free Example 564
Structure

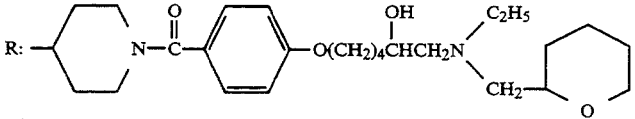

$R^1$: H, q: 1
Bond between 3- and 4-positions in the carbostyril ring: Single bond
NMR analysis: 315)
Form: Free Example 565
Structure

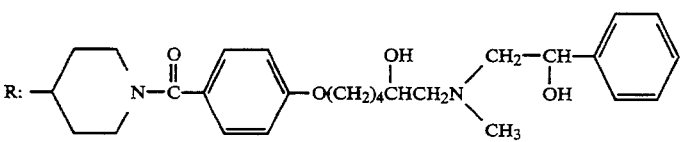

$R^1$: H, q: 1
Bond between 3- and 4-positions in the carbostyril ring: Single bond
NMR analysis: 316)

TABLE 6-continued

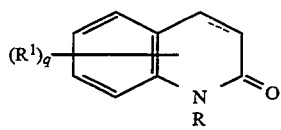

Form: Free

Example 566
Structure

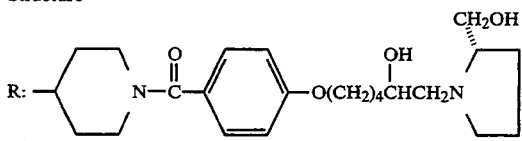

R¹: H, q: 1
between 3- and 4-positions in the carbostyril ring: Single bond
NMR analysis: 317)
Form: Free Example 567
Structure

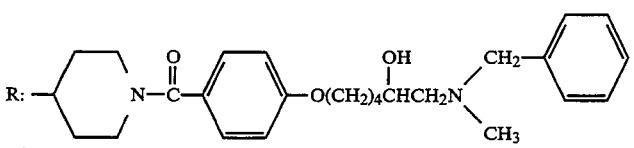

R¹: H, q: 1
Bond between 3- and 4-positions in the carbostyril ring: Single bond
NMR analysis: 318)
Form: Free Example 568
Structure

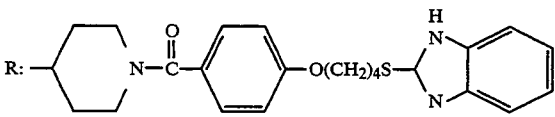

R¹: H, q: 1
Bond between 3- and 4-positions in the carbostyril ring: Single bond
Crystalline form: White amorphous form
NMR analysis: 319)
Form: Free Example 569
Structure

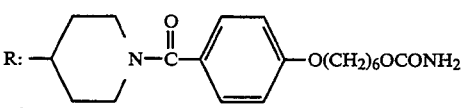

R¹: H, q: 1
Bond between 3- and 4-positions in the carbostyril ring: Single bond
Crystalline form: White amorphous form
NMR analysis: 320)
Form: Free Example 570
Structure

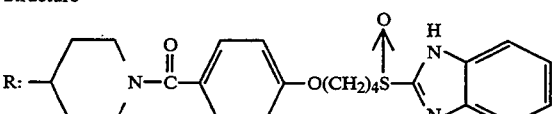

R¹: H, q: 1
Bond between 3- and 4-positions in the carbostyril ring: Single bond
Crystalline form: White amorphous form
NMR analysis: 321)
Form: Free Example 571
Structure

TABLE 6-continued

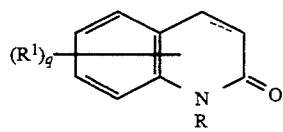

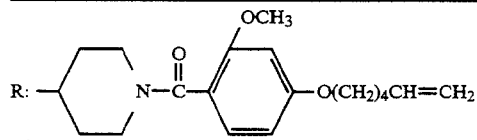

R¹: F (5-, 7-position), q: 2
Bond between 3- and 4-positions in the carbostyril ring: Single bond
Crystalline form: White amorphous form
NMR analysis, 325)
Form: Free Example 572
Structure

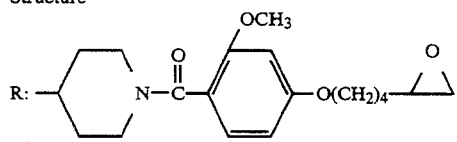

R¹: F (5-, 7-position), q: 2
Bond between 3- and 4-positions in the carbostyril ring: Single bond
Crystalline form: White amorphous form
NMR analysis: 326)
Form: Free Example 573
Structure

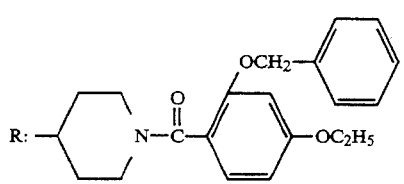

R¹: H, q: 1
Bond between 3- and 4-positions in the carbostyril ring: Single bond
Crystalline form: White powders
Recrystallization solvent: Ethanol
Melting point: 63–65° C.
Form: Free Example 574
Structure

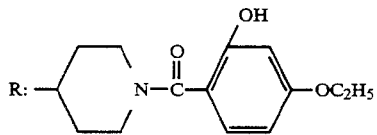

R¹: H, q: 1
Bond between 3- and 4-positions in the carbostyril ring: Single bond
Crystalline form: White powders
Recrystallization solvent: Ethanol
Melting point: 138–140° C.
Form: Free Example 575
Structure

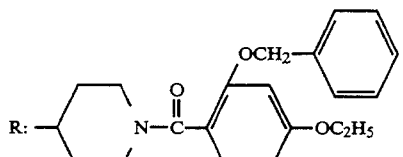

R¹: F (7-position), q: 1
Bond between 3- and 4-positions in the carbostyril ring: Single bond
Crystalline form: White powders
Recrystallization solvent: Ethanol
Melting point: 83–86° C.

TABLE 6-continued

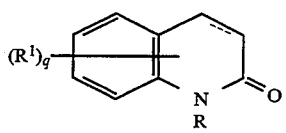

Form: Free

Example 576
Structure

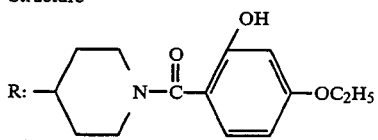

R[1]: F (7-position), q: 1
Bond between 3- and 4-positions in the carbostyril ring: Single bond
Crystalline form: White powders
Recrystallization solvent: Ethanol
Melting point: 140–142° C.
Form: Free Example 577
Structure

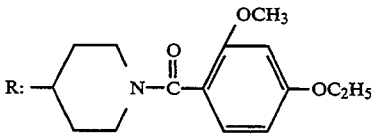

R[1]: CH$_3$ (5-position), q: 1
Bond between 3- and 4-positions in the carbostyril ring: Single bond
Crystalline form: White amorphous form
NMR analysis: 327)
Form: Free Example 577A
Structure

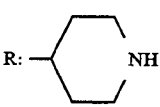

R[1]: CH$_3$ (5-position), q: 1
Bond between 3- and 4-positions in the carbostyril ring: Single bond
Crystalline form: White amorphous form
NMR analysis: 328)
Form: Free The following compounds are obtained in the same manners as in Examples 1 and 385.

TABLE 7

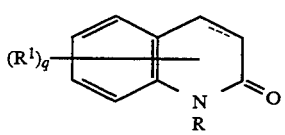

Example 578
Structure

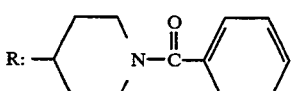

R[1]: F (7-position), q: 1
Bond between 3- and 4-positions in the carbostyril ring: Double bond
Crystalline form: White powders
Recrystallization solvent: Ethanol
Melting point: 181–185° C.
Form: Free Example 579
Structure TABLE 7-continued

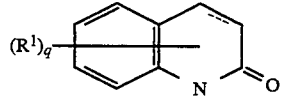

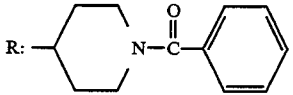

R[1]: (5-, 7-positions), q: 2
Bond between 3- and 4-positions in the carbostyril ring: Double bond
Crystalline form: White powders
Recrystallization solvent: Ethanol
Melting point: 183–185° C.
Form: Free Example 580
Structure

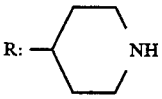

TABLE 7-continued

[Structure: carbostyril ring with (R¹)q and N-R substituent, C=O]

R¹: F (7-position), q: 1
Bond between 3- and 4-positions in the carbostyril ring: Double bond
Crystalline form: White amorphous form
NMR analysis: 243)
Form: Free

Example 581
Structure

R: —⟨cyclohexyl⟩—NH

R¹: F (5-, 7-positions), q: 2
Bond between 3- and 4-positions in the carbostyril ring: Double bond
Crystalline form: White powders
Recrystallization solvent: Ethanol/n-hexane
Melting point: 186–187° C.
Form: Free

Example 582
Structure

R: —⟨cyclohexyl⟩—N—C(=O)—⟨phenyl with OCH₃, OC₂H₅⟩

R¹: F (7-position), q: 1
Bond between 3- and 4-positions in the carbostyril ring: Double bond
Crystalline form: White powders
Recrystallization solvent: Ethanol/diethyl ether
Melting point: 187–188° C.
Form: Free

Example 583
Structure

R: —⟨cyclohexyl⟩—N—C(=O)—⟨phenyl with OCH₃, OCH₃⟩

R¹: F (7-position), q: 1
Bond between 3- and 4-positions in the carbostyril ring: Double bond
Crystalline form: White amorphous form
NMR analysis: 244)
Form: Free

Example 584
Structure

R: —⟨cyclohexyl⟩—N—C(=O)—⟨phenyl with OCH₃, OC₂H₅⟩

R¹: F (5-, 7-positions), q: 2
Bond between 3- and 4-positions in the carbostyril ring: Double bond
Crystalline form: White powders
Recrystallization solvent: Ethanol/diethyl ether
Melting point: 150–152° C.
Form: Free

Example 585
Structure

R: —⟨cyclohexyl⟩—N—C(=O)—⟨phenyl⟩—O(CH₂)₃N—⟨phthalimide⟩

R¹: H, q: 1
Bond between 3- and 4-positions in the carbostyril ring: Double bond
Crystalline form: White amorphous form
NMR analysis: 322)
Form: Free

Example 586
Structure

R: —⟨cyclohexyl⟩—N—C(=O)—⟨phenyl⟩—O(CH₂)₃NH₂

R¹: H, q: 1
Bond between 3- and 4-positions in the carbostyril ring: Double bond
Crystalline form: White amorphous form
NMR analysis: 323)
Form: Free

Example 587
Structure

R: —⟨cyclohexyl⟩—N—C(=O)—⟨phenyl⟩—O(CH₂)₃NHCOCH₃

R¹: H, q: 1
Bond between 3- and 4-positions in the carbostyril ring: Double bond
Crystalline form: White amorphous form
NMR analysis: 324)
Form: Free

TABLE 8

| No. | NMR (CDCl₃) δ value |
|---|---|
| 237 | 1.42(3H, t, J=7.0Hz), 1.58–2.05(2H, m), 2.35–3.47(7H, m), 3.55–3.95(4H, m), 4.04(2H, q, J=7 Hz), 4.38(1H, brs), 4.94(1H, brs), 6.37–6.56 (2H, m), 7.00–7.40(5H, m) |
| 238 | 1.42(3H, t, J=7Hz), 1.52–1.95(2H, m), 2.30–3.93 (13H, m), 4.04(2H, q, J=7Hz), 4.15–5.06(3H, m), 6.40–6.62(2H, m), 6.97–7.50(5H, m) |
| 239 | 1.40(3H, t, J=7Hz), 1.55–2.00(2H, m), 2.30–5.05 (15H, m), 5.30(2H, s), 5.95(1H, brs), 6.50–6.60 (2H, m), 7.02–7.42(10H, m) |
| 240 | 1.42 (3H, t, J=7Hz), 1.55–1.98(2H, m), 2.08(3H, s), 2.40–3.95(7H, m), 4.05(2H, q, J=7Hz), 4.20–4.65(2H, m), 4.90–5.11(1H, m), 6.42–6.73(3H, m) 7.02–7.40(5H, m) |
| 241 | 1.42(3H, t, J=7Hz), 1.50–1.96(2H, m), 2.43(6H, s), 2.51–3.28(7H, m), 3.57–3.95(4H, m), 4.04(2H, q, J=7Hz), 4.33–4.75(1H, m), 4.84–5.06(1H, m), 6.40–6.60(2H, m), 6.99–7.32(5H, m) |
| 242 | 1.68–2.15(4H, m), 2.45–3.20(8H, m), 3.40–3.62 (2H, m); 4.06(2H, t, J=5.9Hz), 4.10–5.10(3H, m), 6.26(1H, brs), 6.68–7.25(5H, m), 7.42(2H, d, J=8.7Hz), 8.15(1H, s) |
| 243 | 1.65–1.88(2H, m), 2.20(1H, brs), 2.60–3.05(4H, m), 3.18–3.42(2H, m), 5.15(1H, brs), 6.59(1H, d, J=9.4Hz), 6.94(1H, m), 7.35–7.65(3H, m) |
| 244 | 1.60–1.97(2H, m), 2.50–3.33(4H, m), 3.54–4.02 (7H, m), 4.95–5.12(1H, m), 6.40–6.65(3H, m), 6.90–7.13(1H, m), 7.15–7.67(4H, m) |

TABLE 8-continued

| No. | NMR (DMSO-d6) δ value |
|---|---|
| 245 | 1.08(6H, t, J=7.1Hz), 1.32–1.90(8H, m), 2.25–3.20(15H, m), 3.60–5.10(9H, m), 6.40–6.85(4H, m), 7.15–7.30(1H, m) |
| 246 | 1.45–1.97(6H, m), 2.16(2H, m), 2.36–3.32(8H, m 2.56(2H, m), 3.60–5.15(2H, m), 3.87(2H, m), 4.32 (2H, m), 4.68(2H, m), 6.19(1H, brs), 6.64(2H, d, J=8.0Hz), 6.83(2H, d, J=8.3Hz), 6.92–7.23(8H, m), 7.36(2H, d, J=8.3Hz) |
| 247 | 0.95(3H, d, J=6.0Hz), 0.98(3H, d, J=6.0Hz), 1.38–1.61(2H, m), 1.62–1.96(6H, m), 2.08(1H, m), 2.27(2H, t, J=7.3Hz), 2.53–3.15 (8H, m), 3.77–4.85(2H, m), 3.97(2H, t, J=6.2Hz), 4.32(2H, m), 5.79(1H, brs), 6.50(2H, m), 6.89(2H, d, J=8.6 Hz), 6.99–7.27(4H, m), 7.42(2H, d, J=8.6Hz) |
| 248 | 1.67–1.96(2H, m), 2.14(2H, quint, J=6.3Hz), 2.40–3.10(8H, m), 2.52(2H, t, J=6.3Hz), 2.96 (3H, s), 3.02(3H, s), 3.85–5.10(2H, m), 4.07(2H, t, J=6.3Hz), 4.37(1H, m), 6.92(2H, d, J=8.6Hz), 6.98–7.33(4H, m), 7.43(2H, d, J=8.6Hz) |
| 249 | 1.65–1.95(2H, m), 2.12(2H, quint, J=6.4Hz), 2.41(2H, t, J=6.4Hz), 2.54–2.85(8H, m), 3.80–5.10(2H, m), 3.98(2H, t, J=6.4Hz), 4.35(1H, m), 4.40(2H, d, J=5.5Hz), 6.54–6.92(1H, brs), 6.83 (2H, d, J=8.6Hz), 6.99–7.31(9H, m), 7.37(2H, d, J=8.6Hz) |

| No. | NMR (CDCl3) δ value |
|---|---|
| 250 | 1.21–1.82(8H, m), 2.08(2H, t, J=7.1Hz), 2.26–3.20(8H, m), 3.39(2H, m), 3.60–4.66(2H, brs), 3.93(2H, t, J=6.4Hz), 4.32(2H, m), 6.71(1H, s), 6.84–7.01(2H, brs), 6.94(2H, d, J=8.7Hz), 7.16–7.31(4H, m), 7.32(2H, d, J=8.7Hz), 7.47(1H, s), 7.88(1H, d, J=8.2Hz), |
| 251 | 1.10–1.97(10H, m), 2.07(2H, t, J=7.6Hz), 2.16 (2H, t, J=7.3Hz), 2.32–3.40(8H, m), 3.60–4.80 (2H, brs), 3.99(2H; t, J=6.4Hz), 4.15(1H, m), 4.28(1H, m), 6.74(1H, brs), 6.98(2H, d, J=8.6 Hz), 7.05(1H, brs), 7.20–7.29(4H, m), 7.36(2H, d, J=8.6Hz), 7.85(1H, d, J=7.7Hz) |
| 252 | 1.38–1.59(2H, m), 1,60–2.18(8H, m), 2.09(3H, s), 2.25(2H, t, J=7.2Hz), 2.44–3.17(8H, m), 2.57 (2H, t, J=6.1Hz), 3.55–5.10(2H, brs), 3.97(2H, t, J=6.1Hz), 4.38(1H, m), 4.64(1H, q, J=7.2Hz), 5.95(1H, brs), 6.78(1H, brs), 6.82(1H, brs), 6.89(2H, d, J=8.7Hz), 6.91–7.28(4H, m), 7.41 (2H, d, J=8.7Hz) |
| 253 | 1.42–1.64(2H, m), 1.64–2.06(6H, m), 2.57(2H, t, J=6.1Hz), 2.64–3.24(8H, m), 3.67–5.15(2H, m), 3.92(2H, t, J=6.1Hz), 4.34(1H, m), 6.84(2H, d, J=8.7Hz), 7.00–7.36(5H, m), 7.40(2H, d, J=8.7 Hz), 8.28(1H, d, J=5.6Hz), 8.80(1H, s) |
| 254 | 1.13–1.96(14H, m), 2.25 (2H, t, J=7.3Hz), 2.46–3.08(8H, m), 3.16(1H, m), 3.72(3H, s), 3.96(2H, t, J=6.2Hz), 4.05–4.97(2H, m), 4.37(1H, m), 4.57 (1H, m), 5.07(1H, brs), 5.08(2H, s), 6.34(1H, d, J=7.5Hz), 6.88(2H, d, J=8.6Hz), 6.98–7.30 (4H, m), 7.34(5H, s), 7.41(2H, d, J=8.6Hz) |
| 255 | 1.30–1.93(14H, m), 2.27(2H, t, J=7.3Hz), 2.53–3.11(10H, m), 3.73(3H, s), 3.98(2H, t, J=6.3 Hz), 4.13–5.06(2H, m), 4.38(1H, m), 4.59(1H, m), 6.46(1H, d, J=7.8Hz), 6.89(2H, d, J=8.6Hz), 6.98–7.30(4H, m), 7.42(2H, d, J=8.6Hz) |
| 256 | 1.14(3H, t, J=7.6Hz), 1.84(2H, m), 2.00(2H, quint, J=6.1Hz), 2.21(2H, q, J=7.6Hz), 2.43–3.23 (8H, m), 3.42(2H, q, J=6.1Hz), 3.65–5.14(2H, m), 4.03(2H, t, J=6.1Hz), 4.36(1H, m), 6.52(1H, brs), 6.89(2H, d, J=8.4Hz), 6.98–7.32(4H, m), 7.42(2H, d, J=8.4Hz) |
| 257 | 0.95(6H, t, J=6.3Hz), 1.84(2H, m), 1.94–2.22 (5H, m), 2.53–3.17(8H, m), 3.46(2H, q, J=6.1Hz), 3.66–5.05(2H, m), 4.05(2H, t, J=6.1Hz), 4.38 (1H, m), 6.00(1H, brs), 6.90(2H, d, J=8.7Hz), 6.99–7.29(4H, m), 7.43(2H, d, J=8.7Hz) |
| 258 | 1.24(3H, t, J=7.1Hz), 1.66–1.93(2H, m), 2.01 (2H, quint, J=6.2Hz), 2.53–3.15(8H, m), 3.39(2H, q, J=6.2Hz), 3.60–5.10(2H, m), 4.05(2H, t, J=6.2 Hz), 4.11(2H, q, J=7.1Hz), 4.39(1H, m), 4.94 (1H, brs), 6.91(2H, d, J=8.7Hz), 6.98–7.29(4H, m), 7.43(2H, d, J=8.7Hz) |
| 259 | 0.92(6H, d, J=6.7Hz), 1.60–1.94(3H, m), 2.02 (2H, quint, J=6.2Hz), 2.53–3.15(8H, m), 3.39(2H, q, J=6.2Hz), 3.60–5.20(2H, m), 3.84(2H, d, J=6.7 Hz), 4.06(2H, t, J=6.2Hz), 4.39(1H, m), 4.95 (1H, brs), 6.91(2H, d, J=8.7Hz), 6.98–7.29(4H, m), 7.43(2H, d, J=8.7Hz) |
| 260 | 1.55–1.87(2H, m), 1.95(2H, quint, J=6.0Hz), 2.52–3.10(8H, m), 3.12(2H, q, J=6.0Hz), 3.66–5.10(2H, m), 3.96(2H, t, J=6.0Hz), 4.37(1H, m), 5.51(1H, brs), 6.81(2H, d, J=8.6Hz), 6.98–7.30 (4H, m), 7.36–7.60(5H, m), 7.85(2H, d, J=8.6Hz) |
| 261 | 1.60–1.90(2H, m), 1.95(2H, quint, J=6.1Hz), 2.40 (3H, 5), 2.50–3.10(8H, m), 3.15(2H, q, J=6.1Hz), 3.70–5.05(2H, m), 3.97(2H, t, J=6.1Hz), 4.38 (1H, m), 5.19(1H, t, J=6.1Hz), 6.82(2H, d, J=8.7 Hz), 6.98–7.28(4H, m), 7.27(2H, d, J=8.7Hz), 7.40(2H, d, J=8.7Hz), 7.74(2H, d, J=8.1Hz), |
| 262 | 1.68–1.93(2H, m), 1.93–2.14(2H, m), 2.02(3H, s), 2.53–3.25(8H, m), 3.46(2H, q, J=5.9Hz), 3.70–5.15(2H, m), 3.86(2H, d, J=4.6Hz), 4.04(2H, t, J=5.9Hz), 4.37(1H, m), 6.65(1H, brs), 6.77(1H, brs), 6.90(2H, d, J=8.6Hz), 6.98–7.33(4H, m), 7.42(2H, d, J=8.6Hz) |
| 263 | 0.93(6H, d, J=6.7Hz), 1.60–1.92(2H, m), 1.93–2.15(3H, m), 2.00(3H, s), 2.33–3.24(8H, m), 3.45 (2H, m), 3.70–5.10(2H, m), 4.03(2H, t, J=5.9Hz), 4.24(1H, t, J=8.5Hz), 4.38(1H, m), 6.63(1H, d, J=8.5Hz), 6.89(2H, d, J=8.6Hz), 6.98–7.29(5H, m), 7.42(2H, d, J=8.6Hz) |
| 264 | 1.67–1.94(2H, m), 2.04(2H, quint, J=6.2Hz), 2.53–3.20(8H, m), 3.51(2H, q, J=6.2Hz), 3.65–5.15(2H, m), 4.06(2H, t, J=6.2Hz), 4.37(1H, m), 6.29(1H, brs), 6.91(2H, d, J=8.7Hz), 6.98–7.29 (4H, m), 7.43(2H, d, J=8.7Hz), 8.14(1H, s) |
| 265 | 1.39–1.62(2H, m), 1.62–1.95(8H, m), 2.20(2H, t, J=7.4Hz), 2.33(6H, s), 2.50(2H, t, J=6.5Hz), 2.56–3.20(8H, m), 3.34(2H, q, J=5.9Hz), 3.66 (1H, brs), 3.86–5.20(1H, m), 3.98(2H, t, J=6.3 Hz), 4.39(1H, m), 6.89(2H, d, J=8.6Hz), 6.98–7.30(5H, m), 7.42(2H, d, J=8.6Hz) |
| 266 | 1.82(2H, m), 2.13(2H, quint, J=5.9Hz), 2.52–3.20 (8H, m), 3.66(2H, q, J=5.9Hz), 3.80–5.10(2H, m), 4.08(2H, t, J=5.9Hz), 4.31(1H, m), 6.86(2H, d, J=8.7Hz), 6.99–7.12(2H, m), 7.16–7.29(2H, m), 7.38(2H, d, J=8.7Hz), 7.59(1H, t, J=5.9Hz), 7.98(2H, dd, J=7.0, 1.9Hz), 8.20(2H, dd, J=7.0, 1.9Hz) |
| 267 | 1.67–1.94(2H, m), 2.09(2H, quint, J=6.0Hz), 2.53–3.20(8H, m), 3.46–5.00(4H, m), 3.60(2H, q, J=6.0Hz), 4.08(2H, t, J=6.0Hz), 4.34(1H, m), 6.63(2H, d, J=8.6Hz), 6.77(1H, t, J=6.0Hz), 6.88(2H, d, J=8.7Hz), 6.98–7.29(4H, m), 7.39 (2H, d, J=8.7Hz), 7.60(2H, d, J=8.6Hz) |
| 268 | 1.60–2.33(4H, m), 2.53–3.20(8H, m), 3,30(2H, m), 3.70–5.17(2H, m), 3.91(2H, t, J=5.9Hz), 4.33 (1H, m), 5.83(1H, brs), 6.82(2H, d, J=8.6Hz), 6.92–7.50(9H, m), 7.37(2H, d, J=8.6Hz), 7.67 (1H, s) |
| 269 | 1.70–2.12(4H, m), 2.00(3H, s), 2.14–2.50(4H, m), 2.53–3.20(8H, m), 3.44(2H, q, J=5.9Hz), 3.80–5.10(2H, brs), 4.03(2H, t, J=5.9Hz), 4.41(2H, m), 6.05(1H, brs), 6.70(1H, brs), 6.91(2H, d, J=8.6Hz), 6.98–7.32(5H, m), 7.41(2H, d, J=8.6 Hz), 7.51(1H, t, J=5.9Hz) |
| 270 | 1.66–1.97(2H, m), 2.04–2.30(2H, m), 2.15(3H, s), 2.44–3.20(8H, m), 3.60(2H, q, J=5.7Hz), 4.05 (2H, t, J=5.7Hz), 4.31(1H, m), 3.80–5.14(2H, m), 6.82(2H, d, J=8.7Hz), 6.99–7.42(5H, m), 7.31 (2H, d, J=8.7Hz), 7.54(2H, d, J=8.6Hz), 7.69 (2H, d, J=8.6Hz), 8.96(1H, brs) |
| 271 | 1.06(3H, t, J=6.8Hz), 1.84(2H, m), 1.92(2H, quint, J=5.9Hz), 2.25–3.20(8H, m), 3.15(2H, quint, J=6.8Hz), 3.30(2H, q, J=5.9Hz), 3.56–5.10 (2H, m), 4.00(2H, t, J=5.9Hz), 4.33(1H, m), 5.29 (1H, t, J=6.8Hz), 5.67(1H, t, J=5.9Hz), 6.89 (2H, d, J=8.4Hz), 6.98–7.32(4H, m), 7.39(2H, d, J=8.4Hz) |
| 272 | 1.40–1.62(2H, m), 1.62–1.94(6H, m), 2.23(2H, t, J=7.6Hz), 2.27(6H, s), 2.46(2H, t, J=5.8Hz), 2.52–3.10(8H, m), 3.34(2H, q, J=5.8Hz), 3.75–5.10(2H, m), 3.98(2H, t, J=6.3Hz), 4.38(1H, m), 6.33(1H, brs), 6.94(2H, d, J=8.7Hz), 6.98–7.30 (4H, m), 7.42(2H, d, J=8.7Hz), |
| 273 | 1.35–1.60(4H, m), 1.61–2.00(8H, m), 2.03–2.21 |

TABLE 8-continued

| | |
|---|---|
| | (4H, m), 2.53-3.14(10H, 3.50(2H, s), 3.60-5.20(2H, m), 3.83 (1H, m,), 3.97(2H, t, J=6.3Hz), 4.39(1H, m), 5.41(1H, d, J=8.0Hz), 6.88(2H, d, J=8.7Hz), 6.99-7.32(4H, m), 7.30(5H, m), 7.42 (2H, d, J=8.7Hz) |
| 274 | 1.70-2.20(6H, m), 1.99(3H, s), 2.08(3H, s), 2.35-3.20(10H, m), 3.45(2H, q, J=6.0Hz), 3.70-5.20(2H, m), 4.03(2H, t, J=6.0Hz), 4.38 (1H, m), 4.57(1H, q, J=7.2Hz), 6.58(1H, d, J=6.0Hz), 6.80-6.98(1H, brs), 6.91(2H, d, J=8.6Hz), 6.99-7.29(4H, m), 7.43(2H, d, J=8.6Hz). |
| 275 | 1.70-2.03(4H, m), 2.05(3H; s), 2.58-3.22(8H, m), 2.99(2H, d, J=7.0Hz), 3.44(2H, d, J=5.9Hz), 3.55-5.30(2H, m), 3.96(2H, t, J=5.9Hz), 4.40 (1H, m), 4.72(1H, q, J=7.0Hz), 6.75(1H, s), 6.92 (2H, d, J=8.6Hz), 7.04-7.60(7H, m), 7.44(2H, d, J=8.6Hz) |
| 276 | 1.33(3H, d, J=7.0Hz), 1.65-1.93(2H, m), 1.93-2.12(2H, m), 1.97(3H, s), 2.53-3.20(8H, m), 3.43 (2H, q, J=6.1Hz), 3.80-5.20(2H, m), 4.02(2H, t, J=6.1Hz), 4.37(1H, m), 4.46(1H, quint, J=7.0 Hz), 6.64(1H, brs), 6.90(2H, d, J=8.7Hz), 6.98-7.29(5H, m), 7.42(2H, d, J=8.7Hz) |
| 277 | 1.38-1.64(4H, m), 1.65-2.10(8H, m), 2.20(2H, t, J=7.3Hz), 2.53-3.10(10H, m), 3.10-3.39(2H, m), 3.45-5.20(2H, m), 3.94(1H, m), 3.98(2H, t, J=6.3 Hz), 4.37(1H, m), 5.82(1H, d, J=7.8Hz), 6.90 (2H, d, J=8.7Hz), 6.98-7.28(4H, m), 7.41(2H, d, J=8.7Hz) |
| 278 | 1.85(4H, m), 2.54-3.24(10H, m), 3.35(2H, m), 3.63-5.00(2H, m), 3.85(2H, m), 4.31(2H, m), 5.11 (2H, s), 5.41(1H, brs), 6.15(1H, brs), 6.45(2H, d, J=8.3Hz), 6.77(2H, d, J=8.6Hz), 6.84(2H, d, J=8.3Hz), 7.00-7.30(4H, m), 7.34(5H, s), 7.37 (2H, d, J=8.6Hz), 8.12(1H, s) |
| 279 | 1.57-1.92(6H, m), 2.19-3.15(18H, m), 3.51-3.61 (2H, m), 3.84-5.22(3H, m), 3.99(2H, t, J=6.3Hz), 6.83-7.46(13H, m) |
| 280 | 1.57-2.05(6H, m), 2.40-3.56(21H, m), 3.73-5.12 (3H, m), 4.02(2H, t, J=5.9Hz), 6.83-7.52(8H, m) |
| 281 | 1.59-1.98(6H, m), 2.32-3.16(14H, m), 3.35-5.18 (7H, m), 3.70(3H, s), 4.01(2H, t, J=6.2Hz), 6.83-7.48(8H, m) |
| 282 | 1.66-2.12(6H, m), 2.32-3.13(12H, m), 3.33-5.10 (13H, m), 6.84-7.49(13H, m) |
| 283 | 1.57-1.95(6H, m), 2.09(3H, s), 2.28-3.28(14H, m), 3.48-5.07(7H, m), 4.01(2H, t, J=6.2Hz), 6.87-7.49(8H, m) |
| 284 | 1.71-1.98(6H, m), 2.15(1H, brs), 2.49-3.16(12H, m), 3.32-5.12(11H, m), 6.85-7.48(8H, m) |
| 285 | 1.34-2.01(8H, m), 2.41-3.23(12H, 3.56-5.18 (8H, m), 6.82-7.48(11H, m) |
| 286 | 1.39-1.96(8H, m), 2.03(2H, brs), 2.43-3.18 (10H, m), 3.35-5.15(4H, m), 3.99(2H, t, J=6.3Hz), 6.84-7.47(8H, m) |
| 287 | 1.42-1.94(8H, m), 1.98(3H, S), 2.08(3H, s), 2.50-3.18(8H, m), 3.30-3.58(2H, m), 3.71-5.07 (4H, m), 3.97(2H, t, J=6.2Hz), 5.90-6.03(1H, m), 6.87-7.49(8H, m) |
| 288 | 1.38-2.08(8H, m), 1.99(3H, s), 2.39-3.56(11H, m), 3.58-5.11(6H, m), 6.17-6.42(1H, m), 6.82-7.48 (8H, m) |
| 289 | 1.37-1.94(8H, m), 2.14-3.15(19H, m), 2.32(3H, s), 3.58-5.07(4H, m), 3.99(2H, t, J=6.4Hz), 6.82-7.48(8H, m) |
| 290 | 1.65-1.98(6H, m), 2.33-3.13(10H, m), 2.39(6H, s), 3.88-4.99(3H, m), 4.02(2H, t, J=5.9Hz), 6.83-7.50(8H, m) |
| 291 | 1.44-2.03(6H, m), 2.21(6H, s), 2.28(2H, t, J=7.2 Hz), 2.52-3.28(10H, m), 3.76-5.13(3H, m), 6.98-7.42(8H, m) |
| 292 | 1.36-1.98(10H, m), 2.12-2.39(2H, m), 2.28(6H, s), 2.52-3.12(10H, m), 3.55-5.13(5H, m), 3.99 (2H, t, J=6.3Hz), 6.86-7.48(8H, m) |
| 293 | 1.04(6H, t, J=7.1Hz), 1.32-1.95(10H, m), 2.20-3.16(16H, m), 3.43-5.13(5H, m), 4.00(2H, t, J=6.4Hz), 6.86-7.49(8H, m) |
| 294 | 0.89(6H, t, J=7.4Hz), 1.32-1.94(16H, m), 2.26-3.12(14H, m), 3.45-4.98(5H, m), 3.99(2H, t, J=6.3Hz), 6.34-7.49(8H, m) |
| 295 | 1.12(3H, t, J=7.1Hz), 1.38-1.96(10H, m), 2.26-3.12(15H, m), 3.46-5.06(5H, m), 3.99(2H, t, J=6.0Hz), 6.89(2H, d, J=8.7Hz), 6.99-7.32(4H, m), 7.42(2H, d, J=8.7Hz) |
| 296 | 1.07(6H, t, J=7.2Hz), 1.28-1.94(8H, m), 2.25-3.17(15H, m), 3.55-5.08(7H, m), 3.96(2H, t, J=6.5Hz), 6.42-7.33(6H, m) |
| 297 | 1.04(6H, t, J=7.1Hz), 1.42-2.14(6H, m), 2.23-3.13(14H, m), 3.56-5.02(7H, m), 6.87-7.49(8H, m) |
| 298 | 1.51-2.13(10H, m), 2.52-3.40(15H, m), 3.78-5.03 (6H, m), 6.83-7.48(8H, m) |
| 299 | 1.35-2.10(12H, m), 2.13-3.12(15H, m), 3.57-4.83 (6H, m), 6.82-7.53(8H, m) |
| 300 | 1.44-2.12(6H, m), 2.20-3.13(15H, m), 3.15-4.86 (10H, m), 6.88-7.57(8H, m) |
| 301 | 1.08(6H, t, J=7.9Hz), 1.43-1.93(8H, m), 2.40-3.16(14H, m), 3.28-5.17(4H, m), 3.45(2H, t, J=5.1Hz), 3.51(2H, t, J=8.0Hz), 3.99(2H, t, J=6.4Hz), 6.84-7.48(4H, m) |
| 302 | 1.48-1.93(8H, m), 2.27-3.13(10H, m), 2.45(6H, s), 3.36-3.67(5H, m), 3.73-5.17(4H, m), 3.99(2H, t, J=6.3Hz), 6.86-7.50(8H, m) |
| 303 | 1.23(6H, t, J=7.2Hz), 1.67-1.94(2H, m), 2.06 (2H, quint, J=6.2Hz), 2.43-3.14(14H, m), 3.38-3.62(4H, m), 3.66(2H, t, J=6.1Hz), 3.87-5.22 (4H, m), 4.08(2H, t, J=6.1Hz), 6.85-7.48(8H, m) |
| 304 | 1.38-1.98(12H, m), 2.25-3.18(14H, m), 3.33-5.13 (7H, m), 6.80-7.50(8H, m) |
| 305 | 1.26-1.92(8H, m), 2.15-3.13(14H, m), 2.32(3H, s), 3.20-5.03(5H, m), 3.98(2H, t, J=6.4Hz), 6.82-7.47(13H, m) |
| 306 | 1.37-1.94(8H, m), 2.28-3.23(14H, m), 2.36(3H, s), 3.54-5.15(4H, m), 3.68(2H, t, J=4.8Hz), 4.00 (2H, t, J=6.3Hz), 6.83-7.52(8H, m) |
| 307 | 1.33-1.98(8H, m), 2.28-3.18(14H, m), 3.38-5.18 (11H, m), 3.98(2H, t, J=6.2Hz), 6.78-7.48 (8H, m) |
| 308 | 1.35-1.98(8H, m), 2.25-3.32(18H, m), 3.38-5.10 (7H, m), 6.78-7.48(13H, m) |
| 309 | 1.38-1.98(16H, m), 2.23-3.15(14H, m), 3.32-5.05 (5H, m), 4.00(2H, t, J=6.3Hz), 6.32-7.50(8H, m) |
| 310 | 1.43(6H, t, J=7.3Hz), 1.35-1.65(4H, m), 1.70-1.98(6H, m), 2.51-3.23(4H, m), 3.77-5.23(3H, m), 3.99(2H, t, J=6.2Hz), 6.85-7.51(8H, m) |
| 311 | 1.34-2.31(14H, m), 2.51-3.65(14H, m), 3.70-5.14 (3H, m), 3.98(2H, t, J=6.2Hz), 6.83-7.50(8H, m) |
| 312 | 1.46-2.06(12H, m), 2.16-3.13(14H, m), 3.33-5.07 (5H, m), 4.00(2H, t, J=6.0Hz), 6.83-7.48(8H, m) |
| 313 | 1.13(3H, t, J=7.2Hz), 1.38-2.02(9H, m), 2.37-3.13(12H, m), 3.53-5.12(3H, m), 3.99(2H, t, J=6.3Hz), 6.82-7.52(8H, m) |
| 314 | 1.11(6H, dd, J=6.3, 1.0Hz), 1.38-1.95(8H, m), 2.55-3.12(13H, m), 3.46-5.09(4H, m), 3.99(2H, t, J=6.3Hz), 6.32-7.49(8H, m) |
| 315 | 1.02 (3H, t, J=7.1Hz), 1.28-2.03(14H, m), 2.21-3.12(14H, m), 3.28-5.12(8H, m), 3.99(2H, t, J=6.4Hz), 6.82-7.48(8H, m) |
| 316 | 1.38-1.96(8H, m), 2.28-3.13(17H, m), 3.62-5.08 (5H, m), 3.99(2H, t, J=6.3Hz), 6.82-7.48(13H, m) |
| 317 | 1.37-2.00(12H, m), 2.18-3.30(15H, m), 3.40-5.16 (4H, m), 3.47(1H, dd, J=11.1, 4.1Hz), 3.62(1H, dd, J=11.1, 4.1Hz), 3.99(2H, t, J=6.4Hz), 6.82-7.48(8H, m) |
| 318 | 1.35-1.95(8H, m), 2.18-3.13(10H, m), 2.24(3H, s), 3.46(1H, d, J=13.0Hz), 3.69(1H, d, J=13.0 Hz), 3.55-5.14(4H, m), 3.99(2H, t, J=6.3Hz), 6.82-7.48(13H, m) |
| 319 | 1.65-2.08(6H, m), 2.46-3.49(10H, m), 3.78-5.08 (5H, m), 6.81(2H, d, J=8.7Hz), 6.95-7.75(10H, m), 11.40(1H, brs) |
| 320 | 1.30-1.99(10H, m), 2.45-3.20(8H, m), 3.74-5.20 (5H, m), 3.98(2H, t, J=6.4Hz), 4.06(2H, t, J=6.6 Hz), 6.90(2H, d, J=8.7Hz), 6.93-7.57(6H, m) |
| 321 | 1.68-2.32(6H, m), 2.49-3.64(10H, m), 3.77-5.10 (5H, m), 6.80(2H, d, J=9.1Hz), 6.96-7.91(10H, m), 12.03(1H, s) |
| 322 | 1.55-1.97(2H, m), 2.07-2.32(2H, m), 2.55-5.17 (7H, m), 3.92(2H, t, J=6.8Hz), 4.06(2H, t, J=6 Hz), 6.65(1H, d, J=9.4Hz), 6.82(2H, d, J=8.7 Hz), 7.10-8.05(11H, m), |
| 323 | 1.61-2.08(6H, m), 2.65-3.34(4H, m), 2.93(2H, t, J=6.8Hz), 3.88-5.20(3H, m), 4.09(2H, t, J=6Hz), 6.65(1H, d, J=9.4Hz), 6.93(2H, d, J=8.8Hz), 7.11-7.77(7H, m) |
| 324 | 1.62-2.09(4H, m), 1.93(3H, s), 2.60-3.49(6H, m), |

TABLE 8-continued

| | |
|---|---|
| | 3.85–5.15(3H, m), 4.00(2H, t, J=5.9Hz), 6.00 (1H, brs), 6.59(1H, d, J=9.4Hz), 6.85(2H, d, J=8.7Hz), 7.08–7.66(7H, m) |
| 325 | 1.30–2.15(8H, m), 2.32–3.20(8H, m), 3.53–4.05 (6H, m), 4.20–4.78(1H, m), 4.80–5.15(3H, m), 5.70–5.93(1H, m), 6.38–6.88(4H, m), 7.10–7.35 (1H, m) |
| 326 | 1.28–1.96(8H, m), 2.30–3.21(11H, m), 3.56–4.10 (6H, m), 4.12–4.78(1H, m), 4.83–5.10(1H, m), 6.40–6.85(4H, m), 7.12–7.32(1H, m) |
| 327 | 1.41(3H, t, J=6.9Hz), 1.52–1.90(2H, m), 2.30 (3H, s), 2.38–3.27(8H, m), 3.55–3.93(4H, m), 4.04 (2H, q, J=6.9Hz), 4.20–4.68(1H, m), 4.80–5.08 (1H, m,), 6.35–6.64(2H, m), 6.78–7.37(4H, m) |
| 328 | 1.64–1.86(3H, m), 2.30(3H, s), 2.40–2.90(8H, m), 3.12–3.31(2H, m), 4.20–4.40(1H, m), 6.82–7.20 (3H, m) |

Example 588

To 1-[1-(2-methoxy-4-ethoxybenzoyl)-4-piperidinyl]-3-ethoxycarbonyl-3,4-dihydrocarbostyril (0.48 g) are added sodium hydroxide (0.2 g), water (4 ml) and ethanol (10 ml) and the mixture is stirred at room temperature for 30 minutes. Water is added to the reaction mixture and the mixture is extracted with ethyl acetate. The aqueous layer is neutralized with acetic acid and extracted with dichloromethane. The extract is concentrated to give 1-[1-(2-methoxy-4-ethoxybenzoyl)-4-piperidinyl]-3-carboxy-3,4-dihydrocarbostyril (0.38 g) as white amorphous form.

NMR (CDCl$_3$) δ ppm: 1.42 (3H, t, J=7.0 Hz), 1.58–2.05 (2H, m), 2.35–3.47 (7H, m), 3.55–3.95 (4H, m), 4.04 (2H, q, J=7 Hz), 4.38 (1H, brs), 4.94 (1H, brs), 6.37–6.56 (2H, m), 7.00–7.40 (5H, m)

Example 589

To 1-[1-(2-methoxy-4-ethoxybenzoyl)-4-piperidinyl]-3-ethoxycarbonyl-3,4-dihydrocarbostyril (1.1 g) are added hydrazine monohydrate (1.1 g) and ethanol (15 ml) and the mixture is refluxed with heating for 7 hours. The reaction mixture is concentrated and the residue is purified by silica gel column chromatography (solvent: dichloromethane→dichloromethane:methanol=20:1) to give 1-[1-(2-methoxy-4-ethoxybenzoyl)4-piperidinyl]-3-hydrazinocarbonyl-3,4-dihydrocarbostyril (0.9 g) as white amorphous form.

NMR (CDCl$_3$) δ ppm: 1.42 (3H, t, J=7.0 Hz), 1.52–1.95 (2H, m), 2.30–3.93 (13H, m), 4.04 (2H, q, J=7 Hz), 4.15–5.06 (3H, m), 6.40–6.62 (2H, m), 6.97–7.50 (5H, m)

Example 590

To 1-[1-(2-methoxy-4-ethoxybenzoyl)-4-piperidinyl]-3-hydrazinocarbonyl-3,4-dihydrocarbostyril (1.4 g) are added dichloromethane (14 ml), 10% hydrochloric acid (5.5 ml) and water (14 ml). To the mixture is added dropwise a solution of sodium nitrite (0.25 g) in water (3 ml) at a temperature below 5° C. The mixture is stirred at 5° C. for 15 minutes. The dichloromethane layer is separated, dried and concentrated. To the resulting residue are added benzyl alcohol (0.5 g) and toluene (7 ml) and the mixture is refluxed with heating for 2 hours. After concentration, the resulting residue is purified by silica gel column chromatography (solvent: dichloromethane) to give 1-[1-(2-methoxy-4-ethoxybenzoyl)-4-piperidinyl]-3-benzyloxycarbonylamino-3,4-dihydrocarbostyril (0.9 g) as white amorphous form.

NMR (CDCl$_3$) δ ppm: 1.40 (3H, t, J=7.0 Hz), 1.55–2.00 (2H, m), 2.30–5.05 (15H, m), 5.30 (2H, s), 5.59 (1H, brs), 6.50–6.60 (2H, m), 7.02–7.42 (10H, m)

Example 591

To 1-[1-(2-methoxy-4-ethoxybenzoyl)-4-piperidinyl]-3-benzyloxycarbonylamino-3,4-dihydrocarbostyril (0.8 g) are added ethanol (20 ml) and 10% palladium-carbon (0.15 g) and the mixture is subjected to catalytic reduction at room temperature for 4 hours. After the catalyst is removed by filtration, the resulting filtrate is concentrated. To the residue are added ethanol (5 ml) and conc. hydrochloric acid (0.2 ml) and the mixture is concentrated again. Diethyl ether is added to the residue and the precipitated crystal is collected by filtration and recrystallized from ethanol to give 1-[1-(2-methoxy-4-ethoxybenzoyl)-4-piperidinyl]-3-amino-3,4-dihydrocarbostyril . hydrochloride (0.52 g) as white powder, m.p.: 257°–260° C.

Example 592

To 1-{1-[4-(5-carboxypentyloxy)benzoyl]-4-piperidinyl}-3,4-dihydrocarbostyril (2.00 g) are added 3,4-diaminopyridine (0.47 g), phosphorus pentoxide (1.00 g) and methanesulfonic acid (7.0 ml) and the mixture is stirred with heating at 100°–120° C. for 3 hours. After cooling, the reaction solution is poured into ice-water (30 ml) and the mixture is adjusted to around pH 11 with aqueous sodium hydroxide solution and extracted with dichloromethane. The extract is dried with magnesium sulfate and the solvent is distilled off. The resulting residue is purified by silica gel column chromatography (solvent: dichloromethane:methanol=20:1→9:1) to give 1-{1-[4-(5-(imidazo[4,5-c]pyridine-2-yl)carboxypentyloxy)benzoyl]-4-piperidinyl]-3,4-dihydrocarbostyril (1.32 g) as white amorphous form.

NMR (CDCl$_3$) δ ppm: 1.42–1.64 (2H, m), 1.64–2.06 (6H, m), 2.57 (2H, t, J=6.1 Hz), 2.64–3.24 (8H, m), 3.67–5.15 (2H, m), 3.92 (2H, t, J=6.1 Hz), 4.34 (1H, m), 6.84 (2H, d, J=8.7 Hz), 7.00–7.36 (5H, m), 7.40 (2H, d, J=8.7 Hz), 8.28 (1H, d, J=5.6 Hz), 8.80 (1H, s)

Example 593

To methyl 2-methyl-5-[(1-benzyl-4-piperidinyl)amino]cinnamate (1.0 g) are added acetic acid (10 ml), conc. hydrochloride acid (3 ml), water (3 ml) and 10% palladium-carbon (0.2 g) and the mixture is subjected to catalytic reduction at 80° C. for 2 hours under atmospheric pressure. After cooling, the catalyst is removed by filtration and the filtrate is concentrated. Water is added to the resulting residue and the mixture is basified with potassium carbonate and then extracted with dichloromethane. The solvent is concentrated to give 5-methyl-1-(4-piperidinyl)-3,4-dihydrocarbostyril (0.6 g) as colorless amorphous form.

NMR (CDCl$_3$) δ ppm: 1.64–1.86 (3H, m), 2.30 (3H, s), 2.40–2.90 (8H, m), 3.12–3.31 (2H, m), 4.20–4.40 (1H, m), 6.82–7.20 (3H, m)

Using the suitable starting materials, the compounds of the above Examples 1–9, 11–164, 169–383C, 435–474A and 482–577A are obtained in the same manners as Example 593.

Using the suitable starting materials, the following compounds are obtained in the same manners as in Examples 1, 384 and 593.

TABLE 9

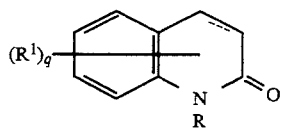

Example 594
Structure

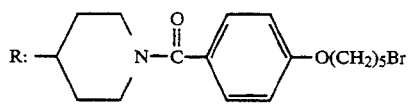

R¹: H, q: 1
Bond between 3- and 4-positions in the carbostyril ring: Single bond
NMR analysis: 491)
Form: Free Example 595
Structure

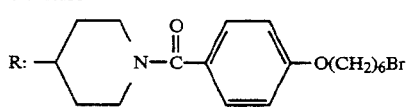

R¹: H, q: 1
Bond between 3- and 4-positions in the carbostyril ring: Single bond
NMR analysis: 492)
Form: Free Example 596
Structure

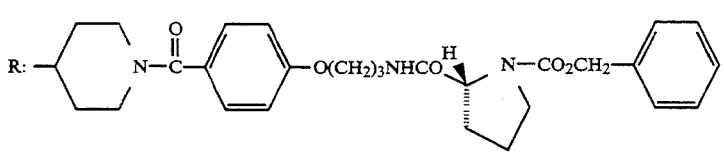

R¹: H, q: 1
Bond between 3- and 4-positions in the carbostyril ring: Single bond
Crystalline form: Colorless amorphous form
NMR analysis: 329)
Form: Free Example 597
Structure

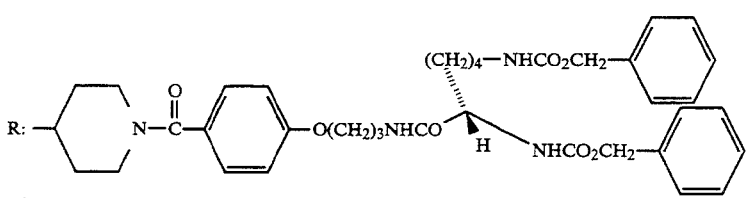

R¹: H, q: 1
Bond between 3- and 4-positions in the carbostyril ring: Single bond
Crystalline form: Colorless amorphous form
NMR analysis: 330)
Form: Free Example 598
Structure

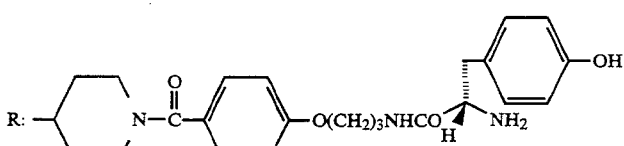

R¹: H, q: 1
Bond between 3- and 4-positions in the carbostyril ring: Single bond
Crystalline form: Colorless amorphous form
NMR analysis: 331)
Form: Free Example 599
Structure TABLE 9-continued

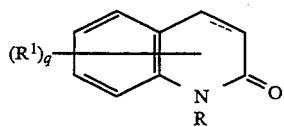

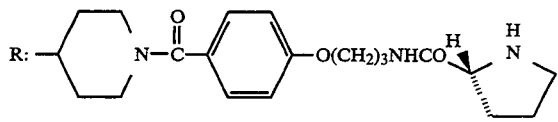

R¹: H, q: 1
Bond between 3- and 4-positions in the carbostyril ring: Single bond
Crystalline form: Colorless amorphous form
NMR analysis: 332)
Form: Free Example 600
Structure

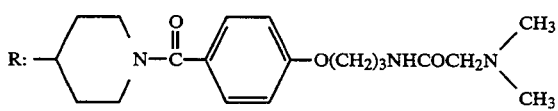

R¹: H, q: 1
Bond between 3- and 4-positions in the carbostyril ring: Single bond
NMR analysis: 333)
Form: Free Example 601
Structure

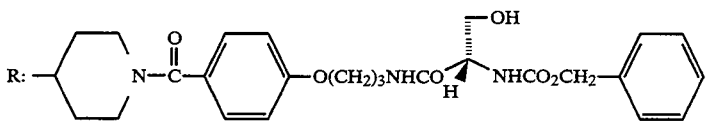

R¹: H, q: 1
Bond between 3- and 4-positions in the carbostyril ring: Single bond
Crystalline form: Colorless amorphous form
NMR analysis: 334)
Form: Free Example 602
Structure

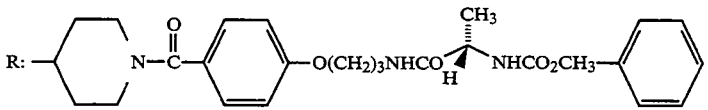

R¹: H, q: 1
Bond between 3- and 4-positions in the carbostyril ring: Single bond
Crystalline form: Colorless amorphous form
NMR analysis: 335)
Form: Free Example 603
Structure

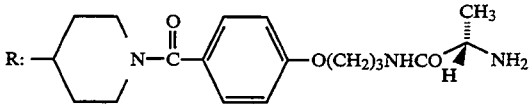

R¹: H, q: 1
Bond between 3- and 4-positions in the carbostyril ring: Single bond
Crystalline form: Colorless amorphous form
NMR analysis: 336)
Form: Free Example 604
Structure

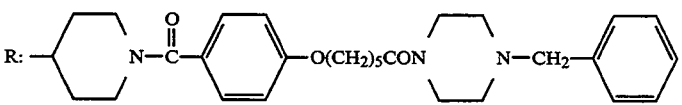

R¹: H, q: 1
Bond between 3- and 4-positions in the carbostyril ring: Single bond
NMR analysis: 337)

TABLE 9-continued

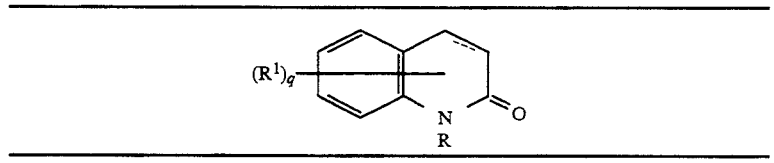

R: 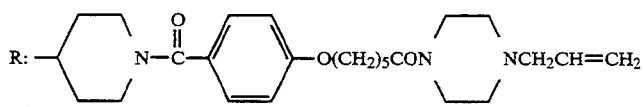 —O(CH₂)₅CON NCH₂CH=CH₂

R¹: H, q: 1
Bond between 3- and 4-positions in the carbostyril ring: Single bond
NMR analysis: 343)
Form: Free Example 611
Structure R: 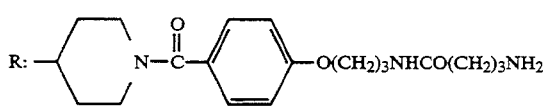 —O(CH₂)₃NHCO(CH₂)₃NH₂

R¹: H, q: 1
Bond between 3- and 4-positions in the carbostyril ring: Single bond
NMR analysis: 344)
Form: Free Example 612
Structure R: 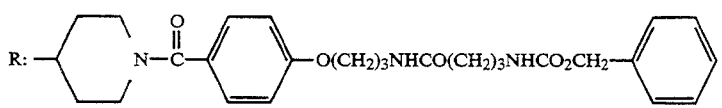 —O(CH₂)₃NHCO(CH₂)₃NHCO₂CH₂—

R¹: H, q: 1
Bond between 3- and 4-positions in the carbostyril ring: Single bond
NMR analysis: 345)
Form: Free Example 613
Structure R: 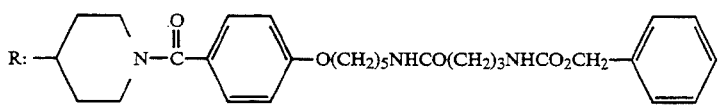 —O(CH₂)₅NHCO(CH₂)₃NHCO₂CH₂—

R¹: H, q: 1
Bond between 3- and 4-positions in the carbostyril ring: Single bond
NMR analysis: 346)
Form: Free Example 614
Structure R: 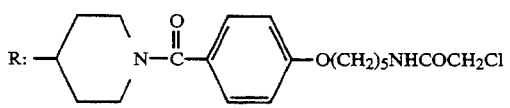 —O(CH₂)₅NHCOCH₂Cl R¹: H, q: 1
Bond between 3- and 4-positions in the carbostyril ring: Single bond
NMR analysis: 347)
Form: Free Example 615
Structure R: 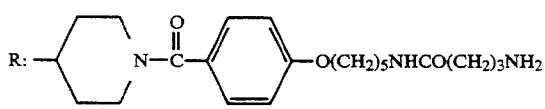 —O(CH₂)₅NHCO(CH₂)₃NH₂

R¹: H, q: 1
Bond between 3- and 4-positions in the carbostyril ring: Single bond
NMR analysis: 348)
Form: Free Example 616
Structure TABLE 9-continued

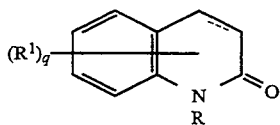

Form: Free

Example 605
Structure

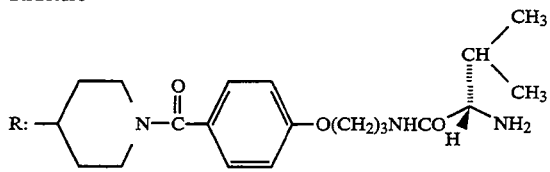

R¹: H, q: 1
Bond between 3- and 4-positions in the carbostyril ring: Single bond
Crystalline form: Colorless amorphous form
NMR analysis: 338)
Form: Free Example 606
Structure

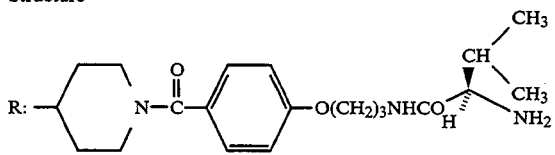

R¹: H, q: 1
Bond between 3- and 4-positions in the carbostyril ring: Single bond
Crystalline form: Colorless amorphous form
NMR analysis: 339)
Form: Free Example 607
Structure

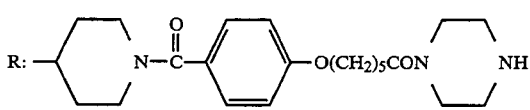

R¹: H, q: 1
Bond between 3- and 4-positions in the carbostyril ring: Single bond
Crystalline form: Colorless amorphous form
NMR analysis: 340)
Form: Free Example 608
Structure

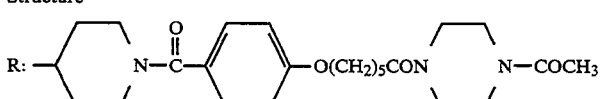

R¹: H, q: 1
Bond between 3- and 4-positions in the carbostyril ring: Single bond
Crystalline form: Colorless amorphous form
NMR analysis: 341)
Form: Free Example 609
Structure

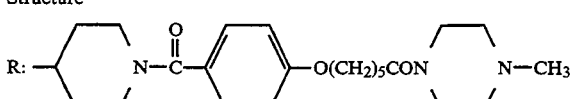

R¹: H, q: 1
Bond between 3- and 4-positions in the carbostyril ring: Single bond
Crystalline form: Colorless amorphous form
NMR analysis: 342)
Form: Free Example 610
Structure TABLE 9-continued

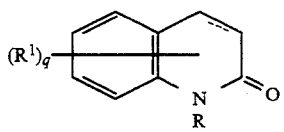

R: 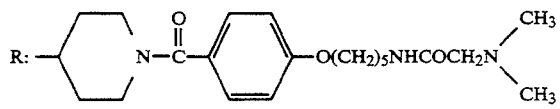

R¹: H, q: 1
Bond between 3- and 4-positions in the carbostyril ring: Single bond
NMR analysis: 349)
Form: Free Example 617
Structure R: 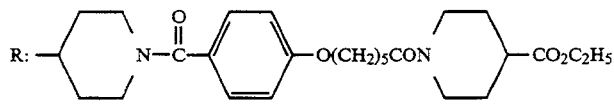

R¹: H, q: 1
Bond between 3- and 4-positions in the carbostyril ring: Single bond
NMR analysis: 350)
Form: Free Example 618
Structure R: 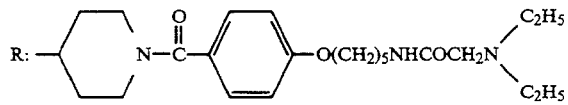

R¹: H, q: 1
Bond between 3- and 4-positions in the carbostyril ring: Single bond
NMR analysis: 351)
Form: Free Example 619
Structure R: 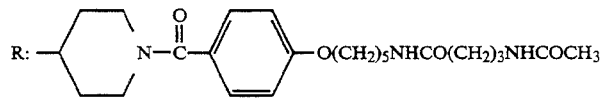

R¹: H, q: 1
Bond between 3- and 4-positions in the carbostyril ring: Single bond
NMR analysis: 352)
Form: Free Example 620
Structure R: 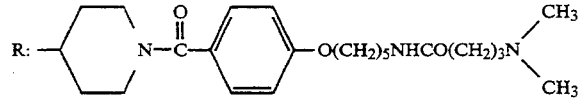

R¹: H, q: 1
Bond between 3- and 4-positions in the carbostyril ring: Single bond
NMR analysis: 353)
Form: Free Example 621
Structure R: 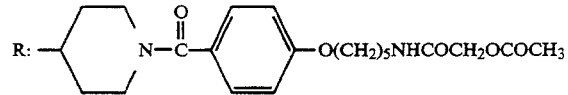

R¹: H, q: 1
Bond between 3- and 4-positions in the carbostyril ring: Single bond
Crystalline form: Colorless amorphous form
NMR analysis: 354)
Form: Free Example 622
Structure TABLE 9-continued

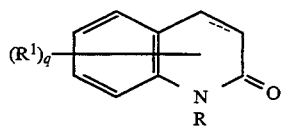

R: 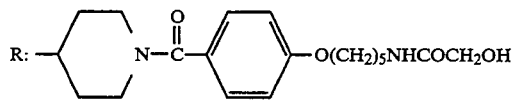 —O(CH$_2$)$_5$NHCOCH$_2$OH

R$^1$: H, q: 1
Bond between 3- and 4-positions in the carbostyril ring: Single bond
Crystalline form: Colorless amorphous form
NMR analysis: 355)
Form: Free Example 623
Structure R: 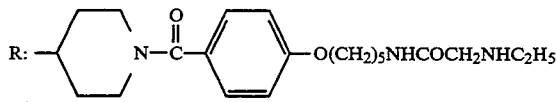 —O(CH$_2$)$_5$NHCOCH$_2$NHC$_2$H$_5$ R$^1$: H, q: 1
Bond between 3- and 4-positions in the carbostyril ring: Single bond
NMR analysis: 356)
Form: Free Example 624
Structure R: 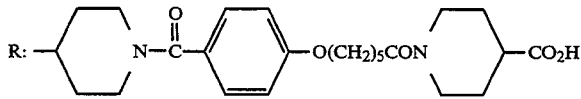 —O(CH$_2$)$_5$CON<the piperidine>—CO$_2$H R$^1$: H, q: 1
Bond between 3- and 4-positions in the carbostyril ring: Single bond
Crystalline form: Colorless amorphous form
NMR analysis: 357)
Form: Free Example 625
Structure R: 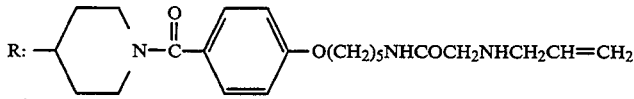 —O(CH$_2$)$_5$NHCOCH$_2$NHCH$_2$CH=CH$_2$ R$^1$: H, q: 1
Bond between 3- and 4-positions in the carbostyril ring: Single bond
NMR analysis: 358)
Form: Free Example 626
Structure R: 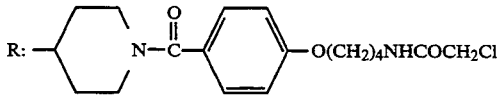 —O(CH$_2$)$_4$NHCOCH$_2$Cl R$^1$: H, q: 1
Bond between 3- and 4-positions in the carbostyril ring: Single bond
NMR analysis: 359)
Form: Free Example 627
Structure R: 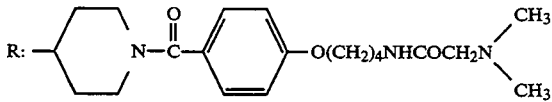 —O(CH$_2$)$_4$NHCOCH$_2$N(CH$_3$)$_2$ R$^1$: H, q: 1
Bond between 3- and 4-positions in the carbostyril ring: Single bond
NMR analysis: 360)
Form: Free Example 628
Structure TABLE 9-continued

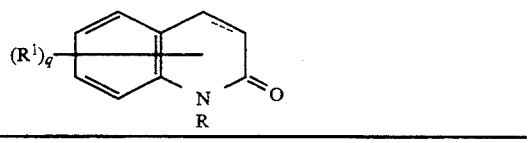

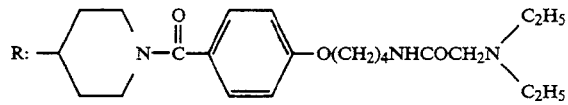

R¹: H, q: 1
Bond between 3- and 4-positions in the carbostyril ring: Single bond
NMR analysis: 361)
Form: Free Example 629
Structure

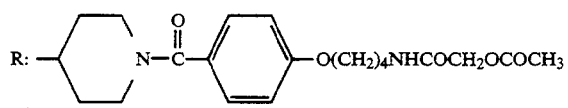

R¹: H, q: 1
Bond between 3- and 4-positions in the carbostyril ring: Single bond
Crystalline form: Colorless amorphous form
NMR analysis: 362)
Form: Free Example 630
Structure

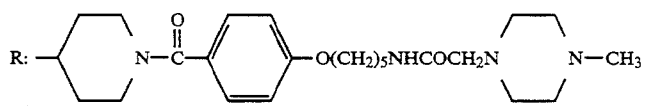

R¹: H, q: 1
Bond between 3- and 4-positions in the carbostyril ring: Single bond
NMR analysis: 363)
Form: Free Example 631
Structure

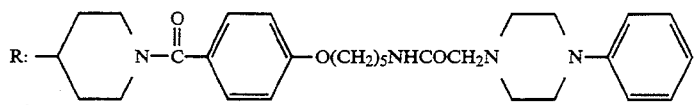

R¹: H, q: 1
Bond between 3- and 4-positions in the carbostyril ring: Single bond
Crystalline form: Colorless amorphous form
NMR analysis, 364)
Form: Free Example 632
Structure

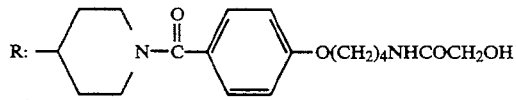

R¹: H, q: 1
Bond between 3- and 4-positions in the carbostyril ring: Single bond
Crystalline form: Colorless amorphous form
NMR analysis: 365)
Form: Free Example 633
Structure

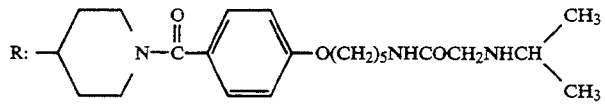

R¹: H, q: 1
Bond between 3- and 4-positions in the carbostyril ring: Single bond
NMR analysis: 366)
Form: Free Example 634

TABLE 9-continued

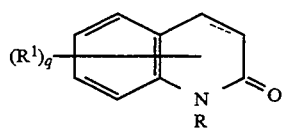

Structure

R: 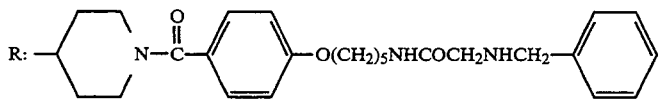

R¹: H, q: 1
Bond between 3- and 4-positions in the carbostyril ring: Single bond
NMR analysis: 367)
Form: Free Example 635
Structure R: 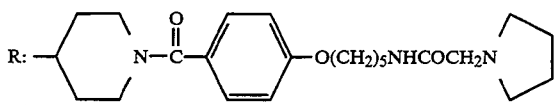

R¹: H, q: 1
Bond between 3- and 4-positions in the carbostyril ring: Single bond
NMR analysis: 368)
Form: Free Example 636
Structure R: 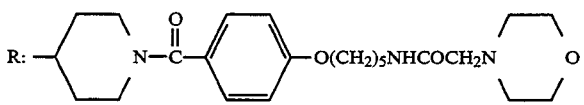

R¹: H, q: 1
Bond between 3- and 4-positions in the carbostyril ring: Single bond
NMR analysis: 369)
Form: Free Example 637
Structure R: 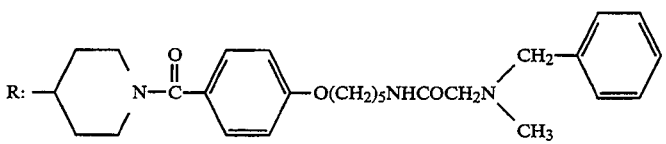

R¹: H, q: 1
Bond between 3- and 4-positions in the carbostyril ring: Single bond
NMR analysis: 370)
Form: Free Example 638
Structure R: 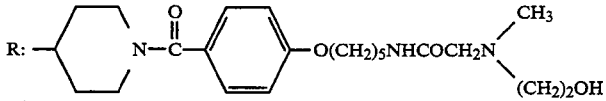

R¹: H, q: 1
Bond between 3- and 4-positions in the carbostyril ring: Single bond
NMR analysis: 371)
Form: Free Example 639
Structure R: 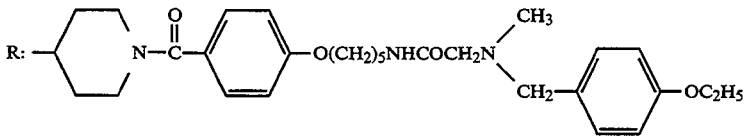

R¹: H, q: 1
Bond between 3- and 4-positions in the carbostyril ring: Single bond
NMR analysis: 372)
Form: Free TABLE 9-continued

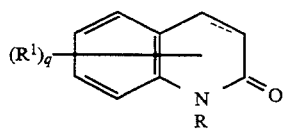

Example 640
Structure

R: 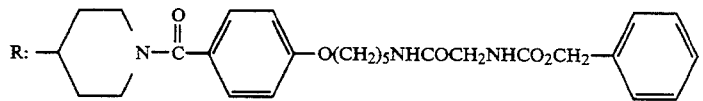

R¹: H, q: 1
Bond between 3- and 4-positions in the carbostyril ring: Single bond
NMR analysis: 373)
Form: Free Example 641
Structure R: 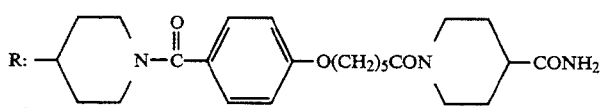

R¹: H, q: 1
Bond between 3- and 4-positions in the carbostyril ring: Single bond
Crystalline form: Colorless amorphous form
NMR analysis: 374)
Form: Free Example 642
Structure R: 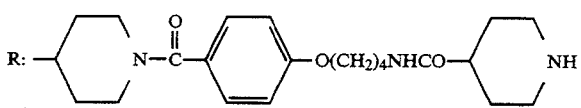

R¹: H, q: 1
Bond between 3- and 4-positions in the carbostyril ring: Single bond
Crystalline form: Colorless amorphous form
NMR analysis: 375)
Form: Free Example 643
Structure R: 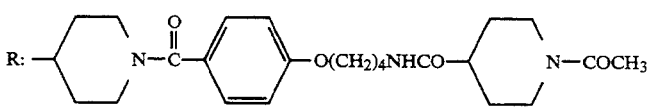

R¹: H, q: 1
Bond between 3- and 4-positions in the carbostyril ring: Single bond
Crystalline form: Colorless amorphous form
NMR analysis: 376)
Form: Free Example 644
Structure R: 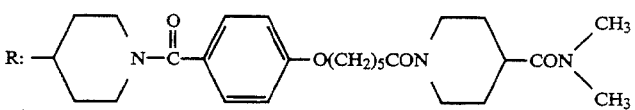

R¹: H, q: 1
Bond between 3- and 4-positions in the carbostyril ring: Single bond
Crystalline form: Colorless amorphous form
NMR analysis: 377)
Form: Free Example 645
Structure R: 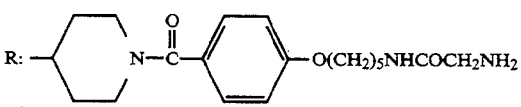

R¹: H, q: 1
Bond between 3- and 4-positions in the carbostyril ring: Single bond

TABLE 9-continued

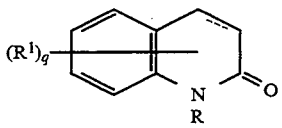

NMR analysis: 378)
Form: Free

Example 646
Structure

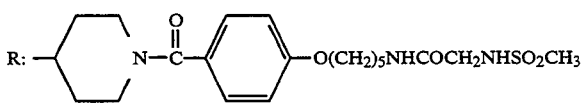

R¹: H, q: 1
Bond between 3- and 4-positions in the carbostyril ring: Single bond
Crystalline form: Colorless amorphous form
NMR analysis: 379)
Form: Free Example 647
Structure

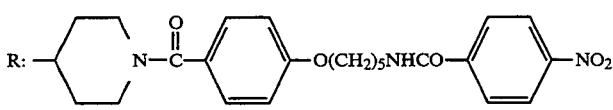

R¹: H, q: 1
Bond between 3- and 4-positions in the carbostyril ring: Single bond
Crystalline form: Colorless amorphous form
NMR analysis: 380)
Form: Free Example 648
Structure

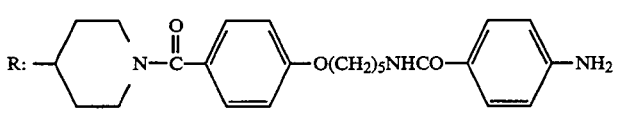

R¹: H, q: 1
Bond between 3- and 4-positions in the carbostyril ring: Single bond
Crystalline form: Colorless amorphous form
NMR analysis: 381)
Form: Free Example 649
Structure

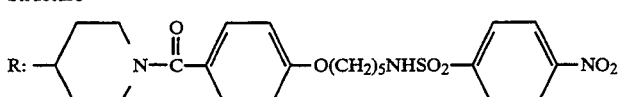

R¹: H, q: 1
Bond between 3- and 4-positions in the carbostyril ring: Single bond
Crystalline form: Colorless amorphous form
NMR analysis: 382)
Form: Free Example 650
Structure

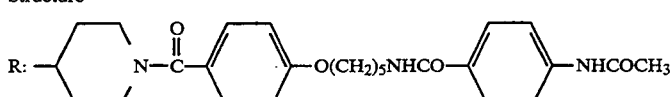

R¹: H, q: 1
Bond between 3- and 4-positions in the carbostyril ring: Single bond
Crystalline form: Colorless amorphous form
NMR analysis: 383)
Form: Free Example 651
Structure TABLE 9-continued

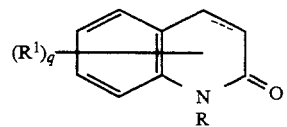

R: 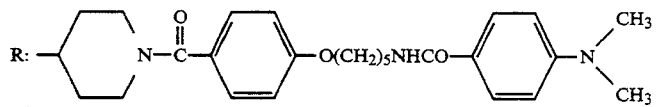

R¹: H, q: 1
Bond between 3- and 4-positions in the carbostyril ring: Single bond
Crystalline form: Colorless amorphous form
NMR analysis: 384)
Form: Free Example 652
Structure R: 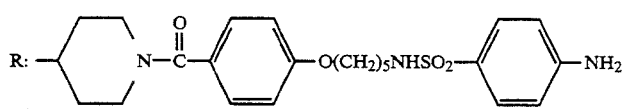

R¹: H, q: 1
Bond between 3- and 4-positions in the carbostyril ring: Single bond
Crystalline form: Colorless amorphous form
NMR analysis: 385)
Form: Free Example 653
Structure R: 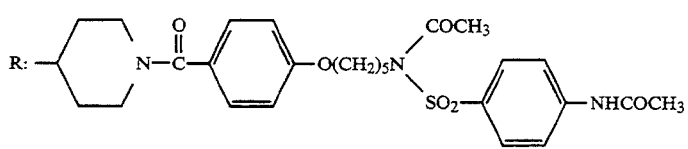

R¹: H, q: 1
Bond between 3- and 4-positions in the carbostyril ring: Single bond
Crystalline form: Colorless amorphous form
NMR analysis: 386)
Form: Free Example 654
Structure R: 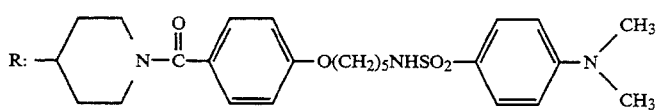

R¹: H, q: 1
Bond between 3- and 4-positions in the carbostyril ring: Single bond
Crystalline form: Colorless amorphous form
NMR analysis: 387)
Form: Free Example 655
Structure R: 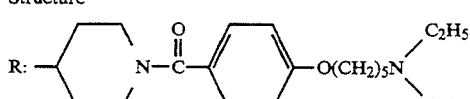

R¹: H, q: 1
Bond between 3- and 4-positions in the carbostyril ring: Single bond
NMR analysis: 388)
Form: Free Example 656
Structure R: 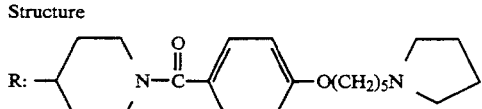

R¹: H, q: 1
Bond between 3- and 4-positions in the carbostyril ring: Single bond
NMR analysis: 389)

TABLE 9-continued

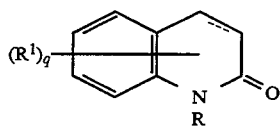

Form: Free

Example 657
Structure

R: 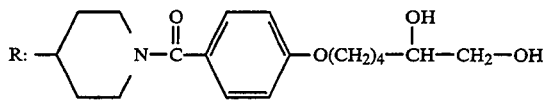

$R^1$: H, q: 1
Bond between 3- and 4-positions in the carbostyril ring: Single bond
NMR analysis: 390)
Form: Free Example 658
Structure R: 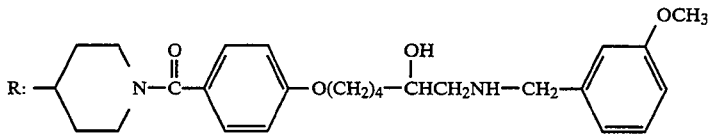

$R^1$: H, q: 1
Bond between 3- and 4-positions in the carbostyril ring: Single bond
NMR analysis: 391)
Form: Free Example 659
Structure R: 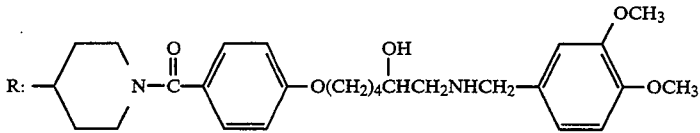

$R^1$: H, q: 1
Bond between 3- and 4-positions in the carbostyril ring: Single bond
Crystalline form: White powders
Recrystallization solvent: ethanol/water
Melting point: 152–155° C.
Form: Oxalate Example 660
Structure R: 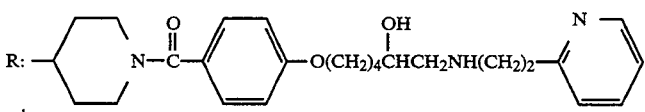

$R^1$: H, q: 1
Bond between 3- and 4-positions in the carbostyril ring: Single bond
NMR analysis: 392)
Form: Free Example 661
Structure R: 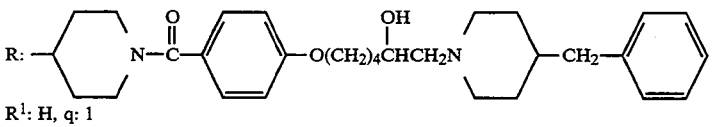

$R^1$: H, q: 1
Bond between 3- and 4-positions in the carbostyril ring: Single bond
NMR analysis: 393)
Form: Free Example 662
Structure R: 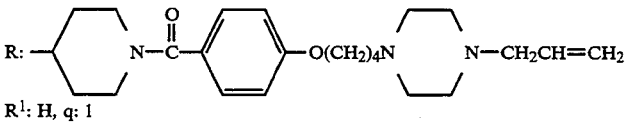

$R^1$: H, q: 1

TABLE 9-continued

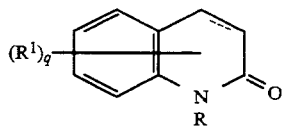

Bond between 3- and 4-positions in the carbostyril ring: Single bond
NMR analysis: 394)
Form: Free Example 663
Structure

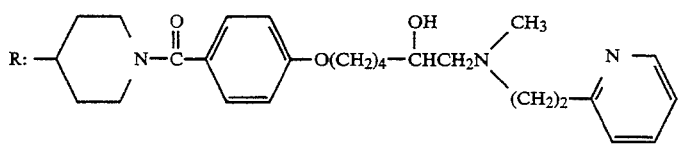

R[1]: H, q: 1
Bond between 3- and 4-positions in the carbostyril ring: Single bond
NMR analysis: 395)
Form: Free Example 664
Structure

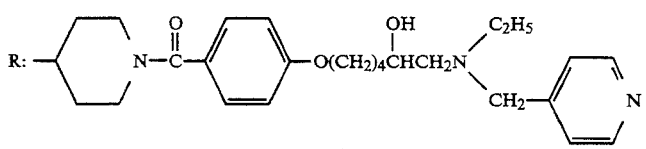

R[1]: H, q: 1
Bond between 3- and 4-positions in the carbostyril ring: Single bond
NMR analysis: 396)
Form: Free Example 665
Structure

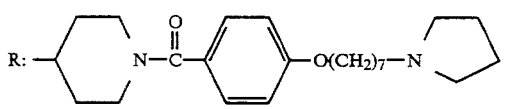

R[1]: H, q: 1
Bond between 3- and 4-positions in the carbostyril ring: Single bond
NMR analysis: 397)
Form: Free Example 666
Structure

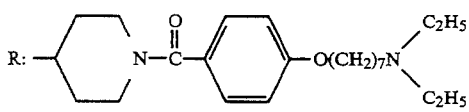

R[1]: H, q: 1
Bond between 3- and 4-positions in the carbostyril ring: Single bond
NMR analysis: 398)
Form: Free Example 667
Structure

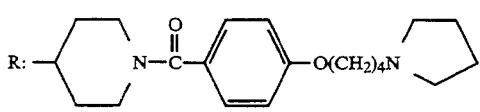

R[1]: H, q: 1
Bond between 3- and 4-positions in the carbostyril ring: Single bond
NMR analysis: 399)
Form: Free Example 668
Structure TABLE 9-continued

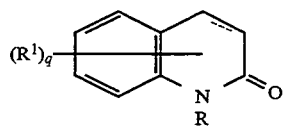

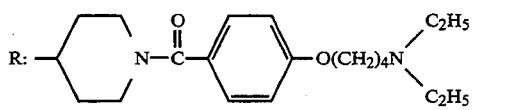

R[1]: H, q: 1
Bond between 3- and 4-positions in the carbostyril ring: Single bond
NMR analysis: 400)
Form: Free Example 669
Structure

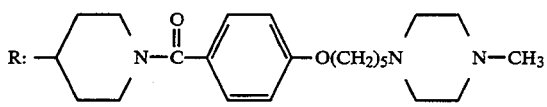

R[1]: H, q: 1
Bond between 3- and 4-positions in the carbostyril ring: Single bond
Crystalline form: Colorless needles
Recrystallization solvent: Ethanol/water
Melting point: 216–217° C.
Form: Dioxalate Example 670
Structure

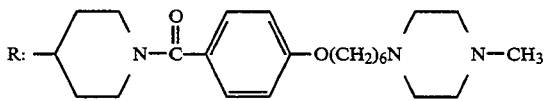

R[1]: H, q: 1
Bond between 3- and 4-positions in the carbostyril ring: Single bond
Crystalline form: Colorless needles
Recrystallization solvent: Ethanol/water
Melting point: 216–217° C.
Form: Dioxalate Example 671
Structure

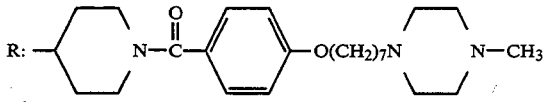

R[1]: H, q: 1
Bond between 3- and 4-positions in the carbostyril ring: Single bond
Crystalline form: White powders
Recrystallization solvent: Ethanol/water
Melting point: 215–218° C.
Form: Dioxalate Example 672
Structure

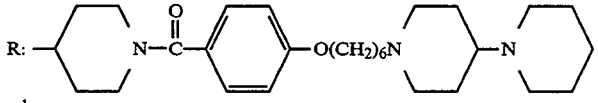

R[1]: H, q: 1
Bond between 3- and 4-positions in the carbostyril ring: Single bond
Crystalline form: White powders
Recrystallization solvent: Ethanol/water
Melting point: 195–196° C.
Form: Dioxalate Example 673
Structure TABLE 9-continued

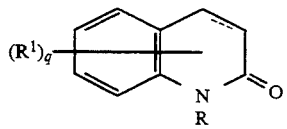

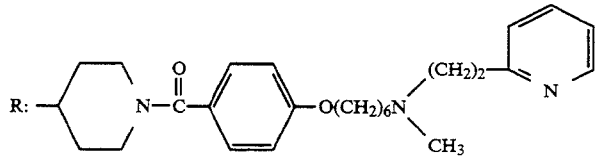

R¹: H, q: 1
Bond between 3- and 4-positions in the carbostyril ring: Single bond
NMR analysis: 401)
Form: Free Example 674
Structure

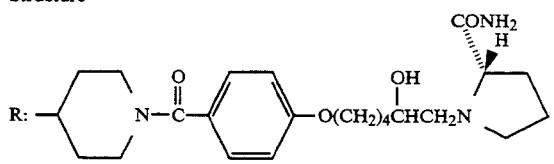

R¹: H, q: 1
Bond between 3- and 4-positions in the carbostyril ring: Single bond
NMR analysis: 402)
Ms (m/z): 562
Form: Free Example 675
Structure

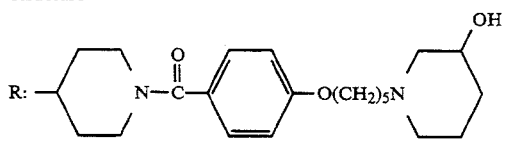

R¹: H, q: 1
Bond between 3- and 4-positions in the carbostyril ring: Single bond
NMR analysis: 403)
Form: Free Example 676
Structure

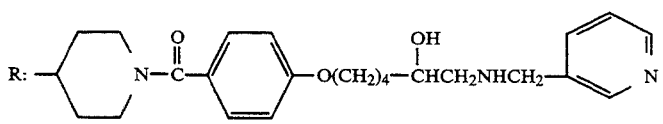

R¹: H, q: 1
Bond between 3- and 4-positions in the carbostyril ring: Single bond
NMR analysis: 404)
Form: Free Example 677
Structure

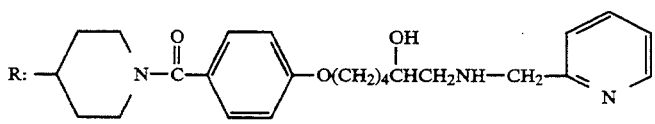

R¹: H, q: 1
Bond between 3- and 4-positions in the carbostyril ring: Single bond
NMR analysis: 405)
Form: Free Example 678
Structure TABLE 9-continued

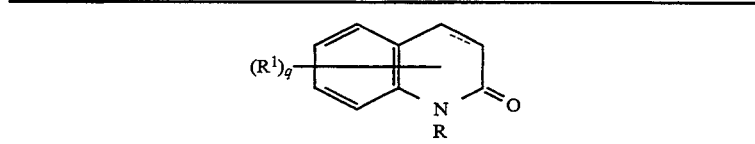

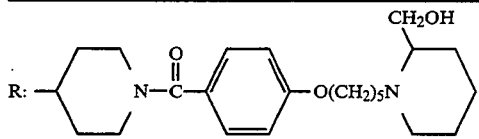

R¹: H, q: 1
Bond between 3- and 4-positions in the carbostyril ring: Single bond
NMR analysis: 406)
Form: Free Example 679
Structure

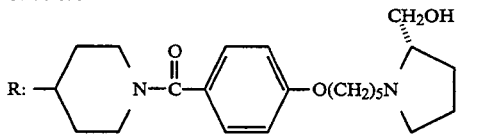

R¹: H, q: 1
Bond between 3- and 4-positions in the carbostyril ring: Single bond
NMR analysis: 407)
Form: Free Example 680
Structure

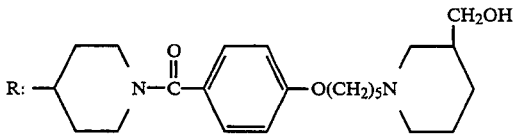

R¹: H, q: 1
Bond between 3- and 4-positions in the carbostyril ring: Single bond
NMR analysis: 408)
Form: Free Example 681
Structure

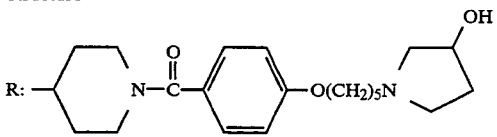

R¹: H, q: 1
Bond between 3- and 4-positions in the carbostyril ring: Single bond
NMR analysis: 409)
Form: Free Example 682
Structure

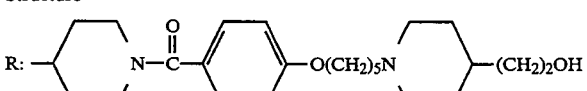

R¹: H, q: 1
Bond between 3- and 4-positions in the carbostyril ring: Single bond
Crystalline form: Colorless amorphous form
NMR analysis: 410)
Form: Hydrochloride Example 683
Structure

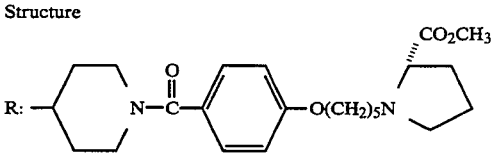

-continued

R¹: H, q: 1
Bond between 3- and 4-positions in the carbostyril ring: Single bond
NMR analysis: 411)
Form: Free Example 684
Structure

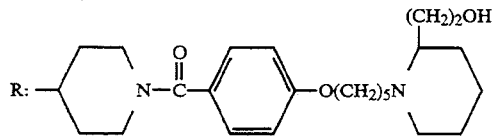

R¹: H, q: 1
Bond between 3- and 4-positions in the carbostyril ring: Single bond
Crystalline form: light yellow amorphous form
NMR analysis: 412)
Form: Hydrochloride Example 685
Structure

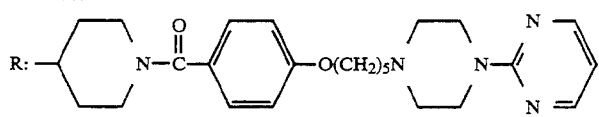

R¹: H, q: 1
Bond between 3- and 4-positions in the carbostyril ring: Single bond
NMR analysis: 413)
Form: Free Example 686
Structure

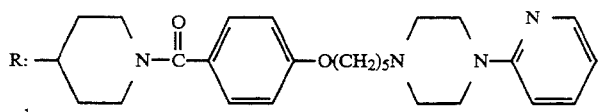

R¹: H, q: 1
Bond between 3- and 4-positions in the carbostyril ring: Single bond
NMR analysis: 414)
Form: Free Example 687
Structure

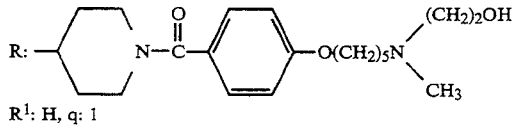

R¹: H, q: 1
Bond between 3- and 4-positions in the carbostyril ring: Single bond
NMR analysis: 415)
Form: Free Example 688
Structure

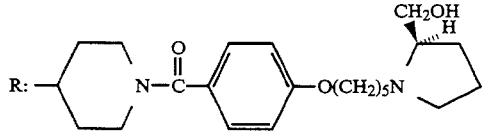

R¹: H, q: 1
Bond between 3- and 4-positions in the carbostyril ring: Single bond
NMR analysis: 416)
Form: Free Example 689
Structure

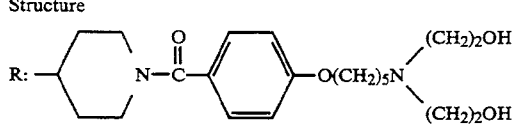

R¹: H, q: 1
Bond between 3- and 4-positions in the carbostyril ring: Single bond
NMR analysis: 417)
Form: Free -continued Example 690
Structure

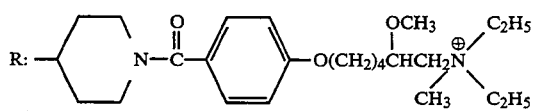

R[1]: H, q: 1
Bond between 3- and 4-positions in the carbostyril ring: Single bond
Crystalline form: Colorless amorphous form
NMR analysis: 418)
FAB-MS (Pos.) (m/z): 551
Form: I$^{\ominus}$ Example 691
Structure

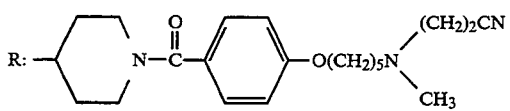

R[1]: H, q: 1
Bond between 3- and 4-positions in the carbostyril ring: Single bond
NMR analysis: 419)
Form: Free Example 692
Structure

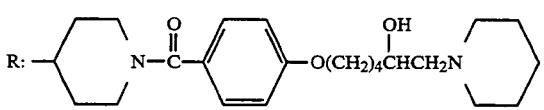

R[1]: H, q: 1
Bond between 3- and 4-positions in the carbostyril ring: Single bond
NMR analysis: 420)
Form: Free Example 693
Structure

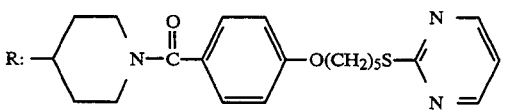

R[1]: H, q: 1
Bond between 3- and 4-positions in the carbostyril ring: Single bond
NMR analysis: 421)
Form: Free Example 694
Structure

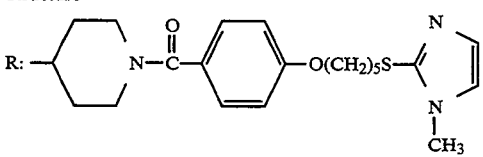

R[1]: H, q: 1
Bond between 3- and 4-positions in the carbostyril ring: Single bond
NMR analysis: 422)
Form: Free Example 695
Structure

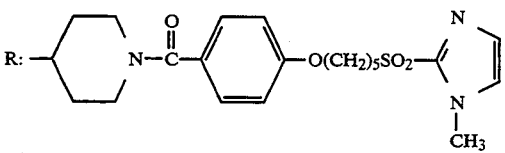

R[1]: H, q: 1
Bond between 3- and 4-positions in the carbostyril ring: Single bond
Crystalline form: Colorless amorphous form
NMR analysis: 423)
Form: Free Example 696

-continued

Structure

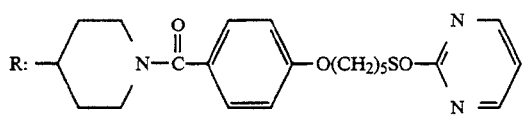

R[1]: H, q: 1
Bond between 3- and 4-positions in ths carbostyril ring: Single bond
NMR analysis: 424)
Form: Free Example 697

Structure

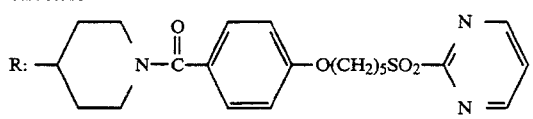

R[1]: H, q: 1
Bond between 3- and 4-positions in the carbostyril ring: Single bond
Crystalline form: Colorless amorphous form
NMR analysis: 425)
Form: Free Example 698

Structure

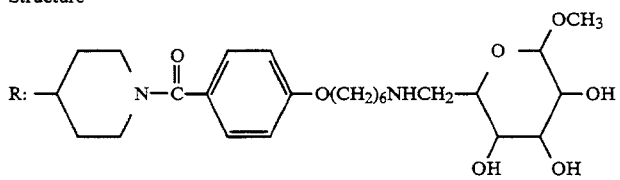

R[1]: H, q: 1
Bond between 3- and 4-positions in the carbostyril ring: Single bond
NMR analysis: 426)
Form: Free Example 699

Structure

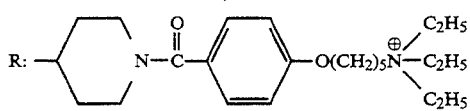

R[1]: H, q: 1
Bond between 3- and 4-positions in the carbostyril ring: Single bond
NMR analysis: 427)
Form: Br$^\ominus$ Example 700

Structure

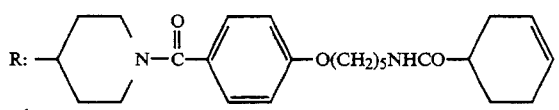

R[1]: H, q: 1
Bond between 3- and 4-positions in the carbostyril ring: Single bond
NMR analysis: 428)
Form: Free Example 701

Structure

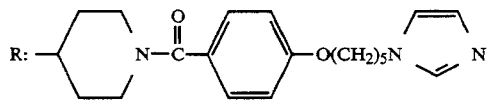

R[1]: H, q: 1
Bond between 3- and 4-positions in the carbostyril ring: Single bond
Crystalline form: Colorless amorphous form
NMR analysis: 429)
Form: Free Example 702

Structure

-continued

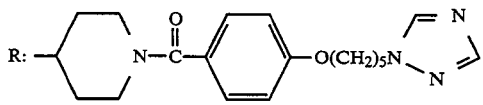

R[1]: H, q: 1
Bond between 3- and 4-positions in the carbostyril ring: Single bond
Crystalline form: Colorless amorphous form
NMR analysis: 430)
Form: Free Example 703
Structure

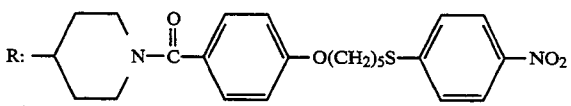

R[1]: H, q: 1
Bond between 3- and 4-positions in the carbostyril ring: Single bond
NMR analysis: 431)
Form: Free Example 704
Structure

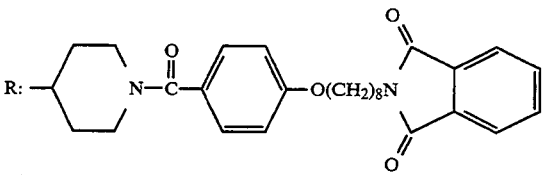

R[1]: H, q: 1
Bond between 3- and 4-positions in the carbostyril ring: Single bond
NMR analysis: 432)
Form: Free Example 705
Structure

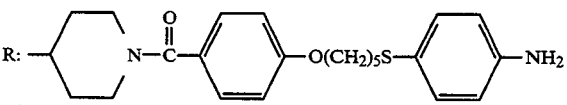

R[1]: H, q: 1
Bond between 3- and 4-positions in the carbostyril ring: Single bond
NMR analysis: 433)
Form: Free Example 706
Structure

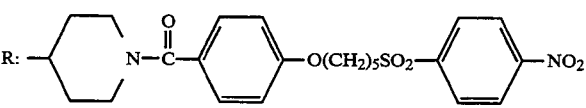

R[1]: H, q: 1
Bond between 3- and 4-positions in the carbostyril ring: Single bond
NMR analysis: 434)
Form: Free Example 707
Structure

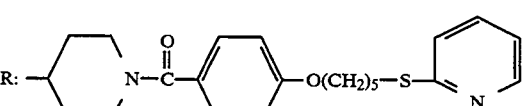

R[1]: H, q: 1
Bond between 3- and 4-positions in the carbostyril ring: Single bond
NMR analysis: 435)
Form: Free Example 708
Structure

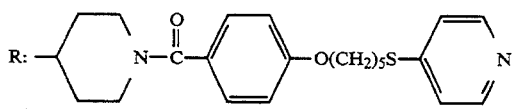

R[1]: H, q: 1
Bond between 3- and 4-positions in the carbostyril ring: Single bond
NMR analysis: 436)
Form: Free Example 709
Structure

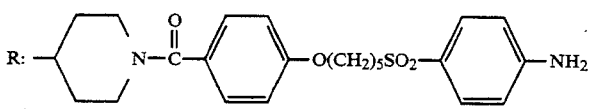

R[1]: H, q: 1
Bond between 3- and 4-positions in the carbostyril ring: Single bond
Crystalline form: Colorless amorphous form
NMR analysis: 437)
Form: Free Example 710
Structure

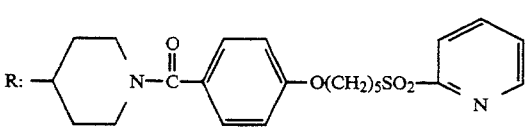

R[1]: H, q: 1
Bond between 3- and 4-positions in the carbostyril ring: Single bond
NMR analysis: 438)
Form: Free Example 711
Structure

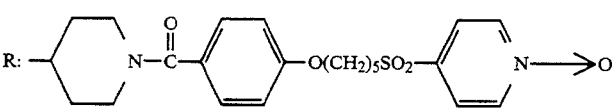

R[1]: H, q: 1
Bond between 3- and 4-positions in the carbostyril ring: Single bond
Crystalline form: Colorless amorphous form
NMR analysis: 439)
Form: Free Example 712
Structure

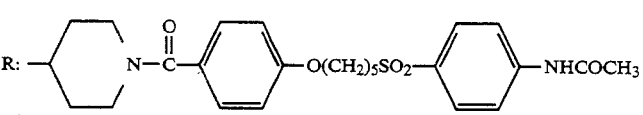

R[1]: H, q: 1
Bond between 3- and 4-positions in the carbostyril ring: Single bond
Crystalline form: Colorless amorphous form
NMR analysis: 440)
Form: Free Example 713
Structure

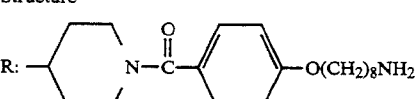

R[1]: H, q: 1
Bond between 3- and 4-positions in the carbostyril ring: Single bond
NMR analysis: 441)
Form: Free Example 714
Structure -continued

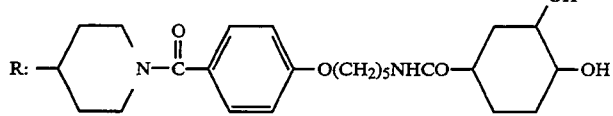

R[1]: H, q: 1
Bond between 3- and 4-positions in the carbostyril ring: Single bond
NMR analysis: 442)
Form: Free Example 715
Structure

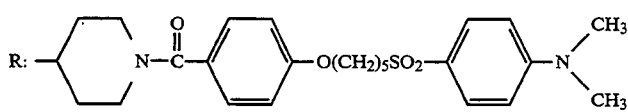

R[1]: H, q: 1
Bond between 3- and 4-positions in the carbostyril ring: Single bond
Crystalline form: Colorless amorphous form
NMR analysis: 443)
Form: Free Example 716
Structure

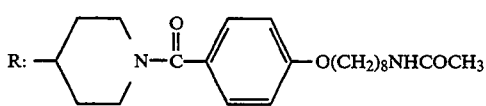

R[1]: H, q: 1
Bond between 3- and 4-positions in the carbostyril ring: Single bond
Crystalline form: Colorless amorphous form
NMR analysis: 444)
Form: Free Example 717
Structure

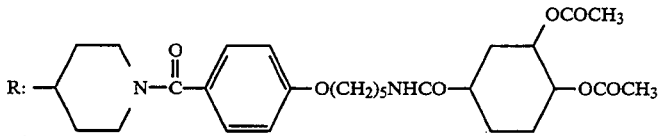

R[1]: H, q: 1
Bond between 3- and 4-positions in the carbostyril ring: Single bond
Crystalline form: Colorless amorphous form
NMR analysis: 445)
Form: Free Example 718
Structure R: 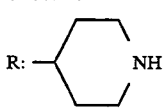

R[1]: —OH (5-position), q: 1
Bond between 3- and 4-positions in the carbostyril ring: Single bond
Crystalline form: White powders
Recrystallization solvent: Methanol/diethyl ether
Melting point: 274° C. (decomposed)
Form: Hydrochloride Example 719
Structure R: 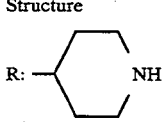

R[1]: —OC$_2$H$_5$ (5-position), q: 1
Bond between 3- and 4-positions in the carbostyril ring: Single bond
Crystalline form: White powders
Recrystallization solvent: Methanol/diethyl ether
Melting point: 250° C. (decomposed)
Form: Hydrochloride Example 720
Structure -continued R: 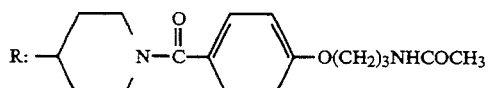

R[1]: OH (5-position), q: 1
Bond between 3- and 4-positions in the carbostyril ring: Single bond
Crystalline form: Colorless amorphous form
NMR analysis: 446)
Form: Free Example 721
Structure R: 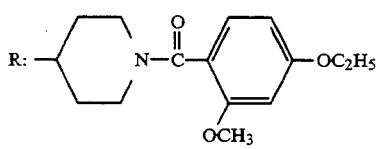

R[1]: H, q: 1
Bond between 3- and 4-positions in the carbostyril ring: Single bond
Crystalline form: Colorless amorphous form
NMR analysis: 447)
Form: Free Example 722
Structure R: 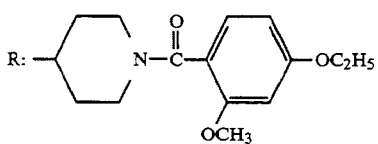

R[1]: —OCH$_3$ (5-position), q: 1
Bond between 3- and 4-positions in the carbostyril ring: Single bond
Crystalline form: Colorless amorphous form
NMR analysis: 448)
Form: Free Example 723
Structure R: 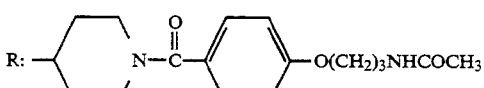

R[1]: —OC$_2$H$_5$ (5-position), q: 1
Bond between 3- and 4-positions in the carbostyril ring: Single bond
Crystalline form: Colorless amorphous form
NMR analysis: 449)
Form: Free Example 724
Structure R: 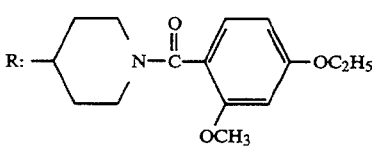

R[1]: —OC$_2$H$_5$ (5-position), q: 1
Bond between 3- and 4-positions in the carbostyril ring: Single bond
Crystalline form: Colorless amorphous form
NMR analysis: 450)
Form: Free Example 725
Structure R: 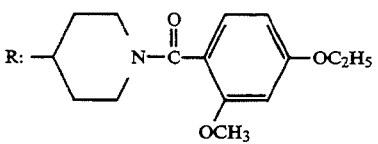

R[1]: —OCOCH$_3$ (5-position), q: 1
Bond between 3- and 4-positions in the carbostyril ring: Single bond
Crystalline form: Colorless amorphous form
NMR analysis: 451)

Form: Free

Example 726
Structure

R: 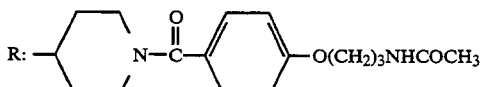 —O(CH$_2$)$_3$NHCOCH$_3$

R$^1$: —OCH$_3$ (5-position), q: 1
Bond between 3- and 4-positions in the carbostyril ring: Single bond
Crystalline form: Colorless amorphous form
NMR analysis: 452)
Form: Free Example 727
Structure R: 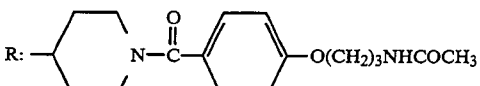 —O(CH$_2$)$_3$NHCOCH$_3$ R$^1$: —OCOCH$_3$, q: 1
Bond between 3- and 4-positions in the carbostyril ring: Single bond
Crystalline form: Colorless amorphous form
NMR analysis: 453)
Form: Free Example 728
Structure R: 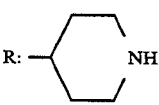

R$^1$: —CH$_3$ (5-, 7-positions), q: 2
Bond between 3- and 4-positions in the carbostyril ring: Single bond
Crystalline form: White powders
Melting point: 278–282° C.
Form: Hydrochloride Example 729
Structure R: 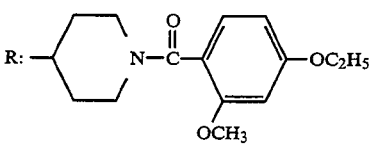 —OC$_2$H$_5$ (OCH$_3$)

R$^1$: —CH$_3$ (5-, 7-positions), q: 2
Bond between 3- and 4-positions in the carbostyril ring: Single bond
Crystalline form: White powders
Melting point: 165–167° C.
Form: Free Example 730
Structure R: 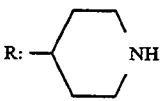

R$^1$: F (5-position), q: 1
Bond between 3- and 4-positions in the carbostyril ring: Single bond
NMR analysis: 454)
Form: Free Example 731
Structure R: 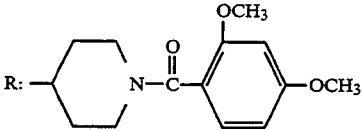 —OCH$_3$ (OCH$_3$)

R$^1$: F (5-position), q: 1
Bond between 3- and 4-positions in the carbostyril ring: Single bond
Crystalline form: Colorless amorphous form
NMR analysis: 455)
Form: Free -continued Example 732
Structure

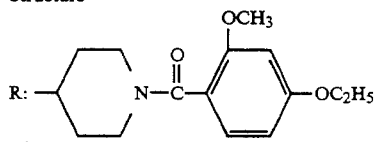

R$^1$: F (5-position), q: 1
Bond between 3- and 4-positions in the carbostyril ring: Single bond
Crystalline form: Colorless amorphous form
NMR analysis: 456)
Form: Free Example 733
Structure

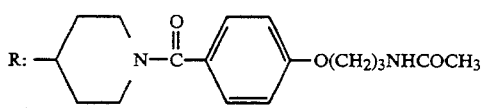

R$^1$: —CH$_3$ (5-position), q: 1
Bond between 3- and 4-positions in the carbostyril ring: Single bond
Crystalline form: Colorless amorphous form
NMR analysis: 457)
Form: Free Example 734
Structure

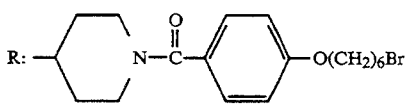

R$^1$: —CH$_3$ (5-position), q: 1
Bond between 3- and 4-positions in the carbostyril ring: Single bond
Crystalline form: Colorless amorphous form
NMR analysis: 458)
Form: Free Example 735
Structure

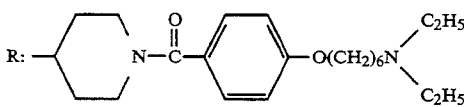

R$^1$: —CH$_3$ (5-position), q: 1
Bond between 3- and 4-positions in the carbostyril ring: Single bond
Crystalline form: Colorless amorphous form
NMR analysis: 459)
Form: Free Example 736
Structure

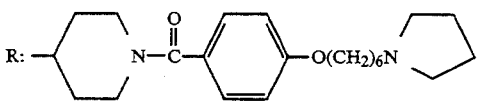

R$^1$: —CH$_3$ (5-position), q: 1
Bond between 3- and 4-positions in the carbostyril ring: Single bond
Crystalline form: Colorless amorphous form
NMR analysis: 460)
Form: Free Example 737
Structure

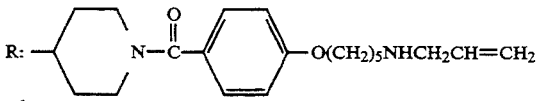

R$^1$: H, q: 1
Bond between 3- and 4-positions in the carbostyril ring: Single bond
NMR analysis: 461)
Form: Free Example 738
Structure -continued

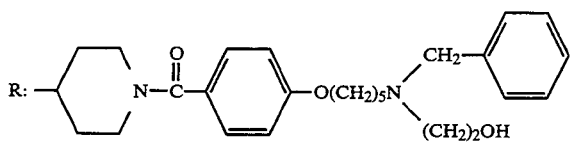
R¹: H, q: 1
Bond between 3- and 4-positions in the carbostyril ring: Single bond
NMR analysis: 462)
Form: Free Example 739
Structure

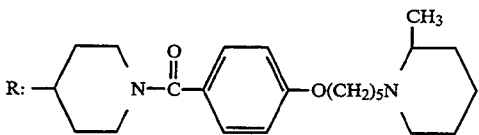
R¹: H, q: 1
Bond between 3- and 4-positions in the carbostyril ring: Single bond
NMR analysis: 463)
Form: Free Example 740
Structure

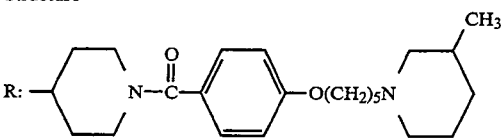
R¹: H, q: 1
Bond between 3- and 4-positions in the carbostyril ring: Single bond
NMR analysis: 464)
Form: Free Example 741
Structure

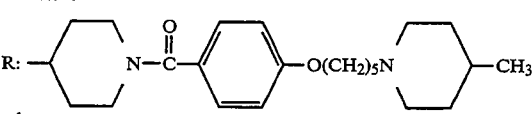
R¹: H, q: 1
Bond between 3- and 4-positions in the carbostyril ring: Single bond
NMR analysis: 465)
Form: Free Example 742
Structure

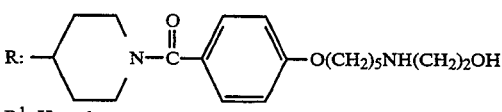
R¹: H, q: 1
Bond between 3- and 4-positions in the carbostyril ring: Single bond
NMR analysis: 466)
Form: Free Example 743
Structure

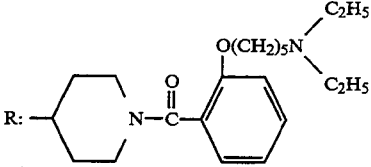
R¹: H, q: 1
Bond between 3- and 4-positions in the carbostyril ring: Single bond
NMR analysis: 467)
Form: Free Example 744
Structure -continued

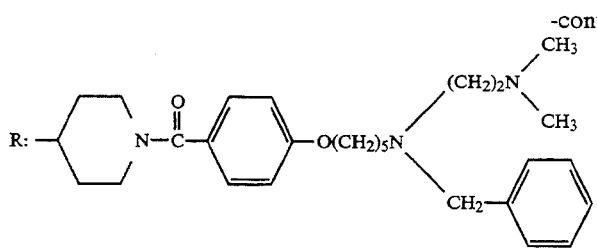

R[1]: H, q: 1
Bond between 3- and 4-positions in the carbostyril ring: Single bond
NMR analysis: 468)
Form: Free Example 745
Structure

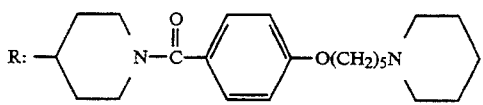

R[1]: H, q: 1
Bond between 3- and 4-positions in the carbostyril ring: Single bond
NMR analysis: 469)
Form: Free Example 746
Structure

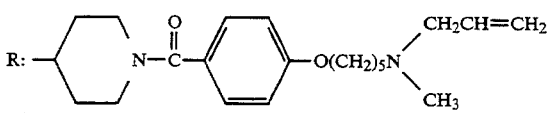

R[1]: H, q: 1
Bond between 3- and 4-positions in the carbostyril ring: Single bond
NMR analysis: 470)
Form: Free Example 747
Structure

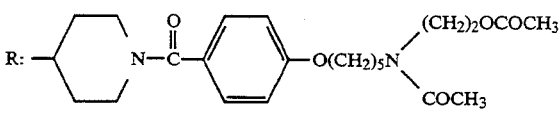

R[1]: H, q: 1
Bond between 3- and 4-positions in the carbostyril ring: Single bond
NMR analysis: 471)
Form: Free Example 748
Structure

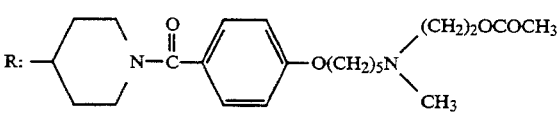

R[1]: H, q: 1
Bond between 3- and 4-positions in the carbostyril ring: Single bond
NMR analysis: 472)
Form: Free Example 749
Structure

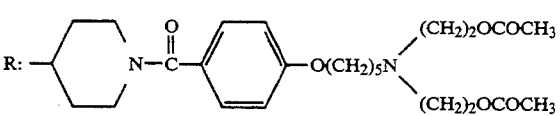

R[1]: H, q: 1
Bond between 3- and 4-positions in the carbostyril ring: Single bond
NMR analysis: 473)
Form: Free Example 750
Structure

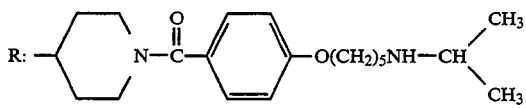

R¹: H, q: 1
Bond between 3- and 4-positions in the carbostyril ring: Single bond
NMR analysis: 474)
Form: Free Example 751
Structure

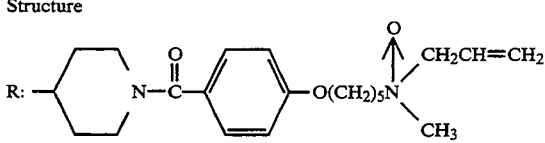

R¹: H, q: 1
Bond between 3- and 4-positions in the carbostyril ring: Single bond
NMR analysis: 475)
Form: Free Example 752
Structure

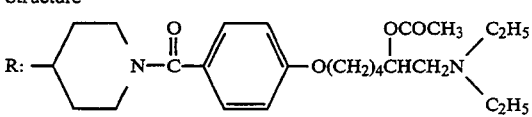

R¹: H, q: 1
Bond between 3- and 4-positions in the carbostyril ring: Single bond
NMR analysis: 476)
Form: Free Example 753
Structure

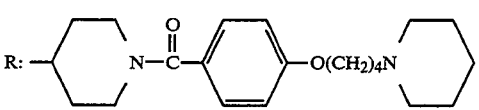

R¹: H, q: 1
Bond between 3- and 4-positions in the carbostyril ring: Single bond
NMR analysis: 477)
Form: Free Example 754
Structure

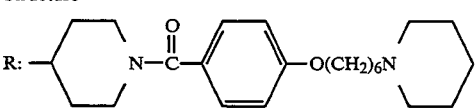

R¹: H, q: 1
Bond between 3- and 4-positions in the carbostyril ring: Single bond
NMR analysis: 478)
Form: Free Example 755
Structure

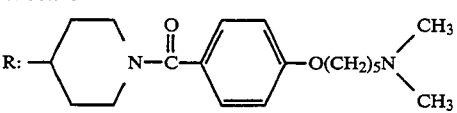

R¹: H, q: 1
Bond between 3- and 4-positions in the carbostyril ring: Single bond
NMR analysis: 479)
Form: Free Example 756
Structure

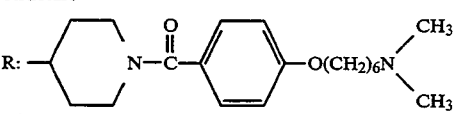

R¹: H, q: 1
Bond between 3- and 4-positions in the carbostyril ring: Single bond
NMR analysis: 480)

-continued

Form: Free

Example 757
Structure

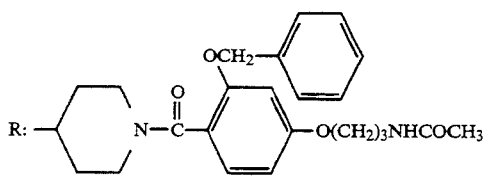

R¹: H, q: 1
Bond between 3- and 4-positions in the carbostyril ring: Single bond
Crystalline form: Colorless amorphous form
NMR analysis: 481)
Form: Free Example 758
Structure

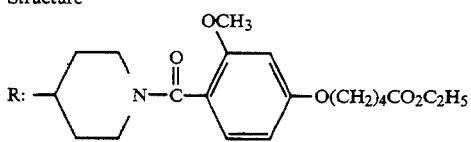

R¹: H, q: 1
Bond between 3- and 4-positions in the carbostyril ring: Single bond
NMR analysis: 482)
Form: Free Example 759
Structure

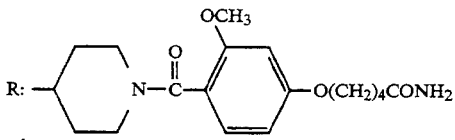

R¹: H, q: 1
Bond between 3- and 4-positions in the carbostyril ring: Single bond
Crystalline form: Colorless amorphous form
NMR analysis: 483)
Form: Free Example 760
Structure

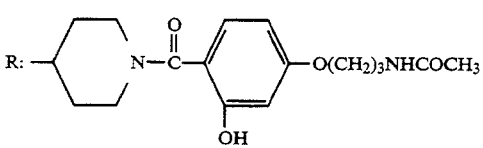

R¹: H, q: 1
Bond between 3- and 4-positions in the carbostyril ring: Single bond
Crystalline form: Colorless needles
Recrystallization solvent: Ethanol/diethyl ether
Melting point: 155–157° C.
Form: Free Example 761
Structure

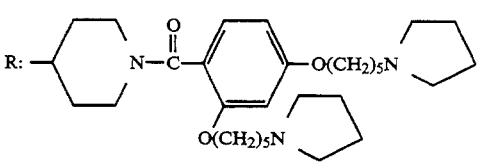

R¹: H, q: 1
Bond between 3- and 4-positions in the carbostyril ring: Single bond
Crystalline form: Colorless amorphous form
NMR analysis: 484)
Form: Free Example 762
Structure

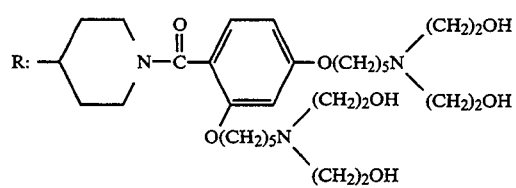

R[1]: H, q: 1
Bond between 3- and 4-positions in the carbostyril ring: Single bond
NMR analysis: 485)
Form: Free Example 763
Structure

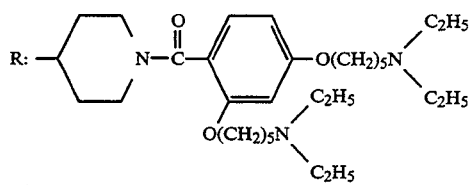

R[1]: H, q: 1
Bond between 3- and 4-positions in the carbostyril ring: Single bond
NMR analysis: 486)
Form: Dihydrochloride Example 764
Structure

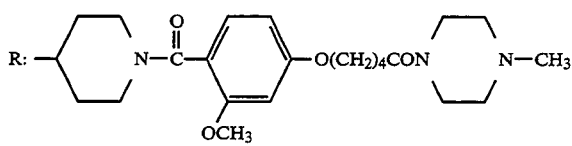

R[1]: H, q: 1
Bond between 3- and 4-positions in the carbostyril ring: Single bond
Crystalline form: Colorless amorphous form
NMR analysis: 487)
Form: Free Example 765
Structure

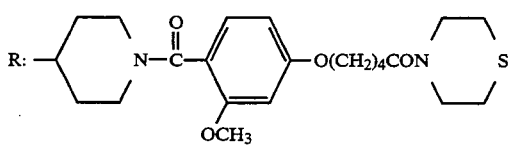

R[1]: H, q: 1
Bond between 3- and 4-positions in the carbostyril ring: Single bond
Crystalline form: Colorless amorphous form
NMR analysis: 488)
Form: Free Example 766
Structure

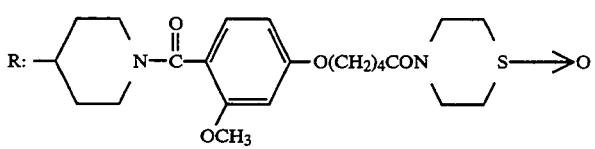

R[1]: H, q: 1
Bond between 3- and 4-positions in the carbostyril ring: Single bond
Crystalline form: Colorless amorphous form
NMR analysis: 489)
Form: Free Example 767
Structure

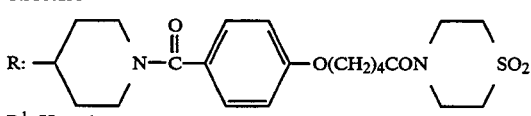

R[1]: H, q: 1

-continued

Bond between 3- and 4-positions in the carbostyril ring: Single bond
Crystalline form: Colorless amorphous form
NMR analysis: 490)
Form: Free Example 768
Structure

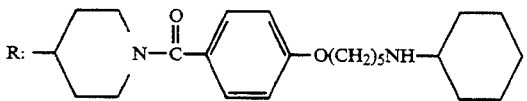

R¹: H, q: 1
Bond between 3- and 4-positions in the carbostyril ring: Single bond
NMR analysis: 493)
Form: Free Example 769
Structure

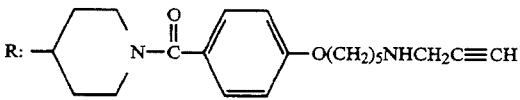

R¹: H, q: 1
Bond between 3- and 4-positions in the carbostyril ring: Single bond
NMR analysis: 494)
Form: Free Example 770

1-{1-[4-(4-Oxiranylbutoxy)benzoyl]-4-piperidinyl}-3,4-dihydrocarbostyril (1.6 g) is dissolved in a mixture of dioxane (30 ml) and water (10 ml). Thereto is added conc. sulfuric acid (0.1 ml) and the mixture is stirred at room temperature overnight. The mixture is neutralized with sodium hydrogen carbonate and then extracted with chloroform. The extract is dried with magnesium sulfate and the solvent is evaporated off. The resulting residue is purified by silica gel column chromatography (solvent: dichloromethane:methanol=50:1) to give 1-{1-[4-(5,6-dihydroxyhexyloxy)benzoyl]-4-piperidinyl]-3,4-dihydrocarbostyril (0.6 g).

NMR (CDCl₃) δ ppm: 1.35–1.93 (8H, m), 2.15–3.15 (10H, m), 3.32–3.78 (3H, m), 3.83–5.22 (3H, m), 3.97 (2H, t, J=6.3 Hz), 6.79–7.48 (8H, m)

Example 771

Using the suitable starting materials, the compounds of the above Examples 718, 719, 728 and 730 are obtained in the same manners as Example 386.

Example 772

Using the suitable starting materials, the compounds of the above Examples 594–717, 720–727, 729, 731–769 are obtained in the same manners as in Examples 390–393.

Example 773

Using the suitable starting materials, the compounds of the above Examples 594–717, 720–727, 729, 731–769 are obtained in the same manners as in Examples 398 and 399.

Example 774

Using the suitable starting materials, the compounds of the above Examples 596–648, 650–651, 653, 700, 712, 714, 716, 717, 720, 723, 726, 727, 733, 747, 757, and 760 are obtained in the same manners as in Examples 403–405.

Example 775

Using the suitable starting materials, the compounds of the above Examples 600, 604, 609, 610, 616, 618, 620, 623, 625, 627, 628, 630, 631, 633, 634, 637–639, 646, 649, 651, 652–655, 658–660, 662, 663, 666, 668–671, 673, 677, 685–687, 689–691, 698, 699, 715, 735–738, 742–744, 746–752, 755, 756, 762–764, 768–769 are obtained in the same manners as in Examples 407–409.

Example 776

Using the suitable starting materials, the compounds of the above Examples 695, 696, 697, 706, 709–712, 715, 751, 766 and 767 are obtained in the same manners as in Example 416.

Example 777

Using the suitable starting materials, the compounds of the above Examples 657–661, 663, 664, 674, 676, 677 and 692 are obtained in the same manners as in Example 421.

Example 778

Using the suitable starting materials, the compounds of the above Examples 596–603, 605, 606, 611–616, 618–623, 625–640, 642, 643, 645–656, 662, 665–673, 675, 678–689, 691, 693, 694, 698, 700–705, 707, 708, 713, 714, 716, 717, 720, 723, 726, 727, 733, 735–750, 753–757, 760–763, 768 and 769 are obtained in the same manners as in Example 426.

TABLE 10

| No. | NMR (CDCl₃) δ value |
|---|---|
| 329 | 1.64–2.44(8H, m), 2.50–3.20(8H, m), 3.25–3.70 (4H, m), 3.80–5.00(2H, brs), 3.99(2H, m), 4.33 (2H, m), 5.07(1H, d, J=12.5Hz), 5.19(1H, d, J=12.5Hz), 6.38(1H, brs), 6.89(2H, d, J=8.4Hz), 6.99–7.29(4H, m), 7.33(5H, m), 7.42(2H, d, J=8.4Hz) |
| 330 | 1.25–2.20(6H, m), 1.80(2H, m), 1.95(2H, m), 2.52–3.04(8H, m), 3.12(2H, m), 3.41(2H, q, J=5.4Hz), 3.80–4.90(2H, brs), 3.98(2H, t, J=5.4Hz), 4.10(1H, m), 4.35(1H, m), 5.29(4H, s), 5.31(1H, brs), 5.70(1H, brs), 6.72(1H, brs), 6.87(2H, d, |

TABLE 10-continued

| No. | |
|---|---|
| | J=8.6Hz), 6.98-7.27(4H, m), 7.30(10H, s), 7.39 (2H, d, J=8.6Hz) |
| 331 | 1.84(2H, m), 2.40-3.15(10H, m), 3.24-3.50(2H, m), 3.56(2H, t, J=6.1Hz), 3.70-5.15(2H, brs), 3.94(2H, t, J=5.6Hz), 4.36(2H, m), 6.61(2H, d, J=8.0Hz,), 6.84(2H, d, J=8.6Hz), 6.92(2H, d, J=8.0Hz), 6.99-7.29(4H, m), 7.40(2H, d, J=8.6Hz), 7.50(1H, brs) |
| 332 | 1.65-2.50(8H, m), 2.50-3.10(10H, m), 3.45(2H, q, J=6.4Hz), 3.60-5.10(2H, brs), 3.81(1H, dd, J=9.0, 5.3Hz), 4.06(2H, t, J=5.9Hz), 4.38(1H, m), 6.92(2H, d, J=8.7Hz), 6.99-7.29(4H, m), 7.43 (2H, d, J=8.7Hz), 8.00(1H, brs) |
| 333 | 1.70-1.93(2H, m), 2.04(2H, quint, J=6.2Hz), 2.30 (6H, s), 2.53-3.20(8H, m), 2.96(2H, s), 3.50(2H, q, J=6.2Hz), 3.80-5.10(2H, brs), 4.08(2H, t, J=6.2Hz), 4.37(1H, m), 6.92(2H, d, J=8.7Hz). 6.99-7.29(4H, m), 7.44(2H, d, J=8.7Hz), 7.53 (1H, brs) |
| 334 | 1.60-1.89(2H, m), 1.97(2H, quint, J=6.0Hz), 2.53-3.20(8H, m), 3.44(2H, q, J=6.0Hz), 3.64 (1H, dd, J=11.2, 5.2Hz), 3.80-5.10(2H, brs), 4.00 (2H, t, J=6.0Hz), 4.12(1H, dd, J=11.2, 5.2Hz), 4.17(1H, m), 4.35(1H, m), 5.10(2H, s), 5.97(1H, d, J=6.0Hz), 6.89(2H, d, J=8.7Hz), 6.99-7.30 (4H, m), 7.33(5H, s), 7.39(2H, d, J=8.7Hz) |
| 335 | 1.37(3H, d, J=7.0Hz), 1.64-1.90(2H, m), 1.97 (2H, m), 2.53-3.20(8H, m), 3.43(2H, q, J=6.2Hz), 3.65-5.00(2H, brs), 4.00(2H, t, J=5.8Hz), 4.21 (1H, quint, J=7.0Hz), 4.37(1H, m), 5.05(1H, d, J=12.2Hz), 5.18(1H, d, J=12.1Hz), 5.55(1H, d, J=7.0Hz), 6.70(1H, brs), 6.88(2H, d, J=8.7Hz), 6.99-7.36(4H, m), 7.33(5H, s), 7.40(2H, d, J=8.7Hz) |
| 336 | 1.33(3H, d, J=6.9Hz), 1.63-1.95(2H, m), 2.03 (2H, quint, J=6.0Hz), 2.53-3.20(8H, m), 3.41-3.55 (3H, m), 3.80-5.20(2H, brs), 4.06(2H, t, J=6.0Hz), 4.37(1H, m), 6.93(2H, d, J=8.6Hz), 6.99-7.89(4H, m), 7.43(2H, d, J=8.6Hz), 7.68(1H, t, J=6.0Hz) |
| 337 | 1.42-1.63(2H, m), 1.62-1.90(6H, m), 2.31-2.44 (6H, m), 2.54-3.10(8H, m), 3.46(2H, m), 3.51(2H, s), 3.63(2H, m), 3.83-5.15(2H, brs), 3.98(2H, t, J=6.4Hz), 4.39(1H, m), 6.89(2H, d, J=8.7Hz), 6.99-7.33(4H, m), 7.31(5H, m), 7.42(2H, d, J=8.7Hz) |
| 338 | 0.82(3H, d, J=6.9Hz), 0.99(3H, d, J=6.9Hz), 1.64-1.90(2H, m), 2.04(2H, m), 2.10-2.41(1H, m), 2.54-3.08(8H, m), 3.24(1H, d, J=3.8Hz), 3.48 (2H, q, J=6.5Hz), 3.67-5.50(2H, brs), 4.06(2H, t, J=5.9Hz), 4.38(1H, m), 6.92(2H, d, J=8.7Hz), 6.99∝7.28(4H, m), 7.43(2H, d, J=8.7Hz), 7.67 (1H, brs) |
| 339 | 0.82(3H, d, J=6.9Hz), 0.99(3H, d, J=6.9Hz), 1.68-1.93(2H, m), 2.03(2H, quint, J=6.1Hz), 2.33 1H, m), 2.54-3.17(8H, m), 3.25(1H, d, J=3.7Hz), 3.49(2H, q, J=6.1Hz), 3.80-5.20(2H brs), 4.07 (2H, t, J=6.1Hz), 4.39(1H, m), 6.92(2H, d, J=8.7Hz), 7.03-7.30(4H, m), 7.43(2H, d, J=8.7Hz), 7.64(1H, brs) |
| 340 | 1.41-1.60(2H, m), 1.61-1.98((6H, m), 2.35(2H, t, J=7.4Hz), 2.54-3.10(12H, m), 3.44(2H, t, J=4.9Hz), 3.59(2H, t, J=4.9Hz), 3.80-5.20(2H, brs), 3.99(2H, t, J=6.3Hz), 4.39(1H, m), 6.89(2H, d, J=8.6Hz), 6.99-7.28(4H, m), 7.42(2H, d, J=8.6Hz) |
| 341 | 1.40-1.65(2H, m), 1.65-2.00(6H, m), 1.76(3H, s), 2.39(2H, t, J=7.4Hz), 2.54-3.20(8H, m), 3.49 (4H, m), 3.61(4H, m), 3.85-5.20(2H, brs), 4.00 (2H, t, J=6.3Hz), 4.39(1H, m), 6.89(2H, d, J=8.7Hz), 6.99-7.25(4H, m), 7.42(2H, d, J=8.7Hz) |
| 342 | 1.40-1.65(2H, m), 1.65-2.02(6H, m), 2.37(2H, t, J=7.3Hz), 2.54-3.30(12H, m), 2.81(3H, s), 3.46-4.10(4H, m), 4.00(2H, t, J=6.2Hz), 4.10-5.20 (2H, brs), 4.37(1H, m), 6.90(2H, d, J=8.7Hz), 7.00-7.26(4H, m), 7.42(2H, d, J=8.7Hz) |
| 343 | 1.42-1.63(2H, m), 1.64-2.00(6H, m), 2.32-2.52 (6H, m), 2.54-3.10(8H, m), 3.01(2H, d, J=6.6Hz), 3.48(2H, m), 3.64(2H, m), 3.80-5.10(2H, brs), 3.99(2H, t, J=6.3Hz), 4.40(1H, m), 5.18(1H, d, J=10.3Hz), 5.20(1H, d, J=16.8Hz), 5.85(1H, ddt, J=16.8, 10.3, 6.6Hz), 6.89(2H, d, J=8.7Hz), 6.99-7.26(4H, m), 7.42(2H, d, J=8.7Hz) |
| 344 | 1.60-1.90(2H, m), 1.81(2H, quint, J=7.0Hz), 1.98 (2H, quint, J=6.2Hz(, 2.25(2H, t, J=7.0Hz), 2.52-3.17(10H, m), 3.39(2H, q, J=6.2Hz), 3.65-5.15(2H, br), 3.90(2H, brs), 4.03(2H, t, J=6.2Hz), 4.33(1H, m), 6.91(2H, d, J=8.5Hz), 6.98-7.28(5H, m), 7.40(2H, d, J=8.5Hz) |
| 345 | 1.70-1.93(2H, m), 1.81(2H, quint, J=6.6Hz), 1.98 (2H, quint, J=6.1Hz), 2.22(2H, t, J=6.6Hz), 2.46-3.10(8H, m), 3.21(2H, q, J=6.6Hz), 3.40 (2H, q, J=6.1Hz), 3.80-5.10)(2H, brs), 4.01(2H, t, J=6.1Hz), 4.34(1H, m), 4.34(1H, m), 5.07(2H, s), 5.73(1H, brs), 6.89(2H, d, J=8.7Hz), 6.91(1H, brs), 6.99-7.25(4H, m), 7.32(5H, s), 7.40(2H, d, J=8.7Hz) |
| 346 | 1.52(4H, m), 1.66-1.97(6H, m), 2.20(2H, t, J=6.8Hz), 2.53-3.05(8H, m), 3.10-3.32(4H, m), 3.70-5.10(2H, br), 3.96(2H, t, J=6.3Hz), 4.37(1H, m), 5.08(2H, s), 5.31(1H, brs), 6.30(1H, brs), 6.88(2H, d, J=8.7Hz)), 6.99-7.27(4H, m), 7.33 (5H, s), 7.41(2H, d, J=8.7Hz) |
| 347 | 1.41-1.71(4H, m), 1.71-1.90(4H, m), 2.54-32.0 (8H, m), 3.34(2H, q, J=6.5Hz), 3.60-5.15(2H, brs), 3.99(2H, t, J=6.2Hz), 4.04(2H, s), 4.38 (1H, m), 6.72(1H, brs), 6.90(2H, d, J=8.7Hz), 6.99-7.28(4H, m), 7.43(2H, d, J=8.7Hz) |
| 348 | 1.32-1.67(4H, m), 1.67-2.00(6H, m), 2.25(2H, t, J=7.3Hz), 2.53-3.10(10H, m), 3.24(2H, q, J=6.2Hz), 3.70-5.20(2H, brs), 3.97(2H, t, J=6.2Hz), 4.36(1H, m), 6.54(1H, m), 6.89(2H, d, J=8.7Hz), 6.99-7.23(4H, m), 7.41(2H, d, J=8.7Hz) |
| 349 | 1.25-1.72(4H, m), 1.73-1.94(4H, m), 2.29(6H, s), 2.54-3.10(8H, m), 2.94(2H, s), 3.31(2H, q, J=6.3Hz), 3.74-5.10(2H, br), 3.99(2H, t, J=6.3Hz), 4.39(1H, m), 6.89(2H, d, J=8.7Hz), 6.99-7.28 (5H, m), 7.43(2H, d, J=8.7Hz) |
| 350 | 1.26(3H, t, J=7.1Hz), 1.42-2.05(12H, m), 2.37 (2H, t, J=7.4Hz), 2.44-3.24(11H, m), 3.50-5.10 (2H, brs), 3.73-3.94(1H, m), 3.99(2H, t, J=6.3Hz), 4.15(2H, q, J=7.1Hz), 4.23-4.53(2H, m), 6.90(2H, d, J=8.7Hz), 6.99-7.29(4H, m), 7.42 (2H, d, J=8.7Hz) |
| 351 | 1.02(6H, t, J=7.1Hz), 1.39-1.71(4H, m), 1.71-2.05(4H, m), 2.38-3.14(8H, m), 2.55(4H, q, J=7.1Hz), 3.01(2H, s), 3.30(2H, q, J=6.3Hz),, 3.70-5.15(2H, brs), 3.98(2H, t, J=6.3Hz), 4.39(1H, m), 6.89(2H, d, J=8.7Hz), 6.99-7.27(4H, m), 7.43 (2H, d, J=8.7Hz), 7.45(1H, brs) |
| 352 | 1.37-1.68(4H, m), 1.68-1.90(6H, m), 1.96(3H, s), 2.16(2H, t, J=6.7Hz), 2.54-3.15(8H, m), 3.15-3.33(4H, m), 3.75-5.20((2H, brs), 3.98(2H, t, J=6.2Hz), 4.36(1H, m), 6.90(2H, d, J=8.5Hz), 6.92(1H, brs), 6.99-7.31(4H, m), 7.41(2H, d, J=8.7Hz) |
| 353 | 1.48-1.64(4H, m), 1.69-1.91(4H, m), 1.91-2.13 (2H, m), 2.21(2H, t, J=6.7Hz), 2.54-3.11(10H, m), 2.66(6H, s), 3.25(2H, q, J=6.2Hz), 3.70-5.10 (2H, brs), 3.98(2H, t, J=6.2Hz), 4.35(1H, m), 6.15(1H, brs), 6.90(2H, d, J=8.7Hz), 6.99-7.28 (4H, m), 7.41(2H, d, J=8.7Hz) |
| 354 | 1.37-1.69(4H, m), 1.69-1.94(4H, m), 2.16(3H, s), 2.53-3.20(8H, m), 3.32(2H, q, J=6.5Hz), 3.65-5.15(2H, br), 3.98(2H, t, J=6.2Hz), 4.54(1H, m), 4.65(2H, s), 6.51(1H, brs), 6.90(2H, d, J=8.7Hz), 6.99-7.30(4H, m), 7.42(2H, d, J=8.7Hz) |
| 355 | 1.49-1.69(4H, m), 1.69-1.98(4H, m), 2.54-3.18 (8H, m), 3.31(2H, q, J=6.3Hz), 3.67(1H, t, J=5.1Hz), 3.80-5.15(2H, brs), 4.00(2H, t, J=6.9Hz), 4.03(2H, d, J=5.1Hz), 4.37(1H, m), 6.64(1H, brs), 6.90(2H, d, J=8.7Hz), 6.99-7.28(4H, m), 7.41(2H, d, J=8.7Hz) |
| 356 | 1.10(3H, t, J=7.1Hz), 1.42-1.70(4H, m), 1.70-1.95(4H, m), 2.54-3.17(8H, m), 2.61(2H, q, J=7.1Hz), 3.24(2H, s), 3.30(2H, q, J=6.5Hz), 3.60-5.20(2H, brs), 3.99(2H, t, J=6.3Hz), 4.37(1H, m), 6.90(2H, d, J=8.6Hz), 6.99-7.30(4H, m), 7.42 (2H, d, J=8.6Hz), 7.45(1H, brs) |
| 357 | 1.30-2.00(12H, m), 2.36(2H, m), 2.52-3.20(11H, m), 3.50-5.15(2H, brs), 3.60-3.84(1H, m), 3.98 (2H, t, J=6.1Hz), 4.22-4.60(2H, m), 6.88(2H, d, J=8.6Hz), 6.99-7.25(4H, m), 7.40(2H, d, J=8.6Hz) |
| 358 | 1.49-1.68(4H, m), 1.68-1.95(4H, m), 2.54-3.10 (8H, m), 3.23(2H, d, J=5.1Hz), 3.27(2H, s), 3.31 (2H, q, J=6.3Hz), 3.70-5.10(2H, brs), 3.98(2H, |

TABLE 10-continued

| No. | |
|---|---|
| | t, J=6.3Hz), 4.39(1H, m), 5.12(1H, d, J=10.2Hz), 5.19(1H, d, J=17.2Hz), 5.85(1H, ddt, J=17.2, 10.2, 5.1Hz), 6.89(2H, d, J=8.7Hz), 6.99–7.38(5H, m), 7.42(2H, d, J=8.7Hz) |
| 359 | 1.63–1.96(6H, m), 2.54–3.20(8H, m), 3.39(2H, q, J=6.4Hz), 3.65–5.20(2H, brs), 4.01(2H, t, J=5.8Hz), 4.05(2H, s), 4.38(1H, m), 6.80(1H, brs), 6.90(2H, d, J=8.7Hz), 6.99–7.25(4H, m), 7.43 (2H, d, J=8.7Hz) |
| 360 | 1.62–1.98(6H, m), 2.28(6H, s), 2.54–3.14(8H, m), 2.94(2H, s), 3.36(2H, q, J=6.5Hz), 3.70–5.10 (2H, brs), 4.01(2H, t, J=5.9Hz), 4.39(1H, m ), 6.90(2H, d, J=8.7Hz), 6.99–7.25(4H, m), 7.27 (1H, brs), 7.43(2H, d, J=8.7Hz) |
| 361 | 1.03(6H, t, J=7.2Hz), 1.59–1.98(6H, m), 2.43–3.20(8H, m), 2.55(4H, q, J=7.2Hz), 3.20(2H, s), 3.35(2H, q, J=6.5Hz), 3.70–5.10(2H, brs), 4.02 (2H, t, J=5.9Hz), 4.39(1H, m), 6.90(2H, d, J=8.7Hz), 6.99–7.29(4H, m), 7.43(2H, d, J=8.7Hz), 7.51(1H, brs) |
| 362 | 1.60–1.94(6H, m), 2.15(3H, s), 2.54–3.20(8H, m), 3.37(2H, q, J=6.5Hz), 3.80–5.10(2H, brs), 4.00 (2H, t, J=5.8Hz), 4.37(1H, m), 4.55(2H, s), 6.60 (1H, bs), 6.90(2H, d, J=8.5Hz), 7.00–7.28(4H, m), 7.42(2H, d, J=8.5Hz) |
| 363 | 1.38–1.72(4H, m), 1.72–1.97(4H, m), 2.30(3H, s), 2.36–3.20(16H, m), 3.10(2H, s), 3.31(2H, q, J=6.4Hz), 3.70–5.15(2H, brs), 3.99(2H, t, J=6.2Hz), 4.36(1H, m), 6.90(2H, d, J=8.7Hz), 6.99–7.30(5H, m), 7.43(2H, d, J=8.7Hz) |
| 364 | 1.36–1.70(4H, m), 1.70–1.97(4H, m), 2.52–3.15 (8H, m), 2.66(4H, s), 3.06(2H, s), 3.20(4H, m), 3.33(2H, q, J=6.4Hz), 3.75–5.10(2H, brs), 3.98 (2H, t, J=6.1Hz), 4.34(1H, m), 6.60–7.36(11H, m), 7.40(2H, d, J=8.5Hz) |
| 365 | 1.56–1.97(6H, m), 2.54–3.22(8H, m), 3.34(2H, q, J=6.4Hz), 3.70–5.10(2H, brs), 3.98(2H, d, J=5.2Hz), 4.00(2H, t, J=5.9Hz), 4.35(1H, m), 4.51 (1H, t, J=5.2Hz), 6.89(1H, brs), 6.90(2H, d, J=8.7Hz), 7.00–7.29(4H, m), 7.40(2H, d, J=8.7Hz), |
| 366 | 1.05(6H, d, J=6.2Hz), 1.38–1.72(4H, m), 1.72–1.95(4H, m), 2.54–3.16(9H, m), 3.24(2H, s), 3.30 (2H, q, J=6.3Hz), 3.70–5.20(2H, brs), 3.98(2H, t, J=6.3Hz), 4.38(1H, m), 6.90(2H, d, J=8.6Hz), 6.99–7.32(94H, m), 7.42(2H, d, J=8.6Hz), 7.49 (1H, brs) |
| 367 | 1.40–1.69(4H, m), 1.69–1.96(4H, m), 2.54–3.16 (8H, m), 3.29(2H, s), 3.29(2H, q, J=6.3Hz), 3.67–5.20(2H, brs), 3.76(2H, s), 3.97(2H, t, J=6.3Hz), 4.38(1H, m), 6.88(2H, d, J=8.7Hz), 7.00–7.39(10H, m), 7.41(2H, d, J=8.7Hz) |
| 368 | 1.37–1.68(4H, m), 1.68–1.98(4H, m), 1.79(4H, m), 2.40–3.15(8H, m), 2.59(4H, m), 3.14(2H, s), 3.31 (2H, q, J=6.4Hz), 3.66–5.20(2H, brs), 3.99(2H, t, J=6.2Hz), 4.37(1H, m), 6.89(2H, d, J=8.6Hz), 6.98–7.29(5H, m), 7.42(2H, d, J=8.6Hz) |
| 369 | 1.37–1.71(4H, m), 1.71–1.94(4H, m), 2.35–3.15 (8H, m), 2.52(4H, m), 3.00(2H, s), 3.31(2H, q, J=6.4Hz), 3.69(4H, m), 3.80–5.20(2H, brs), 3.99 (2H, t, J=6.2Hz), 4.36(1H, m), 6.89(2H, d, J=8.6Hz), 6.98–7.29(5H, m), 7.42(2H, d, J=8.6Hz) |
| 370 | 1.36–1.69(4H, m), 169–1.95(4H, m), 2.28(3H, s), 2.52–3.13(8H, m), 3.02(2H, s), 3.30(2H, q, J=6.4Hz), 3.56(2H, s), 3.80–5.20(2H, brs), 3.96(2H, t, J=6.2Hz), 4.36(1H, m), 6.88(2H, d, J=8.7Hz), 6.98–7.35(5H, m), 7.29(5H, s), 7.42(2H, d, J=8.7Hz) |
| 371 | 1.38–1.69(4H, m), 1.69–1.94(4H, m), 2.33(3H, s), 2.54–3.17(8H, m), 2.58(2H, t, J=5.2Hz), 3.07 2H, s), 3.29(2H, q, J=6.4Hz), 3.65(2H, t, J=5.2Hz), 3.80–5.20(2H, br), 3.98(2H, t, J=6.2Hz), 4.38(1H, m), 6.89(2H, d, J=8.7Hz), 6.99–7.28 (4H, m), 7.29(1H, bs), 7.42(2H, d, J=8.7Hz) |
| 372 | 1.40(3H, t, J=7.0Hz), 1.43–1.68(4H, m), 1.68–1.93(4H, m), 2.26(3H, s), 2.54–3.10(8H, m), 3.01 (2H, s), 3.30(2H, q, J=6.4Hz), 3.49(2H, s), 3.75–5.10(2H, br), 3.97(2H, t, J=6.2Hz), 4.00 (2H, q, J=7.0Hz), 4.39(1H, m), 6.84(2H, d, J=8.5Hz), 6.89(2H, d, J=8.6Hz), 6.99–7.28(5H, m), 7.18(2H, d, J=8.5Hz), 7.42(2H, d, J=8.6Hz) |
| 373 | 1.32–1.65(4H, m), 1.65–1.93(4H, m), 2.53–3.14 (8H, m), 3.24(2H, q, J=6.2Hz), 3.60–5.10(2H, brs), 3.82(2H, d, J=5.7Hz), 3.94(2H, t, J=6.2Hz), 4.37(1H, m), 5.11(2H, s), 5.79(1H, brs), 6.48(1H, brs), 6.88(2H, d, J=8.7Hz), 6.99–7.36 (4H, m), 7.33(5H, s), 7.41(2H, d, J=8.7Hz) |
| 374 | 142–2.02(12H, m), 2.36(2H, t, J=7.4Hz), 2.38 (1H, m), 2.54–3.16(10H, m), 3.53–5.15(2H, brs), 3.76–3.97(1H, m), 4.00(2H, t, J=6.3Hz), 4.38 (1H, m), 4.48–4.67(1H, m), 5.58(1H, brs), 5.81 (1H, brs), 6.90(2H, d, J=8.7Hz), 6.99–7.29(4H, m), 7.42(2H, d, J=8.7Hz) |
| 375 | 1.45–1.98(10H, m), 2.23(1H, m), 2.54–3.10(10H, m), 3.12(1H, m), 3.18(1H, m), 3.32(2H, q, J=6.4Hz), 3.70–5.20(2H, brs), 4.00(2H, t, J=5.8Hz), 4.37(1H, m), 5.95(1H, brs), 6.90(2H, d, J=8.7Hz), 6.99–7.28(4H, m), 7.42(2H, d, J=8.7Hz) |
| 376 | 1.44–2.02(10H, m), 2.09(3H, s), 2.29(1H, m), 2.54–3.20(10H, m), 3.32(2H, q, J=6.4Hz), 3.70–5.20(2H, brs), 3.78–3.94(1H, m), 4.00(2H, t, J=5.8Hz), 4.36(1H, m), 4.52–4.69(1H, m), 5.87 (1H, brs), 6.89(2H, d, J=8.7Hz), 6.99–7.28(4H, m), 7.42(2H, d, J=8.7Hz) |
| 377 | 1.42–2.01(12H, m), 2.38(2H, t, J=7.3Hz), 2.52–3.26(11H, m), 2.94(3H, s), 3.09(3H, s), 3.65–5.20(2H, brs), 3.82–4.14(1H, m), 4.00(2H, t, J=6.2Hz), 4.36(1H, m), 4.53–4.74(1H, m), 6.91 (2H, d, J=8.6Hz), 6.98–7.29(4H, m), 7.42(2H, d, J=8.6Hz) |
| 378 | 1.37–1.71(4H, m), 1.71–1.90(4H, m), 2.53–3.16 (8H, m), 3.30(2H, q, J=6.2Hz), 3.32(2H, s), 3.70–5.20(2H, brs), 3.98(2H, t, J=6.1Hz), 4.35 (1H, m), 6.90(2H, d, J=8.5Hz), 6.99–7.29(4H, m), 7.42(2H, d, J=8.5Hz), 7.44(1H, bs) |
| 379 | 1.33–1.67(4H, m), 1.67–2.00(4H, m), 2.53–3.15 (8H, m), 2.96(3H, s), 3.24(2H, q, J=6.2Hz), 3.50–5.30(2H, brs), 3.71(2H, d, J=5.8Hz), 3.97 (2H, t, J=6.2Hz), 4.36(1H, m), 6.11(1H, t, J=5.8Hz), 6.88(1H, brs), 6.90(2H, d, J=8.7Hz), 6.99–7.29(4H, m), 7.41(2H, d, J=8.7Hz) |
| 380 | 1.41–2.10(8H, m), 2.53–3.30(8H, m), 3.47(2H, q, J=6.2Hz), 3.70–5.20(2H, brs), 3.97(2H, t, J=6.2Hz), 4.34(1H, m), 6.87(1H, d, J=8.7Hz), 6.99–7.29(5H, m), 7.39(2H, d, J=8.7Hz), 7.96(2H, dd, J=6.9, 2.0Hz), 8.22(2H, dd, J=6.9, 2.0Hz) |
| 381 | 1.41–1.73(4H, m), 1.73–2.02(4H, m), 2.53–32.0 (8H, m), 3.43(2H, q, J=6.4Hz), 3.70–5.20(2H, br), 3.97(2H, t, J=6.2Hz), 4.36(1H, m), 6.40 (1H, brs), 6.62(2H, d, J=8.5Hz), 6.87(2H, d, J=8.5Hz), 6.99–7.28(4H, m), 7.40(2H, d, J=8.5Hz), 7.60(2H, d, J=8.5Hz) |
| 382 | 1.30–1.63(4H, m), 1.63–2.05(4H, m), 2.55–3.30 (8H, m), 3.00(2H, q, J=6.2Hz), 3.70–5.20(2H, brs), 3.90(2H, t, J=6.2Hz), 4.37(1H, m), 5.50 (1H, t, J=6.2Hz), 6.86(2H, d, J=8.7Hz), 7.00–7.29(4H, m), 7.41(2H, d, J=8.7Hz), 8.04(2H, dd, J=6.9, 2.0Hz), 8.33(2H, dd, J=6.9, 2.0Hz), |
| 383 | 1.40–1.95(8H, m), 2.15(3H, s), 2.554–3.20(8H, m), 3.44(2H, q, J=6.1Hz), 3.70–5.20(2H, brs), 3.95 (2H, t, J=6.1Hz), 4.33(1H, m), 6.76(1H, brs), 6.83(2H, d, J=8.7Hz), 7.00–7.30(4H, m), 7.34 (2H, d, J=8.7Hz), 7.53(2H, d, J=8.7Hz), 7.68 (2H, d, J=8.7Hz), 8.73(1H, brs) |
| 384 | 1.40–1.95(8H, m), 2.54–3.11(8H, m), 3.01(6H, s), 3.46(2H, q, J=6.5Hz), 3.80–5.30(2H, brs), 3.98(2H, t, J=6.3Hz), 4.39(1H, m), 6.14(1H, brs), 6.65(2H, dd, J=6.9, 2.1Hz), 6.99(2H, d, J=8.8Hz), 6.99–7.28(4H, m), 7.42(2H, d, J=8.8Hz), 7.67(2H, dd, J=6.9, 2.1Hz) |
| 385 | 1.26–1.61(4H, m), 1.61–2.00(4H, m), 2.54–3.30 (8H, m), 2.91(2H, q, J=6.0Hz), 3.70–5.20(2H, brs), 3.90(2H, t, J=6.2Hz), 4.34(1H, m), 4.91 (1H, brs), 6.60(2H, d, J=8.6Hz), 6.85(2H, d, J=8.6Hz, 6.99–7.29(4H, m), 7.40(2H, d, J=8.6Hz), 7.58(2H, d, J=8.6Hz) |
| 386 | 1.48–1.74(4H, m), 1.74–2.02(4H, m), 2.23(3H, s), 2.28(3H, s), 2.54–3.30(8H, m), 3.65–5.20(2H, brs), 3.79(2H, t, J=7.4Hz), 4.00(2H, t, J=5.9Hz), 4.35(1H, m), 6.91(2H, d, J=8.7Hz), 7.00–7.30(4H, m), 7.41(2H, d, J=8.7Hz), 7.26(2H, d, J=8.4Hz), 7.65(2H, d, J=8.4Hz), 9.23(1H, s) |
| 387 | 1.33–1.64(4H, m), 1.64–1.93(4H, m), 2.54–31.5 (8H, m), 2.92(2H, q, J=6.5Hz), 3.02(6H, s), |

TABLE 10-continued

| No. | |
|---|---|
| | 3.70–5.20(2H, brs), 3.90(2H, t, J=6.3Hz), 4.38 (1H, m), 4.81(1H, t, J=6.5Hz), 6.66(2H, d, J=9.1Hz), 6.86(2H, d, J=8.7Hz), 6.99–7.28(4H, m), 7.41(2H, d, J=8.7Hz), 7.69(2H, d, J=9.1Hz) |
| 388 | 1.02(6H, t, J=7.1Hz), 1.34–1.93(8H, m), 2.37–3.12(10H, m), 2.52(4H, q, J=7.1Hz), 3.86–5.08 (3H, m), 3.98(2H, t, J=6.5Hz), 7.83–7.49(8H, m) |
| 389 | 1.42–1.96(12H, m), 2.35–3.15(14H, m), 3.78–5.13 (3H, m), 3.98(2H, t, J=6.4Hz), 6.82–7.50(8H, m) |
| 390 | 1.35–1.93(8H, m), 2.15–3.15(10H, m), 3.32–3.78 (3H, m), 3.83–5.22(3H, m), 3.97(2H, t, J=6.3Hz), 6.79–7.48(8H, m) |
| 391 | 1.38–1.93(8H, m), 2.43–3.40(12H, m), 3.65–5.15 (4H, m), 3.81(3H, s), 3.84(2H, s), 3.97(2H, t, J=6.2Hz), 6.75–7.48(12H, m) |
| 392 | 1.30–1.96(6H, m), 2.49–3.62(16H, m), 3.68–5.05 (4H, m), 3.98(2H, t, J=6.2Hz), 6.78–7.52(8H, m), 7.62(1H, dt, J=7.7, 1.8Hz), 8.43–8.59(1H, m) |
| 393 | 1.18–1.95(14H, m), 2.13–3.10(16H, m), 3.56–5.14 (4H, m), 3.99(2H, t, J=6.3Hz), 6.83–7.48(13H, m), |
| 394 | 1.60–1.93(6H, m), 2.27–3.14(18H, m), 3.02(2H, d, J=6.6Hz), 3.75–5.05(3H, m), 4.00(2H, t, J=6.2Hz), 5.12–5.26(2H, m), 5.78–5.98(1H, m), 6.81–7.47(8H, m) |
| 395 | 1.32–2.03(8H, m), 2.33(3H, s), 2.28–3.13(15H, m), 3.52–5.15(4H, m), 3.98(2H, t, J=6.3Hz), 6.83–7.48(10H, m), 7.60(1H, dt, J=7.6, 1.8Hz), 8.50–8.57(1H, m) |
| 396 | 1.06(3H, t, J=6.7Hz), 1.20–1.96(8H, m), 2.28–3.15(12H, m), 3.22–5.08(5H, m), 3.46(1H, d, J=14.4Hz), 3.83(1H, d, J=14.4Hz), 3.99(2H, t, J=6.7Hz), 6.83–7.52(10H, m), 8.52–8.62(1H, m) |
| 397 | 1.25–1.62(8H, m), 1.65–1.93(8H, m), 2.36–3.13 (14H, m), 3.80–5.05(3H, m), 3.97(2H, t, J=6.5Hz), 6.83–7.49(8H, m) |
| 398 | 1.09(6H, t, J=7.2Hz), 1.22–1.93(12H, m), 2.4–3.12(10H, m), 2.63(4H, q, J=7.2Hz), 3.12–5.11 (3H, m), 3.98(2H, t, J=6.6Hz), 6.84–7.48(8H, m) |
| 399 | 1.63–2.03(10H, m), 2.48–3.13(14H, m), 3.82–5.03 (3H, m), 4.01(2H, t, J=5.9Hz), 6.81–7.49(8H, m) |
| 400 | 1.05(6H, t, J=7.2Hz), 1.57–1.90(6H, m), 2.42–3.15(14H, m), 3.83–5.04(3H, m), 4.01(2H, t, J=6.4Hz), 6.83–7.48(8H, m) |
| 401 | 1.25–1.93(10H, m), 2.36(3H, s), 2.43–3.12(17H, m), 3.82–5.16(3H, m), 3.97(2H, t, J=6.4Hz), 6.85–7.48(10H, m), 7.60(1H, dt, J=7.6, 1.9Hz), 8.49–8.55(1H, m) |
| 402 | 1.35–3.35(26H, m), 3.62–4.42(5H, m), 3.99(2H, t, J=6.6Hz), 5.57(1H, brs), 6.83–7.47(8H, m), |
| 403 | 1.42–2.08(12H, m), 2.43–3.44(15H, m), 3.82–5.04 (4H, m), 3.99(2H, t, J=6.2Hz), 6.83–7.49(8H, m) |
| 404 | 1.32–1.93(8H, m), 2.25(2H, brs), 2.50–3.13(10H, m), 3.80–5.00(4H, m), 3.93(2H, s), 3.97(2H, t, J=6.5Hz), 6.82–7.48(10H, m), 7.65(1H, dt, J=7.6, 1.8Hz), 8.51–8.59(1H, m) |
| 405 | 1.32–1.92(10H, m), 2.48–3.17(10H, m), 3.72–5.18 (4H, m), 3.82(2H, s), 3.97(2H, t, J=6.4Hz), 6.83–7.49(9H, m), 7.65–7.75(1H, m), 8.50(1H, dd, J=4.8, 1.6Hz), 8.56(1H, d, J=1.8Hz) |
| 406 | 1.13–1.92(14H, m), 2.18–3.12(14H, m), 3.47(1H, dd, J=10.7, 4.1Hz), 3.75(1H, dd, J=10.7, 3.8Hz), 3.81–5.08(3H, m), 3.98(2H, t, J=6.4Hz), 6.83–7.48(8H, m) |
| 407 | 1.40–2.03(12H, m), 2.25–3.15(13H, m), 3.20–3.31 (1H, m), 3.45(1H, dd, J=11.0. 3.0Hz), 3.67(1H, dd, J=11.0, 3.6Hz), 3.75–5.13(3H, m), 3.99(2H, t, J=6.3Hz), 6.83–7.50(8H, m) |
| 408 | 1.07–1.93(13H, m), 1.96–3.13(15H, m), 3.53(1H, dd, J=10.5, 5.8Hz), 3.66(1H, dd, J=10.5, 5.0Hz), 3.74–5.13(3H, m), 3.98(2H, t, J=6.4Hz), 6.83–7.47(8H, m) |
| 409 | 1.42–1.93(8H, m), 2.12–3.14(17H, m), 3.83–5.14 (4H, m), 3.99(2H, t, J=6.4Hz), 6.83–6.96(2H, m), 6.96–7.32(4H, m), 7.33–7.48(2H, m) |
| | NMR (DMSO-d6) δ value |
| 410 | 1.33–1.97(15H, m), 2.38–3.28(14H, m), 3.48(2H, t, J=6.3Hz), 3.90–4.83(3H, m), 4.07(2H, t, J=6.2Hz), 6.95–7.49(8H, m), 10.30(1H, brs) |
| | NMR (CDCl3) δ value |

| No. | |
|---|---|
| 411 | 1.40–1.66(4H, m), 1.68–2.22(8H, m), 2.26–3.28 (13H, m), 3.72(3H, s), 3.78–5.10(3H, m), 3.97 (2H, t, J=6.4Hz), 6.83–7.48(8H, m) |
| | NMR (DMSO-d6) δ value |
| 412 | 1.30–2.13(16H, m), 2.33–3.60(16H, m), 3.62–4.93 (3J. ,), 4.02(2H, t, J=6.2Hz), 6.87–7.05(3H, m), 7.18–7.42(5H, m), 10.03(1H, brs) |
| | NMR (CDCl3) δ value |
| 413 | 1.43–1.93(8H, m), 2.35–3.12(14H, m), 3.67–5.24 (3H, m), 3.84(4H, t, J=5.3Hz), 4.00(2H, t, J=6.4Hz), 6.47(1H, t, J=4.7Hz), 6.84–7.50(8H, m), 8.30(2H, d, J=4.7Hz) |
| 412 | 1.40–1.06(8H, m), 2.34–3.13(14H, m), 3.55(4H, t, J=4.8Hz), 3.75–5.21(3H, m), 4.00(2H, t, J=6.4Hz, 6.55–6.67(2H, m), 6.85–7.53(9H, m), 8.12–8.22(1H, m) |
| 415 | 1.40(8H, m), 2.28(3H, s), 2.41–3.12(13H, m), 3.61(2H, t, J=5.5Hz). 3.75–5.25(3H, m), 3.99 (2H, t, J=6.4Hz), 6.85–7.49(8H, m) |
| 416 | 1.37–2.04(12H, m), 2.22–3.16(13H, m), 3.18–3.34 (1H, m), 3.45(1H, dd, J=11.0, 2.8Hz), 3.67(1H, dd, J=11.0, 3.5Hz), 3.85–5.23(2H, m), 3.99(2H, t, J=6.3Hz), 6.83–7.50(8H, m) |
| 417 | 1.38–1.93(8H, m), 2.28–3.13(16H, m), 3.63(4H, t, J=5.4Hz), 3.77–5.08(3H, m), 3.99(2H, t, J=6.3Hz), 6.85–7.50(8H, m) |
| 418 | 1.38(6H, dt, J=7.1, 2.5Hz), 1.42–1.98(8H, m), 2.49–3.14(8H, m), 3.22–3.41(1H, m), 3.27(3H, s), 3.39(3H, s), 3.48–5.13(9H, m), 4.04(2H, t, J=6.2Hz), 6.83–7.47(8H, m) |
| 419 | 1.38–1.95(8H, m), 2.27(3H, s), 2.36–3.19(14H, m), 3.78–5.06(3H, m), 3.99(2H, t, J=6.4Hz), 6.85–6.95(2H, m), 6.97–7.32(4H, m), 7.37–7.48 (2H, m) |
| 420 | 1.32–1.97(14H, m), 1.12–3.12(15H, m), 3.58–5.06 (4H, m), 3.99(2H, t, J=6.4Hz), 6.83–7.54(8H, m) |
| 421 | 1.51–2.00(8H, m), 2.47–3.28(8H, m), 3.18(2H, t, J=6.8Hz), 3.79–5.15(3H, m), 4.00(2H, t, J=6.1Hz), 66.78–3.37(7H, m), 7.42(2H, d, J=8.7Hz), 8.50(2H, d, J=4.8Hz) |
| 422 | 1.45–2.17(8H, m), 2.44–3.24(10H, m), 3.61(3H, s), 3.80–5.12(3H, m), 3.97(2H, t, J=6.3Hz), 6.80–7.38(8H, m), 7.42(2H, d, J=8.7Hz) |
| 423 | 1.52–2.04(8H, m), 2.49–3.15(8H, m), 3.38–3.57 (2H, m), 3.75–5.12(8H, m), 6.88(2H, d, J=8.7Hz), 6.93–7.36(6H, m), 7.42(2H, d, J=8.7Hz) |
| 424 | 1.47–2.20(8H, m), 2.48–3.33(10H, m), 3.75–5.14 (5H, m), 6.87(2H, d, J=8.7Hz), 6.93–7.54(7H, m), 8.88(2H, d, J=4.9Hz) |
| 425 | 1.52–2.13(8H, m), 2.49–3.14(8H, m), 3.47–3.68 (2H, m), 3.85–5.11(3H, m), 3.99(2H, t, J=6.1Hz), 6.87(2H, d, J=8.8Hz), 6.93–7.38(4H, m), 7.42 (2H, d, J=8.8Hz), 7.57(1H, d, J=4.9Hz), 8.95 (1H, d, J=4.9Hz) |
| 426 | 1.09–2.02(10H, m), 2.42–5.21(29H, m), 6.89(2H, d, J=8.7Hz), 6.94–7.36(4H, m), 7.40(2H, d, J=8.7Hz), |
| 427 | 1.38(9H, t, J=7.1Hz), 1.48–2.19(8H, m), 2.49–3.16(8H, m), 3.27–3.45(2H, m), 3.50(6H, q, J=7.1Hz), 3.80–5.11(3H, m), 4.03(2H, t, J=4.7Hz), 6.90(2H, d, J=8.6Hz), 6.97–3.38(4H, m), 7.41 (2H, d, J=8.6Hz) |
| 428 | 1.34–3.39(25H, m), 3.77–5.12(3H, m), 3.97(2H, t, J=6.3Hz), 5.57–5.92(3H, m), 6.88(2H, d, J=8.8Hz), 6.94–7.36(4H, m), 7.42(2H, d, J=8.8Hz) |
| 429 | 1.351.99(8H, m), 2.42–3.20(8H, m), 3.72–5.15 (3H, m), 3.97(4H, t like, J=6.9Hz), 6.81–7.62 (11H, m) |
| 430 | 1.37–2.14(8H, m), 2.45–3.16(8H, m), 3.71–5.15 (3H, m), 3.98(2H, t, J=6.2Hz), 4.21(2H, t, J=7.0Hz), 6.78–7.52(8H, m), 7.94(1H, s), 8.07(1H, s) |
| 431 | 1.53–2.10)8H, m), 2.48–3.17(10H, m), 3.80–5.12 (3H, m), 4.00(2H, t, J=6Hz), 6.89(2H, d, J=8.8Hz), 6.92–7.55(8H, m), 6.05–8.22(1H, m) |
| 432 | 1.22–1.96(14H, m), 2.46–3.16(8H, m), 3.75–5.18 (3H, m), 3.68(2H, t, J=7.2Hz), 3.96(2H, t, J=6.5Hz), 6.89(2H, d, J=8.7Hz), 6.94–7.36(4H, m), 7.42(2H, d, J=8.8Hz), 7.63–7.92(4H, m) |
| 433 | 1.40–2.02(8H, m), 2.41–3.22(10H, m), 3.50–5.15 (3H, m), 3.76(2H, brs), 3.95(2H, t, J=6.2Hz), 6.48–6.68(2H, m), 6.87Z(2H, d, J=8.8Hz), 6.94– |

TABLE 10-continued

| No. | |
|---|---|
| | 7.37(6H, m), 7.42(2H, d, J=8.8Hz) |
| 434 | 1.44–2.11(8H, m), 2.50–3.32(10H, m), 3.83–5.10 (3H, m), 3.96(2H, t, J=5.8Hz), 6.85(2H, d, J=8.7Hz), 6.90–7.38((4H, m), 7.41(2H, d, J=8.7Hz), 8.05–8.21(2H, m), 8.36–8.52(2H, m) |
| 435 | 1.41–2.12(8H, m), 2.45–3.41(8H, m), 3.20(2H, t, J=6.9Hz), 3.70–5.11(3H, m), 3.99(3H, t, J=6.3Hz), 6.75–7.17(11H, m), 8.37–8.52(2H, m) |
| 436 | 1.51–2.05(8H, m), 2.37–3.22(10H, m), 3.76–5.14 (3H, m), 4.00(2H, t, J=6.1Hz), 6.89(2H, d, J=8.7Hz), 6.95–7.38(6H, m), 7.43(2H, d, J=8.7Hz), 8.30–8.49(2H, m) |
| 437 | 1.41–1.92(8H, m), 2.47–3.19(10H, m), 3.70–5.10 (5H, m), 3.93(2H, t, J=6Hz), 6.56–7.70(12H, m) |
| 438 | 1.46–2.02(8H, m), 2.43–3.19(8H, m), 3.31–3.56 (2H, m), 3.70–5.11(3H, m). 3.96(2H, t, J=5.9Hz), 6.75–7.51(8H, m), 7.56(1H, ddd, J=1.3, 4.7, 7.6Hz), 7.89–8.18(2H, m), 8.68–8.81(1H, m) |
| 439 | 1.48–1.97(8H, m), 2.47–3.30(10H, m), 3.78–5.12 (5H, m), 6.87(2H, d, J=8.7Hz), 6.94–7.36(4H, m), 7.43(2H, d, J=8.7Hz), 7.68–7.88(2H, m), 8.23–8.39(2H, m) |
| 440 | 1.41–2.01(8H, m), 2.25(3H, s,), 2.48–3.16(10H, m), 3.71–5.18(3H, m), 3.90(2H, d, J=5.5Hz), 6.78 (2H, d, J=8.7Hz), 6.98–7.54(8H, m), 7.63(2H, d, J=8.7Hz), 9.03(1H, brs) |
| 441 | 1.15–2.16(16H, m), 2.44–3.13(10H, m), 3.75–5.20 (3H, m), 3.98(2H, t, J=6.5Hz), 6.90(2H, d, J=8.7Hz), 6.94–7.37(4H, m), 7.42(2H, d, J=8.7Hz) |
| 442 | 1.22–5.20(34H, m), 5.92–6.19(1H, m), 6.90(2H, d, J=8.5Hz), 6.95–7.34(4H, m), 7.42(2H, d, J=8.5Hz), |
| 443 | 1.42–1.96(8H, m), 2.50–3.19(10H, m), 3.06(6H, s), 3.74–5.11(3H, m), 3.94(2H, t, J=6.2Hz), 6.69 (2H, d, J=9.1Hz), 6.85(2H, d, J=8.8Hz), 6.92–7.34(4H, m), 7.40(2H, d, J=8.8Hz), 7.69(2H, d, J=9.1Hz) |
| 444 | 1.20–2.02(14H, m), 1.97(3H, m), 2.48–3.32(10H, m), 3.77–5.15(3H, m), 3.98(2H, t, J=6.4Hz), 5.61 (1H, brs), 6.90(2H, d, J=8.7Hz), 6.98–7.38(4H, m), 7.42(2H, d, J=8.7Hz) |
| 445 | 1.29–3.40(25H, m), 2.03(3H, s), 2.07(3H, s), 3.81–5.15(7H, m), 5.76(brs), 6.89(2H, d, J=8.4Hz), 6.96–7.51(6H, m) |
| 446 | 1.62–1.94(2H, m), 1.99(3H, s), 2.01(2H, m), 2.46–3.20(8H, m), 3.45(2H, q, J=6.3Hz), 3.70–5.20(2H, brs), 4.05(2H, t, J=5.9Hz)m 4.34(1H, m), 6.00(1H, brs), 6.60(1H, d, J=8.1Hz), 6.67 (1H, d, J=8.1Hz), 6.89(2H, d, J=8.7Hz), 7.10 (1H, t, J=8.1Hz), 7.42(2H, d, J=8.7Hz) |
| 447 | 1.42(3H, t, J=7.0Hz), 1.57–1.75(1H, m), 1.75–1.93(1H, m), 2.40–3.24(8H, m), 3.56–3.92(4H, m), 4.40(2H, q, J=7.0Hz), 4.19–4.66(1H, m), 4.80–5.04(1H, m), 6.37–6.67(1H, m), 6.48(1H, d, J=8.1Hz), 6.60–6.78(1H, m), 6.61(1H, d, J=8.1Hz), 7.01(1H, t, J=8.1Hz), 7.10–7.46(1H, m), 8.36 (1H, brs) |
| 448 | 1.42(3H, t, J=7.0Hz), 1.57–1.75(1H, m), 1.75–1.94(1H, m), 2.35–3.20(8H, m), 3.57–3.73(1H, m), 3.73–3.92(3H, m), 3.84(3H, s), 4.04(2H, q, J=7.0Hz), 4.25–4.75(1H, m), 4.86–5.04(1H, m), 6.43–6.57(1H, m), 6.50(1H, d, J=8.2Hz), 6.64(1H, d, J=8.2Hz), 6.68–6.91(1H, m), 7.12–7.33(1H, m), 7.18(1H, t, J=8.2Hz) |
| 449 | 1.42(3H, t, J=6.9Hz), 1.66–1.91(2H, m), 1.91–2.13(2H, m), 1.97(3H, s), 2.47–3.20(8H, m), 3.42 (2H, q, J=6.3Hz), 3.80–5.20(2H, brs), 4.03(2H, t, J=6.9Hz), 4.05(2H, q, J=6.9Hz), 4.35(1H, m), 6.37(1H, brs), 6.64(1H, d, J=8.2Hz), 6.74(1H, d, J=8.2Hz), 6.89(2H, d, J=8.7Hz), 7.17(1H, t, J=8.2Hz), 7.42(2H, d, J=8.7Hz) |
| 450 | 1.42(6H, t, J=7.0Hz), 1.55–1.76(1H, m), 1.76–1.93(1H, m), 2.35–3.22(8H, m), 3.50–3.75(1H, m), 3.75–3.94(3H, m), 4.40(4H, q, J=7.0Hz), 4.26–4.72(1H, m), 4.82–5.05(1H, m), 6.49–6.58(1H, m), 6.51(1H, d, J=8.2Hz), 6.63(1H, d, J=8.2Hz), 6.68–6.92(1H, m), 7.15(1H, t, J=8.2Hz), 7.20–7.35(1H, m) |
| 451 | 1.42(3H, t, J=7.0Hz), 1.55–1.75(1H, m), 1.75–1.98(1H, m), 2.33(3H, s), 2.41–3.23(8H, m), 3.53–3.96(4H, m), 4.05(2H, q, J=7.9Hz), 4.18–4.68(1H, m), 4.86–5.08(1H, m), 6.46–6.60(1H, m), |

TABLE 10-continued

| No. | |
|---|---|
| | 6.49(1H, d, J=8.0Hz), 6.81(1H, d, J=8.0Hz), 6.94–7.32(2H, m), 7.24(1H, t, J=8.0Hz) |
| 452 | 1.55–1.88(2H, m), 1.88–2.10(2H, m), 1.97(3H, s), 2.47–3.20(8H, m), 3.42(2H, q, J=6.3Hz), 3.60–5.20(2H, brs) 3.84(3H, s), 4.03(2H, t, J=6.0Hz), 4.34(1H, m), 6.30(1H, brs), 6.65(1H, d, J=8.3Hz), 6.75(1H, d, J=8.3Hz), 6.89(2H, d, J=8.7Hz), 7.20(1H, t, J=8.3Hz), 7.41(2H, d, J=8.7Hz) |
| 453 | 1.67–1.93(2H, m), 1.93–2.11(2H, m), 1.98(3H, s), 2.33(3H, s), 2.50–3.15(8H, m), 3.43(2H, q, J=6.4Hz), 3.80–5.20(2H, br), 4.04(2H, t, J=5.9Hz), 4.33(1H, m), 6.13(1H, brs), 6.82(1H, d, J=8.1Hz), 6.90(2H, d, J=8.7Hz), 7.01(1H, d, J=8.1Hz), 7.26(1H, t, J=8.1Hz(, 7.42(2H, d, J=8.7Hz) |
| 454 | 1.60–1.90(3H, m), 2.40–2.95(8H, m), 3.10–3.36 (2H, m), 4.23–4.48(1H, m), 6.70–7.22(3H, m) |
| 455 | 1.55–1.93(2H, m), 2.35–3.27(8H, m), 3.58–4.00 (7H, m), 4.25–4.48(1H, m), 4.86–5.07(1H, m), 6.44–6.60(2H, m), 6.73–7.37(4H, m) |
| 456 | 1.42(3H, t, J=7.0Hz), 1.55–1.90(2H, m), 2.35–3.20(8H, m), 3.60–3.93(4H, m), 4.01(2H, q, J=7.0Hz), 4.25–4.70(1H, m), 4.85–5.05(1H, m), 6.40–6.59(2H, m), 6.72–7.35(4H, m) |
| 457 | 1.70–2.12(4H, m), 1.95(3H, s), 2.31(3H, s), 2.42–3.15(8H, m), 3.35–3.50(2H, m), 3.80–5.10 (5H, m), 6.17(1H, brs), 6.80–7.20(5H, m), 7.42 (2H, d, J=8.5Hz) |
| 458 | 1.40–2.05(10H, m), 2.31(3H, s), 2.42–3.20(8H, m), 3.43(2H, t, J=6.7Hz), 3.70–5.05(5H, m), 6.80–7.22(5H, m), 7.42(2H, d, J=8.7Hz) |
| 459 | 1.03(6H, t, J=7.1Hz), 1.22–2.00(10H, m), 2.31 (3H, s), 2.40–3.23(14H, m), 3.80–5.21(5H, m), 6.85–7.20(5H, m), 7.42(2H, d, J=8.7Hz) |
| 460 | 1.30–2.15(14H, m), 2.31(3H, s), 2.38–3.20(14H, m), 3.80–5.05(5H, m), 6.80–7.22(5H, m), 7.42(2H, d, J=8.7Hz) |
| 461 | 1.42–1.96(8H, m), 2.42–3.13(12H, m), 3.30(2H, d, J=6.1Hz), 3.98(2H, t, J=6.3Hz) 3.80–4.97(3H, m), 4.98–5.28(2H, m), 5.83–6.04(1H, m), 6.82–7.48 (8H, m) |
| 462 | 1.34–1.95((h, m), 2.45–3.15(12H, m), 3.57(2H, t J=5.4Hz), 3.63(2H, s), 3.95(2H, t, J=6.3Hz), 3.78–5.14(3H, m), 6.84–7.50(13H, m) |
| 463 | 1.07(3H, d, J=6.3Hz), 1.24–1.93(14H, m), 2.07–2.48(1H, m), 2.53–3.13(10H, m), 3.98(2H, t, J=6.4Hz), 3.82–5.10(3H, m), 6.84–7.50(8H, m) |
| 464 | 0.76–0.95(1H, m), 0.87(3H, d, J=6.1Hz), 1.38–1.93(14H, m), 2.27–2.41(2H, m), 2.52–3.12(10H, m), 3.98(2H, t, J=6.4Hz), 3.83–5.07(3H, m), 6.83–7.49(8H, m) |
| 465 | 0.92(3H, d, J=5.8Hz), 1.14–2.02(15H, m), 2.26–2.42(2H, m), 2.52–3.13(10H, m), 3.98(2H, t, J=6.4Hz), 3.86–5.06(3H, m), 6.83–7.52(8H, m) |
| 466 | 1.43–1.93(8H, m), 2.52–3.13(14H, m), 3.69(2H, t, J=5.3Hz), 3.99(2H, t, J=6.3Hz), 3.80–5.05(3H, m), 6.83–7.49(8H, m) |
| 467 | 1.04(6H, t, J=7.2Hz), 1.33–2.05(8H, m), 2.30–3.22(14H, m), 3.54–3.75(1H, m), 3.93–4.20(2H, m), 4.30–4.42(1H, m), 4.93–5.07(1H, m), 6.83–7.42 (8H, m) |
| 468 | 1.36–1.92(8H, m), 2.28(6H, s), 2.42–3.13(14H, m), 3.60(2H, s), 3.72–5.07(3H, m), 3.96(2H, t, J=6.4Hz), 6.85–7.48(13H, m) |
| 469 | 1.45–1.98(14H, m), 2.49–31.4(14H, m), 3.82–5.13 (3H, m), 3.99(2H, t, J=6.2Hz), 6.82–7.49(8H, m) |
| 470 | 1.38–1.94(8H, m), 2.22(2H, m), 2.28–2.44(2H, m), 2.49–3.10(8H, m), 3.00(2H, d, J=6.5Hz), 3.88–4.96(3H, m), 3.98(2H, t, J=6.4Hz), 5.08–5.24 (2H, m), 5.87(1H, ddt, J=17.1, 10.2, 6.5Hz), 6.83–7.49(8H, m) |
| 471 | 1.40–1.92(8H, m), 2.05, 2.07, 2.12, 2.14(total: 6H, s), 2.52–3.14(8H, m), 3.28–3.43(2H, m), 3.55 2H, dt, J=8.5, 5.9Hz), 3.99(2H, dt, J=6.1, 6.1Hz), 4.20(2H, dt, J=6.0, 6.0Hz). 3.84–4.98(3H, m), 6.85–7.50(8H, m) |
| 472 | 1.38–1.93(8H, m), 2.07(3H, s), 2.31(3H, s), 2.37–3.13(12H, m), 3.87–5.04(3H, m), 3.98(2H, t, J=6.4Hz), 4.18(2H, t, J=5.9Hz), 6.84–7.49(8H, m) |
| 473 | 1.37–1.94(8H, m), 2.05(6H, s), 2.49–3.12(10H, |

TABLE 10-continued

| No. | |
|---|---|
| | m), 2.77(4H, t, J=6.2Hz), 3.83–5.50(3H, m), 3.98 (2H, t, J=6.3Hz), 4.12(4H, t, J=6.1Hz), 6.85–7.48(8H, m) |
| 474 | 1.13(6H, d, J=6.3Hz), 1.40–1.93(8H, m), 2.49–3.13(12H, m), 3.84–5.03(3H, m), 3.98(2H, t, J=6.4Hz), 6.84–7.48(8H, m) |
| 475 | 1.44–2.08(8H, m), 2.02–3.30(10H, m), 3.09(3H, s), 3.77–5.02(3H, m), 3.87(2H, d, J=7.1Hz), 4.00 (2H, d, J=6.1Hz), 5.41–5.08(2H, m), 6.03–6.27 (1H, m), 6.83–7.48(8H, m) |
| 476 | 1.00(6H, t, J=7.1Hz), 1.41–1.93(8H, m), 2.05 (3H, s), 2.32–3.13(14H, m), 3.86–5.05(3H, m), 3.98(2H, t, J=6.3Hz), 4.90–5.03(1H, m), 6.85–7.48(8H, m) |
| 477 | 1.38–1.93(12H, m), 2.37–3.13(14H, m), 3.87–5.05 (3H, m), 4.01(2H, t, J=6.4Hz), 6.83–7.49(8H, m) |
| 478 | 1.28–1.93(16M, m), 2.32–3.11(14H, m), 3.83–5.07 (3H, m), 3.97(2H, t, J=6.4Hz), 6.85–7.51(8H, m) |
| 479 | 1.43–1.96(8H, m), 2.26(6H, s), 2.26–2.42(2H, m), 2.53–3.07(8H, m), 3.91–5.04(3H, m), 3.99(2H, t, J=6.4Hz), 6.86–7.47(8H, m) |
| 480 | 1.30–1.92(10H, m), 2.30(6H, s), 2.27–2.43(2H, m), 2.53–33.12(8H, m), 3.87–4.87(3H, m), 3.98(2H, t, J=6.4Hz), 6.85–7.48(8H, m) |
| 481 | 1.55–2.16(7H, m), 2.37–5.27(17H, m), 6.38(7.59 (13H, m) |
| 482 | 1.26(3H, t, J=7.2Hz), 1.52–2.01(6H, m), 2.32–3.33(10H, m), 3.53–5.10(8H, m), 4.14(2H, q, J=7.2Hz), 6.40–6.58(2H, m), 6.96–7.33(5H, m) |
| 483 | 1.58–3.32(16H, m), 3.56–5.12(8H, m), 5.52–6.00 (2H, m), 6.48–6.60(2H, m), 6.95–7.48(5H, m) |
| 484 | 1.35–5.15(49H, m), 6.36–6.60(2H, m), 6/92–7.38 (5H, m) |
| 485 | 1.27–4.61(52H, m), 4.78–5.06(1H, m), 6.34–6.60 (2H, m), 6.93–7.40(5H, m) |
| | NMR(DMSO-d$_6$) δ value |
| 486 | 1.24(12H, t, J=7.2Hz), 1.31–2.12(14H, m), 2.25–4.43(26H, m), 4.55–4.79(1H, m), 6.48–6.72(2H, m), 6.94–7.43(5H, m)m 10.49–10.97(2H, m) |
| | NMR (CDCl$_3$) δ value |
| 487 | 1.51–2.02(6H, m), 2.18–4.13(27H, m), 4.28–4.72 (1H, m), 4.88–5.08(1H, m), 6.37–6.59(2H, m), 6.92–7.38(5H, m) |
| 488 | 1.53–1.99(6H, m), 2.30–3.24(14H, m), 3.55–4.12 (10H, m), 4.22–4.75(1H, m), 4.86–5.08(1H, m), 6.39–6.58(2H, m), 6.92–7.38(5H, m) |
| 489 | 1.51–2.10(6H, m), 2.12–3.29(14H, m), 3.52–4.68 (11H, m), 4.77–5.07(1H, m). 6.35–6.62(2H, m), 6.92–7.48(5H, m) |
| 490 | 1.55–2.00(6H, m), 2.34–3.25(14H, m), 3.53–4.72 (11H, m), 4.81–5.07(1H, m), 6.39–6.58(2H, m), 6.92–7.37(5H, m) |
| 491 | 1.49–2.08(8H, m), 2.48–3.13(8H, m), 3.44(2H, t, J=6.7Hz), 3.76–5.08(3H, m), 4.00(2H, t, J=6.3Hz), 6.83–7.48(8H, m) |
| 492 | 1.42–1.63(4H, m), 1.68–2.06(6H, m), 2.48–3.18 (8H, m), 3.43(2H, t, J=6.7Hz), 3.86–5.13(3H, m), 3.99(2H, t, J=6.3Hz), 6.84–7.52(8H, m) |
| 493 | 0.98–2.02(18H, m), 2.23–3.13(12H, m), 3.85–4.97 (3H, m), 3.98(2H, t, J=6.4Hz), 6.83–7.47(8H, m) |
| 494 | 1.42–1.95(9H, m), 2.22(1H, t, J=2.4Hz), 2.48–3.13(10H, m), 3.43(2H, d, J=2.4Hz), 3.84–5.13 (3H, m), 3.99(2H, t, J=6.4Hz), 6.84–7.51(8H, m) |

Using the suitable starting materials, the following compounds are obtained in the same manner as in Examples 1, 384, 390–393, 398, 399, 407–409, 426 and 593.

TABLE 11

(R$^1$)$_q$ — [carbostyril ring structure] — N—R, =O

Example 779

TABLE 11-continued (R$^1$)$_q$ — [carbostyril ring structure] — N—R, =O

Structure

R: —[piperidine]—N—C(=O)—[phenyl]—O(CH$_2$)$_5$NHC(CH$_3$)$_3$

R$^1$: H, q: 1
Bond between 3- and 4-positions in the carbostyril ring: Single bond
NMR analysis: 495)
Form: Free Example 780
Structure R: —[piperidine]—N—C(=O)—[phenyl]—O(CH$_2$)$_5$NHCH$_2$CH(CH$_3$)$_2$ R$^1$: H, q: 1
Bond between 3- and 4-positions in the carbostyril ring: Single bond
NMR analysis: 496)
Form: Free Example 781
Structure R: —[piperidine]—N—C(=O)—[phenyl]—O(CH$_2$)$_5$NHCH$_2$C(CH$_3$)$_3$ R$^1$: H, q: 1
Bond between 3- and 4-positions in the carbostyril ring: Single bond
NMR analysis: 497)
Form: Free Example 782
Structure R: —[piperidine]—N—C(=O)—[phenyl]—O(CH$_2$)$_5$NHCH$_2$C(CH$_3$)=CH$_2$ R$^1$: H, q: 1
Bond between 3- and 4-positions in the carbostyril ring: Single bond
NMR analysis: 498)
Form: Free Example 783
Structure R: —[piperidine]—N—C(=O)—[phenyl]—O(CH$_2$)$_5$NH—[cyclopropyl]

R$^1$: H, q: 1
Bond between 3- and 4-positions in the carbostyril ring: Single bond
NMR analysis: 499)
Form: Free Example 784
Structure R: —[piperidine]—N—C(=O)—[phenyl]—O(CH$_2$)$_5$NH(CH$_2$)$_2$C(CH$_3$)$_3$ R$^1$: H, q: 1
Bond between 3- and 4-positions in the carbostyril ring: Single bond TABLE 11-continued

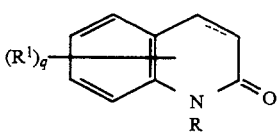

NMR analysis: 500)
Form: Free

Example 785

Structure

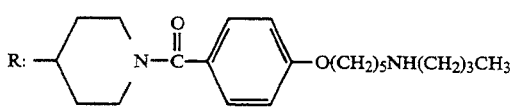

R¹: H, q: 1
Bond between 3- and 4-positions in the carbostyril ring:
Single bond
NMR analysis: 501)
Form: Free Example 786

Structure

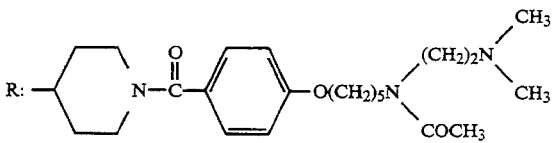

R¹: H, q: 1
Bond between 3- and 4-positions in the carbostyril ring:
Single bond
NMR analysis: 502)
Form: Free Example 787

Structure

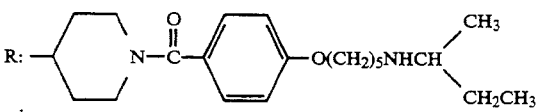

R¹: H, q: 1
Bond between 3- and 4-positions in the carbostyril ring:
Single bond
NMR analysis: 503)
Form: Free Using the suitable starting materials, the following compound is obtained in the same manners as in Examples 1, 384, 390–393, 398, 399, 407–409, 421 and 593.

TABLE 12

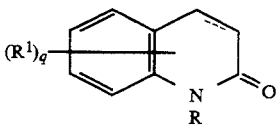

Example 788

Structure

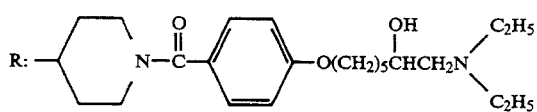

R¹: H, q: 1
Bond between 3- and 4-positions in the carbostyril ring:
Single bond
NMR analysis: 504)
Form: Free

TABLE 13

| No. | NMR (CDCl$_3$) δ value |
|---|---|
| 495 | 1.66(9H, s), 1.42–1.93(8H, m). 2.51–3.22(11H, m), 3.83–5.15(3H, m), 3.98(2H, t, J=6.4Hz), 6.83–7.48(8H, m) |
| 496 | 0.93(6H, d, J=6.6Hz), 1.42–1.94(9H, m), 2.33–3.14(11H, m), 2.46(2H, d, J=6.9Hz), 3.83–5.18 (3H, m), 3.98(2H, t, J=6.4Hz), 6.85–7.48(8H, m) |
| 497 | 0.93(9H, s), 1.43–2.01(9H, m), 2.37(2H, s), 2.50–3.13(10H, m), 3.82–5.03(3H, m), 3.99(2H, t, J=6.4Hz), 6.86–6.94(2H, m), 6.98–7.30(4H, m), 7.38–7.47(2H, m) |
| 498 | 1.43–1.96(9H, m), 1.75(2H, s), 2.52–3.13(10H, m), 3.19(2H, s), 3.88–5.05(3H, m), 3.99(2H, t, J=6.4Hz), 4.85(2H, d, J=6.5Hz), 6.85–7.52(8H, m) |
| 499 | 0.28–0.51(4H, m), 1.41–1.94(9H, m), 2.06–2.21 (1H, m), 2.51–3.17(10H, m), 3.82–5.08(3H, m), 3.98(2H, t, J=6.4Hz), 6.86–7.51(8H, m) |
| 500 | 0.91(9H, s), 1.34–1.94(10H, m), 2.11(1H, brs), 2.49–3.12(12H, m), 3.84–5.03(3H, m), 3.98(2H, t, J=3.4Hz), 6.83–7.48(8H, m) |
| 501 | 0.91(3H, t, J=7.2Hz), 1.24–1.93(12H, m), 2.13 (1H, brs), 2.44–3.15(12H, m), 3.78–5.14(3H, m), 3.98(2H, t, J=6.4Hz), 6.84–7.48(8H, m) |
| 502 | 1.39–1.95(8H, m), 2.11(3H, d, J=1.5Hz), 2.27 (3H, s), 2.33(3H, s), 2.48–3.13(16H, m), 3.26–3.67(4H, m), 3.87–5.10(5H, m), 6.85–7.53(8H, m) |
| 503 | 0.90(3H, t, J=7.4Hz), 1.07(3H, d, J=6.3Hz), 1.20–1.92(10H, m), 2.22(1H, brs), 2.49–3.12(11H, m), 3.85–5.04(3H, m), 3.98(2H, t, J=6.4Hz), 6.83–7.48(8H, m) |
| 504 | 1.02(6H, t, J=7.1Hz), 1.31–1.93(10H, m), 2.16–3.13(15H, m), 3.49–3.67(1H, m), 3.85–4.93(3H, m), 3.98(2H, t, J=6.4Hz), 6.83–7.48(8H, m) |

Reference Example 25

1,3-Cyclohexanedione (10.0 g) is dissolved in toluene (100 ml) with heating and thereto is added 4-amino-1-benzylpiperidine (18.6 ml). The mixture is refluxed for 2 hours by using Dean-Stark apparatus. After cooling, the precipitated crystal is washed with diethyl ether, and recrystallized from toluene to give 1-(1-benzyl-4-piperidinylamino)-1-cyclohexen-3-on (24.2 g) as light yellow prisms, m.p.: 171°–172° C.

Reference Example 26

Acrylic acid (28.9 ml) is added to 1-(1-benzyl-4-piperidinylamino)-1-cyclohexen-3-on (100 g) and the mixture is refluxed with stirring for 6 hours. After cooling, the reaction mixture is dissolved in chloroform containing 10% methanol and purified by silica gel column chromatography (solvent; dichloromethane:-methanol=40:1). The resultant is recrystallized from ethanol/water to give 1-(1-benzyl-4-piperidinyl)-5-oxo-3,4,5,6,7,8-hexahydrocarbostyril (23.98 g) as colorless needles, m.p.: 102°–103° C.

Reference Example 27

1-(1-Benzyl-4-piperidinyl)-5-oxo-3,4,5,6,7,8-hexahydrocarbostyril (10.0 g) is dissolved in chloroform (500 ml) and thereto is added N-bromosuccinimide (5.78 g). The mixture is refluxed with stirring for 2 hours. Thereto are added N-bromosuccinimide (5.00 g) and triethylamine (50 ml) and the mixture is refluxed with stirring for 3 hours. After cooling, the reaction mixture is washed twice with 30% aqueous sodium thiosulfate solution (200 ml) and once with saline solution (500 ml) and then dried with magnesium sulfate. The solvent is evaporated off and the resulting residue is purified by silica gel column chromatography (solvent: dichloromethane:methanol=40:1) and recrystallized from ethanol/water to give 1-(1-benzyl-4-piperidinyl)-5-hydroxy-3,4-dihydrocarbostyril (2.13 g) as colorless needles, m.p.: 183°–184° C.

Reference Example 28

1-(1-Benzyl-4-piperidinyl)-5-hydroxy-3,4-dihydrocarbostyril (500 mg) is dissolved in acetone (20 ml) and thereto are added potassium carbonate (246 mg) and ethyl iodide (0.18 ml). The mixture is refluxed with stirring for 6.5 hours. After the reaction, the insoluble materials are removed by filtration, and the filtrate is concentrated under reduced pressure. Dichloromethane is added to the resulting residue and the mixture is washed with 5% aqueous sodium hydroxide solution and then dried with magnesium sulfate. The solvent is evaporated and the resulting residue is purified by silica gel column chromatography (solvent; dichloromethane:methanol=50:1) to give 1-(1-benzyl-4-piperidinyl)-5-ethoxy-3,4-dihydrocarbostyril (0.27 g).

NMR (CDCl$_3$) δ ppm: 1.41 (3H, t, J=7.0 Hz), 1.58–1.82 (2H, m), 2.03–2.24 (2H, m), 2.47–3.10 (8H, m), 3.54 (2H, s), 4.03 (2H, q, J=7.0 Hz), 4.19–4.36 (1H, m), 6.60 (1H, d, J=8.2 Hz), 6.85 (1H, d, J=8.2 Hz), 7.14 (1H, t, J=8.2 Hz), 7.22–7.37 (5H, m)

Reference Example 29

Using the suitable starting materials, N-(1-benzyl-4-piperidinyl)-3,5-dimethylaniline is obtained in the same manner as in the above Reference Example 1.

NMR (CDCl$_3$) δ ppm: 1.35–1.60 (2H, m), 1.95–2.20 (4H, m), 2.22 (6H, s), 2.70–2.94 (2H, m), 3.15–3.40 (1H, m), 3.52 (2H, s), 6.22 (2H, s), 6.33 (1H, s), 7.20–7.40 (5H, m)

Reference Example 30

Using the suitable starting materials, N-cinnamoyl-N-(1-benzyl-4-piperidinyl)-3,5-dimethylaniline is obtained in the same manners as in the above Reference Example 15 as white powders, m.p.: 151°–154° C.

Reference Example 31

Using the suitable starting materials, 1-(1-benzyl-4-piperidinyl)-5,7-dimethylcarbostyril hydrochloride is obtained in the same manner as in the above Reference Example 16 as white powders, m.p.: 241°–244° C.

Reference Example 32

Using the suitable starting materials, N-(1-benzyl-4-piperidinyl)-2-formyl-3-fluoroaniline is obtained in the same manner as in the above Reference Example 19 as yellow powders, m.p.: 108°–109° C.

Reference Example 33

Using the suitable starting materials, methyl 2-fluoro-5-[(1-benzyl-4-piperidinyl)amino]cinnamate is obtained in the same manner as in the above Reference Example 24 as white powders, m.p.: 130°–133° C.

Reference Example 34

Potassium carbonate (8.9 g), 4-amino-1-benzylpiperidine (18.5 g), cupric oxide (0.6 g) and dimethylformamide (25 ml) are added to 2-chloro-6-fluorobenzoic acid (11.3 g) and the mixture is reacted with heating at 140° C. for 6 hours. After the reaction, the solvent is concentrated and to the resulting residue are added water (200 ml) and active carbon (1 g). The mixture is refluxed for 30 minutes. After filtration, the filtrate is cooled and then adjusted to pH 8.0 with diluted hydrochloric acid. The precipitated crystal is collected by filtration and washed successively with water and methanol to give 2-(1-benzyl-4-piperidinylamino)-6-fluorobenzoic acid (7.6 g) as white powders, m.p.: 233°–236° C.

Reference Example 35

To a solution of lithium aluminum hydride (0.9 g) in anhydrous tetrahydrofuran (160 ml) is added 2-(1-benzyl-4-piperidinylamino)-6-fluorobenzoic acid (8.0 g) and the mixture is refluxed for 1 hour. After cooling, the reaction solution is poured into ice-water and then extracted with dichloromethane. The solvent is concentrated and to the resulting residue is added diethyl ether/n-hexane. The precipitated crystal is collected by filtration to give N-(1-benzyl-4-piperidinyl)-2-hydroxymethyl-3-fluoroaniline (5.6 g) as light yellow powders, m.p.: 167°–170° C. Compounds of formula II are prepared as taught in European patent application EP 0 470514 A1, published Feb. 2, 1992. The carbostryril derivatives of formula II of the present invention can be prepared by various processes, for example, by the processes shown in the following reaction schemes.

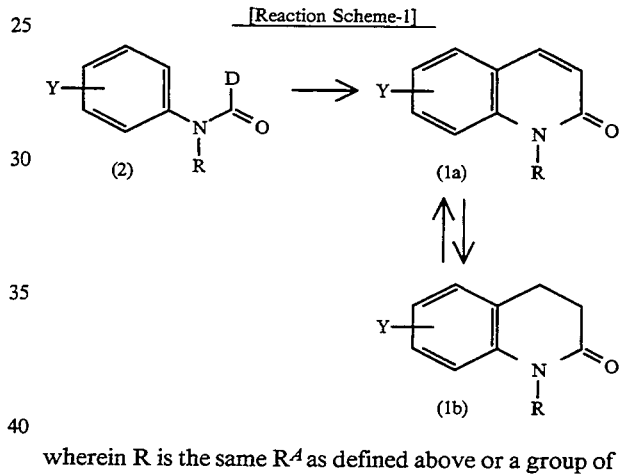

[Reaction Scheme-1]

wherein R is the same R$^4$ as defined above or a group of the formula:

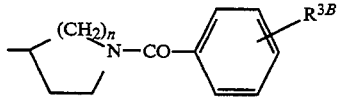

wherein n and R$^{3B}$ are the same as defined above, and D is a group of the formula: —CH=CHR$^{14'}$ (R$^{14'}$ is a lower alkoxy, phenyl or a halogen atom), a group of the formula:

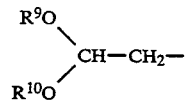

(R$^9$ and R$^{10}$ are each a lower alkyl), or a group of the formula: —C≡CH, and Y is hydrogen atom or a lower alkyl.

The cyclization reaction of the compound of the formula (2) is carried out in an appropriate solvent or without solvent in the presence of an acid. The acid includes any conventional inorganic acids and organic acids, for example, inorganic acids (e.g. hydrochloric acid, hydrobromic acid, sulfuric acid, phosphorus pentoxide, polyphosphoric acid, etc.), Lewis acids (e.g. aluminum chloride, boron trifluoride, titanium tetrachloride, etc.), organic acids (e.g. formic acid, acetic acid, ethanesulfonic acid, p-toluenesulfonic acid, etc.), among which hydrochloric acid, hydrobromic acid and sulfuric acid are preferable. The acid is usually used in at least equivalent amount, preferably in an amount of 10 to 50 times by weight, as much as the amount of the compound (2). The solvent includes any conventional inert solvents, for example, water, lower alcohols (e.g. methanol, ethanol, propanol, etc.), ethers (e.g. dioxane, tetrahydrofuran, etc.), aromatic hydrocarbons (e.g. benzene, chlorobenzene, toluene, etc.), halogenated hydrocarbons (e.g. methylene chloride, chloroform, carbon tetrachloride, etc.), acetone, dimethylsulfoxide, dimethylformamide, hexamethylphosphoric triamide, and the like. The reaction is usually carried out at a temperature of from about 0° to about 200° C., preferably from room temperature to about 150° C., for about 5 minutes to 6 hours.

The reduction of the compound of the formula (1a) is usually carried out under conventional conditions for the usual catalytic reduction. The catalyst includes metals such as palladium, palladium-carbon, platinum, Raney nickel, etc. These metals are used in a conventional catalytic amount. The solvent used therein includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.). The reduction reaction can be carried out under atmospheric pressure or under pressure, usually under atmospheric pressure to 20 kg/cm$^2$, preferably atmospheric pressure to 10 kg/cm$^2$. The reaction temperature is usually in the range of from about 0° C. to about 150° C., preferably from room temperature to about 100° C.

The dehydrogenation reaction of the compound of the formula (1b) is usually carried out in an appropriate solvent with an oxidizing agent. The oxidizing agent includes, for example, benzoquinones (e.g. 2,3-dichloro-5,6-dicyanobenzoquinone, chloranil (=2,3,5,6-tetrachlorobenzoquinone), etc.), halogenating agents (e.g. N-bromosuccinimide, N-chlorosuccinimide, bromine, etc.), hydrogenating catalysts (e.g. selenium oxide, palladium-carbon, palladium black, palladium oxide, Raney nickel, etc.). When a halogenating agent is used, it is used in a wide range of amount but is usually used in an amount of 1 to 5 moles, preferably 1 to 2 moles, to 1 mole of the compound (1b). When a hydrogenating catalyst is used, it is used in a catalytic amount as usual. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar protic solvents (e.g. acetic acid, etc.), aprotic polar solvents (e.g. dimethylformamide, dimethylsulfoxide, hexamethylphosphoric triamide, etc.). The reaction is usually carried out at a temperature of from room temperature to about 300° C., preferably from room temperature to about 200° C., for 1 to 40 hours.

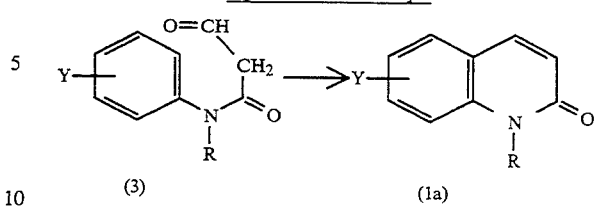

[Reaction Scheme-2]

wherein R and Y are the same as defined above.

The cyclization reaction of the compound (3) is carried out in an appropriate solvent in the presence of a condensation agent. The condensation agent includes, for example, Lewis acids, such as phosphorus pentoxide, hydrogen fluoride, sulfuric acid, polyphosphoric acid, aluminum chloride, zinc chloride, etc. The solvent includes, for example, halogenated hydrocarbons (e.g. chloroform, dichloromethane, 1,2-dichloroethane, etc.), ethers (e.g. diethyl ether, dioxane, etc.), aromatic hydrocarbons (e.g. nitrobenzene, chlorobenzene, etc.). The condensation agent is usually used in an amount of about 1 to 10 moles, preferably about 3 to 6 moles, to 1 mole of the compound (3). The reaction is usually carried out at a temperature of about 50° C. to about 250° C., preferably about 70° C. to about 200° C., for about 20 minutes to about 6 hours.

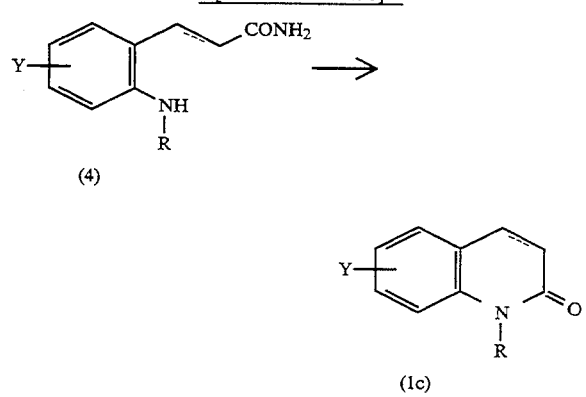

[Reaction Scheme-3]

wherein R, Y and the bond between 3- and 4-positions of the carbostyril nucleus are the same as defined above.

The cyclization reaction of the compound (4) is carried out in an appropriate solvent or without using a solvent in the presence of an acid. The acid includes, for example, inorganic acids (e.g. hydrochloric acid, sulfuric acid, hydrobromic acid, nitric acid, polyphosphoric acid, etc.), organic acids (e.g. p-toluenesulfonic acid, ethanesulfonic acid, trifluoroacetic acid, etc.). The solvent includes any conventional solvents unless they affect on the reaction, for example, water, alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, diphenyl ether, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The reaction is usually carried out at a temperature of from about −20° C. to about 150° C., preferably from about 0° C. to about 150° C., for about 5 minutes to about 30 hours.

[Reaction Scheme-4]

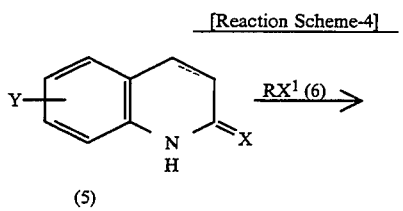

wherein R, X, Y and the bond between 3- and 4-positions of the carbostyril nucleus are the same as defined above, and $X^1$ is a halogen atom.

The reaction of the compound of the formula (5) and the compound of the formula (6) is usually carried out in an appropriate inert solvent in the presence or absence of a basic compound. The inert solvent includes, for example, aromatic hydrocarbons (e.g. benzene, toluene, xylene, etc.), alcohols (e.g. methanol, ethanol, propanol, butanol, 3-methoxy-1-butanol, ethylcellosolve, methylcellosolve, etc.), pyridine, acetone, N-methylpyrrolidone, dimethylsulfoxide, dimethylformamide, hexamethylphosphoric triamide, etc. The basic compound includes, for example, sodium carbonate, potassium carbonate, sodium hydrogen carbonate, potassium, hydrogen carbonate, sodium hydroxide, potassium hydroxide, sodium hydride, potassium hydride, triethylamine, etc.

The amounts of the compound (5) and the compound (6) are not critical, but the composed (6) is usually used at least in equimolar amount, preferably in an amount of 1 to 5 moles to 1 mole of the compound (5). The reaction is usually carried out at a temperature of from room temperature to about 200° C., preferably about 100° C. to about 180° C., for about 3 to 30 hours. In the reaction, a copper powder may also be used as a catalyst, by which the reaction can proceed advantageously.

[Reaction Scheme-5A]

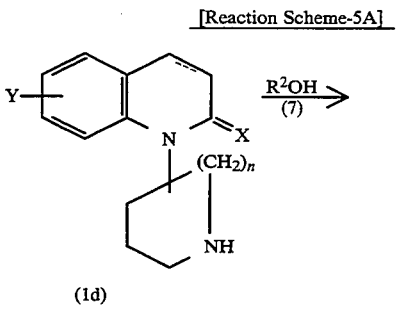

[Reaction Scheme-5A]
-continued

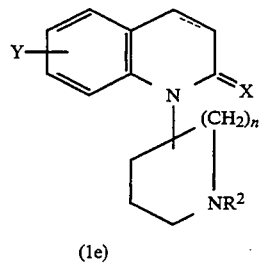

wherein X, Y, n and the bond between 3- and 4-positions of the carbostyril nucleus are the same as defined above, and $R^2$ is the same as $R^{2A}$ as mentioned above or a group of the formula:

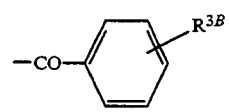

($R^{3B}$ is the same as defined above).

[Reaction Scheme-5B]

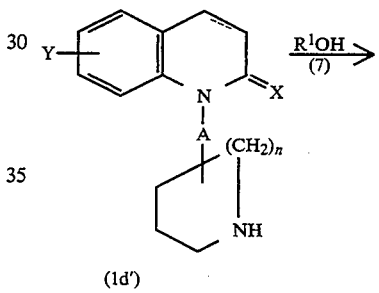

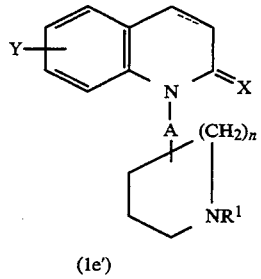

wherein $R^1$, X, Y, A, n and the bond between 3- and 4-positions of the carbostyril nucleus are the same as defined above.

The process of Reaction Schemes-5A and -5B is carried out by reacting a carbostyril derivative of the formula (1d) or (1d') and a carboxylic acid compound of the formula (7) or (7a) by a conventional amido bond producing reaction. The amido bond producing reaction can be carried out under the conditions for the conventional amido bond producing reaction, for example, (a) a mixed acid anhydride process, i.e. a process of reacting the carboxylic acid compound (7) or (7a) with an alkyl-halocarboxylic acid to form a mixed acid anhydride and reacting the resultant with the amine compound (1d) or (1d'), (b) an activated ester process, i.e. a process of converting the carboxylic acid compound (7) or (7a) into an activated ester, such as p-nitrophenyl ester, N-hydroxysuccinimide ester, 1-hydroxybenzotriazole ester, etc., and reacting the resultant with the amine compound (1d) or (1d'), (c) a carbodiimide process, i.e. a process of condensing the carboxylic acid compound (7) or (7a) and the amine compound (1d) or (1d') in the presence of an activating agent such as dicyclohexylcarbodiimide, carbonyldiimidazole, etc., (d) other processes, i.e. a process of converting the carboxylic acid compound (7) or (7a) into a carboxylic anhydride by treating it with a dehydrating agent such as acetic anhydride, and reacting the resultant with the amine compound (1d) or (1d'); a process of reacting an ester of the carboxylic acid compound (7) or (7a) with a lower alcohol and the amine compound (1d) or (1d') at a high temperature under high pressure; a process of reacting an acid halide compound of the carboxylic acid compound (7) or (7a), i.e. a carboxylic acid halide, with the amine compound (1d) or (1d'), and the like.

The mixed acid anhydride used in the above mixed acid anhydride process is obtained by the known Schötten-Baumann reaction, and the reaction product is used without isolation from the reaction mixture for the reaction with the amine compound (1d) or (1d') to give the desired compound of the formula (1e) or (1e'). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylphorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about $-20°$ C. to about $100°$ C., preferably from about $0°$ C. to about $50°$ C., for about 5 minutes to about 10 hours, preferably about 5 minutes to about 2 hours.

The reaction of the thus obtained mixed acid anhydride with the amine compound (1d) or (1d') is usually carried out at a temperature of from about $-20°$ C. to about $150°$ C., preferably about $10°$ C. to about $50°$ C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (7) or (7a), the alkylhalocarboxylic acid and the amine (1d) or (1d') are usually used in each equimolar amount, but preferably, the alkylhalocarboxylic acid and the carboxylic acid compound (7) or (7a) are used each in an amount of about 1 to 1.5 mole to 1 mole of the amine (1d) or (1d').

Among the above other processes (d), in case of the process of reacting the carboxylic acid halide with the amine compound (1d) or (1d'), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride, etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, and the like. The amount of the amine compound (1d) or (1d') and the carboxylic acid halide is not critical, but the carboxylic acid halide is usually used at least in equimolar amount, preferably about 1 to 5 moles to 1 mole of the amine compound (1d) or (1d'). The reaction is usually carried out at a temperature of from about $-20°$ C. to about $180°$ C., preferably from about $0°$ C. to about $150°$ C., for about 5 minutes to about 30 hours.

The amide bond producing reaction in the above Reaction Schemes-5A and -5B may also be carried out by reacting the carboxylic acid compound (7) or (7a) and the amine (1d') in the presence of a condensation agent such as triphenylphosphine, diphenylphosphinyl chloride, phenyl-N-phenylphosphoramide chloridate, diethyl chlorophosphate, diethyl cyanophosphate, bis(2-oxo-3-oxazolidinyl)phosphinic chloride, etc. The reaction is usually carried out in the presence of the solvent and basic compound as used in the above reaction of the carboxylic acid halide and the amine (1d) or (1d') at a temperature of from about $-20°$ C. to about $150°$ C., preferably about $0°$ C. to about $100°$ C., for about 5 minutes to about 30 hours. The condensation agent and the carboxylic acid compound (7) or (7a) are used at least in equimolar amount, preferably about 1 to 2 moles, to 1 mole of the amine (1d) or (1d').

[Reaction Scheme-6A]

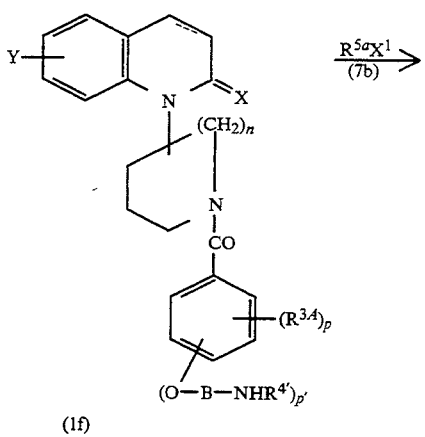

-continued
[Reaction Scheme-6A]

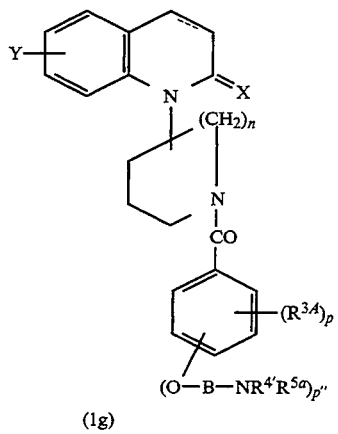

(1g)

wherein X, Y, n, $R^{3A}$, $X^1$, B, A, and the bond between 3- and 4-positions of the carbostyril nucleus are the same as defined above, and $R^{4'}$ is hydrogen atom, $R^{5a}$ is tricyclo[3,3,1,1]decany, a tricyclo[3.3.1.1.]decanyl-lower alkyl, a halogen-substituted lower alkyl, a lower alkoxycarbonyl-lower alkanoyloxy-lower alkyl, or a lower alkenyl, and p' and p" are each an integer of 1 to 3, provided that p+p' and p+p" are each an integer not more than 3.

[Reaction Scheme-6B]

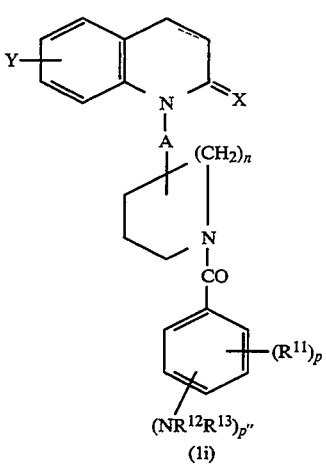

wherein X, Y, n, $X^1$, A, and the bond between 3- and 4-positions of carbostyril nucleus are the same as defined above, and $R^{11}$ is an amino being optionally substituted by a lower alkoxy or a lower alkyl, $R^{12}$ is a lower alkyl, $R^{13}$ is hydrogen atom or a lower alkyl, and p' and p" are each an integer of 1 to 3, provided that p+p' and p+p" are each an integer not more than 3.

[Reaction Scheme-6C]

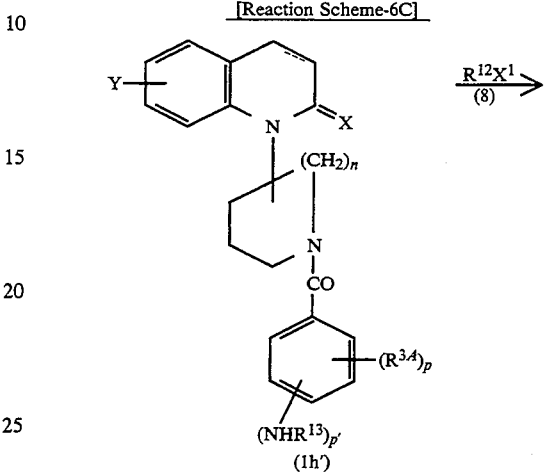

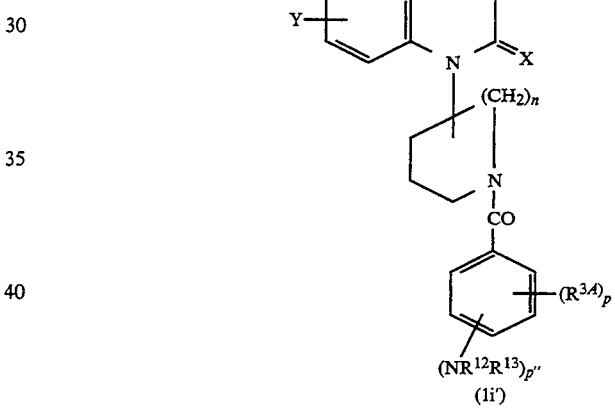

wherein X Y, n, $R^{3A}$, $X^1$, $R^{12}$, $R^{13}$, and the bond between 3- and 4-positions of carbostyril nucleus are the same as defined above, and p' and p" are each an integer of 1 to 3, provided that p+p' and p+p" are each an integer not more than 3.

The reaction of the compound (1f) and the compound (7b) in Reaction Scheme-6A, the reaction of the compound (1h) and the compound (8) in Reaction Scheme-6B, and the reaction of the compound (1h') and the compound (8) in Reaction Scheme-6C are usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), halogenated hydrocarbons (e.g. dichloromethane, dichloroethane, chloroform, carbon tetrachloride, etc.), acetic acid, ethyl acetate, acetone, acetonitrile, dimethylsulfoxide, dimethylformamide, hexamethylphosphoric triamide, and the like. The basic compound includes, for example, metal carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, ethyldiisopropylamine, dimethylaminopyridine, triethylamine, 1,5-diazabicyclo[4.3.0]nonene-(5) (DBN), 1,8-diazabicyclo[5.4.0]undecene-7 (DBU), 1,4-diazabicyclo[2.2.2]octane (DABCO), etc.). The ratio of the compound (7b) or (8) to the compound (1f), (1h), or (1h') is not critical, but the compound (7b) or (8) is usually used at least in equivalent amount, preferably 1 to 5 moles, to 1 mole of the compound (1f), (1h) or (1h'). The reaction is usually carried out at a temperature of from about 0° C. to about 200° C., preferably from about 0° C. to about 170° C., for about 30 minutes to about 30 hours.

Moreover, the compounds (1i) and (1i') wherein $R^{12}$ is a lower alkyl can also be obtained by reacting the compound (1h) or (1h') with a compound of the formula:

$$R^{14}-CO-R^{15} \quad (9)$$

wherein $R^{14}$ and $R^{15}$ are each hydrogen atom or a lower alkyl, respectively.

The reaction is usually carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium borohydride, sodium cyanoborohydride, lithium aluminum hydride, etc.), catalytic reducing agents (e.g. palladium black, palladium-carbon, platinum oxide, platinum black, Raney nickel, etc.). When formic acid is used as the reducing agent, the reaction is usually carried out at a temperature of from room temperature to about 200° C., preferably about 50° C. to about 150° C., for about 1 to 10 hours. The formic acid is usually used in a large excess amount to the compound (1h) or (1h').

When a hydrogenating reducing agent is used, the reaction is usually carried out at a temperature of about $-30°$ C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (1h) or (1h'). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about $-30°$ C. to about 100° C., preferably about 10° C. to about 60° C., for about 1 to 12 hours. The catalytic reducing agent is usually used in an amount of about 0.1 to 40% by weight, preferably about 1 to 20% by weight, of the amount of the compound (1h) or (1h'). The compound (9) is usually used at least in equivalent amount, preferably equivalent to a large excess amount, to the compound (1h) or (1h').

[Reaction Scheme-7]

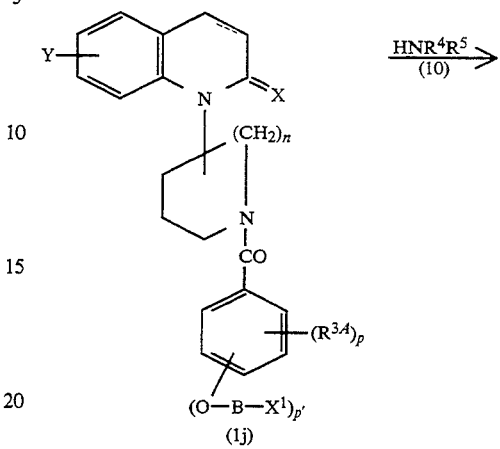

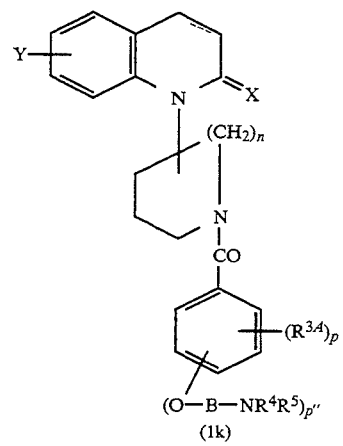

wherein X, Y, p, $R^{34}$, n, $R^4$, $R^5$, p', p'', B, $X^1$, and the bond between 3- and 4-positions of the carbostyril nucleus are the same as defined above.

The reaction of the compound (1j) and the compound (10) is carried out under the same conditions as in the reaction of the compound (1f) and the compound (7b) in the above Reaction Scheme-6A.

[Reaction Scheme-8]

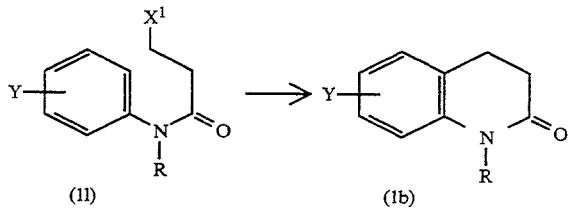

wherein R, Y and $X^1$ are the same as defined above.

The cyclization reaction of the compound (11) is so-called Friedel Craft reaction and is usually carried out in an appropriate solvent in the presence of a Lewis acid. The solvent includes any conventional solvent which is usually used in this kind of reaction, for example, carbon disulfide, nitrobenzene, chlorobenzene, dichloromethane, dichloroethane, tricloroethane, tetrachloroethane, and the like. The Lewis acid includes any conventional acid, for example, aluminum chloride, zinc chloride, iron chloride, tin chloride, boron tribromide, boron trifluoride, conc. sulfuric acid, and the like. The amount of Lewis acid is not critical but is usually in the range of about 2 to 6 moles, preferably about 3 to 4 moles, to 1 mole of the compound (11). The reaction temperature is usually in the range of about 20° C. to 200° C., preferably 40° C. to 180° C. The reaction period of time may vary depending on the kinds of the starting compound, catalyst and reaction temperature, etc., but is usually in the range of about 0.5 to 6 hours. Besides, sodium chloride may be added to the reaction system in order to proceed the reaction advantageously.

[Reaction Scheme-9]

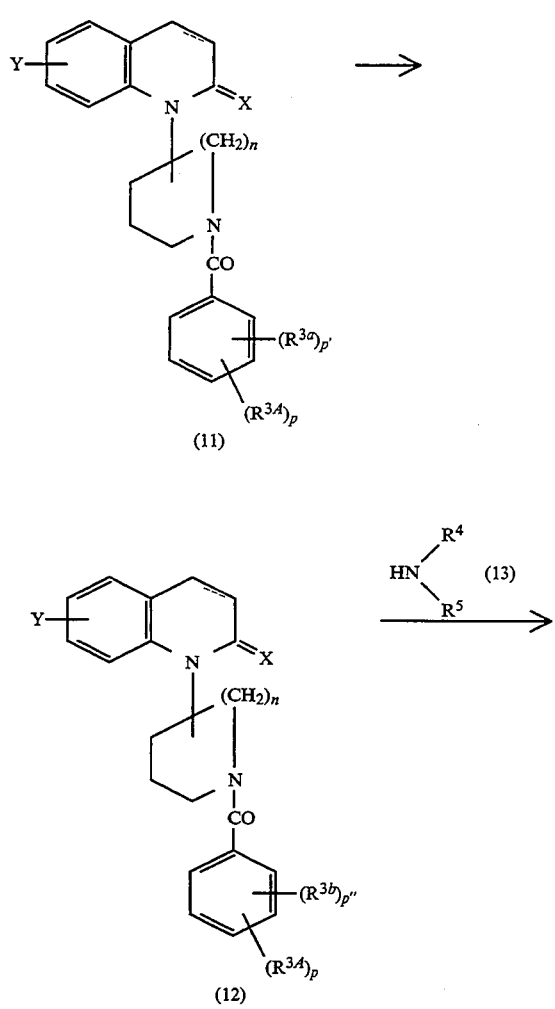

-continued
[Reaction Scheme-9]

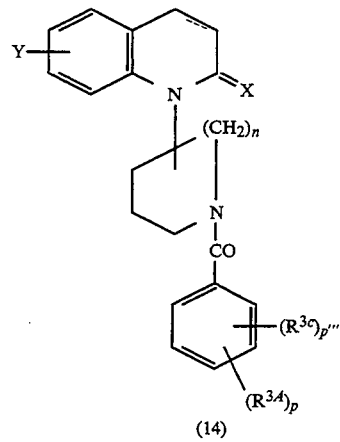

wherein X, Y, $R^{3A}$, n, p, p', p", and the bond between 3- and 4-positions of the carbostyril nucleus are the same as defined above, and $R^{3a}$ is a lower alkenyloxy, $R^{3b}$ is an oxilanyl-substituted lower alkoxy, $R^{3c}$ is a lower alkoxy having a substituent selected from a group of the formula:

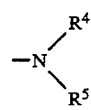

($R^4$ and $R^5$ are as defined above) and hydroxy, and p''' is an integer of 1 to 3, provided that p+p''' is not more than 3.

The reaction of converting the compound (11) into the compound (12) is carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoroperacetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. The above reaction is usually carried out at a temperature of about 0° C. to about 40° C., preferably from about 0° C. to room temperature, for about 1 to 15 hours.

The reaction of the compound (12) and the compound (13) is carried out under the same conditions as in the reaction of the compound (1f) and the compound (7b) in the above Reaction Scheme-6A.

The starting compound (2) can be prepared, for example, by the processes as shown in the following Reaction Schemes-10 and -11.

[Reaction Scheme-10]

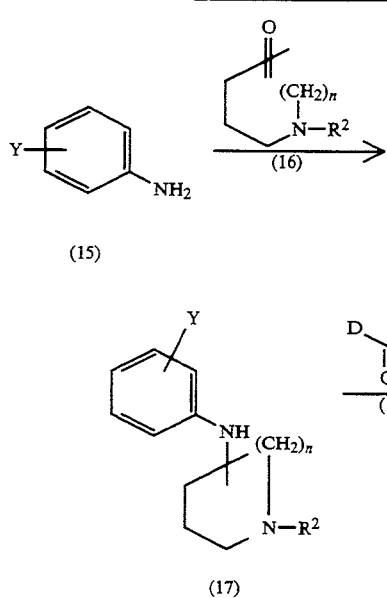

wherein $R^2$, Y, n and D are the same as defined above.

The reaction of the compound (15) and the compound (16) is carried out under the same conditions as in the reaction of the compound (1h) and the compound (9) in the above Reaction Scheme-6B.

The reaction of the compound (17) and the compound (18) is carried out under the same conditions as in the reaction of the compound (1d) and the compound (7) in the above Reaction Scheme-5.

[Reaction Scheme-11]

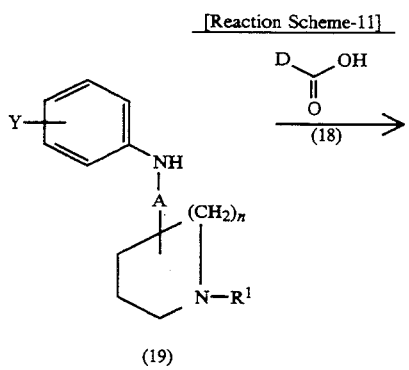

-continued
[Reaction Scheme-11]

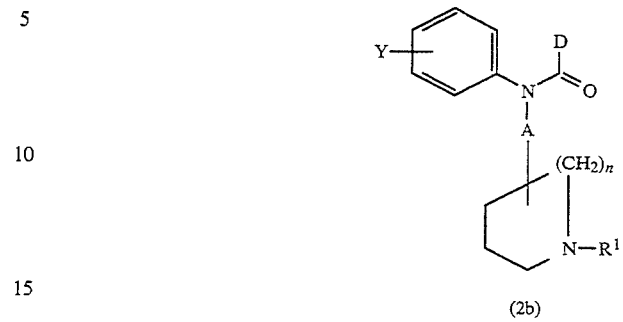

wherein $R^1$, A, Y, n, and D are the same as defined above.

The reaction of the compound (19) and the compound (18) is carried out under the same conditions as the above reaction of the compound (17) and the compound (18).

The starting compound (4) can be prepared, for example, by the process of the following Reaction

[Reaction Scheme-12]

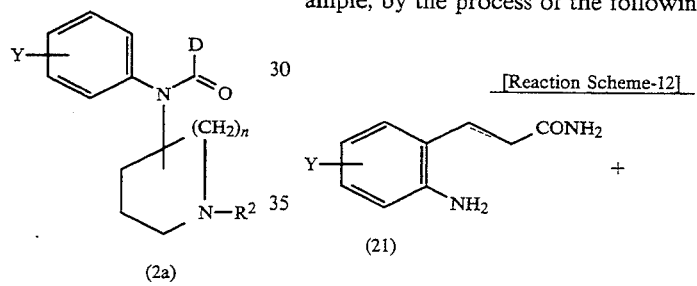

wherein $R^2$, Y, and n are the same as defined above.

The reaction of the compound (21) and the compound (22) is carried out under the same conditions as in the reaction of the compound (15) and the compound (16) in the above Reaction Scheme-10.

The starting compound (11) can be prepared, for example, by the process of the following Reaction Scheme-13.

[Reaction Scheme-13]

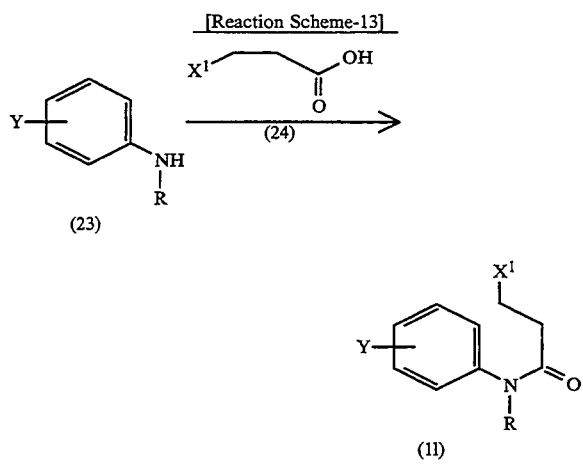

wherein R, Y and $X^1$ are as defined above.

The reaction of the compound (23) and the compound (24) is carried out under the same conditions as in the reaction of the compound (17) and the compound (18) in the above Reaction Scheme-10.

[Reaction Scheme-14]

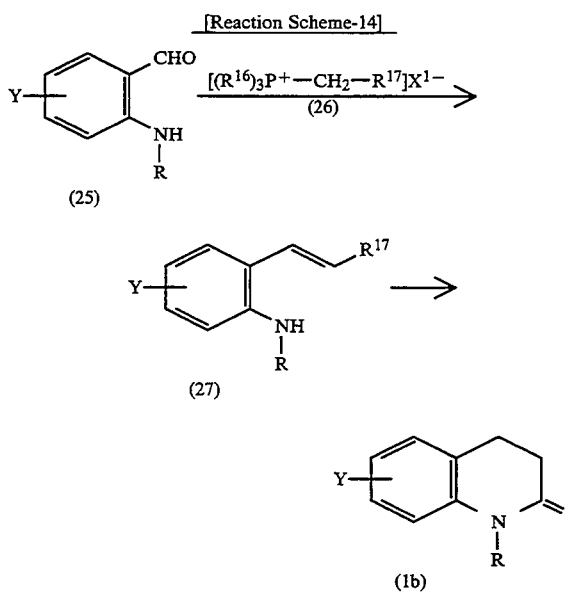

wherein R, Y and $X^1$ are the same as defined above, and $R^{16}$ is phenyl and $R^{17}$ is a lower alkoxycarbonyl.

The reaction of the compound (25) and the compound (26) is carried out in an appropriate solvent in the presence of a basic compound. The basis compound includes inorganic bases (e.g. sodium metal, potassium metal, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about −80° C. to about 150° C., preferably about −80° C. to about 120° C., for about 0.5 to 15 hours.

The cyclization reaction of the compound (27) is carried out in the presence of a catalytic reducing agent and in the presence or absence of a basic compound or an acid, preferably in the presence of an acid, in an appropriate solvent. The basic compound includes, for example, organic bases (e.g. triethylamine, trimethylamine, pyridine, dimethylaniline, N-methylmorpholine, DBN, DBU, DABCO, etc.), and inorganic bases (e.g. potassium carbonate, sodium carbonate, sodium hydroxide, potassium hydroxide, sodium hydride, potassium hydride, potassium hydrogen carbonate, sodium hydrogen carbonate, etc.), and the acid includes, for example, inorganic acids (e.g. hydrochloric acid, sulfuric acid, phosphoric acid, etc.), organic acids (e.g. acetic acid, etc.), or a mixture of these acids. The solvent includes, for example, water, alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. tetrahydrofuran, diethyl ether, dimethoxyethane, etc.), esters (e.g. methyl acetate, ethyl acetate, etc.), N,N-dimethylformamide, dimethylsulfoxide, hexamethylphosphoric triamide, or a mixture of these solvents. The catalytic reducing agent includes the same catalysts as used in the reduction reaction of the compound (1a) in the above Reaction Scheme-1. The reaction is usually carried out under atmospheric pressure to about 20 kg/cm², preferably atmospheric pressure to about 10 kg/cm², at a temperature of about 0° C. to about 200° C., preferably from room temperature to about 150° C., for about 1 to 10 hours. The catalytic reducing agent is preferably used in an amount of 0.02 to 1 part by weight to 1 part by weight of the compound (27).

[Reaction Scheme-15]

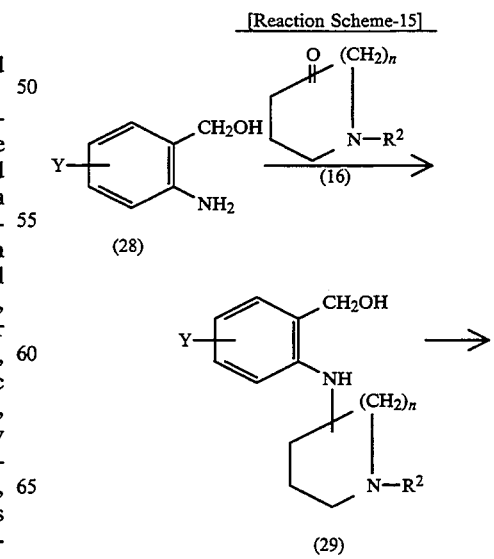

-continued
[Reaction Scheme-15]

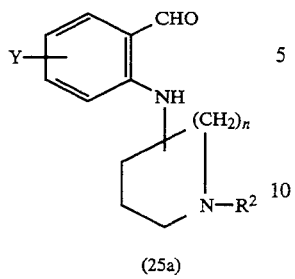

wherein $R^2$, Y and n are as defined above.

The reaction of the compound (28) and the compound (16) is carried out under the same conditions as in the reaction of the compound (15) and the compound (16) in the above Reaction Scheme-10.

The reaction of converting the compound (29) into the compound (25a) is carried out in an appropriate solvent or without solvent in the presence of an oxidizing agent. The solvent includes the above-mentioned aromatic hydrocarbons, lower alcohols, halogenated hydrocarbons, ethers, polar solvents (e.g. dimethylsulfoxide, dimethylformamide, hexamethylphosphoric triamide, etc.). The oxidizing agent includes acetic anhydride-dimethylsulfoxide, phosphorus pentoxide-dimethylsulfoxide, sulfur trioxide.pyridine complex-dimethylsulfoxide, dicyclohexylcarbodiimide-dimethylsulfoxide, oxalyl chloride-dimethylsulfoxide, chromic acid, chromic acid complexes (e.g. chromic acid-pyridine complex, chromic acid-2-pyridine complex, etc.), manganese dioxide, and the like. When oxalyl chloride-dimethylsulfoxide is used as the oxidizing agent, there may be added to the reaction system the basic compound as used in the reaction of the compound (1d) and the carboxylic halide in the above Reaction Scheme-5. The reaction is usually carried out at a temperature of 0° C. to 150° C., preferably from room temperature to about 100° C., for about 1 to 30 hours. The oxidizing agent is usually used in an amount of 1 to 20 moles, preferably 1 to 15 moles, to 1 mole of the compound (29).

[Reaction Scheme-16]

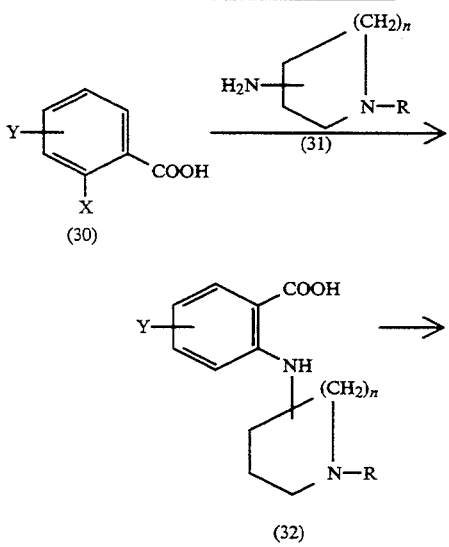

-continued
[Reaction Scheme-16]

wherein R, X, Y and n are the same as defined above.

The reaction of the compound (30) and the compound (31) is carried out under the same conditions as in the reaction of the compound (5) and the compound (6) in the above Reaction Scheme-4. In this reaction, copper monoxide may be added to the reaction system in order to proceed the reaction advantageously.

The reaction of converting the compound (32) into the compound (29) can be carried out by reducing the compound (32). The reduction reaction is preferably carried out by using a hydrogenating reducing agent. The hydrogenating reducing agent includes, for example, lithium aluminum hydride, sodium borohydride, diborane, and the like. The reducing agent is usually used at least in equimolar amount, preferably 1 to 15 moles, to 1 mole of the starting compound. The reducing reaction is usually carried out in an appropriate solvent, for example, water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about −60° C. to about 150° C., preferably −30° C. to 100° C., for about 10 minutes to about 5 hours. When lithium aluminum hydride or diborane is used as the reducing agent, it is preferable to use anhydrous solvents such as tetrahydrofuran, diethyl ether, diisopropyl ether, diglyme, etc.

[Reaction Scheme-17]

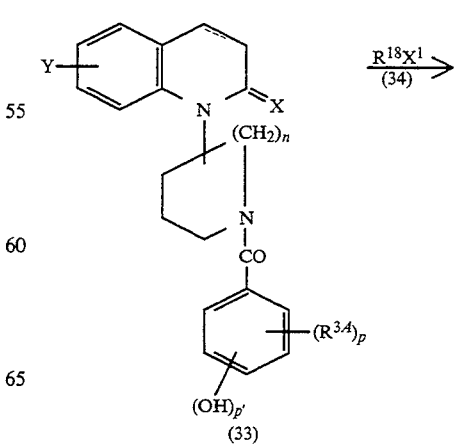

-continued

[Reaction Scheme-17]

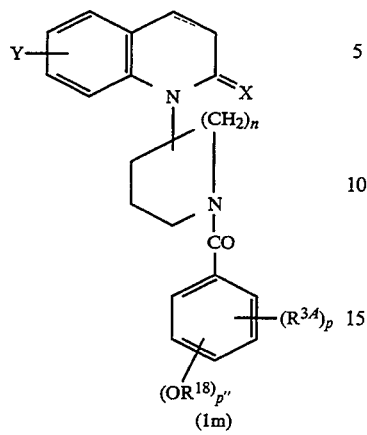
(1m)

wherein $R^{34}$, X, Y, n, p, p', P", $X^1$, and the bond between 3- and 4-positions of the carbostyril nucleus are the same as defined above, and $R^{18}$ is a lower alkyl, a group of the formula:

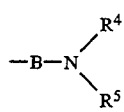

(B, $R^4$ and $R^5$ are the same as defined above), or a lower alkyl having two substituents selected from an aminocarbonyloxy having optionally a lower alkyl and a group of the formula:

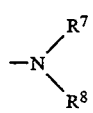

($R^7$ and $R^8$ are the same as defined above).

The reaction of the compound (33) and the compound (34) is carried out under the same conditions as in the reaction of the compound (1f) and the compound (7b) in the above Reaction Scheme-6A. In said reaction, an alkali metal halide (e.g. sodium iodide, potassium iodide, etc.) may be added to the reaction system.

[Reaction Scheme -18]

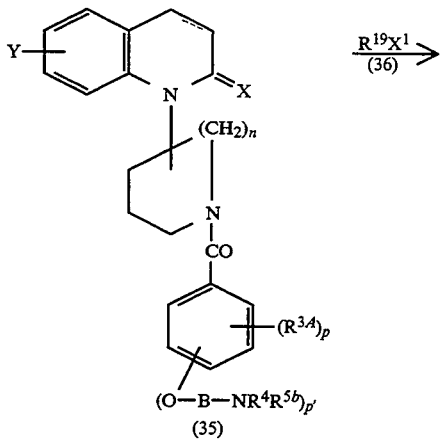

-continued

[Reaction Scheme -18]

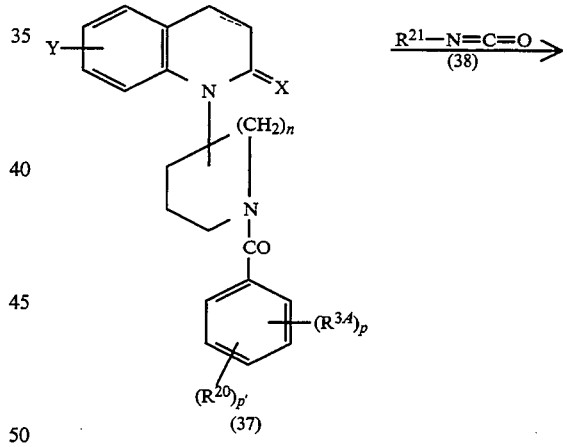
(1n)

wherein $R^{34}$, X, Y, n, p, p', p", B, $R^4$, $X^1$, and the bond between 3- and 4-positions of the carbostyril nucleus are the same as defined above, and $R^{5b}$ is a hydroxy-substituted lower alkyl, $R^{5c}$ is a lower alkoxycarbonyl-lower alkanoyloxy-lower alkyl, and $R^{19}$ is a lower alkoxycarbonyl-lower alkanoyl.

The reaction of the compound (35) and the compound (36) is carried out under the same conditions as in the reaction of the compound (1f) and the compound (7b) in the above Reaction Scheme-6A.

[Reaction Scheme-19]

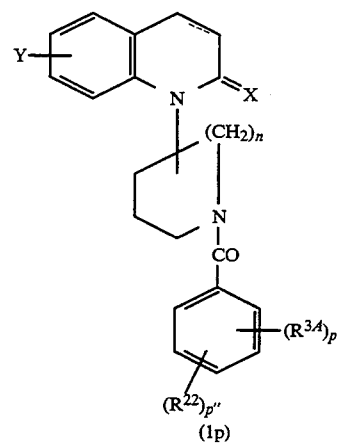
(1p)

wherein X, Y, $R^{34}$, p, p', p'', n, and the bond between 3- and 4-positions of the carbostyril nucleus are the same as defined above, and $R^{20}$ is a lower alkoxy having two substituents selected from hydroxy and a group of the formula:

($R^7$ and $R^8$ are the same as defined above), $R^{21}$ is a lower alkyl, and $R^{22}$ is an aminocarbonyloxy having optionally a lower alkyl substituent, or a group of the formula:

($R^7$ and $R^8$ are the same as defined above).

The reaction of the compound (37) and the compound (38) is carried out in the presence or absence, preferably absence, of a basic compound in an appropriate solvent or without using any solvent. The solvent and basic compound used in the above reaction are the same solvents and basic compounds as used in the reaction of the amine (1d) and the carboxylic acid halide in the above Reaction Scheme-5. The compound (38) is usually used in an amount of about 1 to 5 moles, preferably about 1 to 3 moles, to 1 mole of the compound (37). The reaction is usually carried out at a temperature of about 0° to 200° C., preferably room temperature to about 150° C., for about 5 minutes to about 30 hours. In the reaction, a basic compound (e.g. borane trifluorideethyl etherate, etc.) may be added to the reaction system.

the reaction of the compound (1d) and the compound (7) in the above Reaction Scheme-5.

The reaction of the compound (1p) and the compound (40) is carried out without solvent or in an appropriate solvent in the presence or absence, preferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone pyridine, and the like. The basic compound includes, for example, tertiary amines, (e.g. triethylamine, pyridine, etc.), sodium hydroxide, potassium hydroxide, sodium hydride, and the like. The above reaction may also be carried out in a solvent (e.g. acetic acid, etc.) in the presence of a mineral acid (e.g. sulfuric acid, etc.). The compound (40) is usually used in an equimolar amount or more, preferably about 1 to 10 moles, to 1 mole of the compound (1p). The above reaction is usually carried out at a temperature of about 0° to 200° C., preferably about 0° to 150° C., for about 0.5 to 15 hours.

The hydrolysis of the compound (1q) can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature of from room

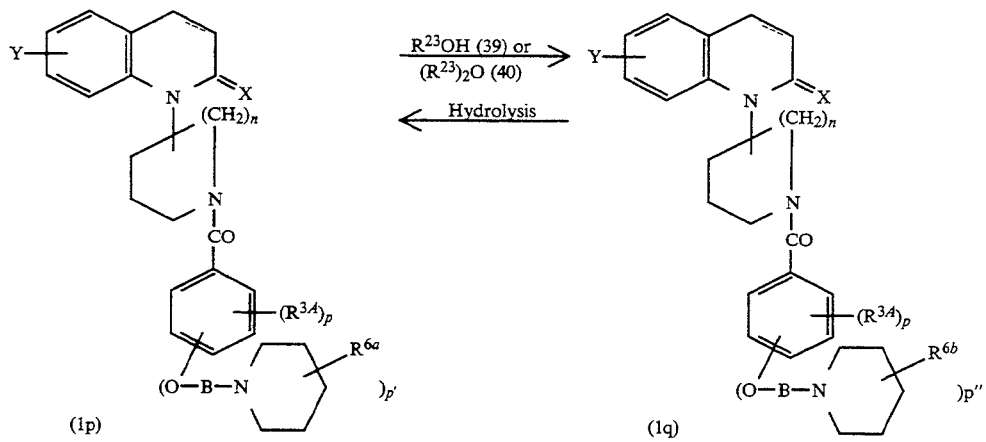

[Reaction Scheme-20]

wherein X, Y, $R^{34}$, B, p, p', p'', and the bond between 3- and 4-positions of the carbostyril nucleus are the same as defined above, and $R^{6a}$ is amino, $R^{6b}$ is an amino substituted by a lower alkanoyl having optionally 1 to 3 halogen substituents, and $R^{23}$ is a lower alkanoyl having optionally 1 to 3 halogen substituents.

The reaction of the compound (1p) and the compound (39) is carried out under the same conditions as in temperature to about 200° C., preferably from room temperature to about 150° C., for about 0.5 to 25 hours.

[Reaction Scheme-21]

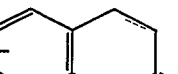

(1c)

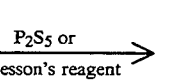

(1t)

wherein R, Y and the bond between 3- and 4-positions of the carbostyril nucleus are the same as defined above.

The reaction of the compound (1c) and phosphorus pentasulfide or Lawesson's reagent (as mentioned in Reference Example 1 hereinafter) is usually carried out in an inert solvent such as aromatic hydrocarbons (e.g. benzene, toluene, xylene, chlorobenzene, etc.), ethers (e.g. diethyl ether, tetrahydrofuran, dioxane, etc.), halogenated hydrocarbons (e.g. methylene chloride, chloroform, etc.), dimethylsulfoxide, hexamethylphosphoric triamide, and the like. The phosphorus pentasulfide or Lawesson's reagent is usually used in an amount of 0.2 mole to large excess amount, preferably 0.4 to 2 moles, to 1 mole of the compound (1c). The reaction is usually carried out at a temperature of from room temperature to 200° C., preferably 50° to 150° C., for 0.5 to 50 hours.

The starting compounds (1d), (1f), (1j), (1l), (33), (35) and (37) can readily be prepared by various processes as shown in the above Reaction Schemes-1 to -5 by using appropriate starting materials.

In the case of the compounds of the formula (1) wherein $R^3$ is thiomorpholino or 1-oxothiomorpholino; or a pyrrolidinyl-substituted lower alkylthio or a pyrrolidinyl-substituted lower alkylsulfinyl can be converted into the corresponding compounds of the formula (1) wherein $R^3$ is 1-oxo- or 1,1-dioxothiomorpholino or 1,1-dioxothiomorpholino; or a pyrrolidinyl-substituted lower alkyl-sulfinyl or -sulfonyl, or a pyrrolidinyl-substituted lower alkyl-sulfonyl, respectively by oxidation thereof.

The above oxidation reaction is carried out in an appropriate solvent in the presence of an oxidizing agent. The solvent includes, for example, water organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates, (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. In case of converting thiomorpholino into 1,1-dioxothiomorpholino or converting pyrrolidinyl-substituted lower alkylthio into pyrrolidinyl-substituted lower alkylsulfonyl, the oxidizing agent is usually used in an amount of at least two moles, preferably 2 to 4 moles, to 1 mole of the starting compound. The above reaction is usually carried out at a temperature of about −40° C. to about 40° C., preferably from about −40° C. to room temperature, for about 10 minutes to about 10 hours.

In the case of the compounds of the formula (1) wherein $R^3$ is a phenylthio having at least one nitro substituent, the compounds can be subjected to a reduction reaction to convert into the corresponding compounds wherein $R^3$ is a phenylthio having at least one amino substituent.

The reduction reaction can be carried out, for example, (1) by reducing them in an appropriate solvent with a catalytic reducing agent, or (2) by reducing them in an appropriate inert solvent with a reducing agent, such as a combination of a metal or metal salt and an acid, or a metal or metal salt and an alkali metal hydroxide, sulfide, ammonium salt, and the like.

In the case of reduction using a catalytic reducing agent (1), the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), and the like. The catalytic reducing agent includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 150° C., preferably from about 0° C. to about 100° C., under a hydrogen pressure of 1 to 10 atm., for about 0.5 to 10 hours.

In the case of the reduction (2), the reducing agent includes a combination of iron, zinc, tin or stannous chloride with a mineral acid (e.g. hydrochloric acid, sulfuric acid, etc.), or of iron, ferrous sulfate, zinc or tin with an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example, water, acetic acid, methanol, ethanol, dioxane, and the like. The conditions of the reduction reaction are determined depending on the kinds of the reducing agent, for example, in case of a combination of stannous chloride and hydrochloric acid, it is advantageously carried out at a temperature of about 0° C. to room temperature for about 0.5 to 10 hours. The reducing agent is usually used in an amount of at least 1 mole, preferably 1 to 5 moles, to 1 mole of the starting compound.

In case of the compounds of the formula (i) wherein $R^3$ is a heterocyclic group where the substituent on at least one nitrogen atom is hydrogen atom, the compounds can be converted into the corresponding compounds wherein $R^3$ is a heterocyclic group where the substituent on at least one nitrogen is a lower alkyl by reacting them with a compound of the formula:

 (34)

wherein $R^{18}$ and $X^1$ are the same as defined above, or a compound of the formula:

 (9)

wherein $R^{14}$ and $R^{15}$ are the same as defined above, under the same conditions as in the reaction of the compound (1f) and the compound (7b) in the above Reaction Scheme-6A or in the reaction of the compound (1h) and the compound (8) in the above Reaction Scheme-6B.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, citric acid, succinic acid, benzoic acid, etc. Besides, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromatography, preparative thin layer chromatography, extraction with a solvent, and the like.

The compounds and their salts of this invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like.

Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspendions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Components | Amount |
| --- | --- |
| 1-{1-[4-(3-Hydroxy-4-allylaminobutoxy)-benzoyl]-4-piperidinyl}-3,4-dihydrocarbostyril | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 1-[1-{4-[(4-Amino-1-piperidinyl)pentyloxy]-benzoyl}-4-piperidinyl]-3,4-dihydrocarbostyril | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screen with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 1-{1-[4-(5-Methylaminocarbonyloxy-6-dimethylaminohexyloxy)benzoyl)-4-piperidinyl]-3,4-dihydrocarbostyril | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

1-(4-Piperidinyl)-3,4-dihydrocarbostyril hydrochloride (5 g) and a Lawesson's Reagent (3.8 g) are dispersed in toluene (20 ml), and the mixture is refluxed for 40 hours. To the reaction mixture is added water, and the mixture is acidified with hydrochloric acid, and the organic layer is separated. The aqueous layer is basified with sodium hydroxide, extracted with chloroform, dried over sodium carbonate and recrystallized from n-hexane. The crystal is collected by filtration, and crystallized from dichloromethane/n-hexane to give 1-(4-piperidinyl)-3,4-dihydrothiocarbostyril (4.1 g) as pale yellow powder, m.p. 94°-97° C.

*) Lawesson's Reagent:

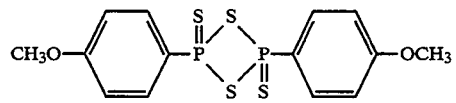

Example 1

1-(4-Piperidinyl)-3,4-dihydrothiocarbostyril (1.1 g), 4-ethoxy-2-methoxybenzoic acid (1.05 g) and bisoxoox-azodinylphosphinyl chloride (1.4 g) are dissolved in dichloromethane (30 ml) and thereto is added triethylamine (1.4 ml), and the mixture is stirred at room temperature overnight. Water is added to the reaction mixture, and the mixture is extracted with chloroform, dried over sodium carbonate, and purified by silica gel column chromatography (eluent: ethyl acetate:n-hexane=1:1) to give 1-[1-(2-methoxy-4-ethoxybenzoyl)-4-piperidinyl]-3,4-dihydrothiocarbostyril (0.9 g) as pale yellow amorphous.

¹H-NMR (CDCL₃) δ ppm; 1.42 (3H, t, J=7.0 Hz), 1.79–2.17 (2H, m), 2.26–2.59 (2H, m), 2.63–3.36 (6H, m), 3.59–3.64 (1H, m), 3.76–3.92 (3H, m), 4.04 (2H, q, J=7.0 Hz), 4.88–5.05 (1H, m), 5.92–6.13 (1H, m), 6.44–6.58 (2H, m), 7.06–7.45 (5H, m)

Using the suitable starting materials, the compounds of the following Table 1 are obtained in the same manner as in Example 1.

TABLE 1

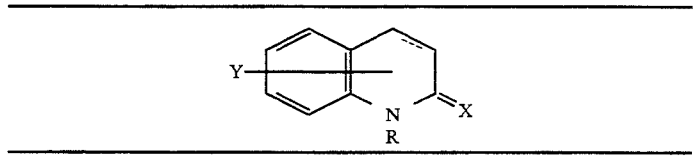

Example 2
Structure

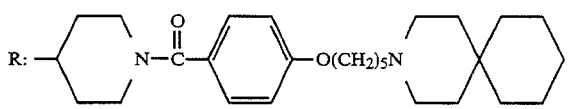

X: O  Y: H
Bond between 3- and 4-positions of the carbosytril nucleus: Single Bond
Crystalline form: Colorless oil
Form: Free
NMR: 1)

Example 3
Structure

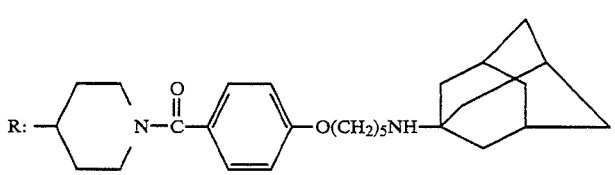

X: O  Y: H
Bond between 3- and 4-positions of the carbosytril nucleus: Single Bond
Crystalline form: White powder
Recrystallization solvent: Ethanol/water
Melting point: 125–129° C.
Form: Hydrochloride

Example 4
Structure

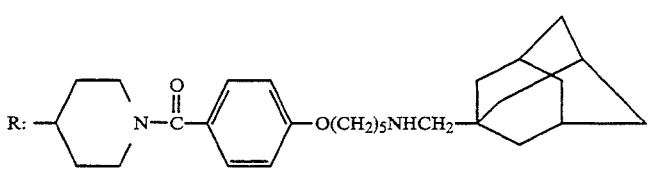

X: O  Y: H
Bond between 3- and 4-positions of the carbosytril nucleus: Single Bond
Crystalline form: Colorless oil
Form: Free
NMR: 2)

Example 5
Structure

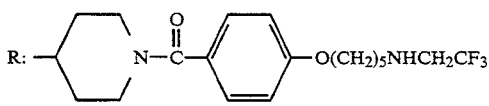

X: O  Y: H
Bond between 3- and 4-positions of the carbosytril nucleus: Single Bond
Crystalline form: Colorless oil
Form: Free
NMR: 3)

Example 6
Structure

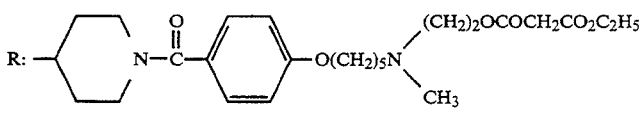

X: O  Y: H
Bond between 3- and 4-positions of the carbosytril nucleus: Single Bond TABLE 1-continued

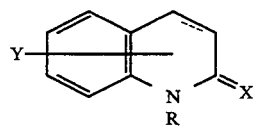

Crystalline form: Colorless oil
Form: Free
NMR: 4)

Example 7
Structure

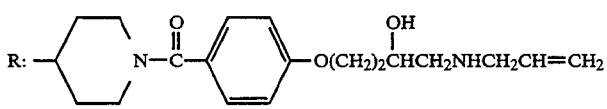

X: O  Y: H
Bond between 3- and 4-positions of the carbosytril nucleus: Single Bond
Crystalline form: Colorless oil
Form: Free
NMR: 5)

Example 8
Structure

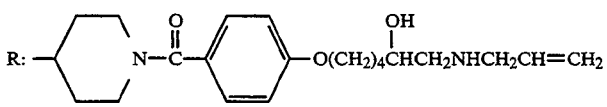

X: O  Y: H
Bond between 3- and 4-positions of the carbosytril nucleus: Single Bond
Crystalline form: Colorless oil
Form: Free
NMR: 6)

Example 9
Structure

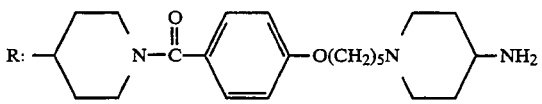

X: O  Y: H
Bond between 3- and 4-positions of the carbosytril nucleus: Single Bond
Crystalline form: Colorless oil
Form: Free
NMR: 7)

Example 10
Structure

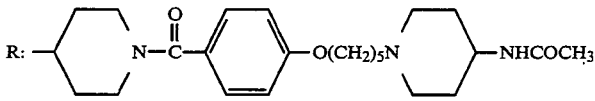

X: O  Y: H
Bond between 3- and 4-positions of the carbosytril nucleus: Single Bond
Crystalline form: Colorless oil
Form: Free
NMR: 8)

Example 11
Structure

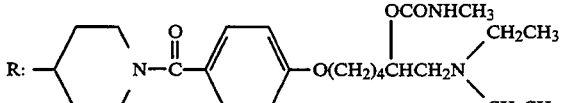

X: O  Y: H
Bond between 3- and 4-positions of the carbosytril nucleus: Single Bond
Crystalline form: Colorless oil
Form: Free
NMR: 9)

Example 12
Structure

TABLE 1-continued

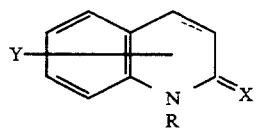

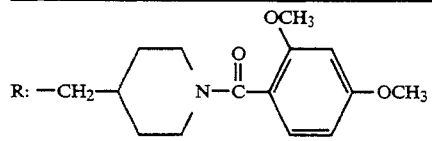

X: O  Y: H
Bond between 3- and 4-positions of the carbosytril nucleus: Single Bond
Crystalline form: Colorless amorphous
Form: Free
NMR: 10)

Example 13
Structure

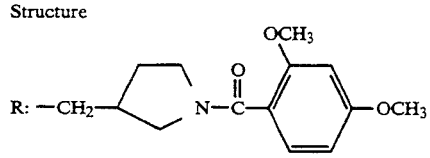

X: O  Y: H
Bond between 3- and 4-positions of the carbosytril nucleus: Single Bond
Crystalline form: Colorless amorphous
Form: Free
NMR: 11)

Example 14
Structure

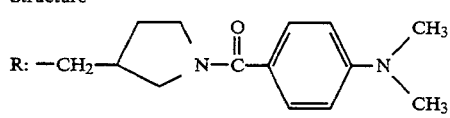

X: O  Y: H
Bond between 3- and 4-positions of the carbosytril nucleus: Single Bond
Crystalline form: Colorless amorphous
Form: Free
NMR: 12)

Example 15
Structure

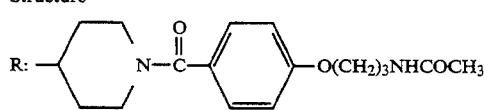

X: S  Y: H
Bond between 3- and 4-positions of the carbosytril nucleus: Single Bond
Crystalline form: Pale yellow powder
Recrystallization solvent: Dichloromethane/n-hexane
Melting point: 182–183° C.
Form: Free Example 16
Structure

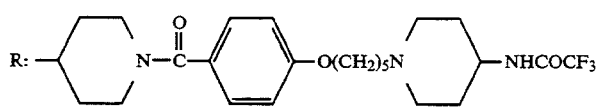

X: O  Y: H
Bond between 3- and 4-positions of the carbosytril nucleus: Single Bond
Crystalline form: Colorless oil
Form: Free
NMR: 13)

Example 17
Structure

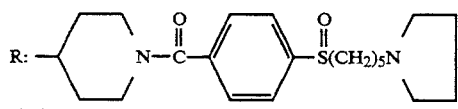

X: O  Y: H

TABLE 1-continued

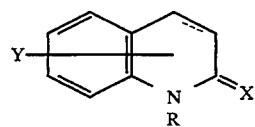

Bond between 3- and 4-positions of the carbosytril nucleus: Single Bond
Crystalline form: White amorphous
Form: Free
NMR: 14)

Example 18
Structure

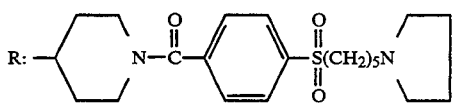

X: O  Y: H
Bond between 3- and 4-positions of the carbosytril nucleus: Single Bond
Crystalline form: White amorphous
Form: Free
NMR: 15)

Example 19
Structure

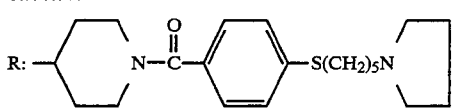

X: O  Y: H
Bond between 3- and 4-positions of the carbosytril nucleus: Single Bond
Crystalline form: White amorphous
Form: Hydrochloride
NMR: 16)

Example 20
Structure

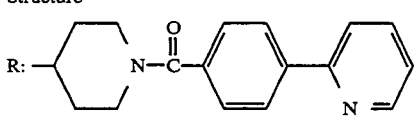

X: O  Y: H
Bond between 3- and 4-positions of the carbosytril nucleus: Single Bond
Crystalline form: Colorless prisms
Recrystallization solvent: Methanol
Melting point: 198–200° C.
Form: Free Example 21
Structure

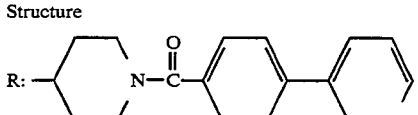

X: O  Y: H
Bond between 3- and 4-positions of the carbosytril nucleus: Single Bond
Crystalline form: Colorless prisms
Recrystallization solvent: Ethyl acetate
Melting point: 151–153° C.
Form: Free Example 22
Structure

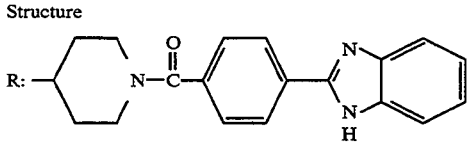

X: O  Y: H
Bond between 3- and 4-positions of the carbosytril nucleus: Single Bond
Crystalline form: Colorless needles
Recrystallization solvent: Methanol
Melting point: 240–243° C.
Form: Free TABLE 1-continued

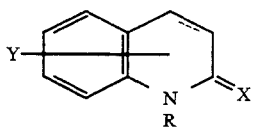

Example 23
Structure

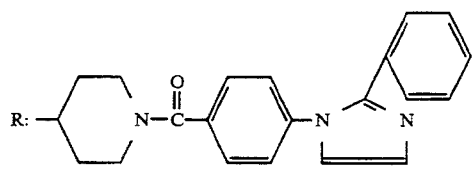

X: O  Y: H
Bond between 3- and 4-positions of the carbosytril nucleus: Single Bond
Crystalline form: White powder
Recrystallization solvent: Methanol
NMR: 17)
Melting point: 107–113° C.
Form: Free Example 24
Structure

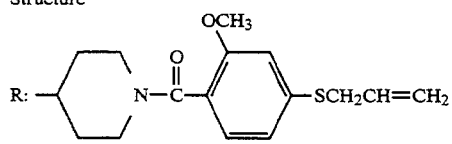

X: O  Y: H
Bond between 3- and 4-positions of the carbosytril nucleus: Single Bond
Crystalline form: White amorphous
Form: Free
NMR: 18)

Example 25
Structure

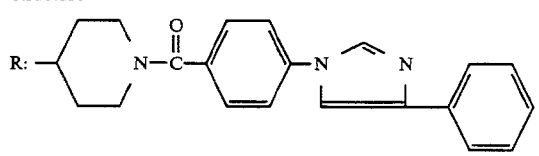

X: O  Y: H
Bond between 3- and 4-positions of the carbosytril nucleus: Single Bond
Crystalline form: Colorless scales
Recrystallization solvent: Ethyl acetate
Melting point: 203–206° C.:
Form: Free Example 26
Structure

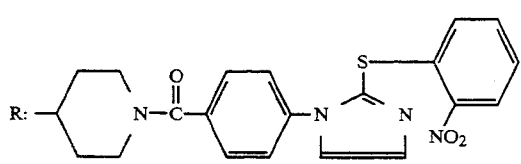

X: O  Y: H
Bond between 3- and 4-positions of the carbosytril nucleus: Single Bond
Crystalline form: Pale yellow powder
Recrystallization solvent: Methanol/chloroform
Melting point: 224–225.5° C.
Form: Free Example 27
Structure

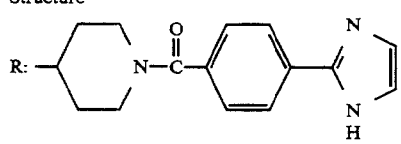

X: O  Y: H

TABLE 1-continued

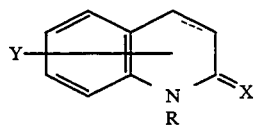

Bond between 3- and 4-positions of the carbosytril nucleus: Single Bond
Crystalline form: White powder
Form: Free
NMR: 19)

Example 28
Structure

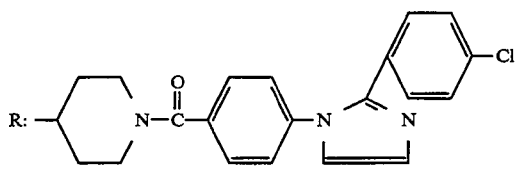

X: O  Y: H
Bond between 3- and 4-positions of the carbosytril nucleus: Single Bond
Crystalline form: Colorless prisms
Recrystallization solvent: Methanol
NMR: 20)
Melting point: Over 100° C. (decomposed)
Form: Free Example 29
Structure

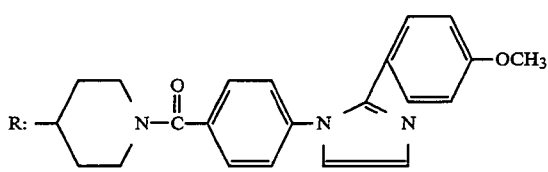

X: O  Y: H
Bond between 3- and 4-positions of the carbosytril nucleus: Single Bond
Crystalline form: Colorless prisms
Recrystallization solvent: Methanol
Melting point: 122–124° C.
Form: Free Example 30
Structure

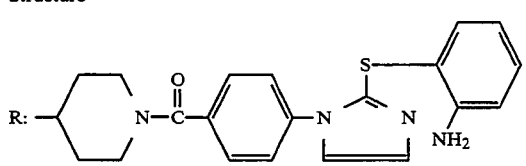

X: O  Y: H
Bond between 3- and 4-positions of the carbosytril nucleus: Single Bond
Crystalline form: White powder
Form: Free
NMR: 21)

Example 31
Structure

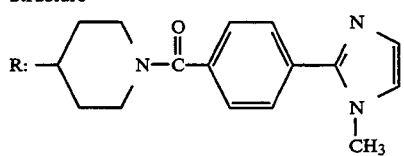

X: O  Y: H
Bond between 3- and 4-positions of the carbosytril nucleus: Single Bond
Crystalline form: Colorless scales
Recrystallization solvent: Ethyl acetate
Melting point: 177–179° C.
Form: Free Example 32
Structure

TABLE 1-continued

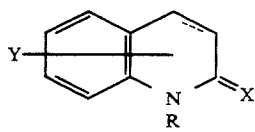

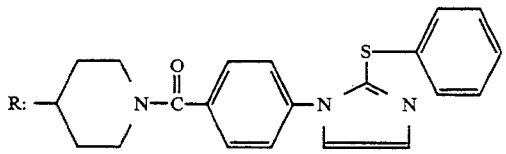

X: O   Y: H
Bond between 3- and 4-positions of the carbosytril nucleus: Single Bond
Crystalline form: White powder
Form: Free
NMR: 22)

Example 33
Structure

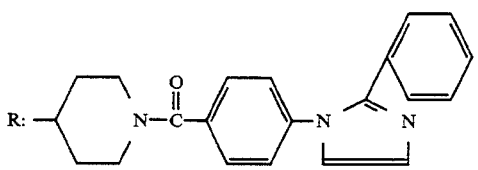

X: O   Y: H
Bond between 3- and 4-positions of the carbosytril nucleus: Double Bond
Crystalline form: Slightly yellow prisms
Recrystallization solvent: Methanol
Melting point: 113–116° C.
Form: Free 1) $^1$H-NMR(CDCl$_3$)δ ppm: 1.23–1.93(22H, m), 2.35–3.12(14H, m), 3.86–4.96(3H, m), 3.98(2H, t, J=6.4Hz), 6.82–6.93(2H, m), 6.96–7.32(4H, m), 7.35–7.48(2H, m)
2) $^1$H-NMR(CDCl$_3$)δ ppm: 1.42–2.03(23H, m), 2.27(2H, s), 2.50–3.13(10H, m), 3.87–4.40(3H, m), 3.98(2H, t, J=6.4Hz), 6.85–6.95(2H, m), 6.97–7.32(4H, m), 7.33–7.48(2H, m)
3) $^1$H-NMR(CDCl$_3$)δ ppm: 1.40–1.97(9H, m), 2.53–3.16(10H, m), 3.18(2H, q, J=9.5Hz), 3.83–4.98(3H, m), 3.99(2H, t, J=6.3Hz), 6.82–6.95(2H, m), 6.97–7.32(4H, m), 7.35–7.48(2H, m)
4) $^1$H-NMR(CDCl$_3$)δ ppm: 1.28(3H, t, J=7.1Hz), 1.38–1.93(8H, m), 2.28(3H, s), 2.35–3.10(12H, m), 3.39(2H, s), 3.82–4.96(3H, m), 3.98(2H, t, J=6.4Hz), 4.19(2H, q, J=7.1Hz), 4.25(2H, t, J=6.5Hz), 6.83–7.46(8H, m)
5) $^1$H-NMR(CDCl$_3$)δ ppm: 1.65–2.08(3H, m), 2.52–3.13(10H, m), 3.27–3.56(5H, m), 3.83–4.98(6H, m), 5.13–5.31(2H, m), 5.81–6.02(1H, m), 6.83–7.46(8H, m)
6) $^1$H-NMR(CDCl$_3$)δ ppm: 1.40–1.92(8H, m), 2.43–3.12(12H, m), 3.21–3.42(2H, m), 3.61–3.76(1H, m), 3.82–3.94(3H, m), 3.99(2H, t, J=6.3Hz), 5.10–5.28(2H, m), 5.80–6.01(1H, m), 6.85–7.48(8H, m)
7) $^1$H-NMR(CDCl$_3$)δ ppm: 1.30–1.68(6H, m), 1.69–2.12(8H, m), 2.15–2.40(4H, m), 2.48–3.12(11H, m), 3.87–5.00(3H, m), 3.98(2H, t, J=6.4Hz), 6.82–7.31(4H, m), 7.35–7.48(2H, m)
8) $^1$H-NMR(CDCl$_3$)δ ppm: 1.41–1.93(12H, m), 1.97(3H, s), 2.08–2.26(2H, m), 2.38–3.29(12H, m), 3.70–5.08(4H, m), 3.99(2H, t, J=6.3Hz), 5.60–5.73(1H, m), 6.83–6.92(2H, m), 6.95–7.31(4H, m), 7.37–7.46(8H, m)
9) $^1$H-NMR(CDCl$_3$)δ ppm: 1.00(6H, t, J=7.1Hz), 1.45–1.97(8H, m), 2.40–3.10(18H, m), 3.90–5.03(4H, m), 3.99(2H, t, J=6.2Hz), 6.82–6.95(2H, m), 6.98–7.33(4H, m), 7.46–7.50(2H, m)
10) $^1$H-NMR(CDCl$_3$)δ ppm: 1.05–2.10(4H, m), 2.55–3.00(7H, m), 3.40–4.15(9H, m), 4.65–4.80(1H, m), 6.35–6.50(2H, m), 6.90–7.30(5H, m)
11) $^1$H-NMR(CDCl$_3$)δ ppm: 1.65–2.15(2H, m), 2.65–3.00(5H, m), 3.05–4.40(12H, m), 6.40–6.55(2H, m), 6.90–7.10(2H, m), 7.10–7.30(3H, m)
12) $^1$H-NMR(CDCl$_3$)δ ppm: 1.65–2.15(2H, m), 2.55–3.05(5H, m), 2.99(6H, s), 3.35–4.50(6H, m), 6.65(2H, d, J=8.9Hz), 6.90–7.10(2H, m), 7.10–7.30(2H, m), 7.48(2H, d, J=8.9Hz)
13) $^1$H-NMR(CDCl$_3$)δ ppm: 1.37–1.63(6H, m), 1.68–2.17(8H, m), 2.30–2.41(2H, m), 2.52–3.10(10H, m), 3.70–5.04(4H, m), 4.00(2H, t, J=6.4Hz), 6.35–6.50(1H, m), 6.85–6.95(2H, m), 6.98–7.31(4H, m), 7.37–7.47(2H, m)
14) $^1$H-NMR(CDCl$_3$)δ ppm: 1.3–2.2(12H, m), 2.3–3.3(16H, m), 3.6–4.0(1H, m), 4.25–4.45(1H, m), 4.7–5.1(1H, m), 7.0–7.35(4H, m), 7.62(2H, d, J=8.5Hz), 7.67(2H, d, J=8.5Hz)
15) $^1$H-NMR(CDCl$_3$)δ ppm: 1.2–2.1(12H, m), 2.3–3.25(16H, m), 3.6–3.85(1H, m), 4.2–4.4(1H, m), 4.8–5.1(1H, m), 6.95–7.15(2H, m), 7.15–7.35(2H, m), 7.65(2H, d, J=8.4Hz), 7.96(2H, d, J=8.4Hz)
16) $^1$H-NMR(DMSO-d$_6$)δ ppm: 1.3–2.1(12H, m), 2.3–2.7(5H, m), 2.7–3.2(10H, m), 3.4–3.9(2H, m), 4.1–4.8(2H, m), 6.95–7.1(1H, m), 7.2–7.5(7H, m), 10.37(1H, brs)
17) $^1$H-NMR(DMSO-d$_6$)δ ppm: 1.5–2.0(2H, m), 2.3–3.3(8H, m), 3.4–3.8(1H, m), 4.2–4.45(1H, m), 4.45–4.8(1H, m), 6.95–7.1(1H, m), 7.2–7.4(11H, m), 7.4–7.6(3H, m)
18) $^1$H-NMR(CDCl$_3$)δ ppm: 1.6–1.9(2H, m), 2.5–3.2(8H, m), 3.5–3.7(3H, m), 3.75–3.95(3H, m), 4.2–4.7(1H, m), 4.85–5.05(1H, m), 5.05–5.3(2H, m), 5.8–6.05(1H, m), 6.85–7.35(7H, m)
19) $^1$H-NMR(CDCl$_3$)δ ppm: 1.6–2.1(2H, m), 2.5–3.2(8H, m), 3.7–4.1(1H, m), 4.2–4.45(1H, m), 4.6–5.2(1H, m), 5.5–6.8(1H, m), 6.95–7.3(6H, m), 7.38(2H, d, J=8.3Hz), 7.85(2H, d, J=8.3Hz)
20) $^1$H-NMR(CDCl$_3$)δ ppm: 1.7–2.1(2H, m), 2.5–3.4(8H, m), 3.6–4.2(1H, m), 4.2–4.5(1H, m), 4.5–5.2(1H, m), 7.0–7.4(12H, m), 7.53(2H, d, J=8.4Hz)
21) $^1$H-NMR(CDCl$_3$)δ ppm: 1.7–2.1(2H, m), 2.5–3.5(10H, m), 3.7–4.2(1H, m), 4.2–4.5(1H, m), 4.6–5.2(1H, m), 6.47(1H, dt, J=1.2Hz, 8.0Hz), 7.62(1H, dd, J=1.2Hz, 8.0Hz), 6.95(1H, dd, J=1.2Hz, 8.0Hz), 7.0–7.3(7H, m), 7.34(2H, d, J=8.4Hz), 7.54(2H, d, J=8.4Hz)
22) $^1$H-NMR(CDCl$_3$)δ ppm: 1.7–2.0(2H, m), 2.5–3.2(8H, m), 3.7–4.0(1H, m), 4.25–4.45(1H, m), 4.7–5.1(1H, m), 7.0–7.4(13H, m), 7.48(2H, d, J=8.4Hz)

Example 34

1-[1-{4-[5-(4-Trifluoroacetylamino-1-piperidinyl)pentyloxy]benzoyl}-4-piperidinyl]-3,4-dihydrocarbostyril (1.8 g) is dissolved in methanol (40 ml), and thereto is added potassium carbonate (0.8 g). The mixture is stirred at room temperature overnight. The reaction solution is concentrated and thereto is added water. The mixture is extracted with chloroform, dried over sodium carbonate, and purified by silica gel column chromatography (eluent; dichloromethane:methanol=10:1) to give 1-[1-{4-[5-(4-amino-1-piperidinyl)pentyloxy]benzoyl}-4-piperidinyl]-3,4-dihydrocarbostyril (1 g) as colorless oil.

$^1$H-NMR (CDCl$_3$) δ ppm: 1.30–1.68 (6H, m), 1.69–2.12 (8H, m), 2.15–2.40 (4H, m), 2.48–3.12 (11H, m), 3.87–5.00 (3H, m), 3.98 (2H, t, J=6.4 Hz), 6.82–6.93 (2H, m), 6.97–7.31 (4H, m), 7.35–7.48 (2H, m)

Example 35

1-[1-{4-[5-(4-Amino-1-piperidinyl)pentyloxy]benzoyl}-4-piperidinyl]-3,4-dihydrocarbostyril (0.6 g) and acetic anhydride (0.2 ml) are dissolved in dichloromethane (20 ml), and thereto are added triethylamine (0.56 ml) and 1,4-dimethylaminopyridine (20 mg), and the mixture is stirred at room temperature overnight. Water is added to the reaction mixture and the mixture is extracted with chloroform, dried over sodium carbonate, and purified by silica gel column chromatography (eluent; dichloromethane:methanol=20:1) to give 1-[1-{4-[5-(4-acetylamino-1-piperidinyl)pentyloxy]benzoyl}-4-piperidinyl]-3,4-dihydrocarbostyril (310 mg) as colorless oil.

$^1$H-NMR (CDCl$_3$) δ ppm: 1.41–1.93 (12H, m), 1.97 (3H, s), 2.08–2.26 (2H, m), 2.38–3.29 (12H, m), 3.70–5.08 (4H, m), 3.99 (2H, t, J=6.3 Hz), 5.60–5.73 (1H, m), 6.83–6.92 (2H, m), 6.95–7.31 (4H, m), 7.37–7.46 (2H, m)

Using the suitable starting materials, the compounds of the above Examples 1 and 14 are obtained in the same manner as in Example 35.

Example 36

1-{1-[4-(6-Diethylamino-5-hydroxyhexyloxy)benzoyl}-4-piperidinyl}-3,4-dihydrocarbostyril (0.7 g) and methyl isocyanate (0.24 ml) are dissolved in acetonitril (20 ml), and thereto is added trifuroboran ethyl ether complex (0.35 ml) under ice-cooling, and the mixture is stirred at room temperature overnight. The reaction mixture is concentrated and purified by silica gel column chromatography (eluent; dichloromethane:methanol=20:1) to give 1-{1-[4-(6-diethylamino-5-methylaminocarbonyloxyhexyloxy)benzoyl]-4-piperidinyl}-3,4-dihydrocarbostyril (314 mg) as colorless oil.

$^1$H-NMR (CDCl$_3$) δ ppm: 1.00 (6H, t, J=7.1 Hz), 1.45–1.97 (8H, m), 2.40–3.10 (18H, m), 3.90–5.03 (4H, m), 3.99 (2H, t, J=6.2 Hz), 6.82–6.95 (2H, m), 6.98–7.33 (4H, m), 7.46–7.50 (2H, m)

Example 37

1-{1-[4-{5-[(N-Methyl-N-(2-hydroxyethyl)amino]pentyloxy}benzoyl]-4-piperidinyl}-3,4-dihydrocarbostyril (0.9 g) and ethylmalonyl chloride (0.28 ml) are dissolved in dichloroethane (10 ml), and thereto is added diisopropylethylamine (0.48 ml) under ice-cooling, and the mixture is stirred at room temperature overnight. The reaction mixture is concentrated and purified by silica gel column chromatography (eluent; dichloromethane:methanol=20:1) to give 1-{1-[4-{5-[(N-methyl-N-(2-ethoxycarbonylacetyloxyethyl)amino]pentyloxy}benzoyl]-4-piperidinyl}-3,4-dihydrocarbostyril (0.28 g) as colorless oil.

$^1$H-NMR (CDCl$_3$) δ ppm: 1.28 (3H, t, J=7.1 Hz), 1.38–1.93 (8H, m), 2.28 (3H, s), 2.35–3.10 (12H, m), 3.39 (2H, s), 3.82–4.96 (3H, m), 3.98 (2H, t, J=6.4 Hz), 4.19 (2H, q, J=7.1 Hz), 4.25 (2H, t, J=6.5 Hz), 6.83–7.46 (8H, m)

Example 38

1-{1-[4-(4-Oxiranylbutoxy)benzoyl]-4-piperidinyl}-3,4-dihydrocarbostyril (4.6 g) is dissolved in methanol (100 ml), and thereto is added allylamine (10 ml), and the mixture is stirred overnight. The reaction mixture is concentrated and purified by silica gel column chromatography (eluent; dichloromethane:methanol=10:1) to give 1-{1-[4-(5-hydroxy-6-allylaminohexyloxy)benzoyl]-4-piperidinyl}-3,4-dihydrocarbostyril (2.5 g) as colorless oil.

$^1$H-NMR (CDCl$_3$) δ ppm: 1.40–1.92 (8H, m), 2.43–3.12 (12H, m), 3.21–3.42 (2H, m), 3.61–3.76 (1H, m), 3.82–3.94 (3H, m), 3.99 (2H, t, J=6.3 Hz), 5.10–5.28 (2H, m), 5.80–6.01 (1H, m), 6.85–7.48 (8H, m)

Using the suitable starting materials, the compound of the above Example 6 is obtained in the same manner as in Example 38.

Example 39

1-{1-[4-(5-Bromopentyloxy)benzoyl]-4-piperidinyl}-3,4-dihydrocarbostyril (2 g) and 4-trifluoroacetylaminopiperidine (2 g) are dissolved in dimethylformamide (40 ml), and thereto is added potassium carbonate (2 g) and the mixture is stirred overnight. The reaction mixture is poured into water, and the mixture is extracted with toluene/ethyl acetate (1:1), dried over magnesium sulfate, and purified by silica gel column chromatography (eluent; dichloromethane:methanol=50:1) to give 1-[1-{4-[5-(4-trifluoroacetylamino-1-piperidinyl)pentyloxy]benzoyl}-4-piperidinyl]-3,4-dihydrocarbostyril (2 g) as colorless oil.

$^1$H-NMR (CDCl$_3$) δ ppm: 1.37–1.63 (6H, m), 1.69–2.17 (8H, m), 2.30–2.41 (2H, m), 2.52–3.10 (10H, m), 3.70–5.04 (4H, m), 4.00 (2H, t, J=6.4 Hz), 6.35–6.50 (1H, m), 6.85–6.95 (2H, m), 6.98–7.31 (4H, m), 7.37–7.47 (2H, m)

Using the suitable starting materials, the compounds of the above Examples 2–10 and 15 are obtained in the same manner as in Example 39.

Example 40

To the mixture of conc. hydrochloric acid (3.2 ml) and ethanol (2 ml) is added 1-[1-{4-[2-(2-nitrophenyl)thio-1-imidazolyl]benzoyl}-4-piperidinyl]-3,4-dihydrocarbostyril (2.0 g), and thereto is added dropwise a solution of stannous chloride dihydrate (2.7 g) in ethanol (4 ml) at a temperature below 25° C. with water-cooling, and the mixture is stirred at room temperature for two hours. The mixture is poured into ice-water and basified with aqueous sodium hydroxide solution, extracted with chloroform, washed with water, and dried over sodium sulfate. After concentrated under reduced pressure, the resulting residue is purified by silica gel column chromatography (eluent; chloroform:methanol=50:1–25:1), and further dissolved in methanol. The mixture is added dropwise with stirring into water (about 40 ml) and the resulting precipitates are collected by filtration and dried to give 1-[1-{4-[2-(2- aminophenyl)thio-1-imidazolyl]benzoyl}-4-piperidinyl}-3,4-dihydrocarbostyril (1.6 g) as white powder.

$^1$H-NMR (CDCl$_3$) δ ppm: 1.7–2.1 (2H, m), 2.5–3.5 (10H, m), 3.7–4.2 (1H, m), 4.2–4.5 (1H, m), 4.6–5.2 (1H, m), 6.47 (1H, dt, J=1.2 Hz, J=8.0 Hz), 7.62 (1H, dd, J=1.2 Hz, J=8.0 Hz), 6.95 (1H, dd, J=1.2 Hz, J=8.0 Hz), 7.0–7.3 (7H, m), 7.34 (2H, d, J=8.4 Hz), 7.54 (2H, d, J=8.4 Hz)

Example 41

To a solution of 1-{1-[4-(2-imidazolyl)benzoyl]-4-piperidinyl}-3,4-dihydrocarbostyril (1.0 g) and potassium carbonate (0.35 g) in dimethylformamide (10 ml) is added methyl iodide (0.16 ml) under ice-cooling, and the mixture is stirred at room temperature overnight. Further, to the mixture are added methyl iodide (0.16 ml) and potassium carbonate (0.3 g), and the mixture is stirred at room temperature for 8 hours. The mixture is poured into ice-water, extracted with ethyl acetate, washed with water and dried over sodium sulfate. After concentrated under reduced pressure, the resulting residue is purified by silica gel column chromatography (eluent; dichloromethane:methanol=25:1) and recrystallized from ethyl acetate to give 1-{1-[4-(1-methyl-2-imidazolyl)benzoyl]-4-piperidinyl}-3,4-dihydrocarbostyril (0.15 g) as colorless scales, m.p. 177°–179° C.

Salts encompass non-toxic salts of the compounds used in this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "Caesarean delivery" shall mean incision through the abdominal and uterine walls for delivery of a fetus.

The ability of the compounds of formula I to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Caesarean delivery.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrlates and cross-linked or amphipathic block copolymers of hydrogels.

RADIOLIGAND BINDING ASSAYS

The high affinity binding of [$^3$H] oxytocin (OT)(-[tyrosyl, 3,5-[$^3$H]OT; 30-60 Ci/mmol; New England Nuclear. Boston, Mass.) to uterine OT receptors was based on an assay (Fuchs, A-R; Fuchs, F; Soloff, MS. 1985 J. Clin. Endocrinol. Metab. 60:37) using a crude membrane preparation of uteri taken from diethylstilbestrol dipropionate (DES)-treated (0.3 mg/kg, ip; 18-24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 μM unlabeled OT and the binding reaction was terminated by filtration through glass fiber filters using a cell harvester (model 7019, Skatron, Inc., Sterling, Va.).

The measurement of [$^3$H]vasopressin (AVP) ([phenylalanyl-3,4 5-$^3$H]AVP; 80-90 Ci/mmol; New England Nuclear) binding to a crude membrane preparation of male rat liver (AVP-V$_1$ sites) or kidney medulla (AVP-V$_2$ sites) was determined according to the method of Butlen, et al. (Butlen, D; Guillon, G; Rajerison, R. M.; Jard, S; Sawyer, W. H.; Manning, M. 1978 Mol Pharmacol 14:1006).

Competition assays were conducted at equilibrium (30 minutes at 30° C.) using 1 nM [$^3$M]AVP (liver) or 2 nM [$^3$H]AVP (kidney) in the following assay buffer: 100 mM Tris-HCl, 5 mM MgCl$_2$, 0.1% BSA, 50 mM phenylmethylsulfonylfluoride, and 50 mg/ml bacitracin, pH 8.0. Nonspecific binding (5-10% of the total binding) was determined using 10 μM unlabeled AVP, and the binding reaction was terminated by filtration as described above for the [$^3$H]OT binding assay.

IC$_{50}$ values were determined for both [$^3$H]OT and [$^3$H]AVP binding assays by linear regression of the relation log concentration of compound vs. percent inhibition of specific binding. Data are also shown as the degree (%) of inhibition of specific binding at a given concentration of compound.

| Example | IC$_{50}$ [$^3$H] OT (rat uterus) | [$^3$H]AVP-V$_1$ (rat liver) |
|---|---|---|
| 1 | 570 | 140 |
| 2 | 1100 | 120 |
| 3 | 2500 | 320 |
| 4 | 1000 | 130 |
| 5 | 560 | 39 |

Radioligand binding for additional subgenera of compounds were additionally performed for each of the following three groups.

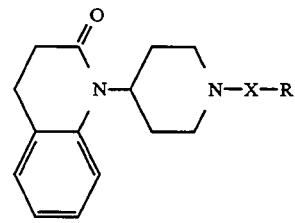

| X | R | IC$_5$, nM or % Inhibition rat OT | rat V1/V2 |
|---|---|---|---|
| CO | phenyl | 69% @ 10 uM | 1,300/ca. 100,000 |
| CO | 1-naphthyl | 69% @ 10 uM | 17%/5% @ 3 uM |
| CO | 2-naphthyl | 75% @ 10 uM | 75%/7% @ 3 uM |
| CO | 5-indolyl | 1,700 nM | 240/56,000 |
| CO | p-CH$_2$—C$_6$H$_4$—OCH$_3$ | 2,400 nM | 6,000/>100,000 |
| CO | p-CH$_2$—C$_6$H$_4$—NH$_2$ | 19% @ 1 uM | 27%/1% @ 3 uM |
| CO | p-CH$_2$—C$_6$H$_4$—NHAc | 2,300 | 950/>100,000 |
| SO$_2$ | p-C$_6$H$_4$—OCH$_3$ | 36% @ 10 uM | 15%/12% @ 3 uM |
| SO$_2$ | (+)-camphor-10-yl | 1,900 | 8,000/72,000 |

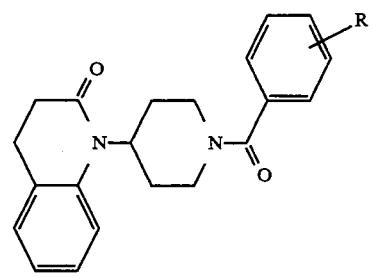

| R | IC$_{50}$, nM or % Inhibition rat OT | rat V1/V2 |
|---|---|---|
| H | 69% @ 10 uM | 1,3000/ca. 100,000 |
| o-OCH$_3$ | 1,100 | 380/66,000 |
| m-OCH$_3$ | 2,700 | 2,100/>100,000 |
| o-Cl, p-Cl | 7% @ 10 uM | 34%/1% @ 3 uM |
| o-CH$_3$, p-CH$_3$ | 79% @ 10 uM | 48%/55% @ 3 uM |
| o-OCH$_3$, p-OCH$_3$ | 560 | 39/28,000 |
| o-Cl, p-NO$_2$ | 15,000 | 34%/6% @ 3 uM |

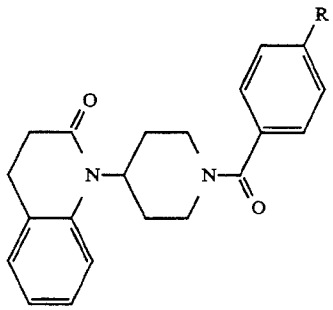

| R | IC50, nM or % Inhibition | |
|---|---|---|
| | rat OT | rat $V_1/V_2$ |
| H | 69% @ 10 μM | 1,300/ca. 100,000 |
| $CH_3$ | 73% @ 10 μM | 370/64,000 |
| $CF_3$ | 69% @ 10 μM | 800/60,000 |
| $CH_2CH_3$ | 80% @ 10 μM | 340/51,000 |
| tert-$C_4H_9$ | 77% @ 10 μM | 800/ca. 70,000 |
| $C_6H_5$ | 3,500 | 65%/2% @ 3 μM |
| F | 69% @ 10 μM | 1,100/≧100,000 |
| $OCH_3$ | 1,000 | 130/38,000 |
| O-n$C_4H_9$ | 38% @ 1 μM | 420/54,000 |
| O—$(CH_2)_3$N═Pth | 1,100 | 120/≧100,000 |
| O—$(CH_2)_3$NHAc | 570 | 140/ca. 100,000 |
| $NO_2$ | 57% @ 10 μM | 1,700/>100,000 |
| CN | 52% @ 10 μM | 59%/3% @ 3 μM |
| $CO_2CH_3$ | 1,400 nM | 35,000/>100,000 |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly.

What is claimed is:

1. A method of preventing preterm labor in a mammal in need thereof, comprising the step of administering to said mammal a pharmacologically effective amount of a compound of the formula:

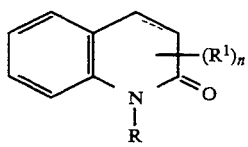

I wherein $R^1$ is hydrogen; nitro; lower alkoxy; lower alkoxycarbonyl; lower alkyl; halogen; amino having one to two substituents selected from the group consisting of lower alkanoyl, lower alkyl, benzoyl and phenyl lower alkoxycarbonyl; hydroxy; cyano; carboxy; lower alkanoyloxy; or hydrazinocarbonyl;

q is an integer of 1 to 3 and

R is a group of the formula

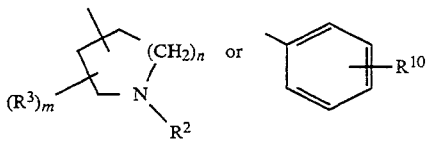

wherein $R^2$ is hydrogen; lower alkoxycarbonyl; phenoxycarbonyl which phenyl ring may be substituted by one to three substituents selected from nitro and an amino having optionally one or two substituents selected from a lower alkanoyl, lower alkyl or benzoyl; phenyl lower alkenylcarbonyl; phenyl lower alkanoyl substituted by amino which in turn is substituted by lower alkoxycarbonyl; alkanoyl; alkenylcarbonyl; phenylsulfonyl substituted by lower alkoxy; a group of the formula

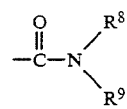

wherein $R^8$ and $R^9$ are the same or different and are each hydrogen or phenyl substituted by lower alkoxy, lower alkyl, halogen, amino substituted by lower alkyl, lower alkanoyl or nitro; carbonyl substituted by a heterocyclic ring substituted by one to three substituents selected from phenyl lower alkoxycarbonyl, phenyl lower alkoxy, oxo, lower alkyl or lower alkylenedioxy; a group of the formula

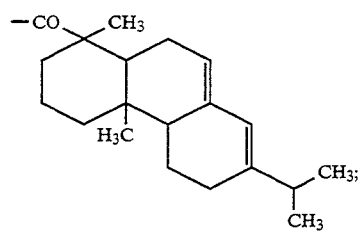

naphthylcarbonyl; thienyl lower alkanoyl; tricyclo[3.3.1.1]decanyl(lower)alkanoyl; tricyclo[3.3.1.1.]-decanylcarbonyl; or a group of the formula

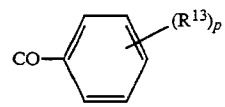

wherein p is 0 or an integer of 1 to 3, and $R^{13}$ is hydroxy; alkoxy; alkoxy having one or two substituents selected from hydroxy, lower alkanoyloxy, tri-lower alkylammonium, lower alkoxy, or a group of the formula

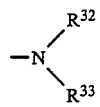

wherein $R^{32}$ and $R^{33}$ are the same or different and are each hydrogen, lower alkyl, hydroxy-substituted lower alkyl, lower alkanoyl, tetrahydropyranyl lower alkyl, phenyl, phenyl lower alkyl wherein the alkyl moiety may optionally be substituted by hydroxy and the phenyl ring may optionally be substituted by a lower alkoxy, or a pyridyl lower alkyl; or $R^{32}$ and $R^{33}$ may be bound to nitrogen to form a 5 or 6 membered saturated heterocyclic ring which may be intervened with nitrogen, oxygen or sulfur wherein the heterocyclic group may optionally be substituted by a member selected from carbamoyl, lower alkyl, phenyl lower alkyl, phenyl or hydroxy-substituted lower alkyl; carboxy-substituted alkoxy; halogen-substituted lower alkoxy; lower alkoxycarbonyl-substituted alkoxy; lower alkanoyloxy-substituted lower alkoxy; lower alkenyloxy substituted lower alkoxy; lower alkoxy lower alkoxy; lower alkylsulfonyloxy-substituted lower alkoxy; benzoyloxy-substituted lower alkoxy; tricyclo[3.3.1.1]decanyl-substituted lower alkoxy; lower alkoxy lower alkoxy substituted by one or two substituents selected from hydroxy and an amino being optionally substituted by lower alkyl; morpholinyl-substituted lower alkoxy; benzimidazolylsulfinyl-substituted lower alkoxy; a group of the formula

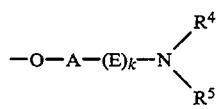

wherein A is alkylene, k is an integer of 0 or 1, E is —CO— or —OCO—, $R^4$ and $R^5$ are the same or different and are each hydrogen; lower alkyl which may optionally be substituted by hydroxy or cyano; lower alkenyl, lower alkynyl; phenyl lower alkyl; lower alkanoyl which may optionally have one to three substituents of a halogen atom; benzoyl which phenyl ring may optionally be substituted by a member selected from nitro and an amino having optionally one or two substituents selected from lower alkyl, lower alkanoyl or phenyl lower alkoxycarbonyl; phenyl; lower alkoxycarbonyl; lower alkoxycarbonyl lower alkyl wherein the lower alkyl moiety may optionally be substituted by hydroxy or an amino having optionally a phenyl lower alkoxycarbonyl substituent; an amido having optionally a lower alkyl substituent; a pyrrolidinyl-substituted carbonyl which pyrrodinyl ring may optionally be substituted by phenyl lower alkoxycarbonyl; amino-substituted lower alkanoyl wherein the lower alkanoyl moiety may optionally be substituted by a member selected from phenyl lower alkoxycarbonyl amino, hydroxy, phenyl optionally having a hydroxy substituent, carbamoyl, imidazolyl or a lower alkylthio, and the amino group may optionally have a substituent selected from a lower alkyl optionally having a hydroxy substituent, lower alkenyl, phenyl lower alkyl optionally having a lower alkoxy substituent on the phenyl ring, lower alkylsulfonyl, lower alkanoyl, lower alkylsulfonyl, a phenylsulfonyl which phenyl ring may optionally be substituted by a lower alkyl group, nitro or amino having optionally one or two substituents selected from a lower alkyl and a lower alkanoyl; amido-substituted lower alkyl wherein the lower alkyl moiety optionally has a substituent selected from phenyl optionally having a hydroxy substituent, imidazolyl, carbamoyl or a lower alkylthio, and the amido group may optionally have a lower alkyl substituent; amino-substituted lower alkyl which may optionally be substituted by a lower alkyl or a lower alkanoyl; anilinocarbonyl; piperidinyl which may optionally be substituted by phenyl lower alkyl; cycloalkyl, cycloalkenylcarbonyl; cycloalkylcarbonyl which may optionally have one to three substituents selected from hydroxy and a lower alkanoyloxy; tetrahydropyranyl-substituted lower alkyl wherein the tetrahydropyranyl ring may optionally have one to four substituents selected from hydroxy and a lower alkoxy; lower alkanoyl which is substituted by a 5 or 6 membered saturated heterocyclic group selected from pyrrolidinyl, piperazinyl, piperidinyl and morpholinyl wherein the heterocyclic group may have optionally a substituent selected from a lower alkyl and phenyl; piperidinyl-substituted carbonyl which may optionally be substituted by a lower alkanoyl; lower alkanoyloxy lower alkyl; pyridyl-substituted lower alkyl; or an amido acid residue which can form an amido group with its amino group or $R^4$ and $R^5$ may bind together with the nitrogen atom to which they bond to form a 5 or 6 membered saturated or unsaturated heterocyclic group which may be intervened or not with nitrogen, oxygen, or sulfur, wherein the heterocyclic group may optionally be substituted by a member selected from a phenyl having optionally a substituent selected from a lower alkoxy and a halogen atom, oxo, hydroxy, lower alkenyl, carboxy, phenyl lower alkyl having an optional hydroxy substituent on the lower alkyl moiety, lower alkanoyl lower alkyl having optionally a hydroxy substituent, benzoyl, an amido having optionally a lower alkyl substituent, anilinocarbonyl, benzoyl lower alkyl lower alkylsulfonyl, piperidinyl, pyrimidyl, pyridyl, and lower alkoxycarbonyl; carbamoyloxy-substituted lower alkoxy; lower alkylthio-substituted lower alkoxy; alkinyloxy; phenoxy; lower alkanoyloxy; lower alkylsulfonyloxy; lower alkynyl; phenyl lower alkoxy; cycloalkyl; cycloalkyloxy; cycloalkenyloxy; imidazo[4,5-c]pyridyl-carbonyl lower alkoxy; a group of the formula

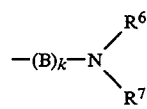

wherein k is as defined above, B is a lower alkylene or a group —CO— and $R^6$ and $R^7$ are the same or different and are each hydrogen, lower alkyl, lower alkanoyl having optionally one to three halogen substituents, carboxy lower alkyl, lower alkoxycarbonyl, lower alkoxycarbonyl lower alkyl, lower alkenyl, amido-substituted lower alkyl having an optional lower alkyl substituent, or a phenyl lower alkoxycarbonyl, or $R^6$ and $R^7$ may bind together with a nitrogen atom to which they bond to form a 5 or 6 membered, saturated or unsaturated heterocyclic group which may be intervened or not with nitrogen, oxygen or sulfur, wherein the heterocyclic group may optionally have a substituent selected from a lower alkoxycarbonyl, lower alkyl, lower alkylthio, or oxo; nitro; halogen; lower alkylsulfonyl; lower alkyl which may optionally have one to three substituents selected from a halogen, hydroxy, phenyl and lower alkoxy; cyano-substituted lower alkoxy, pyrrolyl-substituted lower alkoxy; cyano; lower alkoxycarbonyl; amidino; carbamoyl; carboxy; lower alkanoyl; benzoyl; lower alkoxycarbonyl lower alkyl; carboxy lower alkyl; lower alkoxy lower alkyl; lower alkanoyloxy lower alkyl; hydroxyimino; substituted lower alkyl; phenyl; lower alkylthio; lower alkylsulfinyl; lower alkenyl optionally having a hydroxy substituent; lower alkylenedioxy, lower alkylsilyl; pyrimidylthio-substituted lower alkoxy; pyrimidylsulfinyl-substituted lower alkoxy; pyrimidylsulfonyl-substituted lower alkoxy; imidazolylthio-substituted lower alkoxy which may optionally have a lower alkyl substituent; imidazolylsulfonyl-substituted lower alkoxy which may optionally have a lower alkyl substituent; ammonium-lower alkoxy having three substituents selected from lower alkoxy, lower alkenyl and oxo; phenylthio-substituted lower alkoxy which phenyl ring may optionally have a substituent selected from nitro and amino; phenylsulfonyl-substituted lower alkoxy which phenyl ring may optionally have a substituent selected from nitro and an amino having optionally one or two substituents selected from a lower alkanoyl and lower alkyl; pyridylthio-substituted lower alkoxy; or a pyridylsulfonyl-substituted lower alkoxy which pyridyl ring may optionally be substituted by oxo; n is an integer of 1 or 2; m is 0 or an integer of 1 to 3; $R^3$ is a lower alkyl; $R^{10}$ is a group of the formula

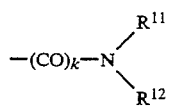

wherein k is as defined above and $R^{11}$ and $R^{12}$ are the same or different and are each hydrogen, lower alkyl, phenyl lower alkyl, lower alkenyl, benzoyl which may optionally have a lower alkoxy substituent, tricyclo[3.3.1.1]decanyl, a phenyl which may optionally have a lower alkoxy substituent or a cycloalkyl, or $R^{11}$ and $R^{12}$ may bind together with the nitrogen atom to which they bond to form a saturated or unsaturated heterocyclic group which may be intervened or not with nitrogen, oxygen or sulfur, wherein the heterocyclic group may optionally have a substituent selected from a benzoyl, a lower alkanoyl, phenyl lower alkyl and a phenyl which may optionally be substituted by a lower alkoxy and a lower alkonoyl; the bond between 3 and 4 positions of the carbostyril ring is a single bond or double bond; provided that when $R^1$ is hydrogen and the k in the formula

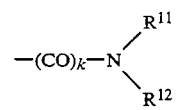

is 0, $R^{11}$ and $R^{12}$ are not simultaneously hydrogen atoms and including the pharmaceutically acceptable salts of the compounds of the formula I.

2. A method of preventing preterm labor in a mammal in need thereof, comprising the step of administering to said mammal a pharmacologically effective amount of a compound of the formula:

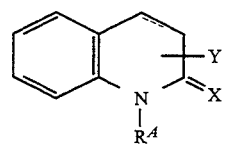

II wherein X is oxygen or sulfur,
Y is hydrogen or lower alkyl;
$R^4$ is a group of the formula

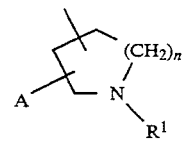

wherein n is 1 or 2, A is a lower alkylene, and $R^1$ is a benzoyl which phenyl may optionally have one to three substituents selected from a lower alkoxy and an amino having optionally a lower alkyl substituent;
or $R^4$ is a group of the formula

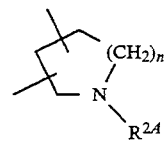

wherein n is as defined above, and $R^{24}$ is a group of the formula

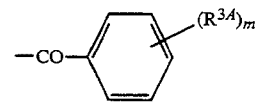

wherein $R^{34}$ is a lower alkoxy; or a 5 or 6 membered heterocyclic ring having 1 to 2 hetero atoms selected from nitrogen, oxygen, or sulfur which may optionally have a substituent selected from lower alkyl, oxo, phenyl optionally having a substituent selected from halogen and a lower alkoxy on the phenyl ring and a phenylthio optionally having a substituent selected from nitro and amino; lower alkynylthio; pyrrolidinyl-substituted lower alkylthio; pyrrolidinyl-substituted lower alkylsulfinyl; pyrrolidinyl-substituted lower alkylsulfonyl; a group of the formula

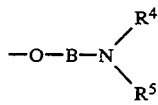

wherein B is a lower alkylene having optionally a hydroxy substituent, R is hydrogen and $R^5$ is tricyclo[3.3.1.1]decanyl, tricyclo[3.3.1.1]decanyl-lower alkyl, halogen-substituted lower alkyl, lower alkoxycarbonyl-lower alkanoyloxy-lower alkyl, lower alkanyl, or lower alkenyl, or $R^4$ and $R^5$ may bind together with the nitrogen atom to which then bond to form a group of the formula

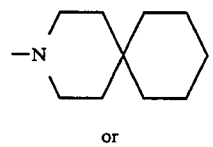

or

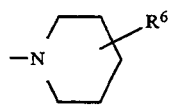

wherein $R^6$ is an amino which may optionally be substituted by a lower alkanoyl having optionally one to three halogen substituents; or lower alkoxy having two substituents selected from an aminocarbonyloxy having optionally a lower alkyl substituent or a group of the formula

wherein $R^7$ and $R^8$ are the same of different and are each hydrogen or lower alkyl;
m is an integer of 1 to 3;
the bond between the 3 and 4 positions of the carbostyril ring is a single bond or a double bond; provided that when all of $R^{3A}$ are lower alkoxy or when $R^5$ is a lower alkanoyl, X is sulfur and that when $R^5$ is lower alkenyl and X is oxygen, B is a lower alkylene having a hydroxy substituent, and further that when $R^{3A}$ is a heterocyclic group having a lower alkyl or oxo substituent, the heterocyclic group is bound to the phenyl ring at the position other then the hetero atom, or a pharmaceutically acceptable salt thereof.

3. A method of preventing preterm labor in a mammal in need thereof, comprising the step of administering to said mammal a pharmacologically effective amount of a compound of the formula:

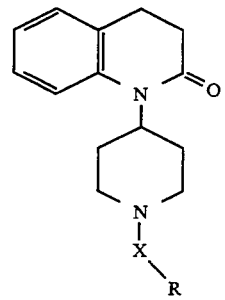

wherein X is CO or $SO_2$;
R is unsubstituted or substituted phenyl where said substituents are $R^1$ or $R^2$; naphthyl; indolyl; p—$CH_2$—$C_6H_4$—$OCH_3$; p—$CH_2C_6H_4$—$NH_2$; p—$CH_2$—$C_6H_4$—NHAc;; or camphor-10-yl;
$R^1$ is halogen, nitro, cyano, lower alkoxycarbonyl, phenyl, hydroxy, O—$(CH_2)_3$N=Pth where Pth is phthaloyl, O—$(CH_2)_3$$NHCOCH_3$ or lower alkoxy; and
$R^2$ is hydrogen, hydroxy; or lower alkoxy which may be substituted wherein said substituent is carbonylamine which may be substituted by lower alkyl; or 5 membered heterocyclic rings having 1 nitrogen heteroatom and where said substituent is phenyl or oxo; and the pharmaceutically acceptable salts thereof.

4. A method of stopping labor prior to Caesarian delivery in a mammal in need thereof, comprising the step of administering to said mammal a pharmacologically effective amount of a compound as claimed in claim 1.

5. A method of treating dysmenorrhea in a mammal in need thereof, comprising the step of administering to said mammal a pharmacologically effective amount of a compound as claimed in claim 1.

* * * * *

UNITED STATES PATENT AND TRADEMARK OFFICE
CERTIFICATE OF CORRECTION

PATENT NO. : 5,356,904
DATED : Oct. 18, 1994
INVENTOR(S) : Freidinger et al

It is certified that error appears in the above-indentified patent and that said Letters Patent is hereby corrected as shown below:

Column 345, line 60, change "$(R^1)n$" to -- $(R^1)q$ --.

Signed and Sealed this

Ninth Day of January, 1996

Attest:

BRUCE LEHMAN

*Attesting Officer*  *Commissioner of Patents and Trademarks*